(12) United States Patent
Mambo et al.

(10) Patent No.: US 8,735,074 B2
(45) Date of Patent: May 27, 2014

(54) MIRNA BIOMARKERS OF LUNG DISEASE

(75) Inventors: Elizabeth Mambo, Austin, TX (US); David Brown, Austin, TX (US); Alex T. Adai, Austin, TX (US); Tiffany Sanford, Round Rock, TX (US); Stephanie Volz, Austin, TX (US); Ashish Choudhary, Austin, TX (US)

(73) Assignee: Asuragen, Inc., Austin, TX (US)

( * ) Notice: Subject to any disclaimer, the term of this patent is extended or adjusted under 35 U.S.C. 154(b) by 542 days.

(21) Appl. No.: 12/870,245

(22) Filed: Aug. 27, 2010

(65) Prior Publication Data

US 2011/0053158 A1    Mar. 3, 2011

Related U.S. Application Data

(60) Provisional application No. 61/237,972, filed on Aug. 28, 2009.

(51) Int. Cl.
*C12Q 1/68* (2006.01)

(52) U.S. Cl.
CPC ............ *C12Q 1/6883* (2013.01); *C12Q 1/6886* (2013.01); *C12Q 2600/112* (2013.01); *C12Q 2600/158* (2013.01); *C12Q 2600/178* (2013.01)
USPC ........................................ 435/6.14; 435/6.12

(58) Field of Classification Search
None
See application file for complete search history.

(56) References Cited

U.S. PATENT DOCUMENTS

| | | | |
|---|---|---|---|
| 6,242,204 | B1 | 6/2001 | Torczynski et al. |
| 6,713,619 | B1 | 3/2004 | Weinberg et al. |
| 7,888,010 | B2 | 2/2011 | Brown et al. |
| 7,919,245 | B2 | 4/2011 | Brown et al. |
| 8,003,320 | B2 | 8/2011 | Brown et al. |
| 2006/0105360 | A1 | 5/2006 | Croce et al. |
| 2006/0204989 | A1 | 9/2006 | Kopreski |
| 2008/0171667 | A1 | 7/2008 | Brown et al. |
| 2009/0075258 | A1 | 3/2009 | Latham et al. |
| 2009/0215865 | A1 | 8/2009 | Plasterk et al. |
| 2010/0173288 | A1 | 7/2010 | Zhang et al. |
| 2010/0323357 | A1* | 12/2010 | Nana-Sinkam et al. .......... 435/6 |
| 2011/0112173 | A1 | 5/2011 | Brown et al. |
| 2013/0017972 | A1 | 1/2013 | Brown et al. |

FOREIGN PATENT DOCUMENTS

| | | |
|---|---|---|
| EP | 2065466 A2 | 6/2009 |
| EP | 2 133 431 | 12/2009 |
| WO | WO 2005/118806 | 12/2005 |
| WO | WO 2007/081720 A2 | 7/2007 |
| WO | WO 2009/052386 A1 | 4/2009 |
| WO | WO 2009/055979 | 5/2009 |
| WO | WO 2009/070653 A1 | 6/2009 |
| WO | WO 2010/004562 | 1/2010 |

OTHER PUBLICATIONS

Chen et al., "Characterization of microRNAs in serum: a novel class of biomarkers for diagnosis of cancer and other diseases," *Cell Research*, 18:997-1006 (2008).

Mascaux et al., "Evolution of microRNA expression during human bronchial squamous carcinogenesis," *Eur. Respir. J.*, 33(2):352-359 (2009).
Raponi et al., "MicroRNA Classifiers for Predicting Prognosis of Squamous Cell Lung Cancer," *Cancer Res.*, 69(14):5776-5783 (2009).
Supplementary European Search Report for European Application No. 10812641.8 dated May 3, 2013, 20 pages.
Takamizawa et al., "Reduced Expression of the *let-7* MicroRNAs in Human Lung Cancers in Association with Shortened Postoperative Survival," *Cancer Research*, 64:3753-3756 (2004).
Ambs et al., "Genomic Profiling of MicroRNA and Messenger RNA Reveals Deregulated MicroRNA Expression in Prostate Cancer," *Cancer Res.* 68(15):6162-6170 (2008).
Bianchi, "Circulating Fetal DNA: Its Origin and Diagnostic Potential—A Review," *Placenta* 25 Suppl. A:S93-S101 (2004).
Bremnes et al., "Circulating tumour-derived DNA and RNA markers in blood: a tool for early detection, diagnostics, and follow-up?," *Lung Cancer* 49:1-12 (2005).
Chen et al., "Telomerase RNA as a detection marker in the serum of breast cancer patients," *Clin. Cancer Res.* 6:3823-3826 (2000).
Chen et al., "Real-time quantification of microRNAs by stem-loop RT-PCR," *Nucl. Acids Res.* 33(20):e179 (2005).
Chen et al., "Characterization of microRNAs in serum: a novel class of biomarkers for diagnosis of cancer and other diseases," *Cell Res.* 18:997-1006 (2008).
Chim et al., "Detection and Characterization of Placental MircoRNAs in Maternal Plasma," *Clin. Chem.* 54:482-490 (2008).
Dasi et al., "Real-time quantification in plasma of human telomerase reverse transcriptase (hTERT) mRNA: a simple blood test to monitor disease in cancer patients," *Lab Invest.* 81:767-769 (2001).
Dodd et al., "Partial AUC Estimation and Regression," *Biometrics* 59:614-623 (2003).
Esquela-Kerscher et al., "The *let-7* microRNA reduces tumor growth in mouse models of lung cancer," *Cell Cycle* 7(6):759-764 (2008).
Fabbri et al., "MicroRNAs," *Cancer J.* 14:1-6 (2008).
Gandellini et al., "miR-205 Exerts Tumor-Suppressive Functions in Human prostate through Down-regulation of Protein Kinase Cε," *Cancer Res.* 69(6):2287-2295 (2009).
Garofalo et al., "MicroRNA signatures of TRAIL resistance in human non-small cell lung cancer," *Oncogene* 27:3845-3855 (2008).
Greenberg et al., "Biomarkers for lung cancer: clinical uses." *Current Opin. Pulm. Med.* 13:249-255 (2007).
International Search Report and Written Opinion dated Oct. 18, 2010, issued in PCT/US2010/046916.
Jackson, "Serum-based microRNAs: Are we blinded by potential?" *PNAS* 106:1 (Jan. 6, 2009).
Jahr et al., "DNA Fragments in the Blood Plasma of Cancer Patients: Quantitations and Evidence for Their Origin from Apoptotic and Necrotic Cells," *Cancer Res.* 61:1659-1665 (2001).

(Continued)

*Primary Examiner* — James Martinell
(74) *Attorney, Agent, or Firm* — Finnegan, Henderson, Farabow, Garrett & Dunner, LLP

(57) ABSTRACT

This application describes miRNAs that may be used as serum or plasma biomarkers for characterizing lung disease in a patient. These miRNA biomarkers may be used alone or in combination with other markers for the diagnosis, prognosis, or monitoring of diseases such as lung cancer.

37 Claims, 26 Drawing Sheets

(56) References Cited

OTHER PUBLICATIONS

Kurreck et al., "Ántisense technologies: Improvement through novel chemical modifications," *Eur. J. Biochem.* 270:1628-1644 (2003).

Lawrie et al., "Detection of elevated levels of tumour-associated microRNAs in serum of patients with diffuse large B-cell lymphoma," *Br. J. Haematol.* 141:672-675 (2008).

Lodes et al., "Detection of Cancer with Serum miRNAs on an Oligonucleotide Microarray," *PLoS ONE* 4(7):e6229:1-12 (2009).

Markou et al., "Prognostic Value of Mature MicroRNA-21 and MicroRNA-205 Overexpression in Non-Small Cell Lung Cancer by Quantitative Real-Time RT-PCR," *Clin. Chem.* 54(10):1696-1704 (2008).

Mattie et al., "Optimized high-throughput microRNA expression profiling provides novel biomarker assessment of clinical prostate and breast cancer biopsies," *Molecular Cancer* 5(24):1-14 (2006).

Mitchell et al., "Circulating microRNAs as stable blood-based markers for cancer detection," *Proc. Natl. Acad. Sci. USA* 105(30):10513-10518 (2008); Supporting Information, pp. 1-29.

Okada et al., "Prognostic Significance of Perioperative Serum Carcinoembryonic Antigen in Non-Small Cell Lung Cancer: Analysis of 1,000 Consecutive Resections for Clinical Stage I Disease," *Ann. Thorac. Surg.* 78:216-221 (2004).

Ozen et al., "Widespread deregulation of microRNA expression in human prostate cancer," *Oncogene* 27:1788-1793 (2008).

Pepe et al., "Combining Predictors for Classification Using the Area under the Receiver Operating Characteristic Curve," *Biometrics* 62:221-229 (2006).

Porkka et al., "MicroRNA Expression Profiling in Prostate Cancer," *Cancer Res* 67(13):6130-6135 (2007).

Press Release, CombiMATRIX Corporation, "CombiMatrix Announces Positive Preliminary Data on Non-Invasive, Cancer Screening Test," GlobeNewswire via COMTEX News Network, (Feb. 26, 2009).

Prueitt et al., "Expression of MicroRNAs and Protein-Coding Genes Associated With Perineural Invasion in Prostate Cancer," *The Prostate* 68:1152-1164 (2008).

Ramirez et al., "Ethylation patterns and K-ras mutations in tumor and paired serum of resected non-small cell lung cancer patients," *Cancer Lett.* 193:207-216 (2003).

Schickel et al., "MicroRNAs: key players in the immune system, differentiation, tumorigenesis and cell death," *Oncogene* 27:5959-5974 (2008).

Schneider et al., "Tumor markers in detection of lung cancer," *Adv. Clin. Chem.* 42:1-41 (2006).

Shi et al., "microRNAs and prostate cancer," *J. Cell. Mol. Med.* 12(5A):1456-1465 (2008).

Siemes et al., "C-Reactive Protein Levels, Variation in the C_reactive Protein Gene, and Cancer Risk: The Rotterdam Study," *J. Clin. Oncol.* 24:5216-5222 (2006).

Suciu et al., "Detection of Cancer with Serum miRNAs on an Oligonucleotide Microarray" Poster presented at Cambridge Healthtech Institute's 16th International Molecular Medicine Tri-Conference, Feb. 25-27, 2009, in San Francisco.

Tanaka et al., "Down-Regulation of miR-92 in Human Plasma is a Novel Marker for Acute Leukemia Patients," *PLoS ONE* 4(7):(e5532):1-5 (2009).

Tong et al., "MicroRNA profile analysis of human prostate cancers," *Cancer Gene Therapy* 16:206-216 (2009).

Weiss et al., "EGFR regulation by microRNA in lung cancer: correlation with clinical response and survival to gefitinib and EGFR expression in cell lines," *Ann Oncol.* 19:1053-1059 (2008).

Yanaihara et al. "Unique microRNA molecular profiles in lung cancer diagnosis and prognosis," *Cancer Cell* 9(3):189-198 (2006).

Yu et al., "MicroRNA Signature Predicts Survival and Relapse in Lung Cancer," *Cancer Cell* 13(1):48-57 (2008).

Ji et al., "Plasma miR-208 as a Biomarker of Myocardial Injury," *Clinical Chemistry* 55(11):1944-1949 (2009).

Li et al., "Serum Circulating Human mRNA Profiling and its Utility for Oral Cancer Detection," *J. Clinical Oncology* 24(11):1754-1760 (2006).

Hunter et al., "Detection of microRNA Expression in Human Peripheral Blood Microvesicles," PLoS ONE, 3(11):1-11 (2008).

Nana-Sinkam et al., "Lung microRNA: from development to disease," Expert Rev. Resp. Med., 3(4):373-385 (2009).

\* cited by examiner

Training Set Results
(Based on Median CV Probability)

| Metric | Est | lower | upper |
|---|---|---|---|
| SENS | .75 | .49 | .93 |
| SPEC | .88 | .67 | .98 |
| NPV | 0.82 | 0.55 | 0.96 |
| PPV | 0.82 | 0.61 | 0.95 |

| | Actual Benign | Actual LuCa |
|---|---|---|
| Predicted Benign | 9 | 2 |
| Predicted Lung Cancer | 3 | 14 |

Test Set Results
(Based on ALL Training Data)

| Metric | Est | lower | upper |
|---|---|---|---|
| SENS | 1 | .72 | 1 |
| SPEC | .94 | .77 | 1 |
| NPV | 0.89 | 0.6 | 0.99 |
| PPV | 1 | 0.85 | 1 |

| | Actual Benign | Actual LuCa |
|---|---|---|
| Predicted Benign | 8 | 1 |
| Predicted Lung Cancer | 0 | 17 |

Figure 4

| pre-miRNA | Sequence | Mature miRNA |
|---|---|---|
| let-7a-1 (SEQ ID NO:1) | UGGGAUGAGGUAGUAGGUUGUAUAGUUUUAGGGUCACACCCACCACUGGGA GAUAACUAUACAAUCUACUGUCUUUCCUA | let-7a |
| let-7a-2 (SEQ ID NO:2) | AGGUUGAGGUAGUAGGUUGUAUAGUUUAGAAUUACAUCAAGGGAGAUAACU GUACAGCCUCCUAGCUUUCCU | let-7a |
| let-7a-3 (SEQ ID NO:3) | GGGUGAGGUAGUAGGUUGUAUAGUUUGGGGCUCUGCCCUGCUAUGGGAUAA CUAUACAAUCUACUGUCUUUCCU | let-7a |
| let-7b (SEQ ID NO:4) | CGGGGUGAGGUAGUAGGUUGUGUGGUUUCAGGGCAGUGAUGUUGCCCCUCG GAAGAUAACUAUACAACCUACUGCCUUCCCUG | let-7b |
| let-7c (SEQ ID NO:5) | GCAUCCGGGUUGAGGUAGUAGGUUGUAUGGUUUAGAGUUACACCCUGGGAG UUAACUGUACAACCUUCUAGCUUUCCUUGGAGC | let-7c |
| let-7d (SEQ ID NO:6) | CCUAGGAAGAGGUAGUAGGUUGCAUAGUUUUAGGGCAGGGAUUUUGCCCAC AAGGAGGUAACUAUACGACCUGCUGCCUUUCUUAGG | let-7d |
| let-7e (SEQ ID NO:7) | CCCGGGCUGAGGUAGGAGGUUGUAUAGUUGAGGAGGACACCCAAGGAGAUC ACUAUACGGCCUCCUAGCUUUCCCCAGG | let-7e |
| let-7f-1 (SEQ ID NO:8) | UCAGAGUGAGGUAGUAGAUUGUAUAGUUGUGGGGUAGUGAUUUUACCCUGU UCAGGAGAUAACUAUACAAUCUAUUGCCUUCCCUGA | let-7f |
| let-7f-2 (SEQ ID NO:9) | UGUGGGAUGAGGUAGUAGAUUGUAUAGUUUUAGGGUCAUACCCCAUCUUGG AGAUAACUAUACAGUCUACUGUCUUUCCCACG | let-7f |
| let-7g (SEQ ID NO:10) | AGGCUGAGGUAGUAGUUUGUACAGUUUGAGGGUCUAUGAUACCACCCGGUA CAGGAGAUAACUGUACAGGCCACUGCCUUGCCA | let-7g |
| let-7i (SEQ ID NO:11) | CUGGCUGAGGUAGUAGUUUGUGCUGUUGGUCGGGUUGUGACAUUGCCCGCU GUGGAGAUAACUGCGCAAGCUACUGCCUUGCUA | let-7i |
| miR-1-1 (SEQ ID NO:12) | UGGGAAACAUACUUCUUUAUAUGCCCAUAUGGACCUGCUAAGCUAUGGAAU GUAAAGAAGUAUGUAUCUCA | miR-1 |
| miR-1-2 (SEQ ID NO:13) | ACCUACUCAGAGUACAUACUUCUUUAUGUACCCAUAUGAACAUACAAUGCU AUGGAAUGUAAAGAAGUAUGUAUUUUUGGUAGGC | miR-1 |
| miR-100 (SEQ ID NO:14) | CCUGUUGCCACAAACCCGUAGAUCCGAACUUGUGGUAUUAGUCCGCACAAG CUUGUAUCUAUAGGUAUGUGUCUGUUAGG | miR-100 |
| miR-101-1 (SEQ ID NO:15) | UGCCCUGGCUCAGUUAUCACAGUGCUGAUGCUGUCUAUUCUAAAGGUACAG UACUGUGAUAACUGAAGGAUGGCA | miR-101 |
| miR-101-2 (SEQ ID NO:16) | ACUGUCCUUUUUCGGUUAUCAUGGUACCGAUGCUGUAUAUCUGAAAGGUAC AGUACUGUGAUAACUGAAGAAUGGUGGU | miR-101 |
| miR-103-1 (SEQ ID NO:17) | UACUGCCCUCGGCUUCUUUACAGUGCUGCCUUGUUGCAUAUGGAUCAAGCA GCAUUGUACAGGGCUAUGAAGGCAUUG | miR-103 |
| miR-103-2 (SEQ ID NO:18) | UUGUGCUUUCAGCUUCUUUACAGUGCUGCCUUGUAGCAUUCAGGUCAAGCA GCAUUGUACAGGGCUAUGAAAGAACCA | miR-103 |

FIG. 5A

| pre-miRNA | Sequence | Mature miRNA |
|---|---|---|
| miR-105-1 (SEQ ID NO:19) | UGUGCAUCGUGGUCAAAUGCUCAGACUCCUGUGGUGGCUGCUCAUGCACCACGGAUGUUUGAGCAUGUGCUACGGUGUCUA | miR-105 |
| miR-105-2 (SEQ ID NO:20) | UGUGCAUCGUGGUCAAAUGCUCAGACUCCUGUGGUGGCUGCUUAUGCACCACGGAUGUUUGAGCAUGUGCUAUGGUGUCUA | miR-105 |
| miR-106a (SEQ ID NO:21) | CCUUGGCCAUGUAAAAGUGCUUACAGUGCAGGUAGCUUUUUGAGAUCUACUGCAAUGUAAGCACUUCUUACAUUACCAUGG | miR-106a |
| miR-106b (SEQ ID NO:22) | CCUGCCGGGGCUAAAGUGCUGACAGUGCAGAUAGUGGUCCUCUCCGUGCUACCGCACUGUGGGUACUUGCUGCUCCAGCAGG | miR-106b |
| miR-107 (SEQ ID NO:23) | CUCUCUGCUUUCAGCUUCUUUACAGUGUUGCCUUGUGGCAUGGAGUUCAAGCAGCAUUGUACAGGGCUAUCAAAGCACAGA | miR-107 |
| miR-10a (SEQ ID NO:24) | GAUCUGUCUGUCUUCUGUAUAUACCCUGUAGAUCCGAAUUUGUGUAAGGAAUUUUGUGGUCACAAAUUCGUAUCUAGGGGAAUAUGUAGUUGACAUAAACACUCCGCUCU | miR-10a |
| miR-10b (SEQ ID NO:25) | CCAGAGGUUGUAACGUUGUCUAUAUAUACCCUGUAGAACCGAAUUUGUGUGGUAUCCGUAUAGUCACAGAUUCGAUUCUAGGGGAAUAUAUGGUCGAUGCAAAAACUUCA | miR-10b |
| miR-122 (SEQ ID NO:26) | CCUUAGCAGAGCUGUGGAGUGUGACAAUGGUGUUUGUGUCUAAACUAUCAAACGCCAUUAUCACACUAAAUAGCUACUGCUAGGC | miR-122a (also called miR-122) |
| miR-124-1 (SEQ ID NO:27) | AGGCCUCUCUCUCCGUGUUCACAGCGGACCUUGAUUUAAAUGUCCAUACAAUUAAGGCACGCGGUGAAUGCCAAGAAUGGGGCUG | miR-124a (also called miR-124) |
| miR-124-2 (SEQ ID NO:28) | AUCAAGAUUAGAGGCUCUGCUCUCCGUGUUCACAGCGGACCUUGAUUUAAUGUCAUACAAUUAAGGCACGCGGUGAAUGCCAAGAGCGGAGCCUACGGCUGCACUUGAA | miR-124a (also called miR-124) |
| miR-124-3 (SEQ ID NO:29) | UGAGGGCCCCUCUGCGUGUUCACAGCGGACCUUGAUUUAAUGUCUAUACAAUUAAGGCACGCGGUGAAUGCCAAGAGAGGCGCCUCC | miR-124a (also called miR-124) |
| miR-125a (SEQ ID NO:30) | UGCCAGUCUCUAGGUCCCUGAGACCCUUUAACCUGUGAGGACAUCCAGGGUCACAGGUGAGGUUCUUGGGAGCCUGGCGUCUGGCC | miR-125a |
| miR-125b-1 (SEQ ID NO:31) | UGCGCUCCUCUCAGUCCCUGAGACCCUAACUUGUGAUGUUUACCGUUUAAAUCCACGGGUUAGGCUCUUGGGAGCUGCGAGUCGUGCU | miR-125b |
| miR-125b-2 (SEQ ID NO:32) | ACCAGACUUUUCCUAGUCCCUGAGACCCUAACUUGUGAGGUAUUUUAGUAACAUCACAAGUCAGGCUCUUGGGACCUAGGCGGAGGGGA | miR-125b |
| miR-126 (SEQ ID NO:33) | CGCUGGCGACGGGACAUUAUUACUUUUGGUACGCGCUGUGACACUUCAAACUCGUACCGUGAGUAAUAAUGCGCCGUCCACGGCA | miR-126; miR-126* |
| miR-127 (SEQ ID NO:34) | UGUGAUCACUGUCUCCAGCCUGCUGAAGCUCAGAGGGCUCUGAUUCAGAAAGAUCAUCGGAUCCGUCUGAGCUUGGCUGGUCGGAAGUCUCAUCAUC | miR-127 |

FIG. 5B

| pre-miRNA | Sequence | Mature miRNA |
|---|---|---|
| miR-128-1 (SEQ ID NO:35) | UGAGCUGUUGGAUUCGGGGCCGUAGCACUGUCUGAGAGGUUUACAUUUCUC ACAGUGAACCGGUCUCUUUUUCAGCUGCUUC | miR-128a |
| miR-128-2 (SEQ ID NO:36) | UGUGCAGUGGGAAGGGGGGCCGAUACACUGUACGAGAGUGAGUAGCAGGUC UCACAGUGAACCGGUCUCUUUUCCCUACUGUGUC | miR-128b |
| miR-129-1 (SEQ ID NO:37) | GGAUCUUUUUGCGGUCUGGGCUUGCUGUUCCUCUCAACAGUAGUCAGGAAG CCCUUACCCCAAAAAGUAUCU | miR-129 |
| miR-129-2 (SEQ ID NO:38) | UGCCCUUCGCGAAUCUUUUUGCGGUCUGGGCUUGCUGUACAUAACUCAAUA GCCGGAAGCCCUUACCCCAAAAAGCAUUUGCGGAGGGCG | miR-129 |
| miR-130a (SEQ ID NO:39) | UGCUGCUGGCCAGAGCUCUUUUCACAUUGUGUCUACUGUCUGCACCUGUCAC UAGCAGUGCAAUGUUAAAAGGGCAUUGGCCGUGUAGUG | miR-130a |
| miR-130b (SEQ ID NO:40) | GGCCUGCCCGACACUCUUUCCCUGUUGCACUACUAUAGGCCGCUGGGAAGC AGUGCAAUGAUGAAAGGGCAUCGGUCAGGUC | miR-130b |
| miR-132 (SEQ ID NO:41) | CCGCCCCCGCGUCUCCAGGGCAACCGUGGCUUUCGAUUGUUACUGUGGGAA CUGGAGGUAACAGUCUACAGCCAUGGUCGCCCCGCAGCACGCCCACGCGC | miR-132 |
| miR-133a-1 (SEQ ID NO:42) | ACAAUGCUUUGCUAGAGCUGGUAAAAUGGAACCAAAUCGCCUCUUCAAUGG AUUUGGUCCCCUUCAACCAGCUGUAGCUAUGCAUUGA | miR-133a |
| miR-133a-2 (SEQ ID NO:43) | GGGAGCCAAAUGCUUUGCUAGAGCUGGUAAAAUGGAACCAAAUCGACUGUC CAAUGGAUUUGGUCCCCUUCAACCAGCUGUAGCUGUGCAUUGAUGGCGCCG | miR-133a |
| miR-133b (SEQ ID NO:44) | CCUCAGAAGAAAGAUGCCCCCUGCUCUGGCUGGUCAAACGGAACCAAGUCC GUCUUCCUGAGAGGUUUGGUCCCCUUCAACCAGCUACAGCAGGGCUGGCAA UGCCCAGUCCUUGGAGA | miR-133b |
| miR-134 (SEQ ID NO:45) | CAGGGUGUGUGACUGGUUGACCAGAGGGGCAUGCACUGUGUUCACCCUGUG GGCCACCUAGUCACCAACCCUC | miR-134 |
| miR-135a-1 (SEQ ID NO:46) | AGGCCUCGCUGUUCUCUAUGGCUUUUUAUUCCUAUGUGAUUCUACUGCUCA CUCAUAUAGGGAUUGGAGCCGUGGCGCACGGCGGGGACA | miR-135a |
| miR-135a-2 (SEQ ID NO:47) | AGAUAAAUUCACUCUAGUGCUUUAUGGCUUUUUAUUCCUAUGUGAUAGUAA UAAAGUCUCAUGUAGGGAUGGAAGCCAUGAAAUACAUUGUGAAAAAUCA | miR-135a |
| miR-135b (SEQ ID NO:48) | CACUCUGCUGUGGCCUAUGGCUUUUCAUUCCUAUGUGAUUGCUGUCCCAAA CUCAUGUAGGGCUAAAAGCCAUGGGCUACAGUGAGGGGCGAGCUCC | miR-135b |
| miR-136 (SEQ ID NO:49) | UGAGCCCUCGGAGGACUCCAUUUGUUUUGAUGAUGGAUUCUUAUGCUCCAU CAUCGUCUCAAAUGAGUCUUCAGAGGGUUCU | miR-136 |
| miR-137 (SEQ ID NO:50) | GGUCCUCUGACUCUCUUCGGUGACGGGUAUUCUUGGGUGGAUAAUACGGAU UACGUUGUUAUUGCUUAAGAAUACGCGUAGUCGAGGAGAGUACCAGCGGCA | miR-137 |

FIG. 5C

| pre-miRNA | Sequence | Mature miRNA |
|---|---|---|
| miR-138-1 (SEQ ID NO:51) | CCCUGGCAUGGUGUGGUGGGGCAGCUGGUGUUGUGAAUCAGGCCGUUGCCAAUCAGAGAACGGCUACUUCACAACACCAGGGCCACACCACACUACAGG | miR-138 |
| miR-138-2 (SEQ ID NO:52) | CGUUGCUGCAGCUGGUGUUGUGAAUCAGGCCGACGAGCAGCGCAUCCUCUUACCCGGCUAUUUCACGACACCAGGGUUGCAUCA | miR-138 |
| miR-139 (SEQ ID NO:53) | GUGUAUUCUACAGUGCACGUGUCUCCAGUGUGGCUCGGAGGCUGGAGACGCGGCCCUGUUGGAGUAAC | miR-139 |
| miR-140 (SEQ ID NO:54) | UGUGUCUCUCUCUGUGUCCUGCCAGUGGUUUUACCCUAUGGUAGGUUACGUCAUGCUGUUCUACCACAGGGUAGAACCACGGACAGGAUACCGGGGCACC | miR-140 |
| miR-141 (SEQ ID NO:55) | CGGCCGGCCCUGGGUCCAUCUUCCAGUACAGUGUUGGAUGGUCUAAUUGUGAAGCUCCUAACACUGUCUGGUAAAGAUGGCUCCCGGGUGGGUUC | miR-141 |
| miR-142 (SEQ ID NO:56) | GACAGUGCAGUCACCCAUAAAGUAGAAAGCACUACUAACAGCACUGGAGGGUGUAGUGUUUCCUACUUUAUGGAUGAGUGUACUGUG | miR-142-3p; miR-142-5p |
| miR-143 (SEQ ID NO:57) | GCGCAGCGCCCUGUCUCCCAGCCUGAGGUGCAGUGCUGCAUCUCUGGUCAGUUGGGAGUCUGAGAUGAAGCACUGUAGCUCAGGAAGAGAGAAGUUGUUCUGCAGC | miR-143 |
| miR-145 (SEQ ID NO:58) | CACCUUGUCCUCACGGUCCAGUUUUCCCAGGAAUCCCUUAGAUGCUAAGAUGGGGAUUCCUGGAAAUACUGUUCUUGAGGUCAUGGUU | miR-145 |
| miR-146a (SEQ ID NO:59) | CCGAUGUGUAUCCUCAGCUUUGAGAACUGAAUUCCAUGGGUUGUGUCAGUGUCAGACCUCUGAAAUUCAGUUCUUCAGCUGGGAUAUCUCUGUCAUCGU | miR-146a |
| miR-146b (SEQ ID NO:60) | CCUGGCACUGAGAACUGAAUUCCAUAGGCUGUGAGCUCUAGCAAUGCCCUGUGGACUCAGUUCUGGUGCCCGG | miR-146b |
| miR-147 (SEQ ID NO:61) | AAUCUAAAGACAACAUUUCUGCACACACACCAGACUAUGGAAGCCAGUGUGGAAAUGCUUCUGCUAGAUU | miR-147 |
| miR-147b (SEQ ID NO:62) | UAUAAAUCUAGUGGAAACAUUUCUGCACAAACUAGAUUCUGGACACCAGUGUGCGGAAAUGCUUCUGCUACAUUUUUAGG | miR-147b |
| miR-148a (SEQ ID NO:63) | GAGGCAAAGUUCUGAGACACUCCGACUCUGAGUAUGAUAGAAGUCAGUGCACUACAGAACUUUGUCUC | miR-148a |
| miR-148b (SEQ ID NO:64) | CAAGCACGAUUAGCAUUUGAGGUGAAGUUCUGUUAUACACUCAGGCUGUGGCUCUCUGAAAGUCAGUGCAUCACAGAACUUUGUCUCGAAAGCUUUCUA | miR-148b |
| miR-149 (SEQ ID NO:65) | GCCGGCGCCCGAGCUCUGGCUCCGUGUCUUCACUCCCGUGCUUGUCCGAGGAGGGAGGGAGGGACGGGGGCUGUGCUGGGGCAGCUGGA | miR-149 |
| miR-150 (SEQ ID NO:66) | CUCCCCAUGGCCCUGUCUCCCAACCCUUGUACCAGUGCUGGGCUCAGACCCUGGUACAGGCCUGGGGGACAGGGACCUGGGGAC | miR-150 |

FIG. 5D

| pre-miRNA | Sequence | Mature miRNA |
|---|---|---|
| miR-151 (SEQ ID NO:67) | UUUCCUGCCCUCGAGGAGCUCACAGUCUAGUAUGUCUCAUCCCCUACUAGACUGAAGCUCCUUGAGGACAGGGAUGGUCAUACUCACCUC | miR-151 |
| miR-152 (SEQ ID NO:68) | UGUCCCCCCGGCCCAGGUUCUGUGAUACACUCCGACUCGGGCUCUGGAGCAGUCAGUGCAUGACAGAACUUGGGCCCGGAAGGACC | miR-152 |
| miR-153-1 (SEQ ID NO:69) | CUCACAGCUGCCAGUGUCAUUUUUGUGAUCUGCAGCUAGUAUUCUCACUCCAGUUGCAUAGUCACAAAAGUGAUCAUUGGCAGGUGUGGC | miR-153 |
| miR-153-2 (SEQ ID NO:70) | AGCGGUGGCCAGUGUCAUUUUUGUGAUGUUGCAGCUAGUAAUAUGAGCCCAGUUGCAUAGUCACAAAAGUGAUCAUUGGAAACUGUG | miR-153 |
| miR-154 (SEQ ID NO:71) | GUGGUACUUGAAGAUAGGUUAUCCGUGUUGCCUUCGCUUUAUUUGUGACGAAUCAUACACGGUUGACCUAUUUUUCAGUACCAA | miR-154; miR-154* |
| miR-155 (SEQ ID NO:72) | CUGUUAAUGCUAAUCGUGAUAGGGGUUUUUGCCUCCAACUGACUCCUACAUAUUAGCAUUAACAG | miR-155 |
| miR-15a (SEQ ID NO:73) | CCUUGGAGUAAAGUAGCAGCACAUAAUGGUUUGUGGAUUUUGAAAAGGUGCAGGCCAUAUUGUGCUGCCUCAAAAAUACAAGG | miR-15a |
| miR-15b (SEQ ID NO:74) | UUGAGGCCUUAAAGUACUGUAGCAGCACAUCAUGGUUUACAUGCUACAGUCAAGAUGCGAAUCAUUAUUUGCUGCUCUAGAAAUUUAAGGAAAUUCAU | miR-15b |
| miR-16-1 (SEQ ID NO:75) | GUCAGCAGUGCCUUAGCAGCACGUAAAUAUUGGCGUUAAGAUUCUAAAAUUAUCUCCAGUAUUAACUGUGCUGCUGAAGUAAGGUUGAC | miR-16 |
| miR-16-2 (SEQ ID NO:76) | GUUCCACUCUAGCAGCACGUAAAUAUUGGCGUAGUGAAAUAUAUAUUAAACACCAAUAUUACUGUGCUGCUUUAGUGUGAC | miR-16 |
| miR-17 (SEQ ID NO:77) | GUCAGAAUAAUGUCAAAGUGCUUACAGUGCAGGUAGUGAUAUGUGCAUCUACUGCAGUGAAGGCACUUGUAGCAUUAUGGUGAC | miR-17-3p; miR-17-5p |
| miR-181a-1 (SEQ ID NO:78) | UGAGUUUUGAGGUUGCUUCAGUGAACAUUCAACGCUGUCGGUGAGUUUGAAUUAAAAUCAAAACCAUCGACCGUUGAUUGUACCCUAUGGCUAACCAUCAUCUACUCCA | miR-181a; miR-213 (also called miR-181a*) |
| miR-181a-2 (SEQ ID NO:79) | AGAAGGGCUAUCAGGCCAGCCUUCAGAGGACUCCAAGGAACAUUCAACGCUGUCGGUGAGUUUGGGAUUUGAAAAAACCACUGACCGUUGACUGUACCUUGGGGUCCUUA | miR-181a |
| miR-181b-1 (SEQ ID NO:80) | CCUGUGCAGAGAUUAUUUUUUAAAAGGUCACAAUCAACAUUCAUUGCUGUCGGUGGGUUGAACUGUGUGGACAAGCUCACUGAACAAUGAAUGCAACUGUGGCCCCGCUU | miR-181b |
| miR-181b-2 (SEQ ID NO:81) | CUGAUGGCUGCACUCAACAUUCAUUGCUGUCGGUGGGUUUGAGUCUGAAUCAACUCACUGAUCAAUGAAUGCAAACUGCGGACCAAACA | miR-181b |
| miR-181c (SEQ ID NO:82) | CGGAAAAUUUGCCAAGGGUUUGGGGGAACAUUCAACCUGUCGGUGAGUUUGGGCAGCUCAGGCAAACCAUCGACCGUUGAGUGGACCCUGAGGCCUGGAAUUGCCAUCCU | miR-181c |

FIG. 5E

| pre-miRNA | Sequence | Mature miRNA |
|---|---|---|
| miR-181d (SEQ ID NO:83) | GUCCCCUCCCCUAGGCCACAGCCGAGGUCACAAUCAACAUUCAUUGUUGUCGGUGGGUUGUGAGGACUGAGGCCAGACCCACCGGGGGAUGAAUGUCACUGUGGCUGGGCCAGACACGGCUUAAGGGGAAUGGGGAC | miR-181d |
| miR-182 (SEQ ID NO:84) | GAGCUGCUUGCCUCCCCCCGUUUUUGGCAAUGGUAGAACUCACACUGGUGAGGUAACAGGAUCCGGUGGUUCUAGACUUGCCAACUAUGGGGCGAGGACUCAGCCGGCAC | miR-182; miR-182* |
| miR-183 (SEQ ID NO:85) | CCGCAGAGUGUGACUCCUGUUCUGUGUAUGGCACUGGUAGAAUUCACUGUGAACAGUCUCAGUCAGUGAAUUACCGAAGGGCCAUAAACAGAGCAGAGACAGAUCCACGA | miR-183 |
| miR-184 (SEQ ID NO:86) | CCAGUCACGUCCCCUUAUCACUUUUCCAGCCCAGCUUUGUGACUGUAAGUGUUGGACGGAGAACUGAUAAGGGUAGGUGAUUGA | miR-184 |
| miR-185 (SEQ ID NO:87) | AGGGGGCGAGGGAUUGGAGAGAAAGGCAGUUCCUGAUGGUCCCCUCCCCAGGGGCUGGCUUUCCUCUGGUCCUUCCCUCCCA | miR-185 |
| miR-186 (SEQ ID NO:88) | UGCUUGUAACUUUCCAAAGAAUUCUCCUUUUGGGCUUUCUGGUUUUAUUUUAAGCCCAAAGGUGAAUUUUUUGGGAAGUUUGAGCU | miR-186 |
| miR-187 (SEQ ID NO:89) | GGUCGGGCUCACCAUGACACAGUGUGAGACCUCGGGCUACAACACAGGACCCGGGCGCUGCUCUGACCCCUCGUGUCUUGUGUUGCAGCCGGAGGGACGCAGGUCCGCA | miR-187 |
| miR-188 (SEQ ID NO:90) | UGCUCCCUCUCUCACAUCCCUUGCAUGGUGGAGGGUGAGCUUUCUGAAAACCCCUCCCACAUGCAGGGUUUGCAGGAUGGCGAGCC | miR-188 |
| miR-18a (SEQ ID NO:91) | UGUUCUAAGGUGCAUCUAGUGCAGAUAGUGAAGUAGAUUAGCAUCUACUGCCCUAAGUGCUCCUUCUGGCA | miR-18a; miR-18a* |
| miR-18b (SEQ ID NO:92) | UGUGUUAAGGUGCAUCUAGUGCAGUUAGUGAAGCAGCUUAGAAUCUACUGCCCUAAAUGCCCCUUCUGGCA | miR-18b |
| miR-190 (SEQ ID NO:93) | UGCAGGCCUCUGUGUGAUAUGUUUGAUAUAUUAGGUUGUUAUUUAAUCCAACUAUAUAUCAAACAUAUUCCUACAGUGUCUUGCC | miR-190 |
| miR-191 (SEQ ID NO:94) | CGGCUGGACAGCGGGCAACGGAAUCCCAAAAGCAGCUGUUGUCUCCAGAGCAUUCCAGCUGCGCUUGGAUUUCGUCCCCUGCUCUCCUGCCU | miR-191 |
| miR-192 (SEQ ID NO:95) | GCCGAGACCGAGUGCACAGGGCUCUGACCUAUGAAUUGACAGCCAGUGCUCUCGUCUCCCCUCUGGCUGCCAAUUCCAUAGGUCACAGGUAUGUUCGCCUCAAUGCCAGC | miR-192 |
| miR-193a (SEQ ID NO:96) | CGAGGAUGGGAGCUGAGGGCUGGGUCUUUGCGGGCGAGAUGAGGGUGUCGGAUCAACUGGCCUACAAAGUCCCAGUUCUCGGCCCCCG | miR-193a |
| miR-193b (SEQ ID NO:97) | GUGGUCUCAGAAUCGGGGUUUUGAGGGCGAGAUGAGUUUAUGUUUUAUCCAACUGGCCCUCAAAGUCCCGCUUUUGGGGUCAU | miR-193b |
| miR-194-1 (SEQ ID NO:98) | AUGGUGUUAUCAAGUGUAACAGCAACUCCAUGUGGACUGUGUACCAAUUUCCAGUGGAGAUGCUGUUACUUUUGAUGGUUACCAA | miR-194 |

FIG. 5F

| pre-miRNA | Sequence | Mature miRNA |
|---|---|---|
| miR-194-2 (SEQ ID NO:99) | UGGUUCCCGCCCCCUGUAACAGCAACUCCAUGUGGAAGUGCCCACUGGUUC CAGUGGGGCUGCUGUUAUCUGGGGCGAGGGCCAG | miR-194 |
| miR-195 (SEQ ID NO:100) | AGCUUCCCUGGCUCUAGCAGCACAGAAAUAUUGGCACAGGGAAGCGAGUCU GCCAAUAUUGGCUGUGCUGCUCCAGGCAGGGUGGUG | miR-195 |
| miR-196a-1 (SEQ ID NO:101) | GUGAAUUAGGUAGUUUCAUGUUGUUGGGCCUGGGUUUCUGAACACAACAAC AUUAAACCACCCGAUUCAC | miR-196a |
| miR-196a-2 (SEQ ID NO:102) | UGCUCGCUCAGCUGAUCUGUGGCUUAGGUAGUUUCAUGUUGUUGGGAUUGA GUUUUGAACUCGGCAACAAGAAACUGCCUGAGUUACAUCAGUCGGUUUUCG UCGAGGGC | miR-196a |
| miR-196b (SEQ ID NO:103) | ACUGGUCGGUGAUUUAGGUAGUUUCCUGUUGUUGGGAUCCACCUUUCUCUC GACAGCACGACACUGCCUUCAUUACUUCAGUUG | miR-196b |
| miR-197 (SEQ ID NO:104) | GGCUGUGCCGGGUAGAGAGGGCAGUGGGAGGUAAGAGCUCUUCACCCUUCA CCACCUUCUCCACCCAGCAUGGCC | miR-197 |
| miR-198 (SEQ ID NO:105) | UCAUUGGUCCAGAGGGGAGAUAGGUUCCUGUGAUUUUUCCUUCUUCUCUAU AGAAUAAAUGA | miR-198 |
| miR-199a-1 (SEQ ID NO:106) | GCCAACCCAGUGUUCAGACUACCUGUUCAGGAGGCUCUCAAUGUGUACAGU AGUCUGCACAUUGGUUAGGC | miR-199a (also called miR-199-5p); miR-199a* (also called miR-199-3p) |
| miR-199a-2 (SEQ ID NO:107) | AGGAAGCUUCUGGAGAUCCUGCUCCGUCGCCCCAGUGUUCAGACUACCUGU UCAGGACAAUGCCGUUGUACAGUAGUCUGCACAUUGGUUAGACUGGGCAAG GGAGAGCA | miR-199a (also called miR-199-5p); miR-199a* (also called miR-199-3p) |
| miR-199b (SEQ ID NO:108) | CCAGAGGACACCUCCACUCCGUCUACCCAGUGUUUAGACUAUCUGUUCAGG ACUCCCAAAUUGUACAGUAGUCUGCACAUUGGUUAGGCUGGGCUGGGUUAG ACCCUCGG | miR-199b |
| miR-19a (SEQ ID NO:109) | GCAGUCCUCUGUUAGUUUUGCAUAGUUGCACUACAAGAAGAAUGUAGUUGU GCAAAUCUAUGCAAAACUGAUGGUGGCCUGC | miR-19a |
| miR-19b-1 (SEQ ID NO:110) | CACUGUUCUAUGGUUAGUUUUGCAGGUUUGCAUCCAGCUGUGUGAUAUUCU GCUGUGCAAAUCCAUGCAAAACUGACUGUGGUAGUG | miR-19b |
| miR-19b-2 (SEQ ID NO:111) | ACAUUGCUACUUACAAUUAGUUUUGCAGGUUUGCAUUUCAGCGUAUAUAUG UAUAUGUGGCUGUGCAAAUCCAUGCAAAACUGAUUGUGAUAAUGU | miR-19b |
| miR-200a (SEQ ID NO:112) | CCGGGCCCCUGUGAGCAUCUUACCGGACAGUGCUGGAUUUCCCAGCUUGAC UCUAACACUGUCUGGUAACGAUGUUCAAAGGUGACCCGC | miR-200a; miR-200a* |
| miR-200b (SEQ ID NO:113) | CCAGCUCGGGCAGCCGUGGCCAUCUUACUGGGCAGCAUUGGAUGGAGUCAG GUCUCUAAUACUGCCUGGUAAUGAUGACGGCGGAGCCCUGCACG | miR-200b |

FIG. 5G

| pre-miRNA | Sequence | Mature miRNA |
|---|---|---|
| miR-200c (SEQ ID NO:114) | CCCUCGUCUUACCCAGCAGUGUUUGGGUGCGGUUGGGAGUCUCUAAUACUG CCGGGUAAUGAUGGAGG | miR-200c |
| miR-202 (SEQ ID NO:115) | CGCCUCAGAGCCGCCCGCCGUUCCUUUUUCCUAUGCAUAUACUUCUUUGAG GAUCUGGCCUAAAGAGGUAUAGGGCAUGGGAAAACGGGGCGGUCGGGUCCU CCCCAGCG | miR-202 |
| miR-203 (SEQ ID NO:116) | GUGUUGGGGCACUCGCGCGCUGGGUCCAGUGGUUCUUAACAGUUCAACAGUU CUGUAGCGCAAUUGUGAAAUGUUUAGGACCACUAGACCCGGCGGGCGCGGC GACAGCGA | miR-203 |
| miR-204 (SEQ ID NO:117) | GGCUACAGUCUUUCUUCAUGUGACUCGUGGACUUCCCUUUGUCAUCCUAUG CCUGAGAAUAUAUGAAGGAGGCUGGGAAGGCAAAGGGACGUUCAAUUGUCA UCACUGGC | miR-204 |
| miR-205 (SEQ ID NO:118) | AAAGAUCCUCAGACAAUCCAUGUGCUUCUCUUGUCCUUCAUUCCACCGGAG UCUGUCUCAUACCCAACCAGAUUUCAGUGGAGUGAAGUUCAGGAGGCAUGG AGCUGACA | miR-205 |
| miR-206 (SEQ ID NO:119) | UGCUUCCCGAGGCCACAUGCUUCUUUAUAUCCCCAUAUGGAUUACUUUGCU AUGGAAUGUAAGGAAGUGUGUGGUUUCGGCAAGUG | miR-206 |
| miR-208a (SEQ ID NO:120) | UGACGGGCGAGCUUUUGGCCCGGGUUAUACCUGAUGCUCACGUAUAAGACG AGCAAAAAGCUUGUUGGUCA | miR-208 (also called miR-208a) |
| miR-20a (SEQ ID NO:121) | GUAGCACUAAAGUGCUUAUAGUGCAGGUAGUGUUUAGUUAUCUACUGCAUU AUGAGCACUUAAAGUACUGC | miR-20a |
| miR-20b (SEQ ID NO:122) | AGUACCAAAGUGCUCAUAGUGCAGGUAGUUUUGGCAUGACUCUACUGUAGU AUGGGCACUUCCAGUACU | miR-20b |
| miR-21 (SEQ ID NO:123) | UGUCGGGUAGCUUAUCAGACUGAUGUUGACUGUUGAAUCUCAUGGCAACAC CAGUCGAUGGGCUGUCUGACA | miR-21 |
| miR-210 (SEQ ID NO:124) | ACCCGGCAGUGCCUCCAGGCGCAGGGCAGCCCCUGCCCACCGCACACUGCG CUGCCCCAGACCCACUGUGCGUGUGACAGCGGCUGAUCUGUGCCUGGGCAG CGCGACCC | miR-210 |
| miR-211 (SEQ ID NO:125) | UCACCUGGCCAUGUGACUUGUGGGCUUCCCUUUGUCAUCCUUCGCCUAGGG CUCUGAGCAGGGCAGGGACAGCAAAGGGGUGCUCAGUUGUCACUUCCCACA GCACGGAG | miR-211 |
| miR-212 (SEQ ID NO:126) | CGGGGCACCCCGCCCGGACAGCGCGCCGGCACCUUGGCUCUAGACUGCUUA CUGCCCGGGCCGCCCUCAGUAACAGUCUCCAGUCACGGCCACCGACGCCUG GCCCCGCC | miR-212 |
| miR-214 (SEQ ID NO:127) | GGCCUGGCUGGACAGAGUUGUCAUGUGUCUGCCUGUCUACACUUGCUGUGC AGAACAUCCGCUCACCUGUACAGCAGGCACAGACAGGCAGUCACAUGACAA CCCAGCCU | miR-214 |
| miR-215 (SEQ ID NO:128) | AUCAUUCAGAAAUGGUAUACAGGAAAAUGACCUAUGAAUUGACAGACAAUA UAGCUGAGUUUGUCUGUCAUUUCUUUAGGCCAAUAUUCUGUAUGACUGUGC UACUUCAA | miR-215 |

FIG. 5H

| pre-miRNA | Sequence | Mature miRNA |
|---|---|---|
| miR-216a (SEQ ID NO:129) | GAUGGCUGUGAGUUGGCUUAAUCUCAGCUGGCAACUGUGAGAUGUUCAUAC AAUCCCUCACAGUGGUCUCUGGGAUUAUGCUAAACAGAGCAAUUUCCUAGC CCUCACGA | miR-216 (also called miR-216a) |
| miR-217 (SEQ ID NO:130) | AGUAUAAUUAUUACAUAGUUUUUGAUGUCGCAGAUACUGCAUCAGGAACUG AUUGGAUAAGAAUCAGUCACCAUCAGUUCCUAAUGCAUUGCCUUCAGCAUC UAAACAAG | miR-217 |
| miR-218-1 (SEQ ID NO:131) | GUGAUAAUGUAGCGAGAUUUUCUGUUGUGCUUGAUCUAACCAUGUGGUUGC GAGGUAUGAGUAAAACAUGGUUCCGUCAAGCACCAUGGAACGUCACGCAGC UUUCUACA | miR-218 |
| miR-218-2 (SEQ ID NO:132) | GACCAGUCGCUGCGGGGCUUUCCUUUGUGCUUGAUCUAACCAUGUGGUGGA ACGAUGGAAACGGAACAUGGUUCUGUCAAGCACCGCGGAAAGCACCGUGCU CUCCUGCA | miR-218 |
| miR-219-1 (SEQ ID NO:133) | CCGCCCCGGGCCGCGGCUCCUGAUUGUCCAAACGCAAUUCUCGAGUCUAUG GCUCCGGCCGAGAGUUGAGUCUGGACGUCCCGAGCCGCCGCCCCCAAACCU CGAGCGGG | miR-219 |
| miR-219-2 (SEQ ID NO:134) | ACUCAGGGGCUUCGCCACUGAUUGUCCAAACGCAAUUCUUGUACGAGUCUG CGGCCAACCGAGAAUUGUGGCUGGACAUCUGUGGCUGAGCUCCGGG | miR-219 |
| miR-22 (SEQ ID NO:135) | GGCUGAGCCGCAGUAGUUCUUCAGUGGCAAGCUUUAUGUCCUGACCCAGCU AAAGCUGCCAGUUGAAGAACUGUUGCCCUCUGCC | miR-22 |
| miR-221 (SEQ ID NO:136) | UGAACAUCCAGGUCUGGGGCAUGAACCUGGCAUACAAUGUAGAUUUCUGUG UUCGUUAGGCAACAGCUACAUUGUCUGCUGGGUUUCAGGCUACCUGGAAAC AUGUUCUC | miR-221 |
| miR-222 (SEQ ID NO:137) | GCUGCUGGAAGGUGUAGGUACCCUCAAUGGCUCAGUAGCCAGUGUAGAUCC UGUCUUUCGUAAUCAGCAGCUACAUCUGGCUACUGGGUCUCUGAUGGCAUC UUCUAGCU | miR-222 |
| miR-223 (SEQ ID NO:138) | CCUGGCCUCCUGCAGUGCCACGCUCCGUGUAUUUGACAAGCUGAGUUGGAC ACUCCAUGUGGUAGAGUGUCAGUUUGUCAAAUACCCCAAGUGCGGCACAUG CUUACCAG | miR-223 |
| miR-224 (SEQ ID NO:139) | GGGCUUUCAAGUCACUAGUGGUUCCGUUUAGUAGAUGAUUGUGCAUUGUUU CAAAAUGGUGCCCUAGUGACUACAAAGCCC | miR-224 |
| miR-23a (SEQ ID NO:140) | GGCCGGCUGGGGUUCCUGGGGAUGGGAUUUGCUUCCUGUCACAAAUCACAU UGCCAGGGAUUUCCAACCGACC | miR-23a |
| miR-23b (SEQ ID NO:141) | CUCAGGUGCUCUGGCUGCUUGGGUUCCUGGCAUGCUGAUUUGUGACUUAAG AUUAAAAUCACAUUGCCAGGGAUUACCACGCAACCACGACCUUGGC | miR-23b |
| miR-24-1 (SEQ ID NO:142) | CUCCGGUGCCUACUGAGCUGAUAUCAGUUCUCAUUUUACACACUGGCUCAG UUCAGCAGGAACAGGAG | miR-24; miR-189 (also called miR-24*) |
| miR-24-2 (SEQ ID NO:143) | CUCUGCCUCCCGUGCCUACUGAGCUGAAACACAGUUGGUUUGUGUACACUG GCUCAGUUCAGCAGGAACAGGG | miR-24 |

FIG. 5I

| pre-miRNA | Sequence | Mature miRNA |
|---|---|---|
| miR-25 (SEQ ID NO:144) | GGCCAGUGUUGAGAGGCGGAGACUUGGGCAAUUGCUGGACGCUGCCCUGGG CAUUGCACUUGUCUCGGUCUGACAGUGCCGGCC | miR-25 |
| miR-26a-1 (SEQ ID NO:145) | GUGGCCUCGUUCAAGUAAUCCAGGAUAGGCUGUGCAGGUCCCAAUGGGCCU AUUCUUGGUUACUUGCACGGGGACGC | miR-26a |
| miR-26a-2 (SEQ ID NO:146) | GGCUGUGGCUGGAUUCAAGUAAUCCAGGAUAGGCUGUUUCCAUCUGUGAGG CCUAUUCUUGAUUACUUGUUUCUGGAGGCAGCU | miR-26a |
| miR-26b (SEQ ID NO:147) | CCGGGACCCAGUUCAAGUAAUUCAGGAUAGGUUGUGUGCUGUCCAGCCUGU UCUCCAUUACUUGGCUCGGGGACCGG | miR-26b |
| miR-27a (SEQ ID NO:148) | CUGAGGAGCAGGGCUUAGCUGCUUGUGAGCAGGGUCCACACCAAGUCGUGU UCACAGUGGCUAAGUUCCGCCCCCCAG | miR-27a |
| miR-27b (SEQ ID NO:149) | ACCUCUCUAACAAGGUGCAGAGCUUAGCUGAUUGGUGAACAGUGAUUGGUU UCCGCUUUGUUCACAGUGGCUAAGUUCUGCACCUGAAGAGAAGGUG | miR-27b |
| miR-28 (SEQ ID NO:150) | GGUCCUUGCCCUCAAGGAGCUCACAGUCUAUUGAGUUACCUUUCUGACUUU CCCACUAGAUUGUGAGCUCCUGGAGGGCAGGCACU | miR-28 |
| miR-296 (SEQ ID NO:151) | AGGACCCUUCCAGAGGGCCCCCCCUCAAUCCUGUUGUGCCUAAUUCAGAGG GUUGGGUGGAGGCUCUCCUGAAGGGCUCU | miR-296 |
| miR-299 (SEQ ID NO:152) | AAGAAAUGGUUUACCGUCCCACAUACAUUUUGAAUAUGUAUGUGGGAUGGU AAACCGCUUCUU | miR-299-3p; miR-299-5p |
| miR-29a (SEQ ID NO:153) | AUGACUGAUUUCUUUUGGUGUUCAGAGUCAAUAUAAUUUUCUAGCACCAUC UGAAAUCGGUUAU | miR-29a |
| miR-29b-1 (SEQ ID NO:154) | CUUCAGGAAGCUGGUUUCAUAUGGUGGUUUAGAUUUAAAUAGUGAUUGUCU AGCACCAUUUGAAAUCAGUGUUCUUGGGGG | miR-29b |
| miR-29b-2 (SEQ ID NO:155) | CUUCUGGAAGCUGGUUUCACAUGGUGGCUUAGAUUUUUCCAUCUUUGUAUC UAGCACCAUUUGAAAUCAGUGUUUUAGGAG | miR-29b |
| miR-29c (SEQ ID NO:156) | AUCUCUUACACAGGCUGACCGAUUUCUCCUGGUGUUCAGAGUCUGUUUUUG UCUAGCACCAUUUGAAAUCGGUUAUGAUGUAGGGGA | miR-29c |
| miR-301a (SEQ ID NO:157) | ACUGCUAACGAAUGCUCUGACUUUAUUGCACUACUGUACUUUACAGCUAGC AGUGCAAUAGUAUUGUCAAAGCAUCUGAAAGCAGG | miR-301 (also called miR-301a) |
| miR-302a (SEQ ID NO:158) | CCACCACUUAAACGUGGAUGUACUUGCUUUGAAACUAAAGAAGUAAGUGCU UCCAUGUUUUGGUGAUGG | miR-302a; miR-302a* |
| miR-302b (SEQ ID NO:159) | GCUCCCUUCAACUUUAACAUGGAAGUGCUUUCUGUGACUUUAAAAGUAAGU GCUUCCAUGUUUUAGUAGGAGU | miR-302b; miR-302b* |

FIG. 5J

| pre-miRNA | Sequence | Mature miRNA |
|---|---|---|
| miR-302d (SEQ ID NO:160) | CCUCUACUUUAACAUGGAGGCACUUGCUGUGACAUGACAAAAAUAAGUGCU UCCAUGUUUGAGUGUGG | miR-302d; miR-302d* |
| miR-30a (SEQ ID NO:161) | GCGACUGUAAACAUCCUCGACUGGAAGCUGUGAAGCCACAGAUGGGCUUUC AGUCGGAUGUUUGCAGCUGC | miR-30a-3p; miR-30a-5p |
| miR-30b (SEQ ID NO:162) | ACCAAGUUUCAGUUCAUGUAAACAUCCUACACUCAGCUGUAAUACAUGGAU UGGCUGGGAGGUGGAUGUUUACUUCAGCUGACUUGGA | miR-30b |
| miR-30c-1 (SEQ ID NO:163) | ACCAUGCUGUAGUGUGUGUAAACAUCCUACACUCUCAGCUGUGAGCUCAAG GUGGCUGGGAGAGGGUUGUUUACUCCUUCUGCCAUGGA | miR-30c |
| miR-30c-2 (SEQ ID NO:164) | AGAUACUGUAAACAUCCUACACUCUCAGCUGUGGAAAGUAAGAAAGCUGGG AGAAGGCUGUUUACUCUUUCU | miR-30c |
| miR-30d (SEQ ID NO:165) | GUUGUUGUAAACAUCCCCGACUGGAAGCUGUAAGACACAGCUAAGCUUUCA GUCAGAUGUUUGCUGCUAC | miR-30d |
| miR-30e (SEQ ID NO:166) | GGGCAGUCUUUGCUACUGUAAACAUCCUUGACUGGAAGCUGUAAGGUGUUC AGAGGAGCUUUCAGUCGGAUGUUUACAGCGGCAGGCUGCCA | miR-30e-3p; miR-30e-5p |
| miR-31 (SEQ ID NO:167) | GGAGAGGAGGCAAGAUGCUGGCAUAGCUGUUGAACUGGGAACCUGCUAUGC CAACAUAUUGCCAUCUUUCC | miR-31 |
| miR-32 (SEQ ID NO:168) | GGAGAUAUUGCACAUUACUAAGUUGCAUGUUGUCACGGCCUCAAUGCAAUU UAGUGUGUGUGAUAUUUUC | miR-32 |
| miR-320a (SEQ ID NO:169) | GCUUCGCUCCCCUCCGCCUUCUCUUCCCGGUUCUUCCCGGAGUCGGGAAAA GCUGGGUUGAGAGGGCGAAAAAGGAUGAGGU | miR-320 (also called miR-320a) |
| miR-323 (SEQ ID NO:170) | UUGGUACUUGGAGAGAGGUGGUCCGUGGCGCGUUCGCUUUAUUUAUGGCGC ACAUUACACGGUCGACCUCUUUGCAGUAUCUAAUC | miR-323 |
| miR-324 (SEQ ID NO:171) | CUGACUAUGCCUCCCCGCAUCCCCUAGGGCAUUGGUGUAAAGCUGGAGACC CACUGCCCCAGGUGCUGCUGGGGGUUGUAGUC | miR-324-3p; miR-324-5p |
| miR-325 (SEQ ID NO:172) | AUACAGUGCUUGGUUCCUAGUAGGUGUCCAGUAAGUGUUUGUGACAUAAUU UGUUUAUUGAGGACCUCCUAUCAAUCAAGCACUGUGCUAGGCUCUGG | miR-325 |
| miR-326 (SEQ ID NO:173) | CUCAUCUGUCUGUUGGGCUGGAGGCAGGGCCUUUGUGAAGGCGGGUGGUGC UCAGAUCGCCUCUGGGCCCUUCCUCCAGCCCCGAGGCGGAUUCA | miR-326 |
| miR-328 (SEQ ID NO:174) | UGGAGUGGGGGGGCAGGAGGGGCUCAGGGAGAAAGUGCAUACAGCCCCUGG CCCUCUCUGCCCUUCCGUCCCCUG | miR-328 |
| miR-329-1 (SEQ ID NO:175) | GGUACCUGAAGAGAGGUUUUCUGGGUUUCUGUUUCUUUAAUGAGGACGAAA CACACCUGGUUAACCUCUUUUCCAGUAUC | miR-329 |
| miR-329-2 (SEQ ID NO:176) | GUGGUACCUGAAGAGAGGUUUUCUGGGUUUCUGUUUCUUUAUUGAGGACGA AACACACCUGGUUAACCUCUUUUCCAGUAUCAA | miR-329 |

FIG. 5K

| pre-miRNA | Sequence | Mature miRNA |
|---|---|---|
| miR-33a (SEQ ID NO:177) | CUGUGGUGCAUUGUAGUUGCAUUGCAUGUUCUGGUGGUACCCAUGCAAUGU UUCCACAGUGCAUCACAG | miR-33 (also called miR-33a) |
| miR-330 (SEQ ID NO:178) | CUUUGGCGAUCACUGCCUCUCUGGGCCUGUGUCUUAGGCUCUGCAAGAUCA ACCGAGCAAAGCACACGGCCUGCAGAGAGGCAGCGCUCUGCCC | miR-330 |
| miR-331 (SEQ ID NO:179) | GAGUUUGGUUUUGUUUGGGUUUGUUCUAGGUAUGGUCCCAGGGAUCCCAGA UCAAACCAGGCCCCUGGGCCUAUCCUAGAACCAACCUAAGCUC | miR-331 |
| miR-335 (SEQ ID NO:180) | UGUUUUGAGCGGGGGUCAAGAGCAAUAACGAAAAAUGUUUGUCAUAAACCG UUUUUCAUUAUUGCUCCUGACCUCCUCUCAUUUGCUAUAUUCA | miR-335 |
| miR-337 (SEQ ID NO:181) | GUAGUCAGUAGUUGGGGGUGGGAACGGCUUCAUACAGGAGUUGAUGCACA GUUAUCCAGCUCCUAUAUGAUGCCUUUCUUCAUCCCCUUCAA | miR-337 |
| miR-338 (SEQ ID NO:182) | UCUCCAACAAUAUCCUGGUGCUGAGUGAUGACUCAGGCGACUCCAGCAUCA GUGAUUUUGUUGAAGA | miR-338 |
| miR-339 (SEQ ID NO:183) | CGGGGCGGCCGCUCUCCCUGUCCUCCAGGAGCUCACGUGUGCCUGCCUGUG AGCGCCUCGACGACAGAGCCGGCGCCUGCCCCAGUGUCUGCGC | miR-339 |
| miR-340 (SEQ ID NO:184) | UUGUACCUGGUGUGAUUAUAAAGCAAUGAGACUGAUUGUCAUAUGUCGUUU GUGGGAUCCGUCUCAGUUACUUUAUAGCCAUACCUGGUAUCUUA | miR-340 |
| miR-342 (SEQ ID NO:185) | GAAACUGGGCUCAAGGUGAGGGGUGCUAUCUGUGAUUGAGGGACAUGGUUA AUGGAAUUGUCUCACACAGAAAUCGCACCCGUCACCUUGGCCUACUUA | miR-342 |
| miR-345 (SEQ ID NO:186) | ACCCAAACCCUAGGUCUGCUGACUCCUAGUCCAGGGCUCGUGAUGGCUGGU GGGCCCUGAACGAGGGGUCUGGAGGCCUGGGUUUGAAUAUCGACAGC | miR-345 |
| miR-346 (SEQ ID NO:187) | GGUCUCUGUGUUGGGCGUCUGUCUGCCCGCAUGCCUGCCUCUCUGUUGCUC UGAAGGAGGCAGGGGCUGGGCCUGCAGCUGCCUGGGCAGAGCGG | miR-346 |
| miR-34a (SEQ ID NO:188) | GGCCAGCUGUGAGUGUUUCUUUGGCAGUGUCUUAGCUGGUUGUUGUGAGCA AUAGUAAGGAAGCAAUCAGCAAGUAUACUGCCCUAGAAGUGCUGCACGUUG UGGGGCCC | miR-34a |
| miR-34b (SEQ ID NO:189) | GUGCUCGGUUUGUAGGCAGUGUCAUUAGCUGAUUGUACUGUGGUGGUUACA AUCACUAACUCCACUGCCAUCAAAACAAGGCAC | miR-34b |
| miR-34c (SEQ ID NO:190) | AGUCUAGUUACUAGGCAGUGUAGUUAGCUGAUUGCUAAUAGUACCAAUCAC UAACCACACGGCCAGGUAAAAAGAUU | miR-34c |
| miR-361 (SEQ ID NO:191) | GGAGCUUAUCAGAAUCUCCAGGGGUACUUUAUAAUUUCAAAAAGUCCCCCA GGUGUGAUUCUGAUUUGCUUC | miR-361 |
| miR-362 (SEQ ID NO:192) | CUUGAAUCCUUGGAACCUAGGUGUGAGUGCUAUUUCAGUGCAACACACCUA UUCAAGGAUUCAAA | miR-362 |

FIG. 5L

| pre-miRNA | Sequence | Mature miRNA |
|---|---|---|
| miR-365-1 (SEQ ID NO:193) | ACCGCAGGGAAAAUGAGGGACUUUUGGGGGCAGAUGUGUUUCCAUUCCACUAUCAUAAUGCCCCUAAAAAUCCUUAUUGCUCUUGCA | miR-365 |
| miR-365-2 (SEQ ID NO:194) | AGAGUGUUCAAGGACAGCAAGAAAAAUGAGGGACUUUCAGGGGCAGCUGUGUUUUCUGACUCAGUCAUAAUGCCCCUAAAAAUCCUUAUUGUUCUUGCAGUGUGCAUCGGG | miR-365 |
| miR-367 (SEQ ID NO:195) | CCAUUACUGUUGCUAAUAUGCAACUCUGUUGAAUAUAAAUUGGAAUUGCACUUUAGCAAUGGUGAUGG | miR-367 |
| miR-369 (SEQ ID NO:196) | UUGAAGGGAGAUCGACCGUGUUAUAUUCGCUUUAUUGACUUCGAAUAAUACAUGGUUGAUCUUUUCUCAG | miR-369-3p; miR-369-5p |
| miR-370 (SEQ ID NO:197) | AGACAGAGAAGCCAGGUCACGUCUCUGCAGUUACACAGCUCACGAGUGCCUGCUGGGGUGGAACCUGGUCUGUCU | miR-370 |
| miR-371 (SEQ ID NO:198) | GUGGCACUCAAACUGUGGGGGCACUUUCUGCUCUCUGGUGAAAGUGCCGCCAUCUUUUGAGUGUUAC | miR-371 |
| miR-372 (SEQ ID NO:199) | GUGGGCCUCAAAUGUGGAGCACUAUUCUGAUGUCCAAGUGGAAAGUGCUGCGACAUUUGAGCGUCAC | miR-372 |
| miR-373 (SEQ ID NO:200) | GGGAUACUCAAAAUGGGGGCGCUUUCCUUUUUGUCUGUACUGGGAAGUGCUUCGAUUUUGGGGUGUCCC | miR-373; miR-373* |
| miR-374a (SEQ ID NO:201) | UACAUCGGCCAUUAUAAUACAACCUGAUAAGUGUUAUAGCACUUAUCAGAUUGUAUUGUAAUUGUCUGUGUA | miR-374 (also called miR-374a) |
| miR-375 (SEQ ID NO:202) | CCCCGCGACGAGCCCCUCGCACAAACCGGACCUGAGCGUUUUGUUCGUUCGGCUCGCGUGAGGC | miR-375 |
| miR-376a-1 (SEQ ID NO:203) | UAAAAGGUAGAUUCUCCUUCUAUGAGUACAUUAUUUAUGAUUAAUCAUAGAGGAAAAUCCACGUUUUC | miR-376a; miR-376a* |
| miR-376a-2 (SEQ ID NO:204) | GGUAUUUAAAAGGUAGAUUUUCCUUCUAUGGUUACGUGUUUGAUGGUUAAUCAUAGAGGAAAAUCCACGUUUUCAGUAUC | miR-376a |
| miR-376b (SEQ ID NO:205) | CAGUCCUUCUUUGGUAUUUAAAACGUGGAUAUUCCUUCUAUGUUUACGUGAUUCCUGGUUAAUCAUAGAGGAAAAUCCAUGUUUUCAGUAUCAAAUGCUG | miR-376b |
| miR-376c (SEQ ID NO:206) | AAAAGGUGGAUAUUCCUUCUAUGUUUAUGUUAUUUAUGGUUAAACAUAGAGGAAAUUCCACGUUUU | miR-368 (also called miR-376c) |
| miR-377 (SEQ ID NO:207) | UUGAGCAGAGGUUGCCCUUGGUGAAUUCGCUUUAUUUAUGUUGAAUCACACAAAGGCAACUUUUGUUUG | miR-377 |
| miR-378 (SEQ ID NO:208) | AGGGCUCCUGACUCCAGGUCCUGUGUGUUACCUAGAAAUAGCACUGGACUUGGAGUCAGAAGGCCU | miR-378; miR-422b (also called miR-378*) |

FIG. 5M

| pre-miRNA | Sequence | Mature miRNA |
|---|---|---|
| miR-379 (SEQ ID NO:209) | AGAGAUGGUAGACUAUGGAACGUAGGCGUUAUGAUUUCUGACCUAUGUAAC AUGGUCCACUAACUCU | miR-379 |
| miR-380 (SEQ ID NO:210) | AAGAUGGUUGACCAUAGAACAUGCGCUAUCUCUGUGUCGUAUGUAAUAUGG UCCACAUCUU | miR-380 (also called miR-380-3p); miR-380* (also called miR-380-5p) |
| miR-381 (SEQ ID NO:211) | UACUUAAAGCGAGGUUGCCCUUUGUAUAUUCGGUUUAUUGACAUGGAAUAU ACAAGGGCAAGCUCUCUGUGAGUA | miR-381 |
| miR-382 (SEQ ID NO:212) | UACUUGAAGAGAAGUUGUUCGUGGUGGAUUCGCUUUACUUAUGACGAAUCA UUCACGGACAACACUUUUUUCAGUA | miR-382 |
| miR-383 (SEQ ID NO:213) | CUCCUCAGAUCAGAAGGUGAUUGUGGCUUUGGGUGGAUAUUAAUCAGCCAC AGCACUGCCUGGUCAGAAAGAG | miR-383 |
| miR-409 (SEQ ID NO:214) | UGGUACUCGGGGAGAGGUUACCCGAGCAACUUUGCAUCUGGACGACGAAUG UUGCUCGGUGAACCCCUUUUCGGUAUCA | miR-409-5p |
| miR-410 (SEQ ID NO:215) | GGUACCUGAGAAGAGGUUGUCUGUGAUGAGUUCGCUUUUAUUAAUGACGAA UAUAACACAGAUGGCCUGUUUUCAGUACC | miR-410 |
| miR-412 (SEQ ID NO:216) | CUGGGGUACGGGGAUGGAUGGUCGACCAGUUGGAAAGUAAUUGUUUCUAAU GUACUUCACCUGGUCCACUAGCCGUCCGUAUCCGCUGCAG | miR-412 |
| miR-422a (SEQ ID NO:217) | GAGAGAAGCACUGGACUUAGGGUCAGAAGGCCUGAGUCUCUCUGCUGCAGA UGGGCUCUCUGUCCCUGAGCCAAGCUUUGUCCUCCCUGG | miR-422a |
| miR-423 (SEQ ID NO:218) | AUAAAGGAAGUUAGGCUGAGGGGCAGAGAGCGAGACUUUUCUAUUUUCCAA AAGCUCGGUCUGAGGCCCCUCAGUCUUGCUUCCUAACCCGCGC | miR-423 |
| miR-424 (SEQ ID NO:219) | CGAGGGGAUACAGCAGCAAUUCAUGUUUUGAAGUGUUCUAAAUGGUUCAAA ACGUGAGGCGCUGCUAUACCCCCUCGUGGGGAAGGUAGAAGGUGGGG | miR-424 |
| miR-425 (SEQ ID NO:220) | GAAAGCGCUUUGGAAUGACACGAUCACUCCCGUUGAGUGGGCACCCGAGAA GCCAUCGGGAAUGUCGUGUCCGCCCAGUGCUCUUUC | miR-425 |
| miR-429 (SEQ ID NO:221) | CGCCGGCCGAUGGGCGUCUUACCAGACAUGGUUAGACCUGGCCCUCUGUCU AAUACUGUCUGGUAAAACCGUCCAUCCGCUGC | miR-429 |
| miR-432 (SEQ ID NO:222) | UGACUCCUCCAGGUCUUGGAGUAGGUCAUUGGGUGGAUCCUCUAUUUCCUU ACGUGGGCCACUGGAUGGCUCCUCCAUGUCUUGGAGUAGAUCA | miR-432; miR-432* |
| miR-433 (SEQ ID NO:223) | CCGGGGAGAAGUACGGUGAGCCUGUCAUUAUUCAGAGAGGCUAGAUCCUCU GUGUUGAGAAGGAUCAUGAUGGGCUCCUCGGUGUUCUCCAGG | miR-433 |
| miR-448 (SEQ ID NO:224) | GCCGGGAGGUUGAACAUCCUGCAUAGUGCUGCCAGGAAAUCCCUAUUUCAU AUAAGAGGGGGCUGGCUGGUUGCAUAUGUAGGAUGUCCCAUCUCCCAGCCC ACUUCGUCA | miR-448 |

FIG. 5N

| pre-miRNA | Sequence | Mature miRNA |
|---|---|---|
| miR-449a (SEQ ID NO:225) | CUGUGUGUGAUGAGCUGGCAGUGUAUUGUUAGCUGGUUGAAUAUGUGAAUG GCAUCGGCUAACAUGCAACUGCUGUCUUAUUGCAUAUACA | miR-449 (also called miR-449a) |
| miR-450a-1 (SEQ ID NO:226) | AAACGAUACUAAACUGUUUUUGCGAUGUGUUCCUAAUAUGCACUAUAAAUA UAUUGGGAACAUUUUGCAUGUAUAGUUUUGUAUCAAUAUA | miR-450 (also called miR-450a) |
| miR-450a-2 (SEQ ID NO:227) | CCAAAGAAAGAUGCUAAACUAUUUUUGCGAUGUGUUCCUAAUAUGUAAUAU AAAUGUAUUGGGGACAUUUUGCAUUCAUAGUUUUGUAUCAAUAAUAUGG | miR-450 (also called miR-450a) |
| miR-451 (SEQ ID NO:228) | CUUGGGAAUGGCAAGGAAACCGUUACCAUUACUGAGUUUAGUAAUGGUAAU GGUUCUCUUGCUAUACCCAGA | miR-451 |
| miR-452 (SEQ ID NO:229) | GCUAAGCACUUACAACUGUUUGCAGAGGAAACUGAGACUUUGUAACUAUGU CUCAGUCUCAUCUGCAAAGAAGUAAGUGCUUUGC | miR-452; miR-452* |
| miR-453 (SEQ ID NO:230) | GCAGGAAUGCUGCGAGCAGUGCCACCUCAUGGUACUCGGAGGGAGGUUGUC CGUGGUGAGUUCGCAUUAUUUAAUGAUGC | miR-453 |
| miR-455 (SEQ ID NO:231) | UCCCUGGCGUGAGGGUAUGUGCCUUUGGACUACAUCGUGGAAGCCAGCACC AUGCAGUCCAUGGGCAUAUACACUUGCCUCAAGGCCUAUGUCAUC | miR-455 |
| miR-483 (SEQ ID NO:232) | GAGGGGGAAGACGGGAGGAAAGAAGGGAGUGGUUCCAUCACGCCUCCUCAC UCCUCUCCUCCCGUCUUCUCCUCUC | miR-483 |
| miR-485 (SEQ ID NO:233) | ACUUGGAGAGAGGCUGGCCGUGAUGAAUUCGAUUCAUCAAAGCGAGUCAUA CACGGCUCUCCUCUCUUUUAGU | miR-485-3p; miR-485-5p |
| miR-486 (SEQ ID NO:234) | GCAUCCUGUACUGAGCUGCCCCGAGGCCCUUCAUGCUGCCCAGCUCGGGGC AGCUCAGUACAGGAUAC | miR-486 |
| miR-487a (SEQ ID NO:235) | GGUACUUGAAGAGUGGUUAUCCCUGCUGUGUUCGCUUAAUUUAUGACGAAU CAUACAGGGACAUCCAGUUUUUCAGUAUC | miR-487a |
| miR-487b (SEQ ID NO:236) | UUGGUACUUGGAGAGUGGUUAUCCCUGUCCUGUUCGUUUUGCUCAUGUCGA AUCGUACAGGGUCAUCCACUUUUUCAGUAUCAA | miR-487b |
| miR-488 (SEQ ID NO:237) | GAGAAUCAUCUCUCCCAGAUAAUGGCACUCUCAAACAAGUUUCCAAAUUGU UUGAAAGGCUAUUUCUUGGUCAGAUGACUCUC | miR-488 |
| miR-489 (SEQ ID NO:238) | GUGGCAGCUUGGUGGUCGUAUGUGUGACGCCAUUUACUUGAACCUUUAGGA GUGACAUCACAUAUACGGCAGCUAAACUGCUAC | miR-489 |
| miR-490 (SEQ ID NO:239) | UGGAGGCCUUGCUGGUUUGGAAAGUUCAUUGUUCGACACCAUGGAUCUCCA GGUGGGUCAAGUUUAGAGAUGCACCAACCUGGAGGACUCCAUGCUGUUGAG CUGUUCACAAGCAGCGGACACUUCCA | miR-490 |
| miR-491 (SEQ ID NO:240) | UUGACUUAGCUGGGUAGUGGGGAACCCUUCCAUGAGGAGUAGAACACUCCU UAUGCAAGAUUCCCUUCUACCUGGCUGGGUUGG | miR-491 |

FIG. 5O

| pre-miRNA | Sequence | Mature miRNA |
|---|---|---|
| miR-493 (SEQ ID NO:241) | CUGGCCUCCAGGGCUUUGUACAUGGUAGGCUUUCAUUCAUUCGUUUGCACA UUCGGUGAAGGUCUACUGUGUGCCAGGCCCUGUGCCAG | miR-493 (also called miR-493-3p); miR-493* (also called miR-493-5p) |
| miR-494 (SEQ ID NO:242) | GAUACUCGAAGGAGAGGUUGUCCGUGUUGUCUUCUCUUUAUUUAUGAUGAA ACAUACACGGGAAACCUCUUUUUUAGUAUC | miR-494 |
| miR-495 (SEQ ID NO:243) | UGGUACCUGAAAAGAAGUUGCCCAUGUUAUUUUCGCUUUAUAUGUGACGAA ACAAACAUGGUGCACUUCUUUUUCGGUAUCA | miR-495 |
| miR-496 (SEQ ID NO:244) | CCCAAGUCAGGUACUCGAAUGGAGGUUGUCCAUGGUGUGUUCAUUUUAUUU AUGAUGAGUAUUACAUGGCCAAUCUCCUUUCGGUACUCAAUUCUUCUUGGG | miR-496 |
| miR-497 (SEQ ID NO:245) | CCACCCCGGUCCUGCUCCCGCCCCAGCAGCACACUGUGGUUUGUACGGCAC UGUGGCCACGUCCAAACCACACUGUGGUGUUAGAGCGAGGGUGGGGGAGGC ACCGCCGAGG | miR-497 |
| miR-498 (SEQ ID NO:246) | AACCCUCCUUGGGAAGUGAAGCUCAGGCUGUGAUUUCAAGCCAGGGGGCGU UUUUCUAUAACUGGAUGAAAAGCACCUCCAGAGCUUGAAGCUCACAGUUUG AGAGCAAUCGUCUAAGGAAGUU | miR-498 |
| miR-499 (SEQ ID NO:247) | GCCCUGUCCCCUGUGCCUUGGGCGGGCGGCUGUUAAGACUUGCAGUGAUGU UUAACUCCUCUCCACGUGAACAUCACAGCAAGUCUGUGCUGCUUCCCGUCC CUACGCUGCCUGGGCAGGGU | miR-499 |
| miR-500 (SEQ ID NO:248) | GCUCCCCCUCUCUAAUCCUUGCUACCUGGGUGAGAGUGCUGUCUGAAUGCA AUGCACCUGGGCAAGGAUUCUGAGAGCGAGAGC | miR-500 |
| miR-501 (SEQ ID NO:249) | GCUCUUCCUCUCUAAUCCUUUGUCCCUGGGUGAGAGUGCUUUCUGAAUGCA AUGCACCCGGGCAAGGAUUCUGAGAGGGUGAGC | miR-501 |
| miR-502 (SEQ ID NO:250) | UGCUCCCCCUCUCUAAUCCUUGCUAUCUGGGUGCUAGUGCUGGCUCAAUGC AAUGCACCUGGGCAAGGAUUCAGAGAGGGGGAGCU | miR-502 |
| miR-503 (SEQ ID NO:251) | UGCCCUAGCAGCGGGAACAGUUCUGCAGUGAGCGAUCGGUGCUCUGGGGUA UUGUUUCCGCUGCCAGGGUA | miR-503 |
| miR-504 (SEQ ID NO:252) | GCUGCUGUUGGGAGACCCUGGUCUGCACUCUAUCUGUAUUCUUACUGAAGG GAGUGCAGGGCAGGGUUUCCCAUACAGAGGGC | miR-504 |
| miR-505 (SEQ ID NO:253) | GAUGCACCCAGUGGGGGAGCCAGGAAGUAUUGAUGUUUCUGCCAGUUUAGC GUCAACACUUGCUGGUUUCCUCUCGGAGCAUC | miR-505 |
| miR-506 (SEQ ID NO:254) | GCCACCACCAUCAGCCAUACUAUGUGUAGUGCCUUAUUCAGGAAGGUGUUA CUUAAUAGAUUAAUAUUUGUAAGGCACCCUUCUGAGUAGAGUAAUGUGCAA CAUGGACAACAUUUGUGGUGGC | miR-506 |
| miR-507 (SEQ ID NO:255) | GUGCUGUGUGUAGUGCUUCACUUCAAGAAGUGCCAUGCAUGUGUCUAGAAA UAUGUUUUGCACCUUUUGGAGUGAAAUAAUGCACAACAGAUAC | miR-507 |

FIG. 5P

| pre-miRNA | Sequence | Mature miRNA |
|---|---|---|
| miR-508 (SEQ ID NO:256) | CCACCUUCAGCUGAGUGUAGUGCCCUACUCCAGAGGGCGUCACUCAUGUAA ACUAAAACAUGAUUGUAGCCUUUUGGAGUAGAGUAAUACACAUCACGUAAC GCAUAUUUGGUGG | miR-508 |
| miR-509-1 (SEQ ID NO:257) | CAUGCUGUGUGUGGUACCCUACUGCAGACAGUGGCAAUCAUGUAUAAUUAA AAAUGAUUGGUACGUCUGUGGGUAGAGUACUGCAUGACACAUG | miR-509 |
| miR-509-2 (SEQ ID NO:258) | CAUGCUGUGUGUGGUACCCUACUGCAGACAGUGGCAAUCAUGUAUAAUUAA AAAUGAUUGGUACGUCUGUGGGUAGAGUACUGCAUGACAC | miR-509 |
| miR-509-3 (SEQ ID NO:259) | GUGGUACCCUACUGCAGACGUGGCAAUCAUGUAUAAUUAAAAAUGAUUGGU ACGUCUGUGGGUAGAGUACUGCAU | miR-509 |
| miR-510 (SEQ ID NO:260) | GUGGUGUCCUACUCAGGAGAGUGGCAAUCACAUGUAAUUAGGUGUGAUUGA AACCUCUAAGAGUGGAGUAACAC | miR-510 |
| miR-511-1 (SEQ ID NO:261) | CAAUAGACACCCAUCGUGUCUUUUGCUCUGCAGUCAGUAAAUAUUUUUUUG UGAAUGUGUAGCAAAAGCACAGAAUGGUGGUCCAUUG | miR-511 |
| miR-511-2 (SEQ ID NO:262) | CAAUAGACACCCAUCGUGUCUUUUGCUCUGCAGUCAGUAAAUAUUUUUUUG UGAAUGUGUAGCAAAAGACAGAAUGGUGGUCCAUUG | miR-511 |
| miR-512-1 (SEQ ID NO:263) | UCUCAGUCUGUGGCACUCAGCCUUGAGGGCACUUUCUGGUGCCAGAAUGAA AGUGCUGUCAUAGCUGAGGUCCAAUGACUGAGG | miR-512-5p |
| miR-512-2 (SEQ ID NO:264) | GGUACUUCUCAGUCUGUGGCACUCAGCCUUGAGGGCACUUUCUGGUGCCAG AAUGAAAGUGCUGUCAUAGCUGAGGUCCAAUGACUGAGGCGAGCACC | miR-512-5p |
| miR-514-1 (SEQ ID NO:265) | AACAUGUUGUCUGUGGUACCCUACUCUGGAGAGUGACAAUCAUGUAUAAUU AAAUUUGAUUGACACUUCUGUGAGUAGAGUAACGCAUGACACGUACG | miR-514 |
| miR-514-2 (SEQ ID NO:266) | GUUGUCUGUGGUACCCUACUCUGGAGAGUGACAAUCAUGUAUAACUAAAUU UGAUUGACACUUCUGUGAGUAGAGUAACGCAUGACAC | miR-514 |
| miR-514-3 (SEQ ID NO:267) | GUUGUCUGUGGUACCCUACUCUGGAGAGUGACAAUCAUGUAUAACUAAAUU UGAUUGACACUUCUGUGAGUAGAGUAACGCAUGACAC | miR-514 |
| miR-515-1 (SEQ ID NO:268) | UCUCAUGCAGUCAUUCUCCAAAAGAAAGCACUUUCUGUUGUCUGAAAGCAG AGUGCCUUCUUUUGGAGCGUUACUGUUUGAGA | miR-515-3p; miR-515-5p |
| miR-515-2 (SEQ ID NO:269) | UCUCAUGCAGUCAUUCUCCAAAAGAAAGCACUUUCUGUUGUCUGAAAGCAG AGUGCCUUCUUUUGGAGCGUUACUGUUUGAGA | miR-515-3p; miR-515-5p |
| miR-516a-1 (SEQ ID NO:270) | UCUCAGGCUGUGACCUUCUCGAGGAAAGAAGCACUUUCUGUUGUCUGAAAG AAAAGAAAGUGCUUCCUUUCAGAGGGUUACGGUUUGAGA | miR-516-3p (also called miR-516a-3p) |
| miR-516a-2 (SEQ ID NO:271) | UCUCAGGUUGUGACCUUCUCGAGGAAAGAAGCACUUUCUGUUGUCUGAAAG AAAAGAAAGUGCUUCCUUUCAGAGGGUUACGGUUUGAGA | miR-516-3p (also called miR-516a-3p) |

FIG. 5Q

| pre-miRNA | Sequence | Mature miRNA |
|---|---|---|
| miR-517a (SEQ ID NO:272) | UCUCAGGCAGUGACCCUCUAGAUGGAAGCACUGUCUGUUGUAUAAAAGAAA AGAUCGUGCAUCCCUUUAGAGUGUUACUGUUUGAGA | miR-517a; miR-517* |
| miR-517b (SEQ ID NO:273) | GUGACCCUCUAGAUGGAAGCACUGUCUGUUGUCUAAGAAAAGAUCGUGCAU CCCUUUAGAGUGUUAC | miR-517b; miR-517* |
| miR-517c (SEQ ID NO:274) | GAAGAUCUCAGGCAGUGACCCUCUAGAUGGAAGCACUGUCUGUUGUCUAAG AAAAGAUCGUGCAUCCUUUUAGAGUGUUACUGUUUGAGAAAAUC | miR-517c; miR-517* |
| mir-518a-1 (SEQ ID NO:275) | UCUCAAGCUGUGACUGCAAAGGGAAGCCCUUUCUGUUGUCUGAAAGAAGAG AAAGCGCUUCCCUUUGCUGGAUUACGGUUUGAGA | mir-518a |
| mir-518a-2 (SEQ ID NO:276) | UCUCAAGCUGUGGGUCUGCAAAGGGAAGCCCUUUCUGUUGUCUAAAAGAAG AGAAAGCGCUUCCCUUUGCUGGAUUACGGUUUGAGA | mir-518a |
| miR-518b (SEQ ID NO:277) | UCAUGCUGUGGCCCUCCAGAGGGAAGCGCUUUCUGUUGUCUGAAAGAAAAC AAAGCGCUCCCCUUUAGAGGUUUACGGUUUGA | miR-518b |
| miR-518c (SEQ ID NO:278) | GCGAGAAGAUCUCAUGCUGUGACUCUCUGGAGGGAAGCACUUUCUGUUGUC UGAAAGAAAACAAAGCGCUUCUCUUUAGAGUGUUACGGUUUGAGAAAAGC | miR-518c; miR-518c* |
| miR-518d (SEQ ID NO:279) | UCCCAUGCUGUGACCCUCUAGAGGGAAGCACUUUCUGUUGUCUGAAAGAAA CCAAAGCGCUUCCCUUUGGAGCGUUACGGUUUGAGA | miR-518d |
| miR-518e (SEQ ID NO:280) | UCUCAGGCUGUGACCCUCUAGAGGGAAGCGCUUUCUGUUGGCUAAAAGAAA AGAAAGCGCUUCCCUUCAGAGUGUUAACGCUUUGAGA | miR-518e |
| miR-518f (SEQ ID NO:281) | UCUCAUGCUGUGACCCUCUAGAGGGAAGCACUUUCUCUUGUCUAAAAGAAA AGAAAGCGCUUCUCUUUAGAGGAUUACUCUUUGAGA | miR-518f |
| miR-519c (SEQ ID NO:282) | UCUCAGCCUGUGACCCUCUAGAGGGAAGCGCUUUCUGUUGUCUGAAAGAAA AGAAAGUGCAUCUUUUUAGAGGAUUACAGUUUGAGA | miR-519c |
| miR-519d (SEQ ID NO:283) | UCCCAUGCUGUGACCCUCCAAAGGGAAGCGCUUUCUGUUUGUUUUCUCUUA AACAAAGUGCCUCCCUUUAGAGUGUUACCGUUUGGGA | miR-519d |
| miR-519e (SEQ ID NO:284) | UCUCAUGCAGUCAUUCUCCAAAAGGGAGCACUUUCUGUUUGAAAGAAAACA AAGUGCCUCCUUUUAGAGUGUUACUGUUUGAGA | miR-519e |
| miR-520a (SEQ ID NO:285) | CUCAGGCUGUGACCCUCCAGAGGGAAGUACUUUCUGUUGUCUGAGAGAAAA GAAAGUGCUUCCCUUUGGACUGUUUCGGUUUGAG | miR-520a; miR-520a* |
| miR-520b (SEQ ID NO:286) | CCCUCUACAGGGAAGCGCUUUCUGUUGUCUGAAAGAAAAGAAAGUGCUUCC UUUUAGAGGG | miR-520b |
| miR-520c (SEQ ID NO:287) | UCUCAGGCUGUCGUCCUCUAGAGGGAAGCACUUUCUGUUGUCUGAAAGAAA AGAAAGUGCUUCCUUUUAGAGGGUUACCGUUUGAGA | miR-510c |

FIG. 5R

| pre-miRNA | Sequence | Mature miRNA |
|---|---|---|
| miR-520d (SEQ ID NO:288) | UCUCAAGCUGUGAGUCUACAAAGGGAAGCCCUUUCUGUUGUCUAAAAGAAAAGAAAGUGCUUCUCUUUGGUGGGUUACGGUUUGAGA | miR-520d; miR-520d* |
| miR-520e (SEQ ID NO:289) | UCUCCUGCUGUGACCCUCAAGAUGGAAGCAGUUUCUGUUGUCUGAAAGGAAAGAAAGUGCUUCCUUUUUGAGGGUUACUGUUUGAGA | miR-520e |
| miR-520f (SEQ ID NO:290) | UCUCAGGCUGUGACCCUCUAAAGGGAAGCGCUUUCUGUGGUCAGAAAGAAAAGCAAGUGCUUCCUUUUAGAGGGUUACCGUUUGGGA | miR-520f |
| miR-520g (SEQ ID NO:291) | UCCCAUGCUGUGACCCUCUAGAGGAAGCACUUUCUGUUUGUUGUCUGAGAAAAAACAAAGUGCUUCCCUUUAGAGUGUUACCGUUUGGGA | miR-520g |
| miR-520h (SEQ ID NO:292) | UCCCAUGCUGUGACCCUCUAGAGGAAGCACUUUCUGUUUGUUGUCUGAGAAAAAACAAAGUGCUUCCCUUUAGAGUUACUGUUUGGGA | miR-520h |
| miR-523 (SEQ ID NO:293) | UCUCAUGCUGUGACCCUCUAGAGGGAAGCGCUUUCUGUUGUCUGAAAGAAAAGAACGCGCUUCCCUAUAGAGGGUUACCCUUUGAGA | miR-523 |
| miR-525 (SEQ ID NO:294) | CUCAAGCUGUGACUCUCCAGAGGGAUGCACUUUCUCUUAUGUGAAAAAAAAGAAGGCGCUUCCCUUUAGAGCGUUACGGUUUGGG | miR-525; miR-525* |
| miR-526a-1 (SEQ ID NO:295) | CUCAGGCUGUGACCCUCUAGAGGGAAGCACUUUCUGUUGCUUGAAAGAAGAGAAAGCGCUUCCUUUUAGAGGAUUACUCUUUGAG | miR-526a |
| miR-526a-2 (SEQ ID NO:296) | GUGACCCUCUAGAGGGAAGCACUUUCUGUUGAAAGAAAAGAACAUGCAUCCUUUCAGAGGGUUAC | miR-526a |
| miR-526b (SEQ ID NO:297) | UCAGGCUGUGACCCUCUUGAGGGAAGCACUUUCUGUUGUCUGAAAGAAGAGAAAGUGCUUCCUUUUAGAGGCUUACUGUCUGA | miR-526b; miR-526b* |
| miR-527 (SEQ ID NO:298) | UCUCAAGCUGUGACUGCAAAGGGAAGCCCUUUCUGUUGUCUAAAAGAAAAGAAAGUGCUUCCCUUUGGUGAAUUACGGUUUGAGA | miR-527 |
| miR-539 (SEQ ID NO:299) | AUACUUGAGGAGAAAUUAUCCUUGGUGUGUUCGCUUUAUUUAUGAUGAAUCAUACAAGGACAAUUUCUUUUUGAGUAU | miR-539 |
| miR-542 (SEQ ID NO:300) | CAGAUCUCAGACAUCUCGGGGAUCAUCAUGUCACGAGAUACCAGUGUGCACUUGUGACAGAUUGAUAACUGAAAGGUCGGGAGCCACUCAUCUUCA | miR-542-3p; miR-542-5p |
| miR-550-1 (SEQ ID NO:301) | UGAUGCUUUGCUGGCUGGUGCAGUGCCUGAGGGAGUAAGAGCCCUGUUGUUGUAAGAUAGUGUCUUACUCCCUCAGGCACAUCUCCAACAAGUCUCU | miR-550 |
| miR-550-2 (SEQ ID NO:302) | UGAUGCUUUGCUGGCUGGUGCAGUGCCUGAGGGAGUAAGAGCCCUGUUGUUGUCAGAUAGUGUCUUACUCCCUCAGGCACAUCUCCAGCGAGUCUCU | miR-550 |
| miR-566 (SEQ ID NO:303) | GCUAGGCGUGGUGGCGGGCGCCUGUGAUCCCAACUACUCAGGAGGCUGGGGCAGCAGAAUCGCUUGAACCCGGGAGGCGAAGGUUGCAGUGAGC | miR-566 |

FIG. 5S

| pre-miRNA | Sequence | Mature miRNA |
|---|---|---|
| miR-576 (SEQ ID NO:304) | UACAAUCCAACGAGGAUUCUAAUUUCUCCACGUCUUUGGUAAUAAGGUUUG GCAAAGAUGUGGAAAAAUUGGAAUCCUCAUUCGAUUGGUUAUAACCA | miR-576 |
| miR-584 (SEQ ID NO:305) | UAGGGUGACCAGCCAUUAUGGUUUGCCUGGGACUGAGGAAUUUGCUGGGAU AUGUCAGUUCCAGGCCAACCAGGCUGGUUGGUCUCCCUGAAGCAAC | miR-584 |
| miR-605 (SEQ ID NO:306) | GCCCUAGCUUGGUUCUAAAUCCCAUGGUGCCUUCUCCUUGGGAAAAACAGA GAAGGCACUAUGAGAUUUAGAAUCAAGUUAGG | miR-605 |
| miR-618 (SEQ ID NO:307) | CUCUUGUUCACAGCCAAACUCUACUUGUCCUUCUGAGUGUAAUUACGUACA UGCAGUAGCUCAGGAGACAAGCAGGUUUACCCUGUGGAUGAGUCUGA | miR-618 |
| miR-638 (SEQ ID NO:308) | GUGAGCGGGCGCGGCAGGGAUCGCGGGCGGGUGGCGGCCUAGGGCGCGGAG GGCGGACCGGGAAUGGCGCGCCGUGCGCCGCCGGCGUAACUGCGGCGCU | miR-638 |
| mir-660 (SEQ ID NO:309) | CUGCUCCUUCUCCCAUACCCAUUGCAUAUCGGAGUUGUGAAUUCUCAAAAC ACCUCCUGUGUGCAUGGAUUACAGGAGGGUGAGCCUUGUCAUCGUG | miR-660 |
| miR-7-1 (SEQ ID NO:310) | UUGGAUGUUGGCCUAGUUCUGUGUGGAAGACUAGUGAUUUUGUUGUUUUUA GAUAACUAAAUCGACAACAAAUCACAGUCUGCCAUAUGGCACAGGCCAUGC CUCUACAG | miR-7 |
| miR-7-2 (SEQ ID NO:311) | CUGGAUACAGAGUGGACCGGCUGGCCCCAUCUGGAAGACUAGUGAUUUUGU UGUUGUCUUACUGCGCUCAACAACAAAUCCCAGUCUACCUAAUGGUGCCAG CCAUCGCA | miR-7 |
| miR-7-3 (SEQ ID NO:312) | AGAUUAGAGUGGCUGUGGUCUAGUGCUGUGUGGAAGACUAGUGAUUUUGUU GUUCUGAUGUACUACGACAACAAGUCACAGCCGGCCUCAUAGCGCAGACUC CCUUCGAC | miR-7 |
| miR-9-1 (SEQ ID NO:313) | CGGGGUUGGUUGUUAUCUUUGGUUAUCUAGCUGUAUGAGUGGUGUGGAGUC UUCAUAAAGCUAGAUAACCGAAAGUAAAAAUAACCCCA | miR-9; miR-9* |
| miR-9-2 (SEQ ID NO:314) | GGAAGCGAGUUGUUAUCUUUGGUUAUCUAGCUGUAUGAGUGUAUUGGUCUU CAUAAAGCUAGAUAACCGAAAGUAAAAACUCCUUCA | miR-9; miR-9* |
| miR-9-3 (SEQ ID NO:315) | GGAGGCCCGUUUCUCUCUUUGGUUAUCUAGCUGUAUGAGUGCCACAGAGCC GUCAUAAAGCUAGAUAACCGAAAGUAGAAAUGAUUCUCA | miR-9; miR-9* |
| miR-92a-1 (SEQ ID NO:316) | CUUUCUACACAGGUUGGGAUCGGUUGCAAUGCUGUGUUUCUGUAUGGUAUU GCACUUGUCCCGGCCUGUUGAGUUUGG | miR-92 (also called miR-92a) |
| miR-92a-2 (SEQ ID NO:317) | UCAUCCCUGGGUGGGGAUUUGUUGCAUUACUUGUGUUCUAUAUAAAGUAUU GCACUUGUCCCGGCCUGUGGAAGA | miR-92 (also called miR-92a) |
| miR-93 (SEQ ID NO:318) | CUGGGGGCUCCAAAGUGCUGUUCGUGCAGGUAGUGUGAUUACCCAACCUAC UGCUGAGCUAGCACUUCCCGAGCCCCCGG | miR-93 |

FIG. 5T

| pre-miRNA | Sequence | Mature miRNA |
|---|---|---|
| miR-95 (SEQ ID NO:319) | AACACAGUGGGCACUCAAUAAAUGUCUGUUGAAUUGAAAUGCGUUACAUUCAACGGGUAUUUAUUGAGCACCCACUCUGUG | miR-95 |
| miR-96 (SEQ ID NO:320) | UGGCCGAUUUUGGCACUAGCACAUUUUUGCUUGUGUCUCUCCGCUCUGAGCAAUCAUGUGCAGUGCCAAUAUGGGAAA | miR-96 |
| miR-98 (SEQ ID NO:321) | AGGAUUCUGCUCAUGCCAGGGUGAGGUAGUAAGUUGUAUUGUUGUGGGGUAGGGAUAUUAGGCCCCAAUUAGAAGAUAACUAUACAACUUACUACUUUCCCUGGUGUGUGGCAUAUUCA | miR-98 |
| miR-99a (SEQ ID NO:322) | CCCAUUGGCAUAAACCCGUAGAUCCGAUCUUGUGGUGAAGUGGACCGCACAAGCUCGCUUCUAUGGGUCUGUGUCAGUGUG | miR-99a |
| miR-99b (SEQ ID NO:323) | GGCACCCACCCGUAGAACCGACCUUGCGGGGCCUUCGCCGCACACAAGCUCGUGUCUGUGGGUCCGUGUC | miR-99b |

FIG. 5U

SEQUENCE LISTING

<160> NUMBER OF SEQ ID NOS: 323

<210> SEQ ID NO 1
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ugggaugagg uaguagguug uauaguuuua gggucacacc caccacuggg agauaacuau     60
acaaucuacu gucuuuccua                                                80

<210> SEQ ID NO 2
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
agguugaggu aguagguugu auaguuuaga auuacaucaa gggagauaac uguacagccu     60
ccuagcuuuc cu                                                        72

<210> SEQ ID NO 3
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gggugaggua guagguugua uaguuugggg cucugcccug cuaugggaua acauaacaau     60
cuacugucuu uccu                                                      74

<210> SEQ ID NO 4
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
cggggugagg uaguagguug ugugguuuca gggcagugau uugcccuc ggaagauaac      60 uauacaaccu acugccuucc cug                                            83

<210> SEQ ID NO 5
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gcauccgggu ugagguagua gguuguaugg uuuagaguua cacccuggga guuaacugua     60
caaccuucua gcuuuccuug gagc                                           84

```
<210> SEQ ID NO 6
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ccuaggaaga gguaguaggu ugcauaguuu uagggcaggg auuuugccca caaggaggua    60
acuauacgac cugcugccuu ucuuagg                                       87

<210> SEQ ID NO 7
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cccgggcuga gguaggaggu uguauaguug aggaggacac ccaaggagau cacuauacgg    60
ccuccuagcu uuccccagg                                                79

<210> SEQ ID NO 8
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ucagagugag guaguagauu guauaguugu gggguaguga uuuuacccug uucaggagau    60
aacuauacaa ucuauugccu ucccuga                                       87

<210> SEQ ID NO 9
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ugugggauga gguaguagau uguauaguuu uagggucaua ccccaucuug gagauaacua    60
uacagucuac ugucuuuccc acg                                           83

<210> SEQ ID NO 10
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
aggcugaggu aguaguuugu acaguuugag ggucuaugau accacccggu acaggagaua    60
acuguacagg ccacugccuu gcca                                          84

<210> SEQ ID NO 11
<211> LENGTH: 84
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 11
cuggcugagg uaguaguuug ugcuguuggu cgguuguga cauugcccgc uguggagaua    60
acugcgcaag cuacugccuu gcua                                         84

<210> SEQ ID NO 12
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ugggaaacau acuucuuuau augcccauau ggaccugcua agcuauggaa uguaaagaag    60
uauguaucuc a                                                        71

<210> SEQ ID NO 13
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
accuacucag aguacauacu ucuuuaugua cccauaugaa cauacaaugc uauggaaugu    60
aaagaaguau guauuuuugg uaggc                                         85

<210> SEQ ID NO 14
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ccuguugcca caaacccgua gauccgaacu ugugguauua guccgcacaa gcuuguaucu    60
auagguaugu gucuguuagg                                               80

<210> SEQ ID NO 15
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ugcccuggcu caguuaucac agugcugaug cugucuauuc uaaagguaca guacugugau    60
aacugaagga uggca                                                    75

<210> SEQ ID NO 16
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16

```
acuguccuuu uucgguuauc augguaccga ugcuguauau cugaaaggua caguacugug      60
auaacugaag aaugguggu                                                   79

<210> SEQ ID NO 17
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uacugcccuc ggcuucuuua cagugcugcc uuguugcaua uggaucaagc agcauuguac      60
agggcuauga aggcauug                                                    78

<210> SEQ ID NO 18
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uugugcuuuc agcuucuuua cagugcugcc uuguagcauu caggucaagc agcauuguac      60
agggcuauga aagaacca                                                    78

<210> SEQ ID NO 19
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ugugcaucgu ggucaaaugc ucagacuccu gugguggcug cucaugcacc acggauguuu      60
gagcaugugc uacggugucu a                                                81

<210> SEQ ID NO 20
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ugugcaucgu ggucaaaugc ucagacuccu gugguggcug cuuaugcacc acggauguuu      60
gagcaugugc uaugugucu a                                                 81

<210> SEQ ID NO 21
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ccuuggccau guaaaagugc uuacagugca gguagcuuuu ugagaucuac ugcaauguaa      60
gcacuucuua cauuaccaug g                                                81
```

```
<210> SEQ ID NO 22
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ccugccgggg cuaaagugcu gacagugcag auaguggucc ucuccgugcu accgcacugu      60
ggguacuugc ugcuccagca gg                                              82

<210> SEQ ID NO 23
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cucucugcuu ucagcuucuu uacaguguug ccuuguggca uggaguucaa gcagcauugu      60
acagggcuau caaagcacag a                                               81

<210> SEQ ID NO 24
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 24
gaucugucug ucuucuguau auacccugua gauccgaauu uguguaagga auuuguggu       60 cacaaauucg uaucuagggg aauauguagu ugacauaaac acuccgcucu                110

<210> SEQ ID NO 25
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 25
ccagagguug uaacguuguc uauauauacc cuguagaacc gaauugugu gguauccgua       60 uagucacaga uucgauucua ggggaauaua uggucgaugc aaaaacuuca               110

<210> SEQ ID NO 26
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ccuuagcaga gcuguggagu gugacaaugg uguuugaguc uaaacuauca aacgccauua     60
ucacacuaaa uagcuacugc uaggc                                           85

<210> SEQ ID NO 27
<211> LENGTH: 85
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 27
aggccucucu cuccguguuc acagcggacc uugauuuaaa uguccauaca auuaaggcac    60
gcggugaaug ccaagaaugg ggcug                                         85

<210> SEQ ID NO 28
<211> LENGTH: 109
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 28
aucaagauua gaggcucugc ucccguguu cacagcggac cuugauuuaa ugucauacaa     60
uuaaggcacg cggugaaugc caagagcgga gccuacggcu gcacuugaa               109

<210> SEQ ID NO 29
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ugagggcccc ucugcguguu cacagcggac cuugauuuaa ugucuauaca auuaaggcac    60
gcggugaaug ccaagagagg cgccucc                                       87

<210> SEQ ID NO 30
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ugccagucuc uaggucccug agacccuuua accgugagg acauccaggg ucacagguga     60
gguucuuggg agccuggcgu cuggcc                                        86

<210> SEQ ID NO 31
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ugcgcuccuc ucaguccccug agacccuaac uugugauguu uaccguuuaa auccacgggu   60
uaggcucuug ggagcugcga gucgugcu                                      88

<210> SEQ ID NO 32
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32

```
accagacuuu uccuagcccu ugagacccua acuugugagg uauuuuagua acaucacaag    60
ucaggcucuu gggaccuagg cggagggga                                      89

<210> SEQ ID NO 33
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
cgcuggcgac gggacauuau uacuuuuggu acgcgcugug acacuucaaa cucguaccgu    60
gaguaauaau gcgccgucca cggca                                          85

<210> SEQ ID NO 34
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ugugaucacu gucuccagcc ugcugaagcu cagagggcuc ugauucagaa agaucaucgg    60
auccgucuga gcuuggcugg ucggaagucu caucauc                             97

<210> SEQ ID NO 35
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ugagcuguug gauucggggc cguagcacug ucugagaggu uuacauuucu cacagugaac    60
cggucucuuu uucagcugcu uc                                             82

<210> SEQ ID NO 36
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ugugcagugg aaggggggc cgauacacug uacgagagug aguagcaggu cucacaguga    60
accggucucu uucccuacug uguc                                           84

<210> SEQ ID NO 37
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ggaucuuuuu gcggucuggg cuugcuguuc cucucaacag uagucaggaa gcccuuaccc    60
caaaaaguau cu                                                        72
```

```
<210> SEQ ID NO 38
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ugcccuucgc gaaucuuuuu gcggucuggg cuugcuguac auaacucaau agccggaagc    60
ccuuacccca aaaagcauuu gcggagggcg                                    90

<210> SEQ ID NO 39
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ugcugcuggc cagagcucuu uucacauugu gcuacugucu gcaccuguca cuagcagugc    60
aauguuaaaa gggcauuggc cguguagug                                     89

<210> SEQ ID NO 40
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ggccugcccg acacucuuuc ccuguugcac uacauaggc cgcugggaag cagugcaaug     60
augaaagggc aucggucagg uc                                            82

<210> SEQ ID NO 41
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 41 ccgccccgc gucuccaggg caaccguggc uuucgauugu uacuguggga acuggaggua     60
acagucuaca gccauggucg ccccgcagca cgcccacgcg c                       101

<210> SEQ ID NO 42
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
acaaugcuuu gcuagagcug guaaaaugga accaaaucgc cucuucaaug gauuuggucc    60
ccuucaacca gcuguagcua ugcauuga                                      88

<210> SEQ ID NO 43
<211> LENGTH: 102
<212> TYPE: RNA
<213> ORGANISM: Artificial Sequence
<220> FEATURE:
```

```
<223> OTHER INFORMATION: Description of Artificial Sequence: Synthetic
      polynucleotide

<400> SEQUENCE: 43
gggagccaaa ugcuuugcua gagcugguaa aauggaacca aaucgacugu ccaauggauu      60 uggucccuu caaccagcug uagcugugca uugauggcgc cg                         102

<210> SEQ ID NO 44
<211> LENGTH: 119
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 44
ccucagaaga aagaugcccc cugcucuggc uggucaaacg gaaccaaguc cgucuuccug      60
agagguuugg uccccuucaa ccagcuacag cagggcuggc aaugcccagu ccuuggaga     119

<210> SEQ ID NO 45
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cagggugugu gacugguuga ccagagggc augcacugug uucacccugu gggccaccua      60
gucaccaacc cuc                                                        73

<210> SEQ ID NO 46
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
aggccucgcu guucucuaug gcuuuuuauu ccuaugugau ucuacugcuc acucauauag      60
ggauuggagc cguggcgcac ggcggggaca                                      90

<210> SEQ ID NO 47
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 47
agauaaauuc acucuagugc uuuauggcuu uuuauuccua ugugauagua auaaagucuc      60
auguagggau ggaagccaug aaauacauug ugaaaaauca                          100

<210> SEQ ID NO 48
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
```

```
cacucugcug uggccuaugg cuuuucauuc cuaugugauu gcugucccaa acucauguag    60
ggcuaaaagc caugggcuac agugaggggc gagcucc                             97

<210> SEQ ID NO 49
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ugagcccucg gaggacucca uuuguuuuga ugauggauuc uuaugcucca ucaucgucuc    60
aaaugagucu ucagaggguu cu                                             82

<210> SEQ ID NO 50
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 50
gguccucuga cucucuucgg ugacggguau ucuugggugg auaauacgga uuacguuguu    60
auugcuuaag aauacgcgua gucgaggaga guaccagcgg ca                      102

<210> SEQ ID NO 51
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cccuggcaug guguggugggg gcagcuggug uugugaauca ggccguugcc aaucagagaa    60
cggcuacuuc acaacaccag ggccacacca cacuacagg                           99

<210> SEQ ID NO 52
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
cguugcugca gcuggugugg ugaaucaggc cgacgagcag cgcauccucu acccggcua    60 uuucacgaca ccagggguugc auca                                          84

<210> SEQ ID NO 53
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
guguauucua cagugcacgu gucuccagug uggcucggag gcuggagacg cggcccuguu    60
ggaguaac                                                             68
```

```
<210> SEQ ID NO 54
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 54
ugugucucuc ucuguguccu gccaguggu uuacccuaug guagguuacg ucaugcuguu    60
cuaccacagg guagaaccac ggacaggaua ccggggcacc                       100

<210> SEQ ID NO 55
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
cggccggccc ugggccauc uccaguaca guguuggaug gucuaauugu gaagcuccua    60
acacugucug guaaagaugg cucccggug gguuc                              95

<210> SEQ ID NO 56
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
gacagugcag ucacccauaa aguagaaagc acuacuaaca gcacuggagg guguaguguu    60
uccuacuuua uggaugagug uacugug                                      87

<210> SEQ ID NO 57
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 57
gcgcagcgcc cugucuccca gccugaggug cagugcugca ucucugguca guugggaguc    60
ugagaugaag cacuguagcu caggaagaga gaaguuguuc ugcagc                106

<210> SEQ ID NO 58
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
caccuugucc ucacggucca guuucccag gaaucccuua gaugcuaaga ugggauucc    60 uggaaauacu guucuugagg ucaugguu                                     88

<210> SEQ ID NO 59
<211> LENGTH: 99
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 59
ccgaugugua uccucagcuu ugagaacuga auuccauggg uugugucagu gucagaccuc    60
ugaaauucag uucuucagcu gggauaucuc ugucaucgu                           99

<210> SEQ ID NO 60
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ccuggcacug agaacugaau uccauaggcu gugagcucua gcaaugcccu guggacucag    60
uucuggugcc cgg                                                       73

<210> SEQ ID NO 61
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
aaucuaaaga caacauuucu gcacacacac cagacuaugg aagccagugu guggaaaugc    60
uucugcuaga uu                                                        72

<210> SEQ ID NO 62
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uauaaaucua guggaaacau uucugcacaa acuagauucu ggacaccagu gugcggaaau    60
gcuucugcua cauuuuuagg                                                80

<210> SEQ ID NO 63
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gaggcaaagu ucugagacac uccgacucug aguaugauag aagucagugc acuacagaac    60
uuugucuc                                                             68

<210> SEQ ID NO 64
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64

```
caagcacgau uagcauuuga ggugaaguuc uguuauacac ucaggcugug gcucucugaa    60
agucagugca ucacagaacu uugucucgaa agcuuucua                            99

<210> SEQ ID NO 65
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
gccggcgccc gagcucuggc uccgugucuu cacucccgug cuugccgag gagggaggga     60 gggacggggg cugugcuggg gcagcugga                                       89

<210> SEQ ID NO 66
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
cuccccaugg cccugucucc caacccuugu accagugcug ggcucagacc cugguacagg     60 ccuggggac agggaccugg ggac                                             84

<210> SEQ ID NO 67
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uuuccugccc ucgaggagcu cacagucuag uaugucucau ccccuacuag acugaagcuc     60
cuugaggaca gggaugguca uacucaccuc                                      90

<210> SEQ ID NO 68
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68 ugucccccc ggcccagguu cugugauaca cuccgacucg ggcucuggag cagucagugc      60
augacagaac uugggcccgg aaggacc                                         87

<210> SEQ ID NO 69
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
cucacagcug ccagugucau uuugugauc ugcagcuagu auucucacuc caguugcaua     60
gucacaaaag ugaucauugg caggguggc                                       90
```

```
<210> SEQ ID NO 70
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
agcgguggcc agugucauuu uugugauguu gcagcuagua auaugagccc aguugcauag    60
ucacaaaagu gaucauugga aacugug                                        87

<210> SEQ ID NO 71
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gugguacuug aagauagguu auccguguug ccuucgcuuu auuugugacg aaucauacac    60
gguugaccua uuuuucagua ccaa                                           84

<210> SEQ ID NO 72
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
cuguuaaugc uaaucgugau aggguuuuu gccuccaacu gacuccuaca uauuagcauu     60
aacag                                                                65

<210> SEQ ID NO 73
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
ccuuggagua aaguagcagc acauaauggu uugguggauuu ugaaaaggug caggccauau   60
ugugcugccu caaaaauaca agg                                            83

<210> SEQ ID NO 74
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uugaggccuu aaaguacugu agcagcacau cauggUUUAC augcuacagu caagaugcga    60
aucauuauuu gcugcucuag aaauuuaagg aaauucau                            98

<210> SEQ ID NO 75
<211> LENGTH: 89
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 75
gucagcagug ccuuagcagc acguaaauau uggcguuaag auucuaaaau uaucuccagu    60
auuaacugug cugcugaagu aagguugac                                     89

<210> SEQ ID NO 76
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
guuccacucu agcagcacgu aaauauuggc guagugaaau auauuaaaa caccaauauu    60 acugugcugc uuuaguguga c                                             81

<210> SEQ ID NO 77
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
gucagaauaa ugucaaagug cuuacagugc agguagugau augugcaucu acugcaguga    60
aggcacuugu agcauuaugg ugac                                          84

<210> SEQ ID NO 78
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 78
ugaguuuuga gguugcuuca gugaacauuc aacgcugucg gugaguuugg aauuaaaauc    60
aaaaccaucg accguugauu guacccuaug gcuaaccauc aucuacucca              110

<210> SEQ ID NO 79
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 79
agaagggcua ucaggccagc cuucagagga cuccaaggaa cauucaacgc ugucggugag    60
uuugggauuu gaaaaaacca cugaccguug acuguaccuu gggguccuua              110

<210> SEQ ID NO 80
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 80

```
ccugugcaga gauuauuuuu uaaaagguca caaucaacau ucauugcugu cgguggguug     60
aacugugugg acaagcucac ugaacaauga augcaacugu ggccccgcuu              110

<210> SEQ ID NO 81
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
cugauggcug cacucaacau ucauugcugu cgguggguuu gagucugaau caacucacug     60
aucaaugaau gcaaacugcg gaccaaaca                                      89

<210> SEQ ID NO 82
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 82
cggaaaauuu gccaaggguu uggggggaaca uucaaccugu cggugaguuu gggcagcuca     60
ggcaaaccau cgaccguuga guggacccug aggccuggaa uugccauccu               110

<210> SEQ ID NO 83
<211> LENGTH: 137
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 83
gucccucccc cuaggccaca gccgagguca caaucaacau ucauuguugu cgguggguug     60
ugaggacuga ggccagaccc accgggggau gaaugucacu guggcugggc cagacacggc   120 uuaagggggaa uggggac                                                  137

<210> SEQ ID NO 84
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 84
gagcugcuug ccuccccccg uuuuuggcaa ugguagaacu cacacugggu agguaacagg     60
auccggugug ucuagacuug ccaacuaugg ggcgaggacu cagccggcac               110

<210> SEQ ID NO 85
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 85
ccgcagagug ugacuccugu ucuguguaug gcacugguag aauucacugu gaacagucuc     60
agucagugaa uuaccgaagg gccauaaaca gagcagagac agauccacga              110
```

<210> SEQ ID NO 86
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
ccagucacgu ccccuuauca cuuuuccagc ccagcuuugu gacuguaagu guuggacgga     60
gaacugauaa ggguagguga uuga                                            84

<210> SEQ ID NO 87
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87 aggggcgag ggauuggaga gaaaggcagu uccugauggu ccccucccca ggggcuggcu      60
uuccucuggu ccuucccucc ca                                              82

<210> SEQ ID NO 88
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ugcuuguaac uuuccaaaga auucuccuuu ugggcuuucu gguuuuauuu uaagcccaaa     60
ggugaauuuu uugggaaguu ugagcu                                          86

<210> SEQ ID NO 89
<211> LENGTH: 109
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 89
ggucgggcuc accaugacac agugugagac cucgggcuac aacacaggac ccgggcgcug     60
cucugacccc ucgugucuug uguugcagcc ggagggacgc agguccgca                109

<210> SEQ ID NO 90
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
ugcucccucu cucacauccc uugcauggug gagggugagc uuucugaaaa ccccucccac     60 augcagggu ugcaggaugg cgagcc                                           86

<210> SEQ ID NO 91
<211> LENGTH: 71
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 91
uguucuaagg ugcaucuagu gcagauagug aaguagauua gcaucuacug cccuaagugc    60
uccuucuggc a                                                        71

<210> SEQ ID NO 92
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
uguguuaagg ugcaucuagu gcaguuagug aagcagcuua gaaucuacug cccuaaaugc    60
cccuucuggc a                                                        71

<210> SEQ ID NO 93
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
ugcaggccuc ugugugauau guuugauaua uuagguuguu auuuaaucca acuauauauc    60
aaacauauuc cuacaguguc uugcc                                         85

<210> SEQ ID NO 94
<211> LENGTH: 92
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
cggcuggaca gcgggcaacg gaaucccaaa agcagcuguu gucccagag cauuccagcu     60 gcgcuuggau uucguccccu gcucuccugc cu                                 92

<210> SEQ ID NO 95
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 95
gccgagaccg agugcacagg gcucugaccu augaauugac agccagugcu cucgucuccc    60
cucuggcugc caauuccaua ggucacaggu auguucgccu caaugccagc               110

<210> SEQ ID NO 96
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 96
cgaggauggg agcugagggc ugggucuuug cgggcgagau gagggugucg gaucaacugg    60
ccuacaaagu cccaguucuc ggccccccg                                      88

<210> SEQ ID NO 97
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
guggucucag aaucggggu uugagggcga gaugaguuua uguuuaucc aacuggcccu      60 caaagucccg cuuuggggu cau                                             83

<210> SEQ ID NO 98
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
augguguuau caaguguaac agcaacucca uguggacugu guaccaauuu ccaguggaga    60
ugcuguuacu uuugaugguu accaa                                          85

<210> SEQ ID NO 99
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
ugguucccgc ccccuguaac agcaacucca uguggaagug cccacugguu ccaguggggc    60
ugcuguuauc uggggcgagg gccag                                          85

<210> SEQ ID NO 100
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
agcuucccug gcucuagcag cacagaaaua uuggcacagg gaagcgaguc ugccaauauu    60
ggcugugcug cuccaggcag gguggug                                        87

<210> SEQ ID NO 101
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
gugaauuagg uaguuucaug uuguugggcc ugguuucug aacacaacaa cauuaaacca    60
cccgauucac                                                           70
```

<210> SEQ ID NO 102
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 102
ugcucgcuca gcugaucugu ggcuuaggua guuucauguu guugggauug aguuuugaac    60
ucggcaacaa gaaacugccu gaguuacauc agucgguuuu cgucgagggc              110

<210> SEQ ID NO 103
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
acuggucggu gauuuaggua guuccuguu guugggaucc accuuucucu cgacagcacg     60
acacugccuu cauuacuuca guug                                          84

<210> SEQ ID NO 104
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
ggcugugccg gguagagagg gcagugggag guaagagcuc uucacccuuc accaccuucu    60
ccacccagca uggcc                                                    75

<210> SEQ ID NO 105
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
ucauuggucc agaggggaga uagguuccug ugauuuuucc uucuucucua agaauaaau     60 ga                                                                  62

<210> SEQ ID NO 106
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
gccaacccag uguucagacu accuguucag gaggcucuca auguguacag uagucugcac    60
auugguuagg c                                                        71

<210> SEQ ID NO 107
<211> LENGTH: 110
<212> TYPE: RNA

```
<213> ORGANISM: Artificial Sequence
<220> FEATURE:
<223> OTHER INFORMATION: Description of Artificial Sequence: Synthetic
      polynucleotide

<400> SEQUENCE: 107
aggaagcuuc uggagauccu gcuccgucgc cccaguguuc agacuaccug uucaggacaa    60
ugccguugua caguagucug cacauugguu agacugggca agggagagca              110

<210> SEQ ID NO 108
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 108
ccagaggaca ccuccacucc gucuacccag uguuuagacu aucguucag gacucccaaa    60 uuguacagua gucugcacau ugguuaggcu gggcugggu agaccucgg               110

<210> SEQ ID NO 109
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
gcaguccucu guuaguuuug cauaguugca cuacaagaag aauguaguug ugcaaaucua    60
ugcaaaacug augguggccu gc                                            82

<210> SEQ ID NO 110
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
cacuguucua ugguuaguuu ugcagguuug cauccagcug ugugauauuc ugcugugcaa    60
auccaugcaa aacugacugu gguagug                                       87

<210> SEQ ID NO 111
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
acauugcuac uuacaauuag uuuugcaggu uugcauuuca gcguauauau guauaugugg    60
cugugcaaau ccaugcaaaa cugauuguga uaaugu                             96

<210> SEQ ID NO 112
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 112 ccgggcccu gugagcaucu uaccggacag ugcuggauuu cccagcuuga cucuaacacu      60
gucugguaac gauguucaaa ggugacccgc                                     90

<210> SEQ ID NO 113
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
ccagcucggg cagccguggc caucuuacug ggcagcauug gauggaguca ggucucuaau      60
acugccuggu aaugaugacg gcggagcccu gcacg                                95

<210> SEQ ID NO 114
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
cccucgucuu acccagcagu guugggugc gguugggagu cucuaauacu gccgguaau       60 gauggagg                                                              68

<210> SEQ ID NO 115
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 115
cgccucagag ccgcccgccg uuccuuuuuc cuaugcauau acuucuuuga ggaucuggcc     60
uaaagaggua uagggcaugg gaaaacgggg cggucggguc cuccccagcg               110

<210> SEQ ID NO 116
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 116 guguuggga cucgcgcgcu gggucccagug guucuuaaca guucaacagu ucuguagcgc     60
aauugugaaa uguuuaggac cacuagaccc ggcgggcgcg cgacagcga                110

<210> SEQ ID NO 117
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 117
ggcuacaguc uuucuucaug ugacucgugg acuucccuuu gcauccuau gccugagaau      60 auaugaagga ggcugggaag gcaaagggac guucaauugu caucacuggc              110
```

```
<210> SEQ ID NO 118
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 118
aaagauccuc agacaaucca ugugcuucuc uguccuuca uuccaccgga gucugucuca      60
uacccaacca gauuucagug gagugaaguu caggaggcau ggagcugaca              110

<210> SEQ ID NO 119
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
ugcuucccga ggccacaugc uucuuuauau ccccauaugg auuacuuugc uauggaaugu      60
aaggaagugu gugguuucgg caagug                                          86

<210> SEQ ID NO 120
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
ugacgggcga gcuuuuggcc cggguuauac cugaugcuca cguauaagac gagcaaaaag      60
cuuguugguc a                                                          71

<210> SEQ ID NO 121
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
guagcacuaa agugcuuaua gugcaggguag uguuuaguua ucuacugcau uaugagcacu      60
uaaaguacug c                                                          71

<210> SEQ ID NO 122
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
aguaccaaag ugcucauagu gcagguaguu uuggcaugac ucacuguag uauggguacu      60 uccaguacu                                                             69

<210> SEQ ID NO 123
<211> LENGTH: 72
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 123
ugucggguag cuuaucagac ugauguugac uguugaaucu cauggcaaca ccagucgaug    60
ggcugucuga ca                                                       72

<210> SEQ ID NO 124
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 124
acccggcagu gccuccaggc gcagggcagc cccugcccac cgcacacugc gcugcccag     60 acccacugug cgugugacag cggcugaucu gugccugggc agcgcgaccc              110

<210> SEQ ID NO 125
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 125
ucaccuggcc augugacuug ugggcuuccc uuugucaucc uucgccuagg gcucugagca    60
gggcagggac agcaaagggg ugcucaguug ucacuuccca cagcacggag              110

<210> SEQ ID NO 126
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 126
cggggcaccc cgcccggaca gcgcgccggc accuuggcuc uagacugcuu acugcccggg    60
ccgcccucag uaacagucuc cagucacggc caccgacgcc uggccccgcc              110

<210> SEQ ID NO 127
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 127
ggccuggcug gacagaguug ucauguqucu gccugucuac acuugcugug cagaacaucc    60
gcucaccugu acagcaggca cagacaggca gucacaugac aacccagccu              110

<210> SEQ ID NO 128
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

```
<400> SEQUENCE: 128
aucauucaga aauggauauac aggaaaauga ccuaugaauu gacagacaau auagcugagu      60
uugucuguca uuucuuuagg ccaauauucu guaugacugu gcuacuucaa                 110

<210> SEQ ID NO 129
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 129
gauggcugug aguuggcuua aucucagcug gcaacuguga gauguucaua caaucccuca      60 cagugguucuc ugggauuaug cuaaacagag caauuuccua gcccucacga                110

<210> SEQ ID NO 130
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 130
aguauaauua uuacauaguu uuugaugucg cagauacugc aucaggaacu gauuggauaa      60
gaaucaguca ccaucaguuc cuaaugcauu gccuucagca ucuaaacaag                 110

<210> SEQ ID NO 131
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 131
gugauaaugu agcgagauuu ucuguugugc uugaucuaac caugugguug cgagguauga      60
guaaaacaug guuccgucaa gcaccaugga acgucacgca gcuuucuaca                 110

<210> SEQ ID NO 132
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 132
gaccagucgc ugcggggcuu uccuuugugc uugaucuaac caugugguug aacgauggaa      60
acggaacaug guucugucaa gcaccgcgga aagcaccgug cucuccugca                 110

<210> SEQ ID NO 133
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 133
ccgccccggg ccgcggcucc ugauugucca aacgcaauuc ucgagcuau ggcuccggcc       60 gagaguugag ucuggacguc ccgagccgcc gcccccaaac cucgagcggg                 110
```

<210> SEQ ID NO 134
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
acucaggggc uucgccacug auuguccaaa cgcaauucuu guacgagucu gcggccaacc    60
gagaauugug gcuggacauc uguggcugag cuccggg                             97

<210> SEQ ID NO 135
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
ggcugagccg caguaguucu ucaguggcaa gcuuuauguc cugacccagc uaaagcugcc    60
aguugaagaa cuguugcccu cugcc                                          85

<210> SEQ ID NO 136
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 136
ugaacaucca ggucuggggc augaaccugg cauacaaugu agauuucugu guucguuagg    60
caacagcuac auugucugcu ggguuucagg cuaccuggaa acauguucuc               110

<210> SEQ ID NO 137
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 137
gcugcuggaa gguguaggua cccucaaugg cucaguagcc aguguagauc cugucuuucg    60
uaaucagcag cuacaucugg cuacugggguc ucgaugggca ucuucuagcu              110

<210> SEQ ID NO 138
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 138
ccuggccucc ugcagugcca cgcuccgugu auuugacaag cugaguugga cacuccaugu    60
gguagagugu caguuuguca aauaccccaa gugcggcaca ugcuuaccag               110

<210> SEQ ID NO 139
<211> LENGTH: 81
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 139
gggcuuucaa gucacuagug guuccguuua guagaugauu gugcauuguu ucaaaauggu    60
gcccuaguga cuacaaagcc c                                             81

<210> SEQ ID NO 140
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 140
ggccggcugg gguuccuggg gaugggauuu gcuuccuguc acaaaucaca uugccaggga    60
uuuccaaccg acc                                                      73

<210> SEQ ID NO 141
<211> LENGTH: 97
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 141
cucaggugcu cuggcugcuu ggguuccugg caugcugauu ugugacuuaa gauuaaaauc    60
acauugccag ggauuaccac gcaaccacga ccuuggc                            97

<210> SEQ ID NO 142
<211> LENGTH: 68
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 142
cuccggugcc uacugagcug auaucaguuc ucauuuuaca cacuggcuca guucagcagg    60
aacaggag                                                            68

<210> SEQ ID NO 143
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 143
cucugccucc cgugccuacu gagcugaaac acaguugguu uguguacacu ggcucaguuc    60
agcaggaaca ggg                                                      73

<210> SEQ ID NO 144
<211> LENGTH: 84
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 144
ggccaguguu gagaggcgga acuugggca auugcuggac gcugcccugg gcauugcacu   60
ugucucgguc ugacagugcc ggcc   84

<210> SEQ ID NO 145
<211> LENGTH: 77
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
guggccucgu ucaaguaauc caggauaggc ugugcagguc ccaaugggcc uauucuuggu   60
uacuugcacg gggacgc   77

<210> SEQ ID NO 146
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
ggcuguggcu ggauucaagu aauccaggau aggcuguuuc caucugugag gccuauucuu   60
gauuacuugu uucuggaggc agcu   84

<210> SEQ ID NO 147
<211> LENGTH: 77
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
ccgggaccca guucaaguaa uucaggauag guugugugcu guccagccug uucuccauua   60
cuuggcucgg ggaccgg   77

<210> SEQ ID NO 148
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
cugaggagca gggcuuagcu gcuugugagc agguccaca ccaagucgug uucacagugg   60
cuaaguuccg cccccag   78

<210> SEQ ID NO 149
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
accucucuaa caaggugcag agcuuagcug auuggugaac agugauuggu uccgcuuug   60 uucacagugg cuaaguucug caccugaaga gaaggug   97

<210> SEQ ID NO 150
<211> LENGTH: 86
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 150
gguccuugcc cucaaggagc ucacagucua uugaguuacc uuucugacuu ucccacuaga    60
uugugagcuc cuggagggca ggcacu    86

<210> SEQ ID NO 151
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 151
aggacccuuc cagagggccc ccccucaauc cuguugugcc uaauucagag gguugggugg    60
aggcucuccu gaagggcucu    80

<210> SEQ ID NO 152
<211> LENGTH: 63
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 152
aagaaauggu uuaccguccc acauacauuu ugaauaugua ugugggaugg uaaaccgcuu    60
cuu    63

<210> SEQ ID NO 153
<211> LENGTH: 64
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 153
augacugauu ucuuuggug uucagaguca auauaauuuu cuagcaccau cugaaaucgg    60
uuau    64

<210> SEQ ID NO 154
<211> LENGTH: 81
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 154
cuucaggaag cugguuucau auggugguuu agauuuaaau agugauuguc uagcaccauu    60
ugaaaucagu guucuugggg g    81

<210> SEQ ID NO 155
<211> LENGTH: 81
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 155
cuucuggaag cugguuucac augguggcuu agauuuuucc aucuuuguau cuagcaccau    60
uugaaaucag uguuuuagga g                                             81

<210> SEQ ID NO 156
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
aucucuuaca caggcugacc gauuucuccu gguguucaga gucuguuuuu gucuagcacc    60
auuugaaauc gguuaugaug uaggggga                                      88

<210> SEQ ID NO 157
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
acugcuaacg aaugcucuga cuuuauugca cuacuguacu uuacagcuag cagugcaaua    60
guauugucaa agcaucugaa agcagg                                        86

<210> SEQ ID NO 158
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
ccaccacuua aacguggaug uacuugcuuu gaaacuaaag aaguaagugc uuccauguuu    60
uggugaugg                                                           69

<210> SEQ ID NO 159
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
gcucccuuca acuuuaacau ggaagugcuu ucgugacuu uaaaaguaag ugcuuccaug     60
uuuuaguagg agu                                                      73

<210> SEQ ID NO 160
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
ccucuacuuu aacauggagg cacuugcugu gacaugacaa aaauaagugc uuccauguuu   60
gagugugg   68

<210> SEQ ID NO 161
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
gcgacuguaa acauccucga cuggaagcug ugaagccaca gaugggcuuu cagucggaug   60
uuugcagcug c   71

<210> SEQ ID NO 162
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
accaaguuuc aguucaugua aacauccuac acucagcugu aauacaugga uuggcuggga   60
gguggauguu uacuucagcu gacuugga   88

<210> SEQ ID NO 163
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
accaugcugu agugugugua aacauccuac acucucagcu gugagcucaa gguggcuggg   60
agaggguugu uuacuccuuc ugccaugga   89

<210> SEQ ID NO 164
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
agauacugua aacauccuac acucucagcu guggaaagua agaaagcugg gagaaggcug   60
uuuacucuuu cu   72

<210> SEQ ID NO 165
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
guuguuguaa acaucccega cuggaagcug uaagacacag cuaagcuuuc agucagaugu   60
uugcugcuac   70

-continued

<210> SEQ ID NO 166
<211> LENGTH: 92
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
gggcagucuu ugcuacugua aacauccuug acuggaagcu guaagguguu cagaggagcu     60
uucagucgga uguuuacagc ggcaggcugc ca                                   92

<210> SEQ ID NO 167
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
ggagaggagg caagaugcug gcauagcugu ugaacuggga accugcuaug ccaacauauu     60
gccaucuuuc c                                                          71

<210> SEQ ID NO 168
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
ggagauauug cacauuacua aguugcaugu ugucacggcc ucaaugcaau uuagugugug     60
ugauauuuuc                                                            70

<210> SEQ ID NO 169
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
gcuucgcucc ccuccgccuu cucuucccgg uucuucccgg agucgggaaa agcuggguug     60
agagggcgaa aaaggaugag gu                                              82

<210> SEQ ID NO 170
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
uugguacuug gagagaggug guccguggcg cguucgcuuu auuuauggcg cacauuacac     60
ggucgaccuc uuugcaguau cuaauc                                          86

<210> SEQ ID NO 171
<211> LENGTH: 83
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 171
cugacuaugc cuccccgcau ccccuagggc auugguguaa agcuggagac ccacugcccc    60
aggugcugcu gggguugua guc                                             83

<210> SEQ ID NO 172
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
auacagugcu ugguuccuag uaggugucca guaaguguuu ugacauaauu uuguuuauug    60
aggaccuccu aucaaucaag cacugugcua ggcucugg                            98

<210> SEQ ID NO 173
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
cucaucuguc uguugggcug gaggcagggc cuuugugaag gcgggugguc cucagaucgc    60
cucugggccc uuccuccagc cccgaggcgg auuca                               95

<210> SEQ ID NO 174
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
uggagugggg gggcaggagg ggcucaggga gaaagugcau acagccccug gcccucucug    60
cccuuccguc cccug                                                     75

<210> SEQ ID NO 175
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
gguaccugaa gagagguuuu cuggguuucu guuucuuuaa ugaggacgaa acacaccugg    60
uuaaccucuu uuccaguauc                                                80

<210> SEQ ID NO 176
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 176
gugguaccug aagagagguu uucuggguuu cuguuucuuu auugaggacg aaacacaccu      60
gguuaaccuc uuuuccagua ucaa                                            84

<210> SEQ ID NO 177
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
cuguggugca uuguaguugc auugcauguu cuggugguac ccaugcaaug uuuccacagu      60
gcaucacag                                                             69

<210> SEQ ID NO 178
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
cuuuggcgau cacugccucu cugggccugu gucuuaggcu cugcaagauc aaccgagcaa      60
agcacacggc cugcagagag gcagcgcucu gccc                                 94

<210> SEQ ID NO 179
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
gaguuugguu uuguuugggu uuguucuagg uaugguccca gggaucccag aucaaaccag      60
gccccugggc cuauccuaga accaaccuaa gcuc                                 94

<210> SEQ ID NO 180
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
uguuuugagc gggggucaag agcaauaacg aaaaauguuu gucauaaacc guuuuucauu      60
auugcuccug accucucuc auuugcuaua uuca                                  94

<210> SEQ ID NO 181
<211> LENGTH: 93
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
guagucagua guuggggggu gggaacggcu ucauacagga guugaugcac aguuauccag      60
cuccuauaug augccuuucu ucaucccuu caa                                   93
```

<210> SEQ ID NO 182
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
ucuccaacaa uauccuggug cugagugaug acucaggcga cuccagcauc agugauuuug    60
uugaaga                                                             67

<210> SEQ ID NO 183
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
cggggcggcc gcucucccug uccuccagga gcucacgugu gccugccugu gagcgccucg    60
acgacagagc cggcgccugc cccagugucu gcgc                                94

<210> SEQ ID NO 184
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
uuguaccugg ugugauuaua aagcaaugag acugauuguc auaugucguu ugugggaucc    60
gucucaguua cuuuauagcc auaccuggua ucuua                               95

<210> SEQ ID NO 185
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
gaaacugggc ucaaggugag gggugcuauc ugugauugag ggacaugguu aauggaauug    60
ucucacacag aaaucgcacc cgucaccuug gccuacuua                           99

<210> SEQ ID NO 186
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
acccaaaccc uaggucugcu gacuccuagu ccagggcucg ugauggcugg ugggcccuga    60 acgaggggguc uggaggccug gguugaauaa ucgacagc                           98

<210> SEQ ID NO 187
<211> LENGTH: 95
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 187
ggucucugug uugggcgucu gucugcccgc augccugccu cucuguugcu cugaaggagg    60
caggggcugg gccugcagcu gccugggcag agcgg                              95

<210> SEQ ID NO 188
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 188
ggccagcugu gaguguuucu uuggcagugu cuuagcuggu uguugugagc aauaguaagg    60
aagcaaucag caaguauacu gcccuagaag ugcugcacgu ugugggggccc             110

<210> SEQ ID NO 189
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
gugcucgguu uguaggcagu gucauuagcu gauuguacug uggugguuac aaucacuaac    60
uccacugcca ucaaaacaag gcac                                          84

<210> SEQ ID NO 190
<211> LENGTH: 77
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
agucuaguua cuaggcagug uaguuagcug auugcuaaua guaccaauca cuaaccacac    60
ggccagguaa aaagauu                                                  77

<210> SEQ ID NO 191
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
ggagcuuauc agaaucucca gggguacuuu auaauuucaa aaagucccccc aggugugauu    60 cugauuugcu uc                                                       72

<210> SEQ ID NO 192
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 192
cuugaauccu uggaaccuag gugugagugc uauuucagug caacacaccu auucaaggau    60
ucaaa                                                               65

<210> SEQ ID NO 193
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
accgcaggga aaaugaggga cuuuuggggg cagauguguu uccauccac uaucauaaug     60 ccccuaaaaa uccuuauugc ucuugca                                       87

<210> SEQ ID NO 194
<211> LENGTH: 111
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 194
agaguguuca aggacagcaa gaaaaaugag ggacuuucag gggcagcugu guuuucugac    60
ucagucauaa ugccccuaaa aauccuuauu guucuugcag ugugcaucgg g            111

<210> SEQ ID NO 195
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
ccauuacugu ugcuaauaug caacucuguu gaauauaaau uggaauugca cuuuagcaau    60
ggugaugg                                                            68

<210> SEQ ID NO 196
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
uugaagggag aucgaccgug uuauauucgc uuuauugacu ucgaauaaua cagguugau     60 cuuuucucag                                                          70

<210> SEQ ID NO 197
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
agacagagaa gccaggucac gucucugcag uuacacagcu cacgagugcc ugcuggggug    60
gaaccugguc ugucu                                                    75
```

```
<210> SEQ ID NO 198
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
guggcacuca aacuguggggg gcacuuucug cucucuggug aaagugccgc caucuuuga      60 guguuac                                                                67

<210> SEQ ID NO 199
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
gugggccuca aauguggagc acuauucuga uguccaagug gaaagugcug cgacauuuga      60
gcgucac                                                                67

<210> SEQ ID NO 200
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
gggauacuca aaauggggggc gcuuccuuu uugucuguac ugggaagugc uucgauuuug      60 gggugnccc                                                              69

<210> SEQ ID NO 201
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
uacaucggcc auuauaauac aaccugauaa guguuauagc acuuaucaga uuguauugua      60
auugucugug ua                                                          72

<210> SEQ ID NO 202
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
ccccgcgacg agccccucgc acaaaccgga ccugagcguu uuguucguuc ggcucgcgug      60
aggc                                                                   64

<210> SEQ ID NO 203
<211> LENGTH: 68
<212> TYPE: RNA
```

<213> ORGANISM: Artificial Sequence
<220> FEATURE:
<223> OTHER INFORMATION: Description of Artificial Sequence: Synthetic
    oligonucleotide

<400> SEQUENCE: 203
uaaaagguag auucuccuuc uaugaguaca uuauuuauga uuaaucauag aggaaaaucc    60
acguuuuc                                                              68

<210> SEQ ID NO 204
<211> LENGTH: 80
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 204
gguauuuaaa agguagauuu uccuucuaug guuacguguu ugaugguuaa ucauagagga    60
aaauccacgu uuucaguauc                                                 80

<210> SEQ ID NO 205
<211> LENGTH: 100
<212> TYPE: RNA
<213> ORGANISM: Artificial Sequence
<220> FEATURE:
<223> OTHER INFORMATION: Description of Artificial Sequence: Synthetic
    polynucleotide

<400> SEQUENCE: 205
caguccuucu uugguauuua aaacguggau auccuucua uguuuacgug auuccugguu    60
aaucauagag gaaauccau guuucagua ucaaaugcug                            100

<210> SEQ ID NO 206
<211> LENGTH: 66
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 206
aaaaggugga uauuccuucu auguuuaugu uauuuauggu uaaacauaga ggaaauucca    60
cguuuu                                                                66

<210> SEQ ID NO 207
<211> LENGTH: 69
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 207
uugagcagag guugcccuug gugaauucgc uuuauuuaug uugaaucaca caaaggcaac    60
uuuuguuug                                                             69

<210> SEQ ID NO 208
<211> LENGTH: 66
<212> TYPE: RNA
<213> ORGANISM: Artificial Sequence
<220> FEATURE:
<223> OTHER INFORMATION: Description of Artificial Sequence: Synthetic
    oligonucleotide

```
<400> SEQUENCE: 208
agggcuccug acuccagguc cugugaguua ccuagaaaua gcacuggacu uggagucaga    60
aggccu                                                              66

<210> SEQ ID NO 209
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
agagauggua gacuauggaa cguaggcguu augauuucug accuauguaa caugguccac    60
uaacucu                                                             67

<210> SEQ ID NO 210
<211> LENGTH: 61
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
aagaugguug accauagaac augcgcuauc ucugugucgu auguaauaug guccacaucu    60
u                                                                   61

<210> SEQ ID NO 211
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
uacuuaaagc gagguugccc uuuguauauu cgguuuauug acauggaaua uacaagggca    60
agcucucugu gagua                                                    75

<210> SEQ ID NO 212
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
uacuugaaga gaaguuguuc gugguggauu cgcuuuacuu augacgaauc auucacggac    60
aacacuuuuu ucagua                                                   76

<210> SEQ ID NO 213
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
cuccucagau cagaagguga uuguggcuuu ggguggauau uaaucagcca cagcacugcc    60
uggucagaaa gag                                                      73
```

<210> SEQ ID NO 214
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
ugguacucgg ggagagguua cccgagcaac uuugcaucug gacgacgaau guugcucggu     60 gaacccuuu ucgguauca                                                  79

<210> SEQ ID NO 215
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
gguaccugag aagagguugu cugugaugag uucgcuuuua uuaaugacga auauaacaca     60
gauggccugu uuucaguacc                                                80

<210> SEQ ID NO 216
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216 cuggggua cg gggauggaug gucgaccagu uggaaaguaa uuguuucuaa uguacuucac    60
cugguccacu agccguccgu auccgcugca g                                   91

<210> SEQ ID NO 217
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
gagagaagca cuggacuuag ggucagaagg ccugagucuc ucugcugcag augggcucuc     60
ugucccugag ccaagcuuug uccucccugg                                     90

<210> SEQ ID NO 218
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
auaaaggaag uuaggcugag gggcagagag cgagacuuuu cuauuuucca aaagcucggu     60
cugaggcccc ucagucuugc uuccuaaccc gcgc                                94

<210> SEQ ID NO 219
<211> LENGTH: 98
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 219
cgaggggaua cagcagcaau ucauguuuug aaguguucua aaugguucaa aacgugaggc    60
gcugcuauac ccccucgugg ggaagguaga aggugggg                            98

<210> SEQ ID NO 220
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
gaaagcgcuu uggaaugaca cgaucacucc cguugagugg gcacccgaga agccaucggg    60
aaugucgugu ccgcccagug cucuuuc                                        87

<210> SEQ ID NO 221
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
cgccggccga ugggcgucuu accagacaug guuagaccug gcccucuguc uaauacuguc    60
ugguaaaacc guccauccgc ugc                                            83

<210> SEQ ID NO 222
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
ugacuccucc aggucuugga guaggucauu ggguggaucc ucuauuuccu uacgugggcc    60
acuggauggc uccuccaugu cuuggaguag auca                                94

<210> SEQ ID NO 223
<211> LENGTH: 93
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
ccggggagaa guacggugag ccugucauua uucagagagg cuagauccuc uguguugaga    60
aggaucauga ugggcucccuc ggguguucucc agg                               93

<210> SEQ ID NO 224
<211> LENGTH: 111
<212> TYPE: RNA
<213> ORGANISM: Artificial Sequence
<220> FEATURE:
<223> OTHER INFORMATION: Description of Artificial Sequence: Synthetic
      polynucleotide
```

```
<400> SEQUENCE: 224
gccggagggu ugaacauccu gcauagugcu gccaggaaau cccuauuuca uauaagaggg      60
ggcuggcugg uugcauaugu aggaugcccc aucucccagc ccacuucguc a              111

<210> SEQ ID NO 225
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
cuguguguga ugagcuggca guguauuguu agcugguuga auaugugaau ggcaucggcu      60
aacaugcaac ugcugucuua uugcauauac a                                    91

<210> SEQ ID NO 226
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
aaacgauacu aaacuguuuu ugcgaugugu uccuaauaug cacauaaau auauuggaa        60 cauuuugcau guauaguuuu guaucaauau a                                    91

<210> SEQ ID NO 227
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 227
ccaaagaaag augcuaaacu auuuuugcga uguguuccua auauguaaua uaaauguauu      60
ggggacauuu ugcauucaua guuuuguauc aauaauaugg                           100

<210> SEQ ID NO 228
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
cuugggaaug gcaaggaaac cguuaccauu acgaguuua guaaugguaa ugguucucuu       60
gcuauaccca ga                                                         72

<210> SEQ ID NO 229
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
gcuaagcacu uacaacuguu ugcagaggaa acugagacuu guaacuaug ucucagucuc       60 aucugcaaag aaguaagugc uuugc                                           85
```

-continued

<210> SEQ ID NO 230
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
gcaggaaugc ugcgagcagu gccaccucau gguacucgga gggagguugu ccguggugag    60
uucgcauuau uuaaugaugc                                                80

<210> SEQ ID NO 231
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
ucccuggcgu gaggguaugu gccuuuggac uacaucgugg aagccagcac caugcagucc    60
augggcauau acacuugccu caaggccuau gucauc                              96

<210> SEQ ID NO 232
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232 gaggggaag acgggaggaa agaagggagu gguuccauca cgccuccuca cuccucuccu     60
cccgucuucu ccucuc                                                    76

<210> SEQ ID NO 233
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
acuuggagag aggcuggccg ugaugaauuc gauucaucaa agcgagucau acacggcucu    60
ccucucuuuu agu                                                       73

<210> SEQ ID NO 234
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
gcauccugua cugagcugcc ccgaggcccu ucaugcugcc cagcucgggg cagcucagua    60
caggauac                                                             68

<210> SEQ ID NO 235
<211> LENGTH: 80
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 235
gguacuugaa gagugguuau cccugcugug uucgcuuaau uuaugacgaa ucauacaggg    60
acauccaguu uuucaguauc                                               80

<210> SEQ ID NO 236
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
uugguacuug gagagugguu aucccugucc uguucguuuu gcucaugucg aaucguacag    60
ggucauccac uuuuucagua ucaa                                          84

<210> SEQ ID NO 237
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
gagaaucauc ucucccagau aauggcacuc ucaaacaagu uccaaauug uuugaaaggc     60 uauuucuugg ucagaugacu cuc                                           83

<210> SEQ ID NO 238
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
guggcagcuu gguggucgua ugugugacgc cauuuacuug aaccuuuagg agugacauca    60
cauauacggc agcuaaacug cuac                                          84

<210> SEQ ID NO 239
<211> LENGTH: 128
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 239
uggaggccuu gcugguuugg aaaguucauu guucgacacc auggaucucc aggugguca     60 aguuuagaga ugcaccaacc uggaggacuc caugcuguug agcuguucac aagcagcgga   120
cacuucca                                                           128

<210> SEQ ID NO 240
<211> LENGTH: 84
<212> TYPE: RNA
<213> ORGANISM: Artificial Sequence
<220> FEATURE:
<223> OTHER INFORMATION: Description of Artificial Sequence: Synthetic
```

```
                        oligonucleotide

<400> SEQUENCE: 240
uugacuuagc uggguagugg ggaacccuuc caugaggagu agaacacucc uuaugcaaga    60
uucccuucua ccuggcuggg uugg                                           84

<210> SEQ ID NO 241
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
cuggccucca gggcuuugua caugguaggc uuucauucau ucguuugcac auucggugaa    60
ggucuacugu gugccaggcc cugugccag                                      89

<210> SEQ ID NO 242
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
gauacucgaa ggagagguug uccguguugu cuucucuuua uuuaugauga aacauacacg    60
ggaaaccucu uuuuuaguau c                                              81

<210> SEQ ID NO 243
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
ugguaccuga aaagaaguug cccauguuau uuucgcuuua uaugugacga aacaaacaug    60
gugcacuucu uuuucggauu ca                                             82

<210> SEQ ID NO 244
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 244
cccaagucag guacucgaau ggagguuguc caugugugu ucauuuuauu uaugaugagu    60
auuacauggc caaucuccuu ucgguacuca auucuucuug gg                      102

<210> SEQ ID NO 245
<211> LENGTH: 112
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 245
ccaccccggu ccugcucccg ccccagcagc acacugguggu uuguacggca cuguggccac    60
```

```
guccaaacca cacugggug uuagagcgag ggugggggag gcaccgccga gg              112
```

<210> SEQ ID NO 246
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 246

```
aacccuccuu gggaagugaa gcucaggcug ugauuucaag ccaggggcg uuuuucuaua      60 acuggaugaa aagcaccucc agagcuugaa gcucacaguu ugagagcaau cgucaagga     120 aguu                                                                 124
```

<210> SEQ ID NO 247
<211> LENGTH: 122
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 247

```
gcccugucc cugugccuug ggcgggcggc uguuaagacu ugcagugaug uuuaacuccu      60
cuccacguga acaucacagc aagucugugc ugcuucccgu cccuacgcug ccugggcagg    120
gu                                                                   122
```

<210> SEQ ID NO 248
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248

```
gcucccccuc ucuaauccuu gcuaccuggg ugagagugcu gucugaaugc aaugcaccug     60
ggcaaggauu cugagagcga gagc                                           84
```

<210> SEQ ID NO 249
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249

```
gcucuuccuc ucuaauccuu ugcccuggg ugagagugcu uucugaaugc aaugcacccg      60
ggcaaggauu cugagagggu gagc                                           84
```

<210> SEQ ID NO 250
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250

```
ugcuccccu cucuaauccu ugcuaucugg gugcuagugc uggcucaaug caaugcaccu      60
```

```
gggcaaggau ucagagaggg ggagcu                                            86

<210> SEQ ID NO 251
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
ugcccuagca gcgggaacag uucugcagug agcgaucggu gcucuggggu auuguuccg        60 cugccagggu a                                                           71

<210> SEQ ID NO 252
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
gcugcuguug ggagacccug gucugcacuc uaucuguauu cuuacugaag ggagugcagg       60
gcaggguuuc ccauacagag ggc                                              83

<210> SEQ ID NO 253
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
gaugcaccca guggggagc caggaaguau ugauguuucu gccaguuuag cgucaacacu        60
ugcugguuuc cucucuggag cauc                                             84

<210> SEQ ID NO 254
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 254
gccaccacca ucagccauac uauguguagu gccuuauuca ggaaggguguu acuuaauaga      60 uuaauauuug uaaggcaccc uucugaguag aguaaugugc aacauggaca acauuugugg      120
uggc                                                                   124

<210> SEQ ID NO 255
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
gugcugugug uagugcuuca cuucaagaag ugccaugcau gugucuagaa auauguuuug       60
caccuuuugg agugaaauaa ugcacaacag auac                                  94
```

```
<210> SEQ ID NO 256
<211> LENGTH: 115
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 256
ccaccuucag cugaguguag ugcccuacuc cagagggcgu cacucaugua aacuaaaaca        60
ugauuguagc cuuuuggagu agaguaauac acaucacgua acgcauauuu ggugg            115

<210> SEQ ID NO 257
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
caugcugugu gugguacccu acugcagaca guggcaauca uguauaauua aaaaugauug        60
guacgucugu ggguagagua cugcaugaca caug                                   94

<210> SEQ ID NO 258
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
caugcugugu gugguacccu acugcagaca guggcaauca uguauaauua aaaaugauug        60
guacgucugu ggguagagua cugcaugaca c                                      91

<210> SEQ ID NO 259
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
gugguacccu acugcagacg uggcaaucau guauaauuaa aaaugauugg uacgucugug        60
gguagaguac ugcau                                                        75

<210> SEQ ID NO 260
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260 guguguccu acucaggaga guggcaauca cauguaauua ggugugauug aaaccucuaa         60
gaguggagua acac                                                         74

<210> SEQ ID NO 261
<211> LENGTH: 87
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 261
caauagacac ccaucguguc uuuugcucug cagucaguaa auauuuuuuu gugaaugugu    60
agcaaaagac agaauggugg uccauug                                        87

<210> SEQ ID NO 262
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
caauagacac ccaucguguc uuuugcucug cagucaguaa auauuuuuuu gugaaugugu    60
agcaaaagac agaauggugg uccauug                                        87

<210> SEQ ID NO 263
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
ucucagucug uggcacucag ccuugagggc acuuucuggu gccagaauga aagugcuguc    60
auagcugagg uccaaugacu gagg                                           84

<210> SEQ ID NO 264
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
gguacuucuc agucuguggc acucagccuu gagggcacuu ucggugcca gaaugaaagu    60 gcugucauag cugaggucca augacugagg cgagcacc                            98

<210> SEQ ID NO 265
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
aacauguugu cuggguacc cuacucugga gagugacaau caugauaau uaaauuugau     60 ugacacuucu gugaguagag uaacgcauga cacguacg                            98

<210> SEQ ID NO 266
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266

-continued

```
guugucugug guacccuacu cuggagagug acaaucaugu auaacuaaau uugauugaca    60
cuucugugag uagaguaacg caugacac                                      88

<210> SEQ ID NO 267
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
guugucugug guacccuacu cuggagagug acaaucaugu auaacuaaau uugauugaca    60
cuucugugag uagaguaacg caugacac                                      88

<210> SEQ ID NO 268
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
ucucaugcag ucauucucca aaagaaagca cuuucuguug ucgaaagca gagugccuuc     60 uuuuggagcg uuacuguuug aga                                           83

<210> SEQ ID NO 269
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
ucucaugcag ucauucucca aaagaaagca cuuucuguug ucgaaagca gagugccuuc     60 uuuuggagcg uuacuguuug aga                                           83

<210> SEQ ID NO 270
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
ucucaggcug ugaccuucuc gaggaaagaa gcacuuucug uugucugaaa gaaaagaaag    60
ugcuuccuuu cagagguua cgguuugaga                                     90

<210> SEQ ID NO 271
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
ucucagguug ugaccuucuc gaggaaagaa gcacuuucug uugucugaaa gaaaagaaag    60
ugcuuccuuu cagagguua cgguuugaga                                     90
```

```
<210> SEQ ID NO 272
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
ucucaggcag ugacccucua gauggaagca cugucuguug uauaaaagaa aagaucgugc       60
aucccuuuag aguguuacug uuugaga                                          87

<210> SEQ ID NO 273
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
gugacccucu agauggaagc acugucuguu gucuaagaaa agaucgugca ucccuuuaga       60
guguuac                                                                67

<210> SEQ ID NO 274
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
gaagaucuca ggcagugacc cucuagaugg aagcacuguc uguugcuaa gaaaagaucg       60 ugcauccuuu uagaguguua cuguuugaga aaauc                                 95

<210> SEQ ID NO 275
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
ucucaagcug ugacugcaaa gggaagcccu uucuguuguc ugaaagaaga gaaagcgcuu      60
cccuuugcug gauuacgguu ugaga                                            85

<210> SEQ ID NO 276
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
ucucaagcug ugggucugca aagggaagcc cuuucuguug ucuaaaagaa gagaaagcgc      60
uucccuuugc uggauuacgg uuugaga                                          87

<210> SEQ ID NO 277
<211> LENGTH: 83
<212> TYPE: RNA
<213> ORGANISM: Artificial Sequence
<220> FEATURE:
```

<223> OTHER INFORMATION: Description of Artificial Sequence: Synthetic
     oligonucleotide

<400> SEQUENCE: 277
ucaugcugug gcccuccaga gggaagcgcu uucguuguc ugaaagaaaa caaagcgcuc    60
cccuuuagag guuuacgguu uga                                          83

<210> SEQ ID NO 278
<211> LENGTH: 101
<212> TYPE: RNA
<213> ORGANISM: Artificial Sequence
<220> FEATURE:
<223> OTHER INFORMATION: Description of Artificial Sequence: Synthetic
     polynucleotide

<400> SEQUENCE: 278
gcgagaagau ucaugcugu gacucucugg agggaagcac uuucguugu cugaaagaaa    60 acaaagcgcu ucucuuuaga guguuacggu uugagaaaag c                     101

<210> SEQ ID NO 279
<211> LENGTH: 87
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 279
ucccaugcug ugacccucua gagggaagca cuuucguug ucugaaagaa accaaagcgc    60
uucccuuugg agcguuacgg uuugaga                                      87

<210> SEQ ID NO 280
<211> LENGTH: 88
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 280
ucucaggcug ugacccucua gagggaagcg cuuucguug gcuaaaagaa aagaaagcgc    60
uucccuucag aguguuaacg cuuugaga                                     88

<210> SEQ ID NO 281
<211> LENGTH: 87
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 281
ucucaugcug ugacccucua gagggaagca cuuucucuug ucuaaaagaa aagaaagcgc    60
uucucuuuag aggauuacuc uuugaga                                      87

<210> SEQ ID NO 282
<211> LENGTH: 87
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 282

```
ucucagccug ugacccucua gagggaagcg cuuucuguug ucugaaagaa aagaaagugc      60
aucuuuuuag aggauuacag uuugaga                                         87

<210> SEQ ID NO 283
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
ucccaugcug ugacccucca aagggaagcg cuuucuguuu guuucucuu aaacaaagug       60 ccucccuuua gaguguuacc guuuggga                                        88

<210> SEQ ID NO 284
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
ucucaugcag ucauucucca aagggagca cuuucuguuu gaaagaaaac aaagugccuc       60
cuuuuagagu guuacuguuu gaga                                            84

<210> SEQ ID NO 285
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
cucaggcugu gacccuccag agggaaguac uuucuguugu cugagagaaa agaaagugcu      60
ucccuuugga cuguuucggu uugag                                           85

<210> SEQ ID NO 286
<211> LENGTH: 61
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
cccucuacag ggaagcgcuu ucuguugucu gaaagaaaag aaagugcuuc cuuuuagagg      60
g                                                                     61

<210> SEQ ID NO 287
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
ucucaggcug ucguccucua gagggaagca cuuucuguug ucugaaagaa aagaaagugc      60
uuccuuuuag aggguuaccg uuugaga                                         87
```

```
<210> SEQ ID NO 288
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
ucucaagcug ugagucuaca aagggaagcc cuuucuguug ucuaaaagaa aagaaagugc    60
uucucuuugg uggguuacgg uuugaga                                       87

<210> SEQ ID NO 289
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
ucuccugcug ugacccucaa gauggaagca guuucuguug ucgaaagga aagaaagugc     60 uuccuuuuug aggguuacug uuugaga                                       87

<210> SEQ ID NO 290
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
ucucaggcug ugacccucua aagggaagcg cuuucugugg ucagaaagaa aagcaagugc    60
uuccuuuuag aggguuaccg uuuggga                                       87

<210> SEQ ID NO 291
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
ucccaugcug ugacccucua gaggaagcac uuucuguuug uugucugaga aaaaacaaag    60 ugcuuccccuu uagaguguua ccguuuggga                                   90

<210> SEQ ID NO 292
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
ucccaugcug ugacccucua gaggaagcac uuucuguuug uugucugaga aaaaacaaag    60
ugcuucccuu uagaguuacu guuuggga                                      88

<210> SEQ ID NO 293
<211> LENGTH: 87
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 293
ucucaugcug ugacccucua gagggaagcg cuuucuguug ucugaaagaa aagaacgcgc    60
uucccuauag aggguuaccc uuugaga                                       87

<210> SEQ ID NO 294
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
cucaagcugu gacucuccag agggaugcac uuucucuuau gugaaaaaaa agaaggcgcu    60
ucccuuuaga gcguuacggu uuggg                                         85

<210> SEQ ID NO 295
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
cucaggcugu gacccucuag agggaagcac uuucuguugc uugaaagaag agaaagcgcu    60
uccuuuuaga ggauuacucu uugag                                         85

<210> SEQ ID NO 296
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
gugacccucu agagggaagc acuuucuguu gaaagaaaag aacaugcauc cuuucagagg    60
guuac                                                               65

<210> SEQ ID NO 297
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
ucaggcugug acccucuuga gggaagcacu uucuguuguc ugaaagaaga gaaagugcuu    60
ccuuuuagag gcuuacuguc uga                                           83

<210> SEQ ID NO 298
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
```

```
ucucaagcug ugacugcaaa gggaagcccu uucuguuguc uaaaagaaaa gaaagugcuu      60
cccuuuggug aauuacgguu ugaga                                           85

<210> SEQ ID NO 299
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
auacuugagg agaaauuauc cuuggugugu ucgcuuuauu uaugaugaau cauacaagga      60
caauuucuuu uugaguau                                                   78

<210> SEQ ID NO 300
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
cagaucucag acaucucggg gaucaucaug ucacgagaua ccagugugca cuugugacag      60
auugauaacu gaaaggucug ggagccacuc aucuuca                              97

<210> SEQ ID NO 301
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
ugaugcuuug cuggcuggug cagugccuga gggaguaaga gcccguugu uguaagauag       60 ugucuuacuc ccucaggcac aucccaaca agucucu                               97

<210> SEQ ID NO 302
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
ugaugcuuug cuggcuggug cagugccuga gggaguaaga gcccguugu ugucagauag       60 ugucuuacuc ccucaggcac aucccagcg agucucu                               97

<210> SEQ ID NO 303
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
gcuaggcgug guggcgggcg ccugugaucc caacuacuca ggaggcuggg gcagcagaau      60
cgcuugaacc cgggaggcga agguugcagu gagc                                 94
```

```
<210> SEQ ID NO 304
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
uacaauccaa cgaggauucu aauuucucca cgucuuuggu aauaagguuu ggcaaagaug       60
uggaaaaauu ggaauccuca uucgauuggu uauaacca                              98

<210> SEQ ID NO 305
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
uagggugacc agccauuaug guuugccugg gacugaggaa uuugcuggga uaugucaguu       60
ccaggccaac caggcugguu ggucucccug aagcaac                               97

<210> SEQ ID NO 306
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
gcccuagcuu gguucuaaau cccauggugc cuucccuug ggaaaaacag agaaggcacu        60
augagauuua gaaucaaguu agg                                              83

<210> SEQ ID NO 307
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
cucuuguuca cagccaaacu cuacuugucc uucugagugu aauuacguac augcaguagc       60
ucaggagaca agcagguuua cccugugggau gagucuga                             98

<210> SEQ ID NO 308
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 308
gugagcgggc gcggcaggga ucgcgggcgg guggcggccu agggcgcgga gggcggaccg      60
ggaauggcgc gccgugcgcc gccggcguaa cugcggcgcu                           100

<210> SEQ ID NO 309
<211> LENGTH: 97
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 309
cugcuccuuc ucccauaccc auugcauauc ggaguuguga auucucaaaa caccuccugu      60
gugcauggau uacaggaggg ugagccuugu caucgug                              97

<210> SEQ ID NO 310
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 310
uuggauguug gccuaguucu guguggaaga cuagugauuu uguuguuuuu agauaacuaa      60
aucgacaaca aaucacaguc ugccauaugg cacaggccau gccucuacag                110

<210> SEQ ID NO 311
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 311
cuggauacag aguggaccgg cuggccccau cuggaagacu agugauuuug uuguugucuu      60
acugcgcuca acaacaaauc ccagucuacc uaauggugcc agccaucgca                110

<210> SEQ ID NO 312
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 312
agauuagagu ggcugugguc uagugcugug uggaagacua gugauuuugu uguucugaug      60
uacuacgaca acaagucaca gccggccuca uagcgcagac ucccuucgac                110

<210> SEQ ID NO 313
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
cgggguuggu uguuaucuuu gguuaucuag cuguaugagu gguguggagu cuucauaaag      60
cuagauaacc gaaaguaaaa auaacccca                                       89

<210> SEQ ID NO 314
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 314
ggaagcgagu uguuaucuuu gguuaucuag cuguaugagu guauuggucu ucauaaagcu        60
agauaaccga aaguaaaaac uccuuca                                            87

<210> SEQ ID NO 315
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
ggaggcccgu uucucucuuu gguuaucuag cuguaugagu gccacagagc cgucauaaag        60
cuagauaacc gaaaguagaa augauucuca                                         90

<210> SEQ ID NO 316
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
cuuucuacac agguugggau cgguugcaau gcuguguuuc uguaugguau ugcacuuguc        60
ccggccuguu gaguuugg                                                      78

<210> SEQ ID NO 317
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
ucaucccugg gugggauuu guugcauuac uuguguucua auaaaguau ugcacuuguc          60 ccggccugug gaaga                                                         75

<210> SEQ ID NO 318
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318 cuggggcuc caaagugcug uucgugcagg uagugugauu acccaaccua cugcugagcu         60
agcacuuccc gagcccccgg                                                    80

<210> SEQ ID NO 319
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
aacacagugg gcacucaaua aaugucuguu gaauugaaau gcguuacauu caacgggu au       60 uuauugagca cccacucugu g                                                  81
```

```
<210> SEQ ID NO 320
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
uggccgauuu uggcacuagc acauuuugc uugugucucu ccgcucugag caaucaugug      60
cagugccaau augggaaa                                                  78

<210> SEQ ID NO 321
<211> LENGTH: 119
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 321
aggauucugc ucaugccagg gugagguagu aaguuguauu guugugggu agggauauua     60 ggccccaauu agaagauaac uauacaacuu acuacuuucc cuggugugug gcauauuca    119

<210> SEQ ID NO 322
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
cccauuggca uaaacccgua gauccgaucu uguggugaag uggaccgcac aagcucgcuu     60 cuauggucu gugucagugu g                                               81

<210> SEQ ID NO 323
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
ggcacccacc cguagaaccg accuugcggg gccuucgccg cacacaagcu cgugucugug    60
gguccguguc                                                           70
```

MIRNA BIOMARKERS OF LUNG DISEASE

This application claims priority to U.S. Provisional Application No. 61/237,972, filed Aug. 28, 2009, which is incorporated by reference in its entirety.

Work described in this application was partially funded by the Federal government under National Cancer Institution/NIH Grant No. 1R43CA141786-01. Accordingly, the Federal government may have certain rights in this invention.

In the United States, lung cancer has the highest incidence and the highest mortality rate of all cancers (http://seer.cancer.gov/statistics/). Lung cancer is divided into two major classes: small cell lung cancer (SCLC) and non-small cell lung cancer (NSCLC), the former affecting 20% of patients and the latter 80%. NSCLC consists of three major subtypes: adenocarcinoma, squamous cell carcinoma (SCC), and large cell carcinoma, with adenocarcinoma and squamous cell carcinoma accounting for the vast majority (Sekido et al., *Biochim Biophys Acta*, 1378:F21-59; Forgacs et al., *Pathol Oncol Res*, 7:6-13 (2001)). An estimated 215,000 new cases of lung cancer and approximately 162,000 deaths from lung cancer occurred in the United States during 2008 (Jemal et al., *J Natl Cancer Inst*, 100:1672-94 (2008)). The high mortality rate of lung cancer has been attributed in part to the fact that more than 75% of lung cancer patients are diagnosed with regional or distant metastasis at first presentation, and in part to the lack of highly effective therapies for lung cancer. Although the current treatment options for lung cancer are limited, it has been shown that patients who are diagnosed at the earliest stage have a better chance of 5-yr survival (50%) than those in later stages (<10%) (see, e.g., http://seer.cancer.gov/statistics; Horner et al. (eds). SEER Cancer Statistics Review, 1975-2006, National Cancer Institute. Bethesda, Md.). Consequently, extensive efforts have been directed to the detection of lung cancer at an early stage so that medical intervention may improve survival.

Risk factors for lung cancer include age and tobacco consumption by smoking (first hand and second hand). Approximately 90% of all lung cancer cases occur in smokers. Additionally, significant differences exist in both incidence and mortality of lung cancer between males and females, suggesting the possibility of inherent biological processes between the two sexes. These differences are among the most consistently reported significant risk factors in lung cancer (Visbal et al, *Ann Thorac Surg*, 78:209-15 (2004)).

Several screening studies designed to detect lung cancer at an earlier stage have been undertaken. Many of these studies have used two major imaging technologies: chest X-ray and computed tomography (CT). A chest X-ray may reveal a mass in the lung that may be biopsied for verification and classification of lung cancer. Improvements in imaging technologies, most notably the development of spiral computed tomography (spiral CT), have enabled clinicians to detect smaller lung tumors in pre-symptomatic individuals. The Early Lung Cancer Action project (ELCAP), designed to screen symptom-free high-risk smokers using chest X-ray and low dose CT, showed that CT greatly improved the detection of smaller, potentially curable lesions (Henschke et al., *Lancet*, 354:99-105 (1999)). However, the major disadvantages were the rate of false positives and high cost (average $600) that were difficult to justify as a screening paradigm. Id.; see also Henschke et al., *N Engl J Med*, 355:1763-71 (2006).

These studies have generated an intense discussion within the scientific community centering on the design of the studies, particularly the lack of randomization, and the conclusions drawn with concerns of high cost and high false positive rate (Henschke et al., 1999; Gould et al., *N Engl J Med*, 356:743-747 (2007)). Between 25 and 60 percent of spiral CT scans of smokers and former smokers show benign abnormalities (Swensen et al., *Am J Respir Crit Care Med*, 165:508-13 (2002)). Imaging screening of asymptomatic patients does not distinguish benign from early malignant lesions. It has also been reported that repeated exposure to low dose CT scans may expose patients to potentially harmful levels of radiation (Brenner et al., *Radiology*, 231:440-5 (2004)).

At present, there is still a need for clinically relevant markers for non-invasive detection of lung disease including cancer, monitoring response to therapy, or detecting lung cancer recurrence. It is also clear that such assays must be highly specific with reasonable sensitivity, and be readily available at a reasonable cost. Circulating biomarkers offer an alternative to imaging with the following advantages: 1) they are found in a minimally-invasive, easy to collect specimen type (blood or blood-derived fluids), 2) they can be monitored frequently over time in a subject to establish an accurate baseline, making it easy to detect changes over time, 3) they can be provided at a reasonably low cost, 4) they may limit the number of patients undergoing repeated expensive and potentially harmful CT scans, and/or 5) unlike CT scans, biomarkers may potentially distinguish indolent from more aggressive lung lesions (see, e.g., Greenberg and Lee, *Opin Pulm Med*, 13:249-55 (2007)).

Existing biomarker assays include several serum protein markers such as CEA (Okada et al., *Ann Thorac Surg*, 78:216-21 (2004)), CYFRA 21-1 (Schneider, *Adv Clin Chem*, 42:1-41 (2006)), CRP (Siemes et al., *J Clin Oncol*, 24:5216-22 (2006)), CA-125 (Schneider, 2006), and neuron-specific enolase and squamous cell carcinoma antigen (Siemes et al., 2006). Low sensitivity and specificity, with a significant number of false positive results due to benign pulmonary diseases have limited the application of these assays.

Circulating nucleic acids such as DNA and mRNA have also been evaluated as possible diagnostic markers for lung cancer. These studies are based on the observations that circulating nucleic acids show differential expression that is suggestive of cancer. (See, e.g., Bremnes et al., *Lung Cancer*, 49:1-12 (2005); Johnson et al., *Cell*, 120:635-47 (2005); Yanaihara et al., *Cancer Cell*, 9:189-98 (2006); Chen et al., *Cell Res*, 18:997-1006 (2008); Fabbri et al., *Cancer J*, 14:1-6 (2008); Garofalo et al., *Oncogene*, 27:3845-55 (2008); Mitchell et al., *Proc Natl Acad Sci*, 105:10513-8 (2008); Schickel et al., *Oncogene*, 27:5959-74 (2008); Weiss et al., *Ann Oncol*, 19:1053-9 (2008); and Yu et al., *Cancer Cell*, 13:48-57 (2008).) The origin of free DNA in circulation is not completely understood, but they are thought to represent the stable remaining fraction from damaged (apoptotic, necrotic) tumor cells (Jahr et al., *Cancer Res*, 61:1659-65 (2001); Bianchi, *Placenta*, 25 Suppl A:S93-S101 (2004)).

We herein describe methods for detecting, diagnosing, or monitoring lung disease by measuring miRNAs from serum or plasma.

In some embodiments, the invention relates to the detection or monitoring of lung diseases such as small cell lung cancer or non-small cell lung cancer by detecting miRNAs from serum or plasma. The methods of the invention include detection of biomarkers that can be used to diagnose disease and/or evaluate the prognosis or aggressiveness of a lung disease. Further, the methods may be used to characterize the progression of a lung disease. In certain embodiments, the methods of the invention may be used to determine whether a lung tumor or lesion in a patient is cancerous or benign. The patients tested using the methods of the invention may also be tested using other known methods in the art.

In certain embodiments of the invention, the diagnosis or prognosis may be achieved by measuring the amount of a miRNA that is present in elevated or reduced levels in the serum or plasma of a subject with lung disease. In some instances, one serum or plasma miRNA may be detected (e.g., amplified and measured) to characterize lung disease, while in other embodiments, two or more miRNAs are detected from serum or plasma. Some embodiments include detecting a pair of miRNAs. In some instances, one miRNA in the pair is elevated in serum or plasma of patients with lung disease or lung cancer, and the other miRNA in the pair is reduced. In other circumstances, both miRNAs in the pair can be elevated or both reduced. In certain embodiments, non-miRNA biomarkers such as protein markers may also be measured. Some embodiments of the invention relate to diagnosis or prognosis of lung cancer, or determining the type of lung cancer in a patient. In some embodiments, the patient has previously been screened for lung disease.

Additional embodiments of the invention are discussed throughout this application. Other objects, features, and advantages of the present invention will become apparent from the following detailed description. Any embodiment discussed with respect to one aspect of the invention applies to other aspects of the invention as well and vice versa. The embodiments in the Example section are understood to be embodiments of the invention that are applicable to all aspects of the invention.

It should be understood, however, that the detailed description and the specific examples, while indicating specific embodiments of the invention, are given by way of illustration only, since various changes and modifications within the spirit and scope of the invention will become apparent to those skilled in the art from this application.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4 shows performance estimates of training and test data from the Linear Discriminate Analysis of Example 5. SENS, sensitivity; SPEC, specificity; NPV, negative predictive value; PPV, positive predictive value. Six differential miRNA pairs were used: miR-142-5p and miR181d; miR-142-3p and miR181d; miR-142-3p and miR-422a; miR-142-5p and miR-422a; miR-92 and miR-27b; and miR-24 and miR-27a.

FIGS. 5A-5U show human precursor miRNA (pre-miRNA) sequences (SEQ ID NOS 1-323, respectively, in order of appearance), as provided by Release 13.0 of the miRBase::Sequences Database (http://microrna.sanger.ac.uk; Griffiths-Jones et al., Nucleic Acids Research, 2008, 36, Database Issue, d154-d158; Griffiths-Jones et al., Nucleic Acids Research, 2006, 34, Database Issue, D140-D144; Griffiths-Jones, Nucleic Acids Research, 2004, 32, Database Issue, D109-D111). The names of mature miRNAs from Tables 1-5 are also provided.

EXEMPLARY EMBODIMENTS

Figure 1:
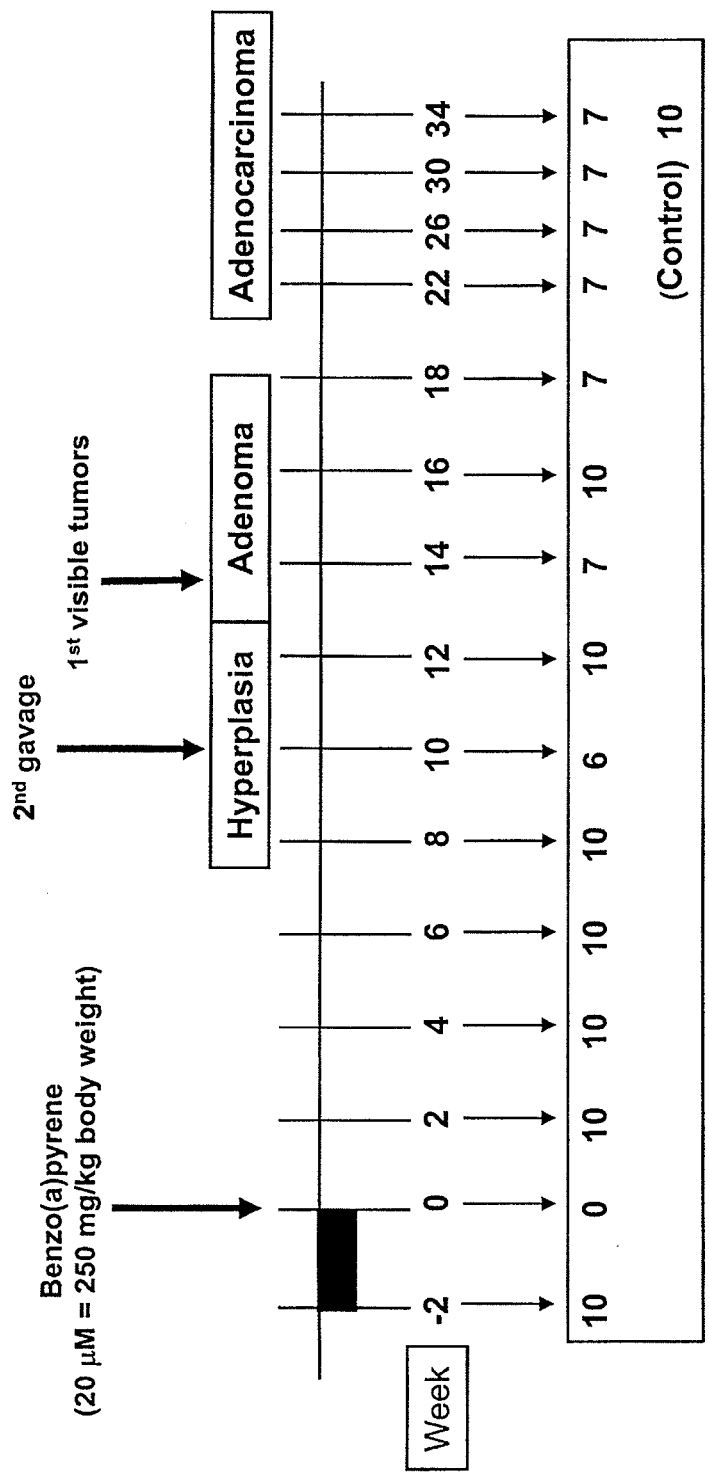
FIG. 1 is a schematic outline of the study design for the mouse model for lung cancer. One hundred fifteen A/J mice were administered with an oral gavage of benzo(a)pyrene at the indicated dose at time (0) and at 10 weeks post the first gavage. Ten control mice received an oral gavage of 200 µl cottonseed oil with no carcinogen at week/day 0. The number of mice sacrificed at each time point is shown below the arrows. The remaining mice were bled every two weeks until 18 weeks and every four weeks thereafter. At the end of 34 weeks, all remaining mice were sacrificed.

In certain aspects, the methods of the invention provide assays for amplifying and measuring the amount of a miRNA in a serum or plasma sample, thereby characterizing a lung disease.

To assist in understanding the present invention, certain terms are first defined. Additional definitions are provided throughout the application.

As used herein, the term "microRNA" (miRNA or miR) includes human miRNAs, mature single stranded miRNAs, precursor miRNAs (pre-miR), and variants thereof, which may be naturally occurring. In some instances, the term "miRNA" also includes primary miRNA transcripts and duplex miRNAs. Unless otherwise noted, when used herein, the name of a specific miRNA refers to the mature miRNA of a precursor miRNA. For example, miR-122a refers to a mature miRNA sequence derived from pre-miR-122. The sequences for particular miRNAs, including human mature and precursor sequences, are reported in the miRBase::Sequences Database (http://microrna.sanger.ac.uk (version 15 released April 2010); Griffiths-Jones et al., Nucleic Acids Research, 2008, 36, Database Issue, D154-D158; Griffiths-Jones et al., Nucleic Acids Research, 2006, 34, Database Issue, D140-D144; Griffiths-Jones, Nucleic Acids Research, 2004, 32, Database Issue, D109-D111). For certain miRNAs, a single precursor contains more than one mature miRNA sequence. In other instances, multiple precursor miRNAs contain the same mature sequence. In some instances, mature miRNAs have been re-named based on new scientific consensus. For example, miR-213, as used herein, refers to a mature miRNA from pre-miR-181a-1, and is also called miR-181a*. Other miRNAs that have been re-named include miR-189 (also called miR-24*), which comes from pre-miR-24-1; miR-368 (also called miR-376c); and miR-422b (also called miR-378*). The skilled artisan will appreciate that scientific consensus regarding the precise nucleic acid sequence for a given miRNA, in particular for mature forms of the miRNAs, may change with time. MiRNAs detected by assays of this application include naturally occurring sequences for the miRNAs.

The term "characterizing" is used herein to encompass detection and prognosis, and it includes detection of a miRNA for making diagnostic or prognostic determinations or predictions of disease. In some instances, the characterization will identify whether a subject has a lung disease such as cancer, or will determine the disease state. Additionally, detection of a miRNA according to the methods herein includes measuring the amount of a miRNA that can used to distinguish patients with lung cancer from patients having other lung diseases, or determine whether a patient with a lung tumor has cancer. In other circumstances, "characterizing" includes detection of a miRNA for determining the stage or aggressiveness of a disease state such as lung cancer, or determining an appropriate treatment method for lung disease.

The use of the word "a", "an" or "the" when used in conjunction with the term "comprising" in the claims and/or the specification may mean "one," but it is also consistent with the meaning of "one or more," "at least one," and "one or more than one."

I. Samples

Serum is typically the fluid, non-cellular portion of coagulated blood. Plasma is also a non-cellular blood sample, but unlike serum, plasma contains clotting factors. In some embodiments, serum or plasma samples are obtained from a human patient previously screened for lung disease using another diagnostic method. In various embodiments, serum or plasma samples are obtained from patients that have tested positive for a tumor or lung lesion. In certain embodiments, the patient has undergone imaging detection, e.g., by chest X-ray or CT scan. In other embodiments, the methods involve detection of miRNA in patients with a positive imaging result for lung disease. In some circumstances, samples are obtained from patients that have a lung tumor or lesion. The tumor or lesion may have been detected by chest X-ray or CT scan, or by other imaging or detection methods known in the art. Additional embodiments include measuring miRNA in samples from patients previously or currently undergoing treatment for a lung disease. In additional embodiments, the sample is from a patient suspected of having lung cancer or at risk of developing lung cancer. The volume of plasma or serum obtained and used for the assay may be varied depending upon clinical intent.

One of skill in the art will recognize that many methods exist for obtaining and preparing serum samples. Generally, blood is drawn into a collection tube using standard methods and allowed to clot. The serum is then separated from the cellular portion of the coagulated blood. In some methods, clotting activators such as silica particles are added to the blood collection tube. In other methods, the blood is not treated to facilitate clotting. Blood collection tubes are commercially available from many sources and in a variety of formats (e.g., Becton Dickenson Vacutainer® tubes—SST™, glass serum tubes, or plastic serum tubes).

In some methods, the blood is collected by venipuncture and processed within three hours after drawing to minimize hemolysis and minimize the release of miRNAs from intact cells in the blood. In some methods, blood is kept on ice until use. The blood may be fractionated by centrifugation to remove cellular components. In some embodiments, centrifugation to prepare serum can be at a speed of at least 500, 1000, 2000, 3000, 4000, or 5000×G. In certain embodiments, the blood can be incubated for at least 10, 20, 30, 40, 50, 60, 90, 120, or 150 minutes to allow clotting. In other embodiments, the blood is incubated for at most 3 hours. When using plasma, the blood is not permitted to coagulate prior to separation of the cellular and acellular components. Serum or plasma can be frozen after separation from the cellular portion of blood until further assayed.

Before analysis, RNA may be extracted from serum or plasma and purified using methods known in the art. Many methods are known for isolating total RNA, or for specifically extracting small RNAs, including miRNAs. The RNA may be extracted using commercially-available kits (e.g., Perfect RNA Total RNA Isolation Kit, Five Prime-Three Prime, Inc.; mirVana™ kits, Ambion, Inc.). Alternatively, RNA extraction methods for the extraction of mammalian intracellular RNA or viral RNA may be adapted, either as published or with modification, for extraction of RNA from plasma and serum. RNA may be extracted from plasma or serum using silica particles, glass beads, or diatoms, as in the method or adaptations described in U.S. Publication No. 2008/0057502.

II. miRNA Markers for Lung Disease

Certain embodiments of the invention provide serum or plasma miRNAs as markers for lung disease. In some embodiments, miRNAs that are present at elevated levels in the serum and/or plasma of patients with lung disease are used as markers. In other embodiments, miRNAs that have reduced levels are used as markers. In some embodiments, more than one miRNA from serum or plasma will be used as markers. When more than one miRNA biomarker is used, the miRNAs may all have elevated levels, all have reduced levels, or a mixture of miRNAs with elevated and reduced levels may be used.

The terms "reduced levels" or "elevated levels" refer to the amount of a miRNA in a serum or plasma sample from a patient compared to the amount of the miRNA in serum or plasma from a cohort or cohorts that do not have the lung disease that the patient is being tested for. For instance, a miRNA that has reduced levels in the sera of lung cancer patients is present at lower amounts in lung cancer patient sera than in serum from a donor who does not have lung cancer (e.g., patients with benign tumors or normal patients). For certain miRNAs, elevated levels in a patient serum or plasma sample indicates presence or prognosis for a lung disease. Other miRNAs are present in reduced levels in patients with lung disease.

Lung disease includes cancer and benign conditions. Lung cancer refers to malignant tumors of the lung, and can be classified as small cell or non-small cell lung cancer. In some embodiments, non-small cell lung cancer can be further characterized as adenocarcinoma, squamous cell carcinoma (SCC), and large cell carcinoma. In addition, cancers can be classified based on X-ray or CT scanning results, aggressiveness, pathology, and measurements of non-miRNA biomarkers, as well as other methods known in the art. In certain aspects, the lung cancer is classified by TNM principles (T-primary tumor, N-regional lymph nodes, M-distant metastasis) and/or stage 0, IA, IB, IIA, IIB, IIIA, IIIB or IV. (See, e.g., Lababede et al., Chest, 115:233-235 (1999).) In some embodiments, the methods described herein can be used to characterize a lung disease in a patient with at least 75, 80, 85, 90, 91, 92, 93, 94, 95, 96, 97, 98, or 99% sensitivity. The degree of sensitivity indicates the percentage of patients with a disease who are positively characterized as having the disease. In additional embodiments, the methods have at least 75, 80, 85, 90, 91, 92, 93, 94, 95, 96, 97, 98, or 99% specificity (e.g., the percentage of non-diseased patients who are correctly characterized). The assay parameters can be adjusted to optimize for both sensitivity and specificity.

In some cases, the level of the miRNA marker will be compared to a control to determine whether the level is reduced or elevated. The control may be an external control, such as a miRNA in a serum or plasma sample from a subject known to be free of lung disease. The external control may be a sample from a normal (non-diseased) subject or from a patient with benign lung disease. In other circumstances, the external control may be a miRNA from a non-serum sample like a tissue sample or a known amount of a synthetic RNA. The external control may be a pooled, average, or individual sample; it may be the same or different miRNA as one being measured. An internal control is a marker from the same serum or plasma sample being tested, such as a miRNA control. See, e.g., US Publication No. US 2009/0075258, which is incorporated by reference in its entirety.

Table 1 lists miRNAs that have elevated or reduced levels in serum from patients with lung disease. These miRNAs may be used in accordance with the invention. Some of the miRNAs are useful for characterizing lung cancer, including distinguishing the type of cancer and/or distinguishing cancer from benign lung disease. In addition, some miRNAs may be used to predict the aggressiveness or outcome of lung cancer.

TABLE 1 miRNAs with elevated or reduced levels in serum from patients with lung cancer. Levels are of miRNA in lung cancer patients compared to patients with benign tumors or lesions.

| miRNA | Level | miRNA | Level | miRNA | Level |
|---|---|---|---|---|---|
| let-7a | reduced | miR-181a | elevated | miR-30b | reduced |
| let-7b | reduced | miR-181b | elevated | miR-30c | reduced |
| let-7c | reduced | miR-181d | elevated | miR-30d | elevated |
| let-7d | reduced | miR-185 | reduced | miR-30e-3p | reduced |
| let-7e | reduced | miR-186 | elevated | miR-30e-5p | reduced |
| let-7f | reduced | miR-18a | reduced | miR-320 | elevated |
| let-7g | reduced | miR-190 | reduced | miR-324-3p | elevated |
| let-7i | reduced | miR-191 | elevated | miR-324-5p | elevated |
| miR-100 | reduced | miR-192 | reduced | miR-328 | elevated |
| miR-101 | reduced | miR-193b | elevated | miR-335 | elevated |
| miR-103 | elevated | miR-194 | elevated | miR-339 | reduced |
| miR-106a | reduced | miR-195 | reduced | miR-340 | reduced |
| miR-106b | reduced | miR-196b | reduced | miR-342 | elevated |
| miR-10a | reduced | miR-197 | elevated | miR-345 | elevated |
| miR-10b | reduced | miR-199a* | reduced | miR-346 | reduced |
| miR-125a | elevated | miR-19a | reduced | miR-361 | elevated |
| miR-126 | reduced | miR-19b | elevated | miR-365 | elevated |
| miR-126* | reduced | miR-202 | elevated | miR-374a | reduced |
| miR-130a | reduced | miR-204 | elevated | miR-375 | elevated |
| miR-130b | elevated | miR-205 | reduced | miR-378 | elevated |
| miR-132 | elevated | miR-206 | reduced | miR-382 | elevated |
| miR-133a | elevated | miR-20a | reduced | miR-422a | elevated |
| miR-133b | reduced | miR-20b | elevated | miR-423 | elevated |
| miR-134 | elevated | miR-21 | reduced | miR-432 | reduced |
| miR-139 | reduced | miR-210 | elevated | miR-433 | elevated |
| miR-140 | reduced | miR-214 | reduced | miR-483 | elevated |
| miR-142-3p | reduced | miR-22 | elevated | miR-485-3p | reduced |
| miR-142-5p | reduced | miR-221 | elevated | miR-486-5p | elevated |
| miR-143 | reduced | miR-222 | elevated | miR-496 | reduced |
| miR-145 | elevated | miR-223 | elevated | miR-497 | reduced |
| miR-146a | elevated | miR-23a | elevated | miR-501 | elevated |
| miR-146b | reduced | miR-24 | elevated | miR-502 | elevated |
| miR-148a | reduced | miR-25 | elevated | miR-505 | elevated |
| miR-150 | elevated | miR-26a | reduced | miR-518b | elevated |
| miR-151 | elevated | miR-26b | reduced | miR-525 | reduced |
| miR-152 | reduced | miR-27a | reduced | miR-566 | elevated |
| miR-155 | elevated | miR-27b | reduced | miR-584 | elevated |
| miR-15a | reduced | miR-296 | reduced | miR-605 | elevated |
| miR-15b | reduced | miR-29a | reduced | miR-638 | reduced |
| miR-16 | reduced | miR-29c | reduced | miR-660 | reduced |
| miR-17-5p | elevated | miR-301 | elevated | miR-92 | elevated |
| | | miR-30a-5p | elevated | miR-93 | elevated |
| | | miR-98 | reduced | miR-99a | elevated |

In certain embodiments, one serum miRNA is used to detect, diagnose, characterize, or monitor lung disease and/or lung cancer. In other embodiments, more than one miRNA is used as a marker. In additional embodiments, two or more miRNAs are used to characterize lung disease. In certain embodiments, at least 2, 3, 4, 5, 6, 7, 8, 9, or 10 miRNAs are detected in the methods of the invention. In certain methods, miRNAs that have reduced levels in serum or plasma from patients with lung disease are used as biomarkers. In other embodiments, a miRNA with elevated levels in serum or plasma can be used as a biomarker. In certain embodiments, the patient has a lung tumor or lesion. In additional embodiments, the patient has previously been screened for lung disease.

In some embodiments, a miRNA for diagnosing lung cancer is chosen from miR-375, miR-499, miR-22, miR-122a, miR-206, miR-103, miR-24, miR-26a, miR-498, miR-205, miR-222, and let-7c.

In certain embodiments, a miRNA is chosen from let-7a, let-7b, let-7c, let-7d, let-7e, let-7f, let-7g, miR-106a, miR-106b, miR-125a, miR-126, miR-130b, miR-132, miR-133a, miR-133b, miR-140, miR-142-3p, miR-143, miR-146a, miR-150, miR-151, miR-155, miR-15a, miR-15b, miR-16, miR-181a, miR-181b, miR-181d, miR-186, miR-18a, miR-190, miR-191, miR-195, miR-197, miR-19b, miR-202, miR-206, miR-20a, miR-210, miR-214, miR-22, miR-221, miR-222, miR-223, miR-23a, miR-24, miR-25, miR-26a, miR-26b, miR-27b, miR-30a-5p, miR-30b, miR-30c, miR-30d, miR-30e-3p, miR-320, miR-324-3p, miR-324-5p, miR-335, miR-342, miR-345, miR-346, miR-361, miR-365, miR-374, miR-378, miR-382, miR-422a, miR-432, miR-485-3p, miR-486, miR-496, miR-502, miR-584, miR-638, miR-660, miR-92, and miR-93.

In additional embodiments, a miRNA is chosen from let-7f, let-7g, let-7i, miR-106b, miR-126, miR-126*, miR-140, miR-142-3p, miR-142-5p, miR-143, miR-145, miR-150, miR-15a, miR-15b, miR-181a, miR-181b, miR-181d, miR-202, miR-214, miR-27a, miR-27b, miR-30e-5p, miR-320, miR-324-3p, miR-340, miR-342, miR-345, miR-374, miR-378, miR-422a, miR-486, miR-518b, and miR-92.

In other embodiments, at least one miRNA is chosen from let-7b, let-7c, let-7d, let-7e, miR-10a, miR-10b, miR-130b, miR-132, miR-133b, miR-139, miR-143, miR-152, miR-155, miR-15b, miR-17-5p, miR-193, miR-194, miR-195, miR-196b, miR-199a*, miR-19b, miR-202, miR-204, miR-205, miR-206, miR-20b, miR-21, miR-210, miR-214, miR-221, miR-27a, miR-27b, miR-296, miR-29a, miR-301, miR-324-3p, miR-324-5p, miR-339, miR-346, miR-365, miR-378, miR-422a, miR-432, miR-485-3p, miR-496, miR-497, miR-505, miR-518b, miR-525, miR-566, miR-605, miR-638, miR-660, and miR-93.

In additional embodiments, a miRNA is chosen from miR-106a, miR-106b, miR-126*, miR-142-3p, miR-15b, miR-181c, miR-182, miR-26b, miR-30b, miR-30e-5p, miR-422b, let-7i, and let-7g.

In further embodiments, a miRNA is chosen from miR-24, miR-92, miR-142-3p, miR-142-5p, miR-181d, miR-27a, miR-27b, miR-422a, miR-29b, miR-15a, miR-106b, miR-126, miR-140, and miR-202. In some embodiments, 2, 3, 4, 5, 6, 7, or 8 of these miRs can be used to distinguish patients with lung cancer from patients with benign lung tumors or lesions. In additional embodiments, 2, 3, 4, 5, 6, 7, or 8 miRNAs are chosen from miR-24, miR-92, miR-142-3p, miR-142-5p, miR-181d, miR-27a, miR-27b, and miR-422a.

In certain embodiments, a miRNA for characterizing lung cancer vs. non-cancer samples is chosen from miR-15b, miR-182, miR-15a, miR-30b, miR-26b, miR-106b, let-7g, miR-142-3p, miR-301, miR-181c, miR-126, miR-346, miR-422b, and miR-92. Non-cancer samples include samples from subjects with benign lung tumors or lesions, or from normal subjects.

Certain embodiments include a method for characterizing lung disease and/or lung cancer in a patient comprising the steps of measuring the level of a miRNA in a serum sample, wherein the miRNA is chosen from let-7b, let-7c, let-7d, let-7e, miR-10a, miR-10b, miR-130b, miR-132, miR-133b, miR-139, miR-143, miR-152, miR-155, miR-15b, miR-17-5p, miR-193, miR-194, miR-195, miR-196b, miR-199a*, miR-19b, miR-202, miR-204, miR-205, miR-206, miR-20b, miR-21, miR-210, miR-214, miR-221, miR-27a, miR-27b, miR-296, miR-29a, miR-301, miR-324-3p, miR-324-5p, miR-339, miR-346, miR-365, miR-378, miR-422a, miR-432, miR-485-3p, miR-496, miR-497, miR-505, miR-518b, miR-525, miR-566, miR-605, miR-638, miR-660, and miR- 93; and determining reduced or elevated levels of the miRNA in the sample, thereby characterizing lung disease or lung cancer.

Table 2 lists miRNAs that have elevated or reduced levels in plasma from patients with lung disease. These miRNAs may be used in accordance with the invention.

TABLE 2 miRNAs with elevated or reduced levels in plasma from patients with lung disease. Levels are of miRNA in lung cancer patients compared to patients without lung cancer.

| miRNA | Level | miRNA | Level |
|---|---|---|---|
| let-7c | elevated | let-7a | reduced |
| miR-100 | elevated | let-7d | reduced |
| miR-10a | elevated | let-7e | reduced |
| miR-10b | elevated | let-7g | reduced |
| miR-122a | elevated | let-7i | reduced |
| miR-125b | elevated | miR-1 | reduced |
| miR-129 | elevated | miR-103 | reduced |
| miR-148a | elevated | miR-106a | reduced |
| miR-150 | elevated | miR-125a | reduced |
| miR-17-5p | elevated | miR-130a | reduced |
| miR-183 | elevated | miR-130b | reduced |
| miR-18a* | elevated | miR-133a | reduced |
| miR-18b | elevated | miR-145 | reduced |
| miR-190 | elevated | miR-148b | reduced |
| miR-192 | elevated | miR-15a | reduced |
| miR-193a | elevated | miR-15b | reduced |
| miR-196b | elevated | miR-17-3p | reduced |
| miR-197 | elevated | miR-181d | reduced |
| miR-19a | elevated | miR-18a | reduced |
| miR-19b | elevated | miR-196a | reduced |
| miR-200c | elevated | miR-198 | reduced |
| miR-203 | elevated | miR-199a | reduced |
| miR-206 | elevated | miR-199a* | reduced |
| miR-20b | elevated | miR-212 | reduced |
| miR-210 | elevated | miR-22 | reduced |
| miR-214 | elevated | miR-221 | reduced |
| miR-218 | elevated | miR-23a | reduced |
| miR-296 | elevated | miR-23b | reduced |
| miR-30a-3p | elevated | miR-26a | reduced |
| miR-31 | elevated | miR-27a | reduced |
| miR-346 | elevated | miR-27b | reduced |
| miR-34c | elevated | miR-29b | reduced |
| miR-375 | elevated | miR-30b | reduced |
| miR-383 | elevated | miR-30d | reduced |
| miR-422a | elevated | miR-30e-3p | reduced |
| miR-429 | elevated | miR-320 | reduced |
| miR-448 | elevated | miR-323 | reduced |
| miR-449 | elevated | miR-326 | reduced |
| miR-452 | elevated | miR-331 | reduced |
| miR-483 | elevated | miR-335 | reduced |
| miR-486 | elevated | miR-339 | reduced |
| miR-489 | elevated | miR-374 | reduced |
| miR-497 | elevated | miR-377 | reduced |
| miR-500 | elevated | miR-379 | reduced |
| miR-501 | elevated | miR-410 | reduced |
| miR-507 | elevated | miR-423 | reduced |
| miR-511 | elevated | miR-433 | reduced |
| miR-514 | elevated | miR-485-3p | reduced |
| miR-516-3p | elevated | miR-485-5p | reduced |
| miR-520d | elevated | miR-487b | reduced |
| miR-527 | elevated | miR-490 | reduced |
| miR-7 | elevated | miR-491 | reduced |
| miR-92 | elevated | miR-493 | reduced |
| miR-93 | elevated | miR-493-3p | reduced |
| miR-99a | elevated | miR-494 | reduced |
|  |  | miR-496 | reduced |
|  |  | miR-502 | reduced |
|  |  | miR-505 | reduced |
|  |  | miR-519d | reduced |
|  |  | miR-539 | reduced |
|  |  | miR-542-3p | reduced |
|  |  | miR-98 | reduced |

In some embodiments, a single plasma miRNA may be used to characterize lung cancer. In other embodiments, one of the miRNAs from Table 2 may be used to characterize lung cancer, either alone or in combination with one or more additional miRNA markers.

In certain embodiments, the methods distinguish lung cancer from benign lung disease. In some circumstances, at least one measured miRNA is elevated in the serum or plasma of lung cancer patients compared to patients with benign conditions or no disease. In some circumstances, at least one measured miRNA is reduced. In certain embodiments at least one measured miRNA is elevated and at least one miRNA is reduced. In other embodiments at least two elevated miRNAs or at least two reduced miRNAs are measured.

In certain embodiments, one of the following miRNAs is used in combination with at least one other miRNA biomarker to determine whether a patient has lung cancer: let-7a, let-7b, let-7d, let-7f, let-7g, let-7i, miR-101, miR-106a, miR-106b, miR-125a, miR-126, miR-126*, miR-130b, miR-132, miR-133b, miR-140, miR-142-3p, miR-142-5p, miR-145, miR-146a, miR-146b, miR-148b, miR-150, miR-151, miR-15a, miR-15b, miR-181a, miR-181b, miR-181d, miR-185, miR-186, miR-190, miR-191, miR-193a, miR-199a*, miR-202, miR-210, miR-214, miR-222, miR-23a, miR-24, miR-26a, miR-26b, miR-27a, miR-27b, miR-29b, miR-301, miR-30a-5p, miR-30b, miR-30c, miR-30d, miR-30e-5p, miR-320, miR-324-3p, miR-326, miR-335, miR-340, miR-342, miR-345, miR-346, miR-34a, miR-374, miR-375, miR-378, miR-422a, miR-422b, miR-425, miR-486, miR-496, miR-518b, miR-660, miR-7, miR-92, miR-93, miR-98, miR-99a, or miR-99b.

In other embodiments, one of the following miRNAs is used in combination with at least one other miRNA biomarker to determine whether a patient has lung cancer or to distinguish lung cancer from benign lung disease: miR-422a; miR-29b; miR-92; miR-142-5p; miR-142-3p; miR-181d; miR-27b; miR-378; miR-27a; miR-30e-5p; miR-181a, miR-126; miR-342; miR-140; miR-15a; miR-324-3p; miR-374; miR-486; miR-518b; miR-106b; miR-145; miR-150; miR-191; miR-345; miR-126*; miR-148b; miR-214; miR-320; let-7g; let-7i; miR-146a; miR-15b; miR-185; miR-186; miR-23a; miR-24; miR-30a-5p; miR-340; miR-34a; miR-101; miR-132; miR-181b; miR-199a*; miR-202; miR-222; miR-422b; miR-660; miR-7; or miR-93.

In other embodiments, one of the following miRNAs is used in combination with at least one other miRNA biomarker to determine whether a patient has lung cancer: let-7g, miR-106b, miR-126, miR-126*, miR-132, miR-140, miR-142-3p, miR-146a, miR-150, miR-15a, miR-15b, miR-181a, miR-181b, miR-181d, miR-214, miR-24, miR-30a-5p, miR-320, miR-342, miR-345, miR-374, miR-422a, miR-422b, miR-486, or miR-92.

Some embodiments of the invention relate to amplifying and measuring at least a pair of miRNAs from serum. Table 3 includes pairs that may be used to characterize lung disease. These pairs may be used in combination with other lung disease biomarkers.

TABLE 3 miRNA pairs measured in serum samples.

miRNA pairs

| | | |
|---|---|---|
| miR-202,miR-29b | miR-324-5p,miR-422a | miR-101,miR-92 |
| miR-142-5p,miR-422a | miR-374,miR-422a | miR-126,miR-92 |
| miR-24,miR-27a | miR-140,miR-345 | miR-126*,miR-422a |
| miR-27b,miR-422a | miR-23a,miR-27a | miR-126*,miR-92 |
| miR-140,miR-422a | miR-29b,miR-378 | miR-150,miR-29a |
| miR-185,miR-93 | miR-30e-5p,miR-422a | miR-15a,miR-92 |
| miR-126,miR-181d | miR-30e-5p,miR-92 | miR-30e-5p,miR-324-3p |

TABLE 3-continued miRNA pairs measured in serum samples.

miRNA pairs

| | | |
|---|---|---|
| miR-142-3p,miR-422a | miR-660,miR-92 | miR-126,miR-378 |
| miR-30e-5p,miR-345 | miR-106b,miR-422a | miR-126,miR-422a |
| miR-29b,miR-422a | let-7g,miR-422a | miR-132,miR-29b |
| miR-26a,miR-422a | miR-148b,miR-92 | miR-142-3p,miR-181a |
| miR-15a,miR-422a | miR-181b,miR-29b | miR-142-3p,miR-378 |
| miR-146a,miR-27b | let-7f,miR-422a | miR-29b,miR-518b |
| miR-148b,miR-422a | miR-181a,miR-27b | miR-142-5p,miR-181d |
| let-7i,miR-422a | miR-29b,miR-324-3p | miR-193b,miR-29b |
| miR-340,miR-422a | miR-132,miR-30e-5p | miR-146a,miR-422a |
| miR-143,miR-150 | miR-214,miR-422b | miR-15b,miR-92 |
| miR-15a,miR-378 | miR-140,miR-378 | miR-142-5p,miR-23a |
| miR-15b,miR-422a | miR-29b,miR-30a-5p | miR-27a,miR-378 |
| miR-27b,miR-92 | let-7a,miR-422a | miR-197,miR-29b |
| miR-30e-3p,miR-422a | miR-142-5p,miR-191 | miR-342,miR-374 |
| miR-30b,miR-422a | miR-24,miR-27b | miR-422a,miR-487b |
| miR-142-3p,miR-92 | miR-126*,miR-181d | miR-142-3p,miR-99b |
| miR-27a,miR-422a | miR-181d,miR-30e-5p | miR-29b,miR-320 |
| miR-142-5p,miR-342 | miR-142-3p,miR-191 | miR-340,miR-378 |
| miR-142-5p,miR-223 | miR-181c,miR-29b | miR-29b,miR-486 |
| miR-27b,miR-378 | miR-181d,miR-27a | miR-23a,miR-422a |
| miR-186,miR-27a | miR-148b,miR-378 | miR-222,miR-27b |
| miR-106b,miR-324-3p | miR-15a,miR-320 | miR-142-5p,miR-24 |
| miR-34a,miR-518b | miR-199a*,miR-422a | miR-148b,miR-181d |
| miR-27a,miR-92 | miR-146a,miR-27a | miR-29b,miR-342 |
| miR-30a-3p,miR-422a | miR-142-5p,miR-181a | miR-152,miR-422a |
| miR-181d,miR-29b | miR-15a,miR-486 | miR-7,miR-92 |
| miR-15b,miR-191 | miR-27b,miR-342 | miR-210,miR-422a |
| miR-192,miR-422a | miR-181a,miR-27a | let-7c,miR-422a |
| miR-422a,miR-576 | let-7g,miR-342 | miR-27b,miR-518b |
| miR-30c,miR-422a | miR-29b,miR-345 | miR-145,miR-374 |
| miR-142-3p,miR-145 | let-7e,miR-422a | miR-27a,miR-324-3p |
| miR-142-3p,miR-181d | miR-29b,miR-422b | miR-140,miR-186 |
| miR-181d,miR-27b | miR-142-3p,miR-202 | miR-185,miR-486 |
| miR-142-5p,miR-186 | miR-214,miR-422a | miR-422a,miR-496 |
| miR-150,miR-29c | miR-142-5p,miR-145 | miR-181a,miR-199a* |
| miR-200c,miR-422a | miR-422a,miR-497 | miR-422a,miR-432 |
| miR-185,miR-92 | miR-29b,miR-433 | miR-181d,miR-23b |
| miR-148a,miR-422a | miR-140,miR-92 | miR-125b,miR-422a |
| miR-34a,miR-422a | miR-142-5p,miR-92 | miR-145,miR-29b |
| miR-32,miR-422a | miR-142-3p,miR-181b | miR-142-5p,miR-146a |
| miR-214,miR-566 | miR-30e-5p,miR-486 | miR-126,miR-320 |
| miR-206,miR-422a | miR-196b,miR-422a | miR-191,miR-374 |
| miR-214,miR-518b | miR-222,miR-29b | miR-126,miR-145 |
| miR-142-3p,miR-320 | miR-142-3p,miR-518b | miR-150,miR-29b |
| miR-331,miR-422a | miR-29b,miR-30d | miR-133b,miR-422a |
| miR-26b,miR-422a | miR-29b,miR-361 | miR-142-5p,miR-324-3p |
| miR-142-5p,miR-345 | miR-342,miR-34a | miR-27b,miR-345 |
| miR-27b,miR-324-3p | miR-106b,miR-181d | miR-374,miR-378 |
| miR-30a-5p,miR-30e-5p | miR-340,miR-92 | let-7b,miR-422a |
| miR-29b,miR-92 | miR-486,miR-7 | miR-346,miR-432* |
| miR-191,miR-27a | miR-21,miR-422a | miR-142-5p,miR-518b |
| miR-140,miR-181d | miR-106b,miR-92 | miR-142-3p,miR-328 |
| miR-422a,miR-660 | let-7i,miR-92 | miR-181a,miR-374 |
| miR-126,miR-181a | miR-101,miR-486 | let-7g,miR-181d |
| miR-126*,miR-378 | miR-181a,miR-29b | miR-106b,miR-378 |
| miR-15a,miR-181d | miR-142-5p,miR-150 | miR-30a-5p,miR-422a |
| miR-224,miR-422a | miR-142-3p,miR-342 | miR-339,miR-422a |
| miR-346,miR-92 | miR-142-5p,miR-93 | let-7i,miR-378 |
| miR-146a,miR-374 | miR-181a,miR-346 | miR-146b,miR-374 |
| miR-181d,miR-346 | miR-15a,miR-425 | miR-181b,miR-346 |
| let-7f,miR-146a | let-7g,miR-146a | let-7d,miR-92 |
| miR-106a,miR-15b | let-7a,miR-92 | miR-146a,miR-15b |
| miR-106a,miR-422b | miR-126*,miR-26b | miR-106a,miR-26b |
| miR-15b,miR-30a-5p | let-7i,miR-26b | let-7g,miR-106a |
| miR-126*,miR-15b | miR-126*,miR-30b | miR-106a,miR-106b |
| miR-126*,miR-30 | miR-126,miR-15b | miR-126*,miR-15a |
| miR-15b,miR-27b | miR-106b,miR-30a-5p | miR-15b,miR-30d |
| miR-15b,miR-27a | | |
| miR-15a,miR-30a-5p | miR-15a,miR-27b | miR-15b,miR-30b |
| miR-126,miR-15a | miR-15a,miR-30d | miR-15b,miR-26b |
| miR-106b,miR-30d | miR-106b,miR-126* | miR-15a,miR-422a |
| miR-106a,miR-30a-5p | miR-106a,miR-30d | miR-15b,miR-301 |
| miR-26b,miR-27b | miR-182,miR-27b | miR-106b,miR-27b |

In certain embodiments, the pair of miRNAs is chosen from miR-202 and miR-29b; miR-142-5p and miR-422a; miR-24 and miR-27a; miR-27b and miR-422a; miR-140 and miR-422a; miR-185 and miR-93; miR-126 and miR-181d; miR-142-3p and miR-422a; miR-30e-5p and miR-345; miR-29b and miR-422a; miR-324-5p and miR-422a; miR-374 and miR-422a; miR-140 and miR-345; miR-23a and miR-27a; miR-29b and miR-378; miR-30e-5p and miR-422a; miR-30e-5p and miR-92; miR-660 and miR-92; miR-106b and miR-422a; let-7g and miR-422a; miR-101 and miR-92; miR-126 and miR-92; miR-126* and miR-422a; miR-126* and miR-92; miR-150 and miR-29a; miR-15a and miR-92; miR-30e-5p and miR-324-3p; miR-126 and miR-378; miR-126 and miR-422a; miR-132 and miR-29b; miR-142-3p and miR-181a; miR-142-3p and miR-378; miR-148b and miR-92; miR-181b and miR-29b; miR-26a and miR-422a; miR-15a and miR-422a; miR-146a and miR-27b; miR-148b and miR-422a; let-7i and miR-422a; miR-340 and miR-422a; miR-143 and miR-150; miR-15a and miR-378; miR-15b and miR-422a; miR-27b and miR-92; miR-30e-3p and miR-422a; miR-30b and miR-422a; miR-142-3p and miR-92; miR-27a and miR-422a; miR-142-5p and miR-342; miR-142-5p and miR-223; miR-27b and miR-378; miR-186 and miR-27a; miR-106b and miR-324-3p; miR-34a and miR-518b; miR-27a and miR-92; miR-30a-3p and miR-422a; miR-181d and miR-29b; miR-15b and miR-191; miR-192 and miR-422a; miR-422a and miR-576; miR-30c and miR-422a; miR-142-3p and miR-145; miR-142-3p and miR-181d; miR-181d and miR-27b; miR-142-5p and miR-186; miR-150 and miR-29c; miR-200c and miR-422a; miR-185 and miR-92; miR-148a and miR-422a; miR-34a and miR-422a; miR-32 and miR-422a; miR-214 and miR-566; miR-206 and miR-422a; miR-214 and miR-518b; miR-142-3p and miR-320; miR-331 and miR-422a; miR-26b and miR-422a; miR-142-5p and miR-345; miR-27b and miR-324-3p; miR-30a-5p and miR-30e-5p; miR-29b and miR-92; miR-191 and miR-27a; miR-140 and miR-181d; miR-422a and miR-660; miR-126 and miR-181a; miR-126* and miR-378; miR-15a and miR-181d; let-7f and miR-422a; miR-181a and miR-27b; miR-29b and miR-324-3p; miR-132 and miR-30e-5p; miR-214 and miR-422b; miR-140 and miR-378; miR-29b and miR-30a-5p; let-7a and miR-422a; miR-142-5p and miR-191; miR-24 and miR-27b; miR-126* and miR-181d; miR-181d and miR-30e-5p; miR-142-3p and miR-191; miR-181c and miR-29b; miR-181d and miR-27a; miR-148b and miR-378; miR-15a and miR-320; miR-199a* and miR-422a; miR-146a and miR-27a; miR-142-5p and miR-181a; miR-15a and miR-486; miR-27b and miR-342; miR-181a and miR-27a; let-7g and miR-342; miR-29b and miR-345; let-7e and miR-422a; miR-29b and miR-422b; miR-142-3p and miR-202; miR-214 and miR-422a; miR-142-5p and miR-145; miR-422a and miR-497; miR-29b and miR-433; miR-140 and miR-92; miR-142-5p and miR-92; miR-142-3p and miR-181b; miR-30e-5p and miR-486; miR-196b and miR-422a; miR-222 and miR-29b; miR-142-3p and miR-518b; miR-29b and miR-30d; miR-29b and miR-361; miR-342 and miR-34a; miR-106b and miR-181d; miR-340 and miR-92; miR-486 and miR-7; miR-21 and miR-422a; miR-106b and miR-92; let-7i and miR-92; miR-101 and miR-486; miR-181a and miR-29b; miR-142-5p and miR-150; miR-142-3p and miR-342; miR-29b and miR-518b; miR-142-5p and miR-181d; miR-193b and miR-29b; miR-146b and miR-422a; miR-15b and miR-92; miR-142-5p and miR-23a; miR-27a and miR-378; miR-197 and miR-29b; miR-342 and miR-374; miR-422a and miR-487b; miR-142-3p and miR-99b; miR-29b and miR-320; miR-340 and miR-378; miR-29b and miR-486; miR-23a and miR-422a; miR-222 and miR-27b; miR-142-5p and miR-24; miR-148b and miR-181d; miR-29b and miR-342; miR-152 and miR-422a; miR-7 and miR-92; miR-210 and miR-422a; let-7c and miR-422a; miR-27b and miR-518b; miR-145 and miR-374; miR-27a and miR-324-3p; miR-140 and miR-186; miR-185 and miR-486; miR-422a and miR-496; miR-181a and miR-199a*; miR-422a and miR-432; miR-181d and miR-23b; miR-125b and miR-422a; miR-145 and miR-29b; miR-142-5p and miR-146a; miR-126 and miR-320; miR-191 and miR-374; miR-126 and miR-145; miR-150 and miR-29b; miR-133b and miR-422a; miR-142-5p and miR-324-3p; miR-27b and miR-345; miR-374 and miR-378; let-7b and miR-422a; miR-346 and miR-432*; miR-142-5p and miR-518b; miR-142-3p and miR-328; miR-181a and miR-374; let-7g and miR-181d; miR-106b and miR-378; miR-30a-5p and miR-422a; miR-339 and miR-422a; let-7i and miR-378; miR-142-5p and miR-93; and miR-224 and miR-422a.

In certain embodiments, the pair of miRNAs is chosen from let-7a and miR-181a; let-7a and miR-181d; let-7b and miR-150; let-7b and miR-181d; let-7b and miR-92; let-7c and miR-150; let-7c and miR-181d; let-7c and miR-92; let-7e and miR-378; let-7f and miR-181a; let-7f and miR-181d; let-7f and miR-342; let-7f and miR-92; let-7g and miR-150; let-7g and miR-181a; let-7g and miR-181d; let-7g and miR-342; let-7g and miR-92; let-7i and miR-486; let-7i and miR-92; miR-106b and miR-150; miR-106b and miR-181d; miR-106b and miR-92; miR-125a and miR-142-3p; miR-125a and miR-374; miR-126* and miR-181d; miR-126* and miR-30a-5p; miR-126* and miR-92; miR-126 and miR-146a; miR-126 and miR-150; miR-126 and miR-181a, miR-126 and miR-181d; miR-126 and miR-342; miR-126 and miR-92; miR-130b and miR-142-3p; miR-132 and miR-142-3p; miR-132 and miR-214; miR-140 and miR-150; miR-140 and miR-30a-5p; miR-140 and miR-345; miR-140 and miR-92; miR-142-3p and miR-146a; miR-142-3p and miR-150; miR-142-3p and miR-151; miR-142-3p and miR-181a; miR-142-3p and miR-181b; miR-142-3p and miR-181d; miR-142-3p and miR-186; miR-142-3p and miR-210; miR-142-3p and miR-22; miR-142-3p and miR-23a; miR-142-3p and miR-24; miR-142-3p and miR-30a-5p; miR-142-3p and miR-342; miR-142-3p and miR-345; miR-142-3p and miR-425; miR-142-3p and miR-486; miR-142-3p and miR-92; miR-142-3p and miR-99b; miR-142-5p and miR-30a-5p; miR-143 and miR-223; miR-143 and miR-486; miR-150 and miR-15b; miR-150 and miR-214; miR-150 and miR-29b; miR-150 and miR-374; miR-150 and miR-576; miR-15a and miR-181a; miR-15a and miR-181b; miR-15a and miR-181d; miR-15a and miR-210; miR-15a and miR-30a-5p; miR-15a and miR-342; miR-15a and miR-345; miR-15a and miR-486; miR-15a and miR-92; miR-15b and miR-17-5p; miR-15b and miR-181a; miR-15b and miR-181d; miR-15b and miR-24; miR-15b and miR-342; miR-15b and miR-92; miR-16 and miR-486; miR-16 and miR-92; miR-181a and miR-214; miR-181a and miR-26a; miR-181a and miR-26b; miR-181a and miR-30b; miR-181a and miR-30c; miR-181a and miR-374; miR-181a and miR-98; miR-181b and miR-214; miR-181b and miR-374; miR-181d and miR-214; miR-181d and miR-26b; miR-181d and miR-30b; miR-181d and miR-30c; miR-181d and miR-374; miR-181d and miR-432; miR-181d and miR-496; miR-181d and miR-638; miR-181d and miR-98; miR-193a and miR-422a; miR-195 and miR-486; miR-199a* and miR-92; miR-20a and miR-92; miR-214 and miR-342; miR-214 and miR-422b; miR-214 and miR-92; miR-24 and miR-374; miR-26a and miR-342; miR-26b and miR-342; miR-26b and miR-92; miR-27a and miR-30a-5p; miR-27b and miR-30d; miR-29b and miR-30a-5p; miR-30b and miR-342; miR-30b and miR-92; miR-30c and miR-342; miR-30c and miR-92; miR-320 and miR-98; miR-342 and miR-374; miR-346 and miR-422a; miR-346 and miR-518b; miR-346 and miR-566; miR-374 and miR-92; miR-422a and miR-496; miR-422a and miR-638; miR-422a and miR-98; miR-432 and miR-92; miR-496 and miR-92; and miR-7 and miR-92.

In other embodiments, the pair of miRNAs is chosen from miR-142-5p and miR181d; miR-142-3p and miR181d; miR-142-3p and miR-422a; miR-142-5p and miR-422a; miR-92 and miR-27b; and miR-24 and miR-27a. In additional embodiments, the pair of miRNAs is chosen from miR-106a and miR-422b; miR-126* and miR-26b; miR-106a and miR-26b; miR-15b and miR-30a-5p; let-7a and miR-26b; let-7g and miR-106a; miR-126* and miR-15b; miR-126* and miR-30b; and miR-106a and miR-106b.

In some embodiments, the pair is measured in a serum sample. Optionally, one or more additional miRNAs are measured.

In additional embodiments, certain miRNA pairs may be used to characterize lung disease in female or male patients (Table 4). In certain embodiments, the methods detect sex-specific miRNA biomarkers.

TABLE 4 miRNA pairs for characterizing lung disease in female or male patients

| miRNA Biomarker Pair (Females) | miRNA Biomarker Pair (Males) |
| --- | --- |
| miR-15a,miR-422a | miR-185,miR-93 |
| miR-181d,miR-27b | miR-30e-5p,miR-433 |
| miR-27b,miR-422a | miR-126,miR-378 |
| miR-15b,miR-191 | miR-342,miR-497 |
| miR-181d,miR-29b | let-7f,miR-342 |
| miR-142-3p,miR-422a | miR-142-5p,miR-422a |
| miR-23a,miR-27a | miR-145,miR-200c |
| miR-222,miR-27a | miR-148a,miR-19b |
| miR-126,miR-422a | miR-191,miR-340 |
| miR-142-5p,miR-145 | miR-200b,miR-422a |
| miR-142-3p,miR-145 | miR-340,miR-378 |
| miR-143,miR-223 | |
| miR-324-5p,miR-422a | |
| miR-30e-5p,miR-422a | |
| miR-27a,miR-422a | |
| miR-126*,miR-222 | |
| miR-140,miR-422a | |
| miR-101,miR-92 | |
| miR-202,miR-29b | |
| miR-29b,miR-422a | |
| miR-30e-5p,miR-324-3p | |
| miR-181b,miR-29b | |
| miR-142-5p,miR-181a | |
| miR-126*,miR-422a | |
| miR-195,miR-93 | |
| miR-140,miR-222 | |
| miR-126,miR-181d | |
| miR-142-5p,miR-422a | |
| miR-24,miR-27a | |
| miR-27a,miR-361 | |
| miR-346,miR-518b | |
| miR-222,miR-27b | |
| miR-15b,miR-181a | |
| miR-142-5p,miR-191 | |
| miR-433,miR-487b | |
| miR-29b,miR-518b | |
| miR-106b,miR-422a | |
| miR-21,miR-422a | |
| miR-15b,miR-422a | |
| miR-181a,miR-27a | |
| miR-142-5p,miR-345 | |
| miR-32,miR-422a | |
| miR-30e-5p,miR-92 | |
| miR-148b,miR-422a | |
| miR-192,miR-422a | |
| let-7i,miR-422a | |

TABLE 4-continued miRNA pairs for characterizing lung disease in female or male patients

| miRNA Biomarker Pair (Females) | miRNA Biomarker Pair (Males) |
|---|---|
| miR-19b,miR-486 | |
| miR-15a,miR-181d | |
| miR-142-3p,miR-26a | |
| miR-142-3p,miR-181a | |
| miR-29b,miR-378 | |
| miR-15a,miR-181b | |
| miR-142-3p,miR-342 | |
| miR-195,miR-20b | |
| miR-145,miR-27a | |
| miR-374,miR-422a | |
| miR-27b,miR-361 | |
| miR-142-3p,miR-518b | |
| miR-140,miR-181d | |
| miR-27b,miR-326 | |
| miR-139,miR-422a | |
| let-7g,miR-422a | |
| miR-140,miR-345 | |
| miR-148b,miR-326 | |
| miR-20a,miR-92 | |
| miR-133b,miR-181b | |
| miR-132,miR-30e-5p | |
| miR-19b,miR-92 | |
| miR-181a,miR-30c | |
| miR-197,miR-422a | |
| miR-142-5p,miR-222 | |
| miR-148a,miR-422a | |
| let-7g,miR-181d | |
| miR-197,miR-29b | |
| miR-331,miR-422a | |
| miR-15a,miR-181a | |
| miR-339,miR-422a | |
| miR-181b,miR-215 | |
| miR-145,miR-374 | |
| miR-206,miR-518b | |
| miR-106b,miR-486 | |
| miR-126*,miR-181a | |
| miR-422a,miR-576 | |
| miR-17-5p,miR-422a | |
| miR-106b,miR-345 | |
| miR-126,miR-342 | |
| miR-139,miR-181d | |
| miR-140,miR-30a-5p | |
| miR-142-3p,miR-26b | |
| miR-142-3p,miR-361 | |
| miR-19a,miR-92 | |
| miR-222,miR-422a | |
| miR-296,miR-422a | |
| miR-29b,miR-382 | |

Some embodiments of the invention relate to amplifying and measuring two or more miRNAs from plasma. One of the following miRNA plasma biomarkers may be used in combination with at least one other miRNA: miR-10b, miR-192, miR-206, miR-101, miR-205, miR-16, miR-151, miR-137, miR-215, miR-181a, miR-218, miR-126*, miR-125b, miR-326, miR-100, miR-31, miR-197, miR-222, miR-191, miR-200c, miR-186, miR-145, miR-155, miR-29c, let-7c, miR-181c, miR-125a, miR-134, miR-181d, let-7b, miR-127, miR-146a, miR-139, miR-152, miR-190, miR-30e-5p, miR-106b, miR-10a, miR-132, miR-148a, miR-213, miR-29a, miR-375, miR-133b, miR-15a, miR-107, miR-148b, miR-19a, miR-106a, miR-130a, miR-17-3p, miR-18a*, miR-195, miR-20b, miR-301, miR-339, miR-410, miR-188, miR-193a, let-7g, let-7i, miR-140, miR-181b, miR-25, miR-328, miR-133a, miR-150, miR-17-5p, miR-21, miR-214, miR-370, miR-383, miR-130b, miR-199a, miR-212, miR-221, miR-27b, miR-30e-3p, miR-338, miR-361, miR-141, miR-142-5p, miR-30a-3p, miR-30a-5p, miR-451, miR-142-3p, miR-146b, miR-15b, miR-18a, miR-210, miR-296, miR-323, miR-362, let-7a, miR-196b, miR-223, miR-29b, miR-324-5p, miR-376a, miR-379, miR-491, let-7d, miR-126, miR-182, miR-185, miR-204, miR-23a, miR-27a, miR-324-3p, miR-342, miR-34c, miR-382, miR-425, miR-432*, miR-103, miR-193b, miR-196a, miR-199a*, miR-199b, miR-28, miR-30d, miR-330, miR-423, miR-433, miR-485-5p, miR-20a, miR-23b, miR-26a, miR-30b, miR-30c, miR-320, miR-345, miR-422b, miR-335, miR-365, miR-486, miR-24, miR-26b, miR-331, miR-340, miR-34a, miR-374, miR-452, miR-483, miR-512-5p, let-7e, miR-32, miR-422a, miR-424, miR-432, miR-485-3p, miR-487b, miR-496, miR-505, miR-7, miR-202, miR-369-3p, miR-495, miR-502, miR-511, miR-516-3p, miR-517c, miR-92, miR-93, miR-99a, or miR-99b.

Table 5 includes pairs of miRNAs that may be used to characterize lung cancer from plasma samples. Optionally, one or more additional miRNAs are measured.

TABLE 5 miRNA pairs measured in plasma samples miRNA pairs

| | | |
|---|---|---|
| let-7c:miR-326 | miR-330:miR-375 | miR-181a:miR-218 |
| miR-326:miR-7 | miR-134:miR-206 | miR-151:miR-218 |
| miR-206:miR-491 | miR-432*:miR-491 | miR-491:miR-512-5p |
| miR-339:miR-375 | miR-181d:miR-375 | miR-326:miR-375 |
| miR-30a-3p:miR-326 | miR-191:miR-200c | miR-200c:miR-326 |
| miR-151:miR-206 | miR-23a:miR-326 | miR-20b:miR-30b |
| miR-10b:miR-30b | miR-125b:miR-146a | miR-491:miR-516-3p |
| miR-16,miR-487b | let-7i,miR-206 | miR-192,miR-339 |
| miR-326,miR-345 | miR-200c,miR-339 | miR-192,miR-196b |
| miR-140,miR-192 | miR-16,miR-191 | miR-7,miR-99b |
| miR-383,miR-491 | miR-15a,miR-375 | miR-213,miR-31 |
| miR-339,miR-7 | miR-17-5p,miR-30b | miR-16,miR-30b |
| miR-375,miR-99b | miR-206,miR-212 | miR-137,miR-151 |
| miR-199a,miR-375 | miR-192,miR-30b | miR-218,miR-361 |
| miR-206,miR-376a | miR-148b,miR-192 | miR-190,miR-326 |
| miR-375,miR-505 | miR-16,miR-24 | miR-204,miR-375 |
| miR-200c,miR-301 | miR-206,miR-320 | miR-10b,miR-191 |
| miR-451,miR-487b | miR-326,miR-34c | miR-125b,miR-30d |
| miR-218,miR-326 | miR-191,miR-7 | miR-126*,miR-375 |
| miR-206,miR-213 | miR-218,miR-410 | miR-17-3p,miR-326 |
| miR-206,miR-422b | miR-181a,miR-206 | miR-31,miR-326 |
| miR-192,miR-326 | miR-206,miR-370 | miR-151,miR-31 |
| miR-205,miR-326 | miR-222,miR-30a-3p | miR-125b,miR-326 |
| miR-218,miR-491 | miR-326,miR-423 | miR-375,miR-433 |
| miR-206,miR-361 | miR-137,miR-491 | miR-361,miR-432* |
| miR-206,miR-410 | miR-192,miR-342 | miR-142-5p,miR-375 |
| miR-30a-3p,miR-99b | miR-206,miR-382 | miR-126*,miR-192 |
| miR-151,miR-383 | miR-375,miR-423 | miR-502,miR-512-5p |
| miR-218,miR-338 | miR-17-5p,miR-487b | miR-326,miR-451 |
| miR-212,miR-512-5p | miR-326,miR-511 | miR-192,miR-324-3p |
| miR-375,miR-496 | miR-155,miR-218 | miR-200c,miR-222 |
| | | miR-191,miR-19b |

Other miRNAs and groups of miRNAs that can be used in the methods of the invention will be apparent from the Examples described herein.

III. Methods To Measure The Level Of A Mirna

Many methods of measuring the levels or amounts of miRNAs are contemplated. Any reliable, sensitive, and specific method can be used. In some embodiments, a miRNA is amplified prior to measurement. In other embodiments, the level of miRNA is measured during the amplification process. In still other methods, the miRNA is not amplified prior to measurement.

A. Amplification Reactions

Many methods exist for amplifying miRNA nucleic acid sequences such as mature miRNAs, precursor miRNAs, and primary miRNAs. Suitable nucleic acid polymerization and amplification techniques include reverse transcription (RT), polymerase chain reaction (PCR), real-time PCR (quantitative PCR (q-PCR)), nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. In certain embodiments, more than one amplification method is used, such as reverse transcription followed by real time quantitative PCR (qRT-PCR) (Chen et al., Nucleic Acids Research, 33(20):e179 (2005)).

A typical PCR reaction includes multiple amplification steps, or cycles that selectively amplify target nucleic acid species: a denaturing step in which a target nucleic acid is denatured; an annealing step in which a set of PCR primers (forward and reverse primers) anneal to complementary DNA strands; and an elongation step in which a thermostable DNA polymerase elongates the primers. By repeating these steps multiple times, a DNA fragment is amplified to produce an amplicon, corresponding to the target DNA sequence. Typical PCR reactions include 20 or more cycles of denaturation, annealing, and elongation. In many cases, the annealing and elongation steps can be performed concurrently, in which case the cycle contains only two steps. Since mature miRNAs are single-stranded, a reverse transcription reaction (which produces a complementary cDNA sequence) may be performed prior to PCR reactions. Reverse transcription reactions include the use of, e.g., a RNA-based DNA polymerase (reverse transcriptase) and a primer.

In PCR and q-PCR methods, for example, a set of primers is used for each target sequence. In certain embodiments, the lengths of the primers depends on many factors, including, but not limited to, the desired hybridization temperature between the primers, the target nucleic acid sequence, and the complexity of the different target nucleic acid sequences to be amplified. In certain embodiments, a primer is about 15 to about 35 nucleotides in length. In other embodiments, a primer is equal to or fewer than 15, 20, 25, 30, or 35 nucleotides in length. In additional embodiments, a primer is at least 35 nucleotides in length.

In a further aspect, a forward primer can comprise at least one sequence that anneals to a miRNA biomarker and alternatively can comprise an additional 5' non-complementary region. In another aspect, a reverse primer can be designed to anneal to the complement of a reverse transcribed miRNA. The reverse primer may be independent of the miRNA biomarker sequence, and multiple miRNA biomarkers may be amplified using the same reverse primer. Alternatively, a reverse primer may be specific for a miRNA biomarker.

In some embodiments, two or more miRNAs are amplified in a single reaction volume. One aspect includes multiplex q-PCR, such as qRT-PCR, which enables simultaneous amplification and quantification of at least two miRNAs of interest in one reaction volume by using more than one pair of primers and/or more than one probe. The primer pairs comprise at least one amplification primer that uniquely binds each miRNA, and the probes are labeled such that they are distinguishable from one another, thus allowing simultaneous quantification of multiple miRNAs. Multiplex qRT-PCR has research and diagnostic uses, including but not limited to detection of miRNAs for diagnostic, prognostic, and therapeutic applications.

The qRT-PCR reaction may further be combined with the reverse transcription reaction by including both a reverse transcriptase and a DNA-based thermostable DNA polymerase. When two polymerases are used, a "hot start" approach may be used to maximize assay performance (U.S. Pat. Nos. 5,411,876 and 5,985,619). For example, the components for a reverse transcriptase reaction and a PCR reaction may be sequestered using one or more thermoactivation methods or chemical alteration to improve polymerization efficiency (U.S. Pat. Nos. 5,550,044, 5,413,924, and 6,403,341).

B. Detection of miRNAs

In certain embodiments, labels, dyes, or labeled probes and/or primers are used to detect amplified or unamplified miRNAs. The skilled artisan will recognize which detection methods are appropriate based on the sensitivity of the detection method and the abundance of the target. Depending on the sensitivity of the detection method and the abundance of the target, amplification may or may not be required prior to detection. One skilled in the art will recognize the detection methods where miRNA amplification is preferred.

A probe or primer may include Watson-Crick bases or modified bases. Modified bases include, but are not limited to, the AEGIS bases (from Eragen Biosciences), which have been described, e.g., in U.S. Pat. Nos. 5,432,272, 5,965,364, and 6,001,983. In certain aspects, bases are joined by a natural phosphodiester bond or a different chemical linkage. Different chemical linkages include, but are not limited to, a peptide bond or a Locked Nucleic Acid (LNA) linkage, which is described, e.g., in U.S. Pat. No. 7,060,809.

In a further aspect, oligonucleotide probes or primers present in an amplification reaction are suitable for monitoring the amount of amplification product produced as a function of time. In certain aspects, probes having different single stranded versus double stranded character are used to detect the nucleic acid. Probes include, but are not limited to, the 5'-exonuclease assay (e.g., TaqMan™) probes (see U.S. Pat. No. 5,538,848), stem-loop molecular beacons (see, e.g., U.S. Pat. Nos. 6,103,476 and 5,925,517), stemless or linear beacons (see, e.g., WO 9921881, U.S. Pat. Nos. 6,485,901 and 6,649,349), peptide nucleic acid (PNA) Molecular Beacons (see, e.g., U.S. Pat. Nos. 6,355,421 and 6,593,091), linear PNA beacons (see, e.g. U.S. Pat. No. 6,329,144), non-FRET probes (see, e.g., U.S. Pat. No. 6,150,097), Sunrise™/AmplifluorB™ probes (see, e.g., U.S. Pat. No. 6,548,250), stem-loop and duplex Scorpion™ probes (see, e.g., U.S. Pat. No. 6,589,743), bulge loop probes (see, e.g., U.S. Pat. No. 6,590,091), pseudo knot probes (see, e.g., U.S. Pat. No. 6,548,250), cyclicons (see, e.g., U.S. Pat. No. 6,383,752), MGB Eclipse™ probe (Epoch Biosciences), hairpin probes (see, e.g., U.S. Pat. No. 6,596,490), PNA light-up probes, antiprimer quench probes (Li et al., Clin. Chem. 53:624-633 (2006)), self-assembled nanoparticle probes, and ferrocene-modified probes described, for example, in U.S. Pat. No. 6,485,901.

In certain embodiments, one or more of the primers in an amplification reaction can include a label. In yet further embodiments, different probes or primers comprise detectable labels that are distinguishable from one another. In some embodiments a nucleic acid, such as the probe or primer, may be labeled with two or more distinguishable labels.

In some aspects, a label is attached to one or more probes and has one or more of the following properties: (i) provides a detectable signal; (ii) interacts with a second label to modify the detectable signal provided by the second label, e.g., FRET (Fluorescent Resonance Energy Transfer); (iii) stabilizes hybridization, e.g., duplex formation; and (iv) provides a member of a binding complex or affinity set, e.g., affinity, antibody-antigen, ionic complexes, hapten-ligand (e.g., biotin-avidin). In still other aspects, use of labels can be accomplished using any one of a large number of known techniques employing known labels, linkages, linking groups, reagents, reaction conditions, and analysis and purification methods.

MiRNAs can be detected by direct or indirect methods. In a direct detection method, one or more miRNAs are detected by a detectable label that is linked to a nucleic acid molecule. In such methods, the miRNAs may be labeled prior to binding to the probe. Therefore, binding is detected by screening for the labeled miRNA that is bound to the probe. The probe is optionally linked to a bead in the reaction volume.

In certain embodiments, nucleic acids are detected by direct binding with a labeled probe, and the probe is subsequently detected. In one embodiment of the invention, the nucleic acids, such as amplified miRNAs, are detected using FlexMAP Microspheres (Luminex) conjugated with probes to capture the desired nucleic acids. Some methods may involve detection with polynucleotide probes modified with fluorescent labels or branched DNA (bDNA) detection, for example.

In other embodiments, nucleic acids are detected by indirect detection methods. For example, a biotinylated probe may be combined with a streptavidin-conjugated dye to detect the bound nucleic acid. The streptavidin molecule binds a biotin label on amplified miRNA, and the bound miRNA is detected by detecting the dye molecule attached to the streptavidin molecule. In one embodiment, the streptavidin-conjugated dye molecule comprises Phycolink® Streptavidin R-Phycoerythrin (PROzyme). Other conjugated dye molecules are known to persons skilled in the art.

Labels include, but are not limited to: light-emitting, light-scattering, and light-absorbing compounds which generate or quench a detectable fluorescent, chemiluminescent, or bioluminescent signal (see, e.g., Kricka, L., Nonisotopic DNA Probe Techniques, Academic Press, San Diego (1992) and Garman A., Non-Radioactive Labeling, Academic Press (1997).). Fluorescent reporter dyes useful as labels include, but are not limited to, fluoresceins (see, e.g., U.S. Pat. Nos. 5,188,934, 6,008,379, and 6,020,481), rhodamines (see, e.g., U.S. Pat. Nos. 5,366,860, 5,847,162, 5,936,087, 6,051,719, and 6,191,278), benzophenoxazines (see, e.g., U.S. Pat. No. 6,140,500), energy-transfer fluorescent dyes, comprising pairs of donors and acceptors (see, e.g., U.S. Pat. Nos. 5,863, 727; 5,800,996; and 5,945,526), and cyanines (see, e.g., WO 9745539), lissamine, phycoerythrin, Cy2, Cy3, Cy3.5, Cy5, Cy5.5, Cy7, FluorX (Amersham), Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, Tetramethylrhodamine, and/or Texas Red, as well as any other fluorescent moiety capable of generating a detectable signal. Examples of fluorescein dyes include, but are not limited to, 6-carboxyfluorescein; 2',4',1,4,-tetrachlorofluorescein; and 2',4',5',7',1, 4-hexachlorofluorescein. In certain aspects, the fluorescent label is selected from SYBR-Green, 6-carboxyfluorescein ("FAM"), TET, ROX, VICTM, and JOE. For example, in certain embodiments, labels are different fluorophores capable of emitting light at different, spectrally-resolvable wavelengths (e.g., 4-differently colored fluorophores); certain such labeled probes are known in the art and described above, and in U.S. Pat. No. 6,140,054. A dual labeled fluorescent probe that includes a reporter fluorophore and a quencher fluorophore is used in some embodiments. It will be appreciated that pairs of fluorophores are chosen that have distinct emission spectra so that they can be easily distinguished.

In still a further aspect, labels are hybridization-stabilizing moieties which serve to enhance, stabilize, or influence hybridization of duplexes, e.g., intercalators and intercalating dyes (including, but not limited to, ethidium bromide and SYBR-Green), minor-groove binders, and cross-linking functional groups (see, e.g., Blackburn et al., eds. "DNA and RNA Structure" in Nucleic Acids in Chemistry and Biology (1996)).

In further aspects, methods relying on hybridization and/or ligation to quantify miRNAs may be used, including oligonucleotide ligation (OLA) methods and methods that allow a distinguishable probe that hybridizes to the target nucleic acid sequence to be separated from an unbound probe. As an example, HARP-like probes, as disclosed in U.S. Publication No. 2006/0078894 may be used to measure the quantity of miRNAs. In such methods, after hybridization between a probe and the targeted nucleic acid, the probe is modified to distinguish the hybridized probe from the unhybridized probe. Thereafter, the probe may be amplified and/or detected. In general, a probe inactivation region comprises a subset of nucleotides within the target hybridization region of the probe. To reduce or prevent amplification or detection of a HARP probe that is not hybridized to its target nucleic acid, and thus allow detection of the target nucleic acid, a post-hybridization probe inactivation step is carried out using an agent which is able to distinguish between a HARP probe that is hybridized to its targeted nucleic acid sequence and the corresponding unhybridized HARP probe. The agent is able to inactivate or modify the unhybridized HARP probe such that it cannot be amplified.

In an additional embodiment of the method, a probe ligation reaction may be used to quantify miRNAs. In a Multiplex Ligation-dependent Probe Amplification (MLPA) technique (Schouten et al., *Nucleic Acids Research* 30:e57 (2002)), pairs of probes which hybridize immediately adjacent to each other on the target nucleic acid are ligated to each other only in the presence of the target nucleic acid. In some aspects, MLPA probes have flanking PCR primer binding sites. MLPA probes can only be amplified if they have been ligated, thus allowing for detection and quantification of miRNA biomarkers.

IV. EXAMPLES

The following examples illustrate various embodiments of the invention and are not intended to limit the scope of the invention.

The examples described herein include the use of qRT-PCR, which includes real-time monitoring of PCR products during the exponential phase instead of by an end-point measurement. The threshold cycle ($C_t$) measurements in the examples refer to the number of cycles it takes to reach a pre-defined point in the fluorescent signal.

The examples also describe the use of Receiver Operator Characteristic (ROC) analysis. A Receiver Operator Characteristic curve is a graphical plot of the sensitivity vs. specificity for a binary classifier system as its discrimination threshold is varied. ROC analysis provides a tool to select possibly optimal models and to discard suboptimal ones independently from (and prior to specifying) the class distribution. Numerous examples of ROC analysis are present in the literature, including applications in selecting and applying biomarkers for the diagnosis of disease (Pepe et al., *Biometrics* 62:221-229 (2006); Dodd et al., *Biometrics* 59:614-623

(2003)). ROC analysis captures the continuum of sensitivity and specificity, but it can be summarized as a single quantity, i.e., the area under the curve (AUC) of the ROC. The AUC is closely related to the nonparametric Wilcox test and summarizes the separation of classes over all the thresholds. Advantages of the ROC technique include (1) it does not assume a parametric form of the class probability as required in the logistic regression method, (2) it is adaptable to outcome-dependent samplings, e.g. the case-control design, which are widely used in medical studies, and (3) it is relatively straightforward to assign different 'costs' to false positives and false negatives (Dodd 2003; Pepe 2006).

Example 1

Mouse Model for Early Detection of Lung Cancer

The A/J mouse model was used to chemically induce lung tumors and monitor the miRNA expression profile in plasma. Benzo[a]pyrene (Sigma-Aldrich, St. Louis, Mo., USA; cat. no. 48564) served as a carcinogen to chemically induce lung tumors in mice. A/J mice (67 male and 68 female) were purchased from The Jackson Laboratory (Bar Harbor, Me., USA; Stock Number 000646) and sent to Perry Scientific Inc. (San Diego, Calif., USA), at the age of six weeks. Perry Scientific performed all the animal related experiments including carcinogen administration, animal monitoring, blood withdrawal and plasma processing.

To obtain baseline data, two weeks prior to carcinogen administration, 125 mice were bled via orbital sinus and 10 mice were sacrificed by isofluorane inhalation and bled out by cardiac puncture. On day 0, mice in the experimental group were dosed with carcinogen via oral gavage at a dose equivalent to 20 µM in 200 µl (250 mg/kg body weight) in cotton-seed oil (Sigma-Aldrich, cat. no. C7767). Ten control mice (5 males and 5 females) received an oral gavage of 200 µl cottonseed oil with no carcinogen. A second carcinogen dose (250 mg/kg body weight) was administered to the test group at 10 weeks post the first gavage, with the control animals receiving a second gavage of cottonseed oil as described above. Mice were sacrificed at specific time points (FIG. 1), and the remaining mice were bled every two weeks (FIG. 1). At termination, animals were weighed, bled via cardiac puncture, and lung lobes collected. Control mice were bled throughout the study and sacrificed at week 34 post-carcinogen administration.

Blood samples were processed individually into plasma. For plasma preparation, blood samples were collected into BD Vacutainer® K2EDTA tubes (Becton, Dickinson and Company; Franklin Lakes, N.J., USA; cat. no. 367841). Blood was centrifuged at 2,000×g for 10 minutes, after which the plasma layer was aspirated and put into a fresh tube and centrifuged at 2,500×g for 10 minutes. The resulting plasma was immediately stabilized by the addition of 2× denaturing buffer from the mirVana™ miRNA Isolation Kit (Ambion Inc., Austin, Tex., USA; cat no. AM1560) to achieve a final concentration of 1×. Plasma and buffer were mixed by vortexing and immediately frozen at −80° C. until shipment to Asuragen on dry ice. Cell pellets were also frozen at −80° C. and shipped to Asuragen with plasma samples.

Plasma RNA was purified using the organic extraction of the mirVana PARIS™ Kit (Ambion, Inc.; Part No. AM1556), with the following modifications. Following the addition of acid phenol:chloroform and vortexing, samples were incubated on ice for 5 min then centrifuged at 13,000×g for 10 min at 4° C. The aqueous layer was removed, extracted with chloroform, and centrifuged again. The aqueous layer was removed from the second extraction, and 3M NaOAc (1/10 volume), glycogen (5 mg/ml), and 100% ethanol (1.5 volume) were added to the samples. Lysate/ethanol mixtures were passed through a mirVana PARIS™ filter cartridge, and filters were washed once with 650 µl of Wash 1 buffer and twice with 650 µl of Wash 2/3 buffer. RNA was eluted with two aliquots of nuclease free water (50 µl) and stored at −80° C.

One half of the lung lobes from each mouse were fixed in 10% buffered formalin overnight, embedded in paraffin (FFPE), and processed for hematoxylin and eosin (H&E) stained slides. The other half were snap frozen at −80° C. FFPE lung sections were step-sectioned at 5 mm intervals. The following sectioning guidelines were used: If no grossly visible tumors were present in either lung, three random 5×5×5 mm sections from each lung were taken for snap-freezing and for FFPE preparation. If grossly visible tumors were present, one 5×5×5 mm section of one tumor from each lung was snap-frozen and the other half was prepared for FFPE. If only one lung had tumors, random regions from the uninvolved lung were snap-frozen and FFPE prepared. For histopathology, the lung lobes preserved in formalin were sent to Pacific Pathology Inc. (San Diego, Calif., USA) where they were embedded in paraffin, sectioned, stained with hematoxylin and eosin, and prepared into slides.

H&E-stained slides were sent to Asuragen and analyzed by a board certified pathologist and classified as normal, hyperplasia, adenoma, or adenocarcinoma of the lung. Table 6 shows the number of visible tumors observed in each sacrificed animals, and the pathological diagnosis in each of the lung lobes.

TABLE 6

Lung tumors and pathological diagnosis from experimental and control mice. SCC, squamous cell carcinoma.

| Mouse Number | Sex | Pathology-Based Diagnosis Right Lobes | Pathology-Based Diagnosis Left Lobes | Number of Visible Tumors | Week of Termination |
|---|---|---|---|---|---|
| Experimental Animals ||||||
| 8864 | F | Normal | Normal | 0 | 0 |
| 8865 | F | Normal | Normal | 0 | 0 |
| 8866 | F | Normal | Normal | 0 | 0 |
| 8867 | F | Normal | Normal | 0 | 0 |
| 8868 | F | Normal | Normal | 0 | 0 |
| 8931 | M | Normal | Normal | 0 | 0 |
| 8932 | M | Normal | Normal | 0 | 0 |
| 8933 | M | Normal | Normal | 0 | 0 |
| 8934 | M | Normal | Normal | 0 | 0 |

TABLE 6-continued

Lung tumors and pathological diagnosis from experimental and control mice. SCC, squamous cell carcinoma.

| Mouse Number | Sex | Pathology-Based Diagnosis Right Lobes | Pathology-Based Diagnosis Left Lobes | Number of Visible Tumors | Week of Termination |
|---|---|---|---|---|---|
| 8935 | M | Normal | Normal | 0 | 0 |
| 8858 | F | Normal | Normal | 0 | 2 |
| 8859 | F | Normal | Adenoma | 0 | 2 |
| 8860 | F | Normal | Normal | 0 | 2 |
| 8861 | F | Normal | Normal | 0 | 2 |
| 8862 | F | Normal | Normal | 0 | 2 |
| 8926 | M | Normal | Normal | 0 | 2 |
| 8927 | M | Normal | Normal | 0 | 2 |
| 8928 | M | Normal | Normal | 0 | 2 |
| 8929 | M | Normal | Normal | 0 | 2 |
| 8930 | M | Normal | Normal | 0 | 2 |
| 8853 | F | Normal | Normal | 0 | 4 |
| 8854 | F | Normal | Normal | 0 | 4 |
| 8855 | F | Normal | Normal | 0 | 4 |
| 8856 | F | Normal | Normal | 0 | 4 |
| 8857 | F | Normal | Normal | 0 | 4 |
| 8921 | M | Normal | Normal | 0 | 4 |
| 8922 | M | Normal | Normal | 0 | 4 |
| 8923 | M | Normal | Normal | 0 | 4 |
| 8924 | M | Normal | Normal | 0 | 4 |
| 8925 | M | Normal | Normal | 0 | 4 |
| 8509 | M | Normal | Normal | 0 | 6 |
| 8847 | F | Normal | Normal | 0 | 6 |
| 8848 | F | Normal | Normal | 0 | 6 |
| 8850 | F | Normal | Normal | 0 | 6 |
| 8851 | F | Normal | Normal | 0 | 6 |
| 8852 | F | Normal | Normal | 0 | 6 |
| 8917 | M | Normal | Normal | 0 | 6 |
| 8918 | M | Normal | Normal | 0 | 6 |
| 8919 | M | Normal | Normal | 0 | 6 |
| 8920 | M | Normal | Normal | 0 | 6 |
| 8507 | M | Normal | Normal | 0 | 8 |
| 8508 | M | Normal | Normal | 0 | 8 |
| 8841 | F | Normal | Normal | 0 | 8 |
| 8842 | F | Normal | Normal | 0 | 8 |
| 8843 | F | Normal | Normal | 0 | 8 |
| 8845 | F | Normal | Normal | 0 | 8 |
| 8846 | F | Normal | Normal | 0 | 8 |
| 8912 | M | Normal | Normal | 0 | 8 |
| 8915 | M | Normal | Normal | 0 | 8 |
| 8941 | M | Normal | Normal | 0 | 8 |
| 8838 | F | Normal | Normal | 0 | 10 |
| 8839 | F | Normal | Normal | 0 | 10 |
| 8840 | F | Normal | Normal | 0 | 10 |
| 8907 | M | Normal | Normal | 0 | 10 |
| 8908 | M | Normal | Normal | 0 | 10 |
| 8909 | M | Normal | Normal | 0 | 10 |
| 8506 | M | Normal | Normal | 0 | 12 |
| 8833 | F | Normal | Normal | 0 | 12 |
| 8834 | F | Normal | Normal | 0 | 12 |
| 8835 | F | Normal | Normal | 0 | 12 |
| 8836 | F | Normal | Normal | 0 | 12 |
| 8837 | F | Normal | Normal | 0 | 12 |
| 8902 | M | Normal | Normal | 0 | 12 |
| 8903 | M | Normal | Normal | 0 | 12 |
| 8904 | M | Normal | Normal | 0 | 12 |
| 8940 | M | Normal | Normal | 0 | 12 |
| 8505 | M | Normal | Normal | 4 | 14 |
| 8828 | F | Normal | Hyperplasia | 0 | 14 |
| 8830 | F | Normal | Normal | | 14 |
| 8831 | F | Adenomas papillary (2) | Hyperplasia | 3 | 14 |
| 8832 | F | Hyperplasia | Adenocarcinoma | 1 | 14 |
| 8899 | M | Normal | Normal | 1 | 14 |
| 8900 | M | Normal | Normal | 0 | 14 |
| 8816 | F | Normal | Normal | 0 | 16 |
| 8825 | F | Adenocarcinoma in adenoma | Hyperplasia | | 16 |
| 8826 | F | Hyperplasia | Adenoma | 2 | 16 |
| 8827 | F | Normal | Normal | 2 | 16 |
| 8829 | F | Normal | Normal | 2 | 16 |
| 8895 | M | Normal | Normal | 2 | 16 |
| 8896 | M | Normal | Normal | 1 | 16 |

TABLE 6-continued

Lung tumors and pathological diagnosis from experimental and control mice.
SCC, squamous cell carcinoma.

| Mouse Number | Sex | Pathology-Based Diagnosis Right Lobes | Pathology-Based Diagnosis Left Lobes | Number of Visible Tumors | Week of Termination |
|---|---|---|---|---|---|
| 8897 | M | Adenocarcinoma | Normal | 5 | 16 |
| 8898 | M | Adenoma | Normal | 2 | 16 |
| 8939 | M | Normal | Normal | 0 | 16 |
| 8822 | F | Hyperplasia | Normal | 2 | 18 |
| 8823 | F | Adenocarcinoma in adenoma | Hyperplasia | 1 | 18 |
| 8824 | F | Adenoma | Hyperplasia | 2 | 18 |
| 8890 | M | Adenocarcinomas (2) | Hyperplasia | 2 | 18 |
| 8892 | M | Adenocarcinoma | Hyperplasia | 4 | 18 |
| 8893 | M | Adenocarcinomas (2) | Hyperplasia | 8 | 18 |
| 8938 | M | Normal | Normal | 3 | 18 |
| 8808 | F | Normal | Normal | 0 | 22 |
| 8820 | F | Adenomas papillary (2) | Hyperplasia | 3 | 22 |
| 8821 | F | Normal | Normal | 2 | 22 |
| 8886 | M | Adenocarcinoma | Hyperplasia | 1 | 22 |
| 8887 | M | Normal | Normal | 0 | 22 |
| 8888 | M | Adenoma | Hyperplasia | 4 | 22 |
| 8889 | M | Hyperplasia | Normal | 1 | 22 |
| 8811 | F | Normal | Normal | 2 | 26 |
| 8812 | F | Adenocarcinoma in adenoma | Normal | 4 | 26 |
| 8813 | F | Adenocarcinoma | Adenoma papillary | 8 | 26 |
| 8814 | F | Hyperplasia | Mucinous Adenocarcinoma | 6 | 26 |
| 8885 | M | Normal | Normal | 1 | 26 |
| 8936 | M | Adenocarcinoma in adenoma | Normal | 4 | 26 |
| 8937 | M | Adenocarcinoma in adenoma | Adenoma | 2 | 26 |
| 8504 | M | Adenoma, papillary | Normal | 3 | 30 |
| 8806 | F | Adenocarcinoma | Normal | 6 | 30 |
| 8815 | F | Hyperplasia | Adenoma | 3 | 30 |
| 8819 | F | Adenocarcinoma in adenoma | Adenoma | 3 | 30 |
| 8874 | M | Adenocarcinoma | Adenocarcinoma | 11 | 30 |
| 8883 | M | Adenocarcinoma | Adenocarcinoma | 6 | 30 |
| 8884 | M | Adenocarcinomas (2) | Normal | 5 | 30 |
| 8805 | F | Normal | Normal | 0 | 34 |
| 8807 | F | Adenocarcinoma | Normal | 2 | 34 |
| 8810 | F | Hyperplasia | Adenocarcinoma papillary | 6 | 34 |
| 8875 | M | SCC | Adenoma | 3 | 34 |
| 8878 | M | Adenocarcinoma | Adenoma papillary | 8 | 34 |
| 8880 | M | Adenomas papillary (2) | Hyperplasia | 6 | 34 |
| Control Animals | | | | | |
| 8870 | M | Hyperplasia | Normal | 0 | 34 |
| 8873 | M | Normal | Normal | 1 | 34 |
| 8502 | M | Adenocarcinoma in adenoma | Normal | 0 | 34 |
| 8501 | F | Normal | Normal | 0 | 34 |
| 8503 | M | Normal | Normal | 0 | 34 |
| 8801 | F | Normal | Normal | 0 | 34 |
| 8802 | F | Normal | Normal | 0 | 34 |
| 8803 | F | Normal | Normal | 0 | 34 |
| 8805 | F | Normal | Normal | 0 | 34 | miRNA expression was evaluated in plasma samples from mice with pathology-confirmed adenocarcinoma of the lung and from control mice that did not receive carcinogen. Control mice were age matched to the mice with adenocarcinoma. Expression levels of 329 miRNAs, were determined by qRT-PCR using TaqMan® MicroRNA Assays (Applied Biosystems) specific for each miRNA. A subset of the miRNAs (170) have identical mature sequences in both mice and humans and the remainder are mouse homologues of corresponding human miRNAs. Reverse transcription (RT) reaction components (Table 7) were assembled on ice prior to the addition of RNA template, and included ~1 ng plasma RNA per each 10 µl reaction. RT reactions were incubated in a 384-well GeneAmp® PCR System 9700 (Applied Biosystems) at 16° C. for 30 minutes, then at 42° C. for 30 minutes, then at 85° C. for 5 minutes. RT reactions were then frozen at −20° C.

TABLE 7

Reverse transcription reaction components.

| RT Reagent | Final Concentration |
| --- | --- |
| 10X RT Buffer (Asuragen, Inc.) | 1X |
| dNTPs (2.5 mM each) (GE Healthcare, Piscataway, NJ, USA; cat. no. 28-4065-53) | 1 mM |
| 5X TaqMan MicroRNA RT primers (Applied Biosystems, Inc.) | 0.25X |
| RNasin plus RNase Inhibitor (40 U/mL) (Promega, Corp., Madison, WI, USA; cat. no. N251X) | 0.4 U/μl |
| Moloney Murine Leukemia Virus Reverse Transcriptase (MMLV-RT), (200 U/μL) (Invitrogen Corp., Carlsbad, CA, USA; cat. no. 28025-021 | 1 U/μl |
| Mouse Plasma RNA | ~1 ng |

PCR components (Table 8) were assembled on ice prior to the addition of cDNA (2 μl) from the RT reaction. Reactions were incubated in an ABI PRISM™ 7900HT Fast Real-Time PCR system (Applied Biosystems) at 95° C. for 1 minute, then for 50 cycles at 95° C. for 5 seconds and 60° C. for 30 seconds. Results were analyzed with the 7900HT Fast Real-Time PCR system SDS V2.3 software (Applied Biosystems).

TABLE 8

PCR components.

| qPCR Reagents | Final Concentration |
| --- | --- |
| MgCl$_2$ (50 mM) | 5 mM |
| 10X Platinum PCR Buffer, Minus MgCl$_2$ (Invitrogen; cat. no. 53286) | 1X |
| dNTPs (2.5 mM each) (GE Healthcare; cat. no. 28-4065-53) | 1 mM |
| 20X TaqMan miRNA primer/probe mix (Applied Biosystems) | 0.4X |
| 50X ROX (Asuragen, Inc.) | 1X |
| Platinum Taq DNA Polymerase (5 U/μl) (Invitrogen, Corp.; cat. no. 10966-083) | 0.033 U/μl |
| cDNA from RT-reaction | 2 μl |

Table 9 shows the average Ct data and ddCt values for cancer vs. control mice from the qRT-PCR experiment. miRNAs with p-values of 0.1 or less are shown.

TABLE 9 miRNA expression in plasma samples from mice with pathology-confirmed adenocarcinoma of the lung and from control mice that did not receive carcinogen.

| miR-ID | Normal Ave dCT | Normal SD | Cancer Ave dCT | Cancer SD | cancer − normal ddCT | t-test p-value |
| --- | --- | --- | --- | --- | --- | --- |
| miR-124a | 5.024 | 0.207 | 1.823 | 0.400 | −3.201 | 0.009745 |
| miR-141 | −2.319 | 1.108 | −4.446 | 1.887 | −2.127 | 0.011532 |
| miR-183 | 1.025 | 1.294 | −1.054 | 1.848 | −2.080 | 0.02066 |
| miR-182 | −2.074 | 1.340 | −3.989 | 1.711 | −1.915 | 0.020695 |
| mmu-miR-718 | 5.556 | 0.220 | 3.416 | 0.997 | −2.140 | 0.030195 |
| miR-27b | −1.343 | 1.872 | −3.049 | 0.996 | −1.705 | 0.036353 |
| miR-452 | 1.601 | 0.674 | −0.313 | 1.708 | −1.914 | 0.040553 |
| miR-379 | 3.021 | 0.764 | 1.287 | 0.988 | −1.735 | 0.041625 |
| mmu-miR-429 | −4.873 | 0.781 | −6.663 | 1.970 | −1.790 | 0.042703 |
| mmu-miR-83 | 3.704 | 1.371 | 1.304 | 0.781 | −2.400 | 0.043659 |
| miR-433 | 2.504 | 1.310 | 0.867 | 1.784 | −1.636 | 0.046172 |
| mmu-miR-715 | 3.353 | 1.520 | 1.169 | 1.327 | −2.185 | 0.050614 |
| miR-200a | −4.099 | 1.544 | −5.861 | 1.901 | −1.762 | 0.052236 |
| mmu-miR-694 | −0.132 | 3.124 | 2.744 | 2.058 | 2.875 | 0.059031 |
| miR-205 | −3.726 | 1.365 | −5.323 | 1.875 | −1.597 | 0.060958 |
| miR-423 | −3.359 | 6.935 | −12.157 | 11.792 | −8.797 | 0.076461 |
| mmu-miR-706 | 0.017 | 1.072 | −1.309 | 1.650 | −1.327 | 0.077327 |
| miR-422b | −0.914 | 1.839 | −2.576 | 1.930 | −1.662 | 0.089258 |
| miR-324-5p | 0.864 | 1.571 | −0.388 | 0.503 | −1.252 | 0.089557 |
| miR-200c | −5.662 | 1.485 | −7.159 | 1.966 | −1.497 | 0.09453 |
| miR-378 | −0.322 | 2.275 | −1.960 | 0.738 | −1.638 | 0.095018 |
| miR-365 | −3.013 | 1.678 | −4.707 | 2.275 | −1.694 | 0.098461 |
| mmu-miR-542-5p | 2.291 | 1.603 | 0.917 | 0.836 | −1.374 | 0.099749 |

Figure 2A:
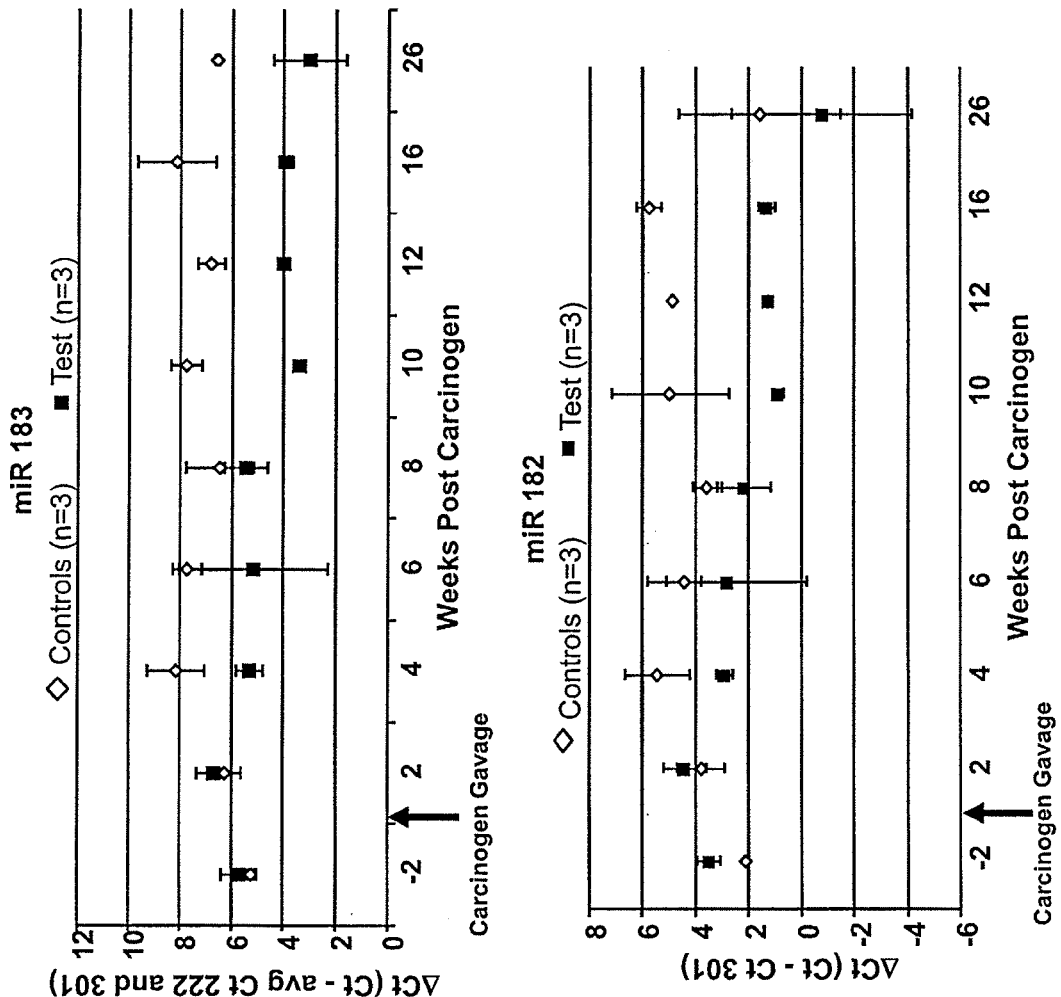
FIG. 2A and FIG. 2B show temporal changes of miR-183 and miR-182 (FIG. 2A) and miR-365 and miR-141 (FIG. 2B) plasma miRNA expression in mice that developed lung tumors and in control mice.
Figure 2B:
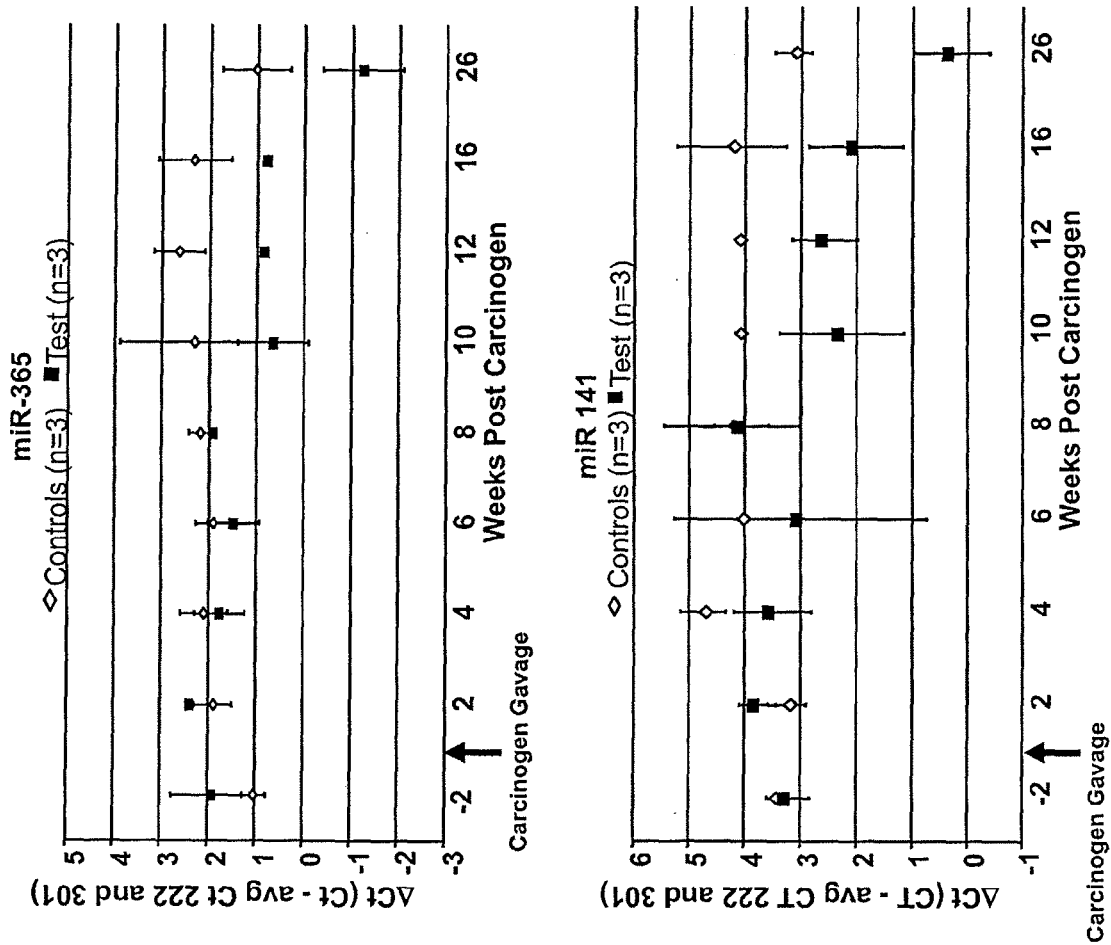

In addition, a temporal study was performed to examine miRNA expression in animals that had been diagnosed with lung adenocarcinomas. FIG. 2A and FIG. 2B show the changes in expression of selected miRNAs over time, prior to the detection of tumors. This figure shows that differential expression of miRNAs can be detected as early as 10 weeks after carcinogen administration—at least 6 weeks prior to the detection of tumors. These results demonstrate that miRNA can be used to detect lung cancer at an early stage and are suitable for screening for lung cancer.

Example 2 qRT-PCR Identification of miRNA Biomarkers for the Detection of Lung Cancer

The expression of 12 miRNAs were evaluated in serum samples from eight lung cancer patients and eight normal patients. Blood from lung cancer patients and normal donors was collected into BD Vacutainer® Plus Plastic Serum Tubes. All blood was collected at the time of diagnosis but prior to any medical intervention, such as tumor resection or treatment. Blood was centrifuged at 1,000×g for 10 min and serum transferred to a fresh tube and immediately frozen at −80° C. Serum RNA was extracted using the organic extraction of the mirVana PARIS™ Kit (Ambion, Inc., Austin, Tex., USA; Part No. AM1556), with the following modifications. Following the addition of acid phenol:chloroform and vortexing, samples were incubated on ice for 5 min then centrifuged at 13,000×g for 10 min at 4° C. The aqueous layer was removed, extracted with chloroform, and centrifuged again. The aqueous layer was removed from the second extraction, and 3M NaOAc (1/10 volume), glycogen (5 mg/ml), and 100% ethanol (1.5 volume) were added to the samples. Lysate/ethanol mixtures were passed through a mirVana PARIS™ filter cartridge, and filters were washed once with 650 μl of Wash 1 buffer and twice with 650 μl of Wash 2/3 buffer. RNA was eluted with two aliquots of nuclease free water (50 μl) and stored at −80° C.

miRNA expression levels were determined by qRT-PCR using TaqMan® MicroRNA Assays (Applied Biosystems; Foster City, Calif., USA) specific for each miRNA. Reverse transcription (RT) reactions were performed using the Taq-Man® MicroRNA Reverse Transcription Kit (Applied Biosystems, Foster City, Calif., USA; cat. no. 4366597). Reaction components listed in Table 10 were assembled on ice prior to the addition of RNA template. All reaction components were as provided by the manufacturer (Applied Biosystems; Foster City, Calif., USA) as a kit with multiple components. Serum RNA (1 ng total RNA per reaction) was added and mixed. RT reactions were incubated in a 384-well Gene-Amp® PCR System 9700 (Applied Biosystems) at 16° C. for 30 minutes, then at 42° C. for 30 minutes, then at 85° C. for 5 minutes. RT reactions were then frozen at −20° C.

TABLE 10

Reverse transcription reaction components.

| RT Reagent | Final Concentration |
| --- | --- |
| 10X RT Buffer | 1X |
| dNTPs (100 mM) | 1 mM |
| 5X TaqMan MicroRNA RT primers | 0.25X |
| RNase Inhibitor (20 U/µl) | 0.26 U/µl |
| Multiscribe MMLV-RT enzyme (50 U/µl) | 3.35 U/µl |
| Human Serum RNA | ~1 ng |

PCR components (Table 11) were assembled on ice prior to the addition of cDNA (4 µl) from the RT reaction. Reactions were incubated in an ABI PRISM™ 7900HT Fast Real-Time PCR system (Applied Biosystems) at 95° C. for 1 minute, then for 50 cycles at 95° C. for 5 seconds and 60° C. for 30 seconds. Results were analyzed with the 7900HT Fast Real-Time PCR system SDS V2.3 software (Applied Biosystems).

TABLE 11

PCR components.

| qPCR Reagents | Final Concentration |
| --- | --- |
| MgCl$_2$ (50 mM) (Invitrogen, Corp.; cat. no. 52723) | 5 mM |
| 10X Platinum PCR Buffer, Minus Mg (Invitrogen Corp.; cat. no. 53286) | 1X |

TABLE 11-continued

PCR components.

| qPCR Reagents | Final Concentration |
| --- | --- |
| dNTPs (2.5 mM each) (GE Healthcare; cat. no. 28-4065-53) | 1 mM |
| 20X TaqMan miRNA primer/probe mix (Applied Biosystems) | 0.4X |
| 50X ROX Internal Marker (Asuragen, Inc.) | 1X |
| Platinum Taq DNA Polymerase (5 U/µl) (Invitrogen, Corp.; cat. no. 10966-083) | 0.033 U/µl |

Table 12 provides average dCt values for cancer and normal samples for each miRNA. In addition, ddCt values represent the difference in expression between cancer and normal samples.

TABLE 12

Expression of miRNAs in serum from patients with and without lung cancer.

| miR-ID | Normal Ave dCT | Normal SD | Cancer Ave dCT | Cancer SD | Cancer-normal ddCT | ttest p-value |
| --- | --- | --- | --- | --- | --- | --- |
| miR-375 | 2.595 | 1.470 | −0.284 | 1.624 | −2.878 | 0.002304 |
| miR-499 | 9.492 | 2.276 | 13.093 | 1.348 | 3.600 | 0.022561 |
| miR-22 | −1.705 | 1.115 | −2.715 | 0.787 | −1.010 | 0.055164 |
| miR-122a | 2.547 | 1.088 | 3.925 | 1.642 | 1.378 | 0.067827 |
| miR-206 | 1.039 | 1.870 | 2.816 | 1.781 | 1.777 | 0.071915 |
| miR-103 | −5.317 | 1.051 | −4.264 | 1.195 | 1.053 | 0.08225 |
| miR-24 | −6.105 | 0.998 | −6.920 | 1.020 | −0.815 | 0.12848 |
| miR-26a | −7.577 | 1.080 | −6.754 | 1.316 | 0.823 | 0.193305 |
| miR-498 | 9.488 | 2.253 | 10.945 | 3.831 | 1.457 | 0.439918 |
| miR-205 | 5.380 | 1.864 | 6.265 | 2.862 | 0.886 | 0.497533 |
| miR-222 | −4.169 | 1.014 | −4.005 | 0.888 | 0.164 | 0.735768 |
| let7c | −1.414 | 1.090 | −1.300 | 0.688 | 0.114 | 0.805489 |

In an expanded panel, the expression of 180 miRNAs were evaluated in serum samples from sixteen lung cancer patients and from twelve individuals with benign lung conditions (Table 13). In Table 13, Diff stands for differential status of the tumor; MOD stands for moderate; AC for adenocarcinoma; SCC for squamous cell carcinoma; R for right; RUL for right upper lobe; RML for right mid lobe; RLL for right lower lobe; LUL for left upper lobe; and LLL for left lower lobe.

TABLE 13

Histopathological and patient information for lung cancer and benign specimens.

| AGE | SEX | Tumor Size (cm) | Diagnosis | Cell Type | Diff | Lobe |
| --- | --- | --- | --- | --- | --- | --- |
| 69 | M | 5.5 | Cancer | SCC | MOD | LLL |
| 69 | M | 3.0 | Cancer | Adenocarcinoma | POOR | RUL |
| 63 | M | 2.0 | Cancer | Adenocarcinoma | POOR | RUL |
| 60 | M | 3.3 | Cancer | Adenocarcinoma | MOD/POOR | RUL |
| 56 | M | 3.0 | Cancer | SCC | MOD | RUL |
| 64 | F | 2.5 | Cancer | Adenocarcinoma | MOD | LUL |
| 72 | F | 6.0 | Cancer | SCC | MOD/POOR | LLL |
| 73 | F | 7.5 | Cancer | SCC | MOD | RLL |
| 71 | M | 3.0 | Cancer | SCC | WELL | LUL |
| 72 | M | 2.8 | Cancer | Adenocarcinoma | MOD | RLL |
| 59 | F | 3.5 & 2.6 | Cancer | Adenocarcinoma | POOR/WELL | RUL |
| 69 | M | 3.8 | Cancer | SCC | POOR | LUL |
| 66 | F | 3.2 | Cancer | Adenocarcinoma | POOR | RUL |
| 66 | F | 3.5 | Cancer | SCC | POOR | RUL |
| 66 | M | 3.5 | Cancer | SCC | WELL | LLL |

TABLE 13-continued

Histopathological and patient information for lung cancer and benign specimens.

| AGE | SEX | Tumor Size (cm) | Diagnosis | Cell Type | Diff | Lobe |
|---|---|---|---|---|---|---|
| 73 | F | 5.5 | Cancer | SCC | POOR | RLL |
| 71 | M | NA | Benign | Infarct | NA | LLL Wedge |
| 64 | F | NA | Benign | Granuloma | NA | Wedge |
| 59 | F | NA | Benign | Lymphoplasmacytic | NA | LLL |
| 60 | M | NA | Benign | Necrotizing Granuloma | NA | RML |
| 58 | M | NA | Benign | Decortocation | NA | LLL Decortocation |
| 60 | F | NA | Benign | Granuloma | NA | Wedge |
| 73 | F | NA | Benign | Granuloma | NA | RML |
| 77 | F | 2.0 | Benign | Hamartoma | NA | Wedge |
| 69 | F | 2.3 | Benign | Hamartoma | NA | LUL |
| 71 | F | NA | Benign | Hamartoma | NA | Wedge |
| 56 | M | 0.5 | Benign | No abnormalities identified | WELL | R |
| 69 | M | 0.7 nodule | Benign | Granulomas | NA | RUL Wedge |

Blood from lung cancer patients and comparator donors was collected into BD Vacutainer® Plus Plastic Serum Tubes and processed as described above for the initial human samples.

Table 14 provides differential expression data for miRNAs in the form of average dCt values for cancer and benign samples. In addition, ddCt values represent the difference in expression between cancer and benign samples.

TABLE 14

Expression of miRNAs in serum from patients with lung cancer or benign lung conditions.

| miR-ID | Benign Ave dCT | Benign SD | Cancer Ave dCT | Cancer SD | Cancer - Benign ddCT | ttest P-value |
|---|---|---|---|---|---|---|
| miR-422a | 2.6793 | 0.3602 | 1.0741 | 0.9172 | −1.6052 | 5.10E−06 |
| miR-27b | 0.7835 | 0.4918 | 1.7571 | 0.5307 | 0.9735 | 4.94E−05 |
| miR-181d | 0.8962 | 0.6161 | −0.1954 | 0.7101 | −1.0916 | 2.40E−04 |
| miR-126 | −4.0254 | 0.3338 | −3.2872 | 0.5391 | 0.7382 | 2.99E−04 |
| miR-142-3p | −4.6372 | 0.3449 | −3.6120 | 0.8137 | 1.0252 | 3.76E−04 |
| miR-27a | −2.2922 | 0.6007 | −1.3131 | 0.6512 | 0.9791 | 3.92E−04 |
| miR-142-5p | −0.4216 | 0.7273 | 0.7481 | 0.8222 | 1.1697 | 5.91E−04 |
| miR-126* | −3.5995 | 0.2867 | −3.0059 | 0.4729 | 0.5935 | 7.08E−04 |
| miR-92 | −6.8925 | 0.6114 | −8.1185 | 0.9946 | −1.2260 | 8.70E−04 |
| miR-378 | −1.3378 | 0.4795 | −2.2688 | 0.7699 | −0.9310 | 1.07E−03 |
| miR-374 | −1.0404 | 0.3363 | −0.3476 | 0.6435 | 0.6928 | 2.25E−03 |
| miR-15b | −1.3417 | 0.4185 | −0.8038 | 0.4658 | 0.5379 | 4.02E−03 |
| miR-30e-5p | −2.5626 | 0.7111 | −1.7810 | 0.6035 | 0.7816 | 4.15E−03 |
| miR-140 | −0.6399 | 0.5506 | 0.0188 | 0.5949 | 0.6587 | 6.01E−03 |
| miR-181a | 1.7785 | 0.9882 | 0.8296 | 0.6985 | −0.9489 | 6.16E−03 |
| miR-15a | 1.7754 | 0.5195 | 2.4577 | 0.6611 | 0.6822 | 6.62E−03 |
| miR-486 | −6.1701 | 1.0226 | −7.4543 | 1.2676 | −1.2842 | 7.98E−03 |
| miR-340 | −1.0291 | 0.5294 | −0.3092 | 0.7436 | 0.7199 | 8.45E−03 |
| miR-518b | 5.7505 | 1.1729 | 4.3957 | 1.3343 | −1.3548 | 9.58E−03 |
| miR-342 | 0.8380 | 0.5664 | 0.0741 | 0.8180 | −0.7639 | 1.02E−02 |
| miR-145 | 1.5007 | 0.7105 | 0.7670 | 0.6990 | −0.7337 | 1.12E−02 |
| let-7i | −1.8912 | 0.5005 | −1.4026 | 0.5160 | 0.4886 | 1.86E−02 |
| miR-150 | −2.5234 | 0.8088 | −3.7092 | 1.5066 | −1.1858 | 2.06E−02 |
| miR-320 | −4.9158 | 0.7410 | −5.7428 | 1.0027 | −0.8270 | 2.37E−02 |
| miR-345 | 0.2934 | 0.9660 | −0.4029 | 0.5695 | −0.6963 | 2.44E−02 |
| miR-214 | 2.3882 | 1.1670 | 3.8445 | 1.9139 | 1.4563 | 2.94E−02 |
| let-7f | 0.2969 | 0.6481 | 0.9345 | 0.7784 | 0.6376 | 2.98E−02 |
| miR-324-3p | 1.3654 | 0.6871 | 0.7783 | 0.6976 | −0.5871 | 3.55E−02 |
| miR-106b | −2.0518 | 0.7547 | −1.5215 | 0.5235 | 0.5302 | 3.71E−02 |
| miR-143 | 0.9101 | 1.0014 | 1.8296 | 1.2023 | 0.9195 | 4.13E−02 |
| let-7g | −2.8322 | 0.3171 | −2.3913 | 0.6574 | 0.4410 | 4.21E−02 |
| miR-181b | 1.1157 | 0.6983 | 0.4448 | 0.9198 | −0.6708 | 4.48E−02 |
| miR-202 | 1.3920 | 0.8357 | 0.6625 | 0.9352 | −0.7295 | 4.51E−02 |
| miR-191 | −2.5784 | 0.6352 | −2.9762 | 0.4085 | −0.3978 | 5.42E−02 |
| miR-199a* | −1.5205 | 0.5713 | −1.0752 | 0.6451 | 0.4453 | 6.91E−02 |
| miR-193b | 2.3794 | 0.7481 | 1.5532 | 1.3659 | −0.8262 | 7.02E−02 |
| miR-496 | 4.3400 | 1.0930 | 5.3754 | 1.6993 | 1.0353 | 7.72E−02 |
| miR-132 | 1.6586 | 1.1201 | 1.0688 | 0.6675 | −0.5899 | 9.36E−02 |
| miR-328 | 0.8189 | 0.8011 | 0.2829 | 0.8614 | −0.5361 | 1.05E−01 |
| miR-29a | −2.3257 | 0.6459 | −1.6683 | 1.2372 | 0.6574 | 1.06E−01 |

TABLE 14-continued

Expression of miRNAs in serum from patients with lung cancer or benign lung conditions.

| miR-ID | Benign Ave dCT | Benign SD | Cancer Ave dCT | Cancer SD | Cancer - Benign ddCT | ttest P-value |
|---|---|---|---|---|---|---|
| miR-26a | −3.1762 | 0.4130 | −2.8524 | 0.5688 | 0.3238 | 1.08E−01 |
| miR-30b | −2.2309 | 0.5773 | −1.9028 | 0.5152 | 0.3281 | 1.25E−01 |
| miR-222 | −1.9205 | 0.6562 | −2.2670 | 0.4896 | −0.3466 | 1.28E−01 |
| miR-433 | 3.8847 | 1.0349 | 3.2175 | 1.1667 | −0.6673 | 1.28E−01 |
| miR-148a | −0.9623 | 0.8328 | −0.5361 | 0.6067 | 0.4262 | 1.29E−01 |
| miR-24 | −3.1600 | 0.5440 | −3.4913 | 0.5632 | −0.3313 | 1.30E−01 |
| miR-185 | −0.4549 | 0.9216 | 0.1325 | 1.0365 | 0.5874 | 1.32E−01 |
| let-7e | −2.6734 | 0.4214 | −2.2989 | 0.7579 | 0.3745 | 1.36E−01 |
| miR-29c | −0.5739 | 0.7037 | −0.0001 | 1.1417 | 0.5737 | 1.38E−01 |
| miR-566 | 2.4771 | 1.1749 | 1.7666 | 1.2689 | −0.7104 | 1.42E−01 |
| miR-432 | 2.3089 | 0.9280 | 2.9279 | 1.2706 | 0.6190 | 1.66E−01 |
| let-7c | 1.2401 | 0.5373 | 1.6456 | 0.8681 | 0.4055 | 1.67E−01 |
| miR-26b | −3.6560 | 0.4932 | −3.3775 | 0.5238 | 0.2785 | 1.71E−01 |
| miR-186 | −1.2855 | 0.6674 | −1.6027 | 0.5389 | −0.3172 | 1.76E−01 |
| miR-30c | −2.3656 | 0.5170 | −2.0711 | 0.5893 | 0.2945 | 1.80E−01 |
| miR-21 | −4.6211 | 0.6501 | −4.2927 | 0.5931 | 0.3284 | 1.83E−01 |
| miR-196b | 3.5790 | 0.8693 | 4.1100 | 1.1353 | 0.5310 | 1.89E−01 |
| miR-206 | 3.3545 | 1.2404 | 4.0606 | 1.5185 | 0.7062 | 2.00E−01 |
| miR-133b | 3.0461 | 1.0602 | 3.6031 | 1.1841 | 0.5570 | 2.09E−01 |
| miR-101 | −0.1229 | 1.0697 | 0.3882 | 1.0225 | 0.5111 | 2.11E−01 |
| miR-30d | −2.3000 | 0.4638 | −2.6151 | 0.7742 | −0.3152 | 2.23E−01 |
| miR-125a | 0.9380 | 0.7768 | 0.5229 | 0.9426 | −0.4151 | 2.26E−01 |
| miR-423 | 2.3856 | 0.7807 | 1.9988 | 0.8556 | −0.3869 | 2.30E−01 |
| miR-98 | 2.3292 | 0.6178 | 2.7845 | 1.1810 | 0.4553 | 2.36E−01 |
| miR-30a-5p | −3.5098 | 0.4451 | −3.7597 | 0.6011 | −0.2499 | 2.37E−01 |
| miR-382 | 3.0718 | 1.3008 | 2.5268 | 1.1063 | −0.5449 | 2.42E−01 |
| miR-146a | −3.3154 | 0.7922 | −3.6180 | 0.5646 | −0.3026 | 2.48E−01 |
| miR-210 | 0.9449 | 0.6478 | 0.5916 | 0.8745 | −0.3533 | 2.50E−01 |
| miR-10b | 1.8909 | 0.8881 | 2.3531 | 1.1545 | 0.4622 | 2.60E−01 |
| miR-501 | 4.2875 | 1.8588 | 3.5968 | 1.3891 | −0.6907 | 2.70E−01 |
| miR-16 | −9.0423 | 1.1022 | −8.5257 | 1.3039 | 0.5165 | 2.79E−01 |
| miR-195 | −3.3951 | 1.2516 | −2.8590 | 1.3747 | 0.5361 | 2.99E−01 |
| miR-93 | −3.5061 | 0.9429 | −3.8992 | 1.0384 | −0.3931 | 3.12E−01 |
| let-7a | −1.5300 | 0.4402 | −1.2614 | 0.8211 | 0.2686 | 3.15E−01 |
| miR-497 | 2.2971 | 1.0066 | 2.6427 | 0.8125 | 0.3456 | 3.24E−01 |
| let-7b | −2.3849 | 0.6326 | −2.1077 | 0.7862 | 0.2772 | 3.26E−01 |
| miR-130a | −2.1333 | 1.1347 | −1.7624 | 0.8643 | 0.3709 | 3.35E−01 |
| miR-346 | 2.9259 | 1.0873 | 3.5397 | 1.9410 | 0.6138 | 3.35E−01 |
| miR-192 | −0.1533 | 0.7412 | 0.1308 | 0.9346 | 0.2841 | 3.94E−01 |
| miR-130b | −0.4571 | 0.8988 | −0.7298 | 0.7741 | −0.2727 | 3.97E−01 |
| miR-133a | 2.1153 | 1.5110 | 1.2847 | 3.0632 | −0.8307 | 3.97E−01 |
| miR-17-5p | −0.6945 | 0.6588 | −0.9188 | 0.7430 | −0.2243 | 4.15E−01 |
| miR-20a | −4.6339 | 0.9997 | −4.2700 | 1.2843 | 0.3640 | 4.29E−01 |
| miR-483 | 2.9376 | 1.2951 | 2.5331 | 1.3943 | −0.4045 | 4.41E−01 |
| miR-660 | −1.6504 | 0.5269 | −1.4526 | 0.8660 | 0.1978 | 4.91E−01 |
| miR-30e-3p | 3.9566 | 0.8947 | 4.1763 | 0.7757 | 0.2197 | 4.93E−01 |
| miR-22 | −0.4382 | 0.7316 | −0.6420 | 0.8160 | −0.2038 | 5.06E−01 |
| miR-301 | 1.9104 | 0.7844 | 1.7216 | 0.7036 | −0.1888 | 5.09E−01 |
| miR-296 | 2.8720 | 0.3686 | 2.7212 | 0.8082 | −0.1508 | 5.54E−01 |
| let-7d | −0.2621 | 0.4927 | −0.1031 | 0.8485 | 0.1591 | 5.68E−01 |
| miR-335 | 0.6203 | 0.9959 | 0.4327 | 0.7237 | −0.1876 | 5.68E−01 |
| miR-99a | 2.0535 | 0.9928 | 1.8082 | 1.2768 | −0.2453 | 5.86E−01 |
| miR-151 | −0.0065 | 0.6454 | −0.1485 | 0.7022 | −0.1419 | 5.89E−01 |
| miR-197 | −0.2610 | 0.5401 | −0.3910 | 0.7156 | −0.1300 | 6.03E−01 |
| miR-139 | 2.4268 | 0.8325 | 2.5865 | 0.8012 | 0.1598 | 6.12E−01 |
| miR-638 | 0.5473 | 1.1720 | 0.7616 | 1.0756 | 0.2143 | 6.20E−01 |
| miR-25 | −2.6351 | 1.1161 | −2.8617 | 1.2709 | −0.2267 | 6.31E−01 |
| miR-223 | −7.0503 | 0.9827 | −7.2432 | 1.0912 | −0.1930 | 6.33E−01 |
| miR-19b | −5.0280 | 0.7599 | −5.1783 | 0.8950 | −0.1504 | 6.43E−01 |
| miR-134 | 3.4474 | 1.2533 | 3.2173 | 1.4493 | −0.2300 | 6.64E−01 |
| miR-525 | 5.3500 | 1.2998 | 5.5719 | 1.3734 | 0.2220 | 6.69E−01 |
| miR-194 | 3.2777 | 0.9298 | 3.1344 | 0.8584 | −0.1432 | 6.77E−01 |
| miR-23a | 0.1782 | 0.5417 | 0.0918 | 0.5748 | −0.0865 | 6.90E−01 |
| miR-584 | 2.1971 | 1.6012 | 2.0072 | 0.8763 | −0.1899 | 6.91E−01 |
| miR-10a | 2.3596 | 0.8173 | 2.4861 | 0.9602 | 0.1266 | 7.16E−01 |
| miR-605 | 3.1671 | 1.0273 | 2.9048 | 2.4778 | −0.2622 | 7.34E−01 |
| miR-152 | 1.2288 | 0.7870 | 1.3077 | 0.5498 | 0.0789 | 7.57E−01 |
| miR-361 | 1.4327 | 0.7048 | 1.3446 | 0.9835 | −0.0881 | 7.94E−01 |
| miR-339 | 1.7024 | 0.6148 | 1.7631 | 0.6041 | 0.0607 | 7.96E−01 |
| miR-18a | 0.1604 | 0.5327 | 0.2132 | 0.7051 | 0.0528 | 8.30E−01 |
| miR-365 | 1.4310 | 0.9063 | 1.3636 | 1.0200 | −0.0674 | 8.58E−01 |
| miR-100 | 2.5049 | 1.3365 | 2.5891 | 1.3062 | 0.0842 | 8.69E−01 |
| miR-103 | 0.0781 | 0.9976 | 0.0383 | 0.7868 | −0.0398 | 9.07E−01 |
| miR-146b | −1.4331 | 0.5367 | −1.4051 | 0.6798 | 0.0280 | 9.07E−01 |

TABLE 14-continued

Expression of miRNAs in serum from patients with lung cancer or benign lung conditions.

| miR-ID | Benign Ave dCT | Benign SD | Cancer Ave dCT | Cancer SD | Cancer - Benign ddCT | ttest P-value |
|---|---|---|---|---|---|---|
| miR-19a | −3.9132 | 0.7972 | −3.8742 | 0.9759 | 0.0390 | 9.11E−01 |
| miR-505 | 3.1605 | 1.3641 | 3.1189 | 0.9145 | −0.0415 | 9.24E−01 |
| miR-204 | 4.9078 | 1.2588 | 4.8708 | 1.1407 | −0.0369 | 9.37E−01 |
| miR-221 | −1.9235 | 0.8297 | −1.9439 | 0.8326 | −0.0204 | 9.49E−01 |
| miR-324-5p | 2.4533 | 0.4286 | 2.4384 | 0.8683 | −0.0149 | 9.57E−01 |
| miR-485-3p | 3.7173 | 1.7214 | 3.7477 | 1.3047 | 0.0303 | 9.58E−01 |
| miR-155 | 1.7078 | 0.7514 | 1.7018 | 1.0942 | −0.0061 | 9.87E−01 |
| miR-20b | −1.2419 | 0.9574 | −1.2497 | 1.4402 | −0.0078 | 9.87E−01 |
| miR-190 | 2.6134 | 0.7303 | 2.6156 | 0.9347 | 0.0022 | 9.95E−01 |
| miR-502 | 3.8339 | 1.1577 | 3.8302 | 1.7387 | −0.0038 | 9.95E−01 |
| miR-106a | −3.8355 | 0.7495 | −3.8341 | 0.9729 | 0.0014 | 9.97E−01 |

Pairs of miRNA biomarkers were also evaluated for their abilities to distinguish serum from patients for these samples. Un-normalized qRT-PCR data were used to calculate dCt values for each miRNA pair that was evaluated. The dCt values of the various miRNA pairs were analyzed using Receiver Operator Characteristic (ROC) analysis to identify the diagnostic miRNA pairs for lung cancer. In this example, ROC curves were used to evaluate the capacities of individual and combinations of biomarker candidates to distinguish patient classes. The abundance(s) of biomarker candidates were measured, and the measurements were used to develop classifiers whose true positive and false positive rates were plotted in a ROC curve. The AUC was then calculated for each classifier. An ideal classifier has an ROC AUC value of 1, and classifiers were ranked based upon how close their ROC AUC is to 1.

Table 15 includes miRNA pairs that distinguish patients with lung cancer from those with benign lung conditions. The miRNA pairs in Table 15 are listed in order of decreasing ROC AUC. Serum miRNA biomarker pairs for classifying patients with cancer vs. patients with benign lung conditions are presented. Mean values represent the average difference in Ct values between the two miRNAs in the pair. In Table 15, "Benign mean" represents the mean of data from 12 subjects with benign lung conditions; "Cancer mean" is the mean for data from 16 lung cancer patients; "Benign SD" is the standard deviation for data from patients with benign lung conditions; "Cancer SD" is the standard deviation for data from lung cancer patients; "Benign vs Cancer Assoc." refers to the p-value associated with the diagnosis of benign/lung cancer; ROC stands for receiver operating characteristic; and AUC is area under curve.

TABLE 15 microRNA biomarker pairs - benign lung and lung cancer patient sera.

| miRNA Biomarker Pair | Benign mean - Cancer mean | Benign mean | Benign SD | Cancer mean | Cancer SD | AUC ROC | Benign vs Cancer Assoc. |
|---|---|---|---|---|---|---|---|
| miR-202,miR-29b | 2.33 | −1.53 | 0.64 | −3.86 | 1.09 | 0.99 | 5.74E−07 |
| miR-142-5p,miR-422a | −2.77 | −3.10 | 0.92 | −0.33 | 1.31 | 0.98 | 1.34E−06 |
| miR-24,miR-27a | 1.31 | −0.87 | 0.41 | −2.18 | 0.56 | 0.98 | 2.71E−07 |
| miR-27b,miR-422a | −2.57 | −1.90 | 0.51 | 0.67 | 1.09 | 0.98 | 4.84E−08 |
| miR-140,miR-422a | −2.26 | −3.32 | 0.63 | −1.06 | 1.10 | 0.97 | 9.36E−07 |
| miR-185,miR-93 | −0.98 | 3.05 | 0.39 | 4.03 | 0.48 | 0.97 | 4.03E−06 |
| miR-126,miR-181d | −1.83 | −4.92 | 0.63 | −3.09 | 0.85 | 0.97 | 1.27E−06 |
| miR-142-3p,miR-422a | −2.63 | −7.32 | 0.56 | −4.69 | 1.09 | 0.97 | 4.07E−08 |
| miR-30e-5p,miR-345 | −1.48 | −2.86 | 0.81 | −1.38 | 0.68 | 0.97 | 1.85E−05 |
| miR-29b,miR-422a | −3.10 | 0.18 | 1.00 | 3.27 | 1.43 | 0.96 | 8.31E−07 |
| miR-324-5p,miR-422a | −1.59 | −0.23 | 0.58 | 1.37 | 0.81 | 0.96 | 4.37E−06 |
| miR-374,miR-422a | −2.30 | −3.72 | 0.56 | −1.42 | 1.23 | 0.96 | 2.35E−06 |
| miR-140,miR-345 | −1.36 | −0.93 | 0.75 | 0.42 | 0.78 | 0.96 | 3.97E−05 |
| miR-23a,miR-27a | 1.06 | 2.47 | 0.37 | 1.41 | 0.56 | 0.96 | 5.10E−06 |
| miR-29b,miR-378 | −2.42 | 4.30 | 1.00 | 6.72 | 1.21 | 0.96 | 6.22E−06 |
| miR-30e-5p,miR-422a | −2.39 | −5.24 | 0.85 | −2.86 | 1.19 | 0.96 | 3.23E−06 |
| miR-30e-5p,miR-92 | −2.01 | 4.33 | 0.68 | 6.34 | 0.97 | 0.96 | 1.83E−06 |
| miR-660,miR-92 | −1.42 | 5.24 | 0.71 | 6.67 | 0.55 | 0.96 | 2.80E−06 |
| miR-106b,miR-422a | −2.13 | −4.73 | 0.93 | −2.60 | 0.95 | 0.96 | 2.91E−06 |
| let-7g,miR-422a | −2.05 | −5.51 | 0.46 | −3.47 | 1.31 | 0.95 | 2.24E−05 |
| miR-101,miR-92 | −1.74 | 6.77 | 0.69 | 8.51 | 0.83 | 0.95 | 3.63E−06 |
| miR-126,miR-92 | −1.96 | 2.87 | 0.73 | 4.83 | 1.18 | 0.95 | 2.77E−05 |
| miR-126*,miR-422a | −2.20 | −6.28 | 0.42 | −4.08 | 1.17 | 0.95 | 1.42E−06 |
| miR-126*,miR-92 | −1.82 | 3.29 | 0.59 | 5.11 | 1.11 | 0.95 | 2.37E−05 |
| miR-150,miR-29a | 1.84 | −0.20 | 0.86 | −2.04 | 0.80 | 0.95 | 3.74E−06 |
| miR-15a,miR-92 | −1.91 | 8.67 | 0.58 | 10.58 | 0.92 | 0.95 | 1.10E−06 |
| miR-30e-5p,miR-324-3p | −1.37 | −3.93 | 0.78 | −2.56 | 0.58 | 0.95 | 1.33E−05 |
| miR-126,miR-378 | −1.67 | −2.69 | 0.58 | −1.02 | 0.92 | 0.95 | 9.56E−06 |
| miR-126,miR-422a | −2.34 | −6.70 | 0.49 | −4.36 | 1.06 | 0.95 | 1.47E−07 |
| miR-132,miR-29b | 2.22 | −1.20 | 1.23 | −3.42 | 1.13 | 0.95 | 3.82E−05 |

TABLE 15-continued microRNA biomarker pairs - benign lung and lung cancer patient sera.

| miRNA Biomarker Pair | Benign mean - Cancer mean | Benign mean | Benign SD | Cancer mean | Cancer SD | AUC ROC | Benign vs Cancer Assoc. |
|---|---|---|---|---|---|---|---|
| miR-142-3p,miR-181a | −1.97 | −6.42 | 0.85 | −4.44 | 0.94 | 0.95 | 5.06E−06 |
| miR-142-3p,miR-378 | −1.96 | −3.30 | 0.60 | −1.34 | 1.06 | 0.95 | 5.05E−06 |
| miR-148b,miR-92 | −1.76 | 7.75 | 0.70 | 9.51 | 0.86 | 0.95 | 4.27E−06 |
| miR-181b,miR-29b | 2.31 | −1.82 | 0.98 | −4.13 | 1.16 | 0.95 | 7.59E−06 |
| miR-26a,miR-422a | −1.93 | −5.85 | 0.62 | −3.93 | 1.08 | 0.95 | 8.71E−06 |
| miR-15a,miR-422a | −2.29 | −0.90 | 0.62 | 1.38 | 1.05 | 0.94 | 4.15E−07 |
| miR-146a,miR-27b | 1.24 | −4.10 | 0.66 | −5.34 | 0.45 | 0.94 | 3.44E−06 |
| miR-148b,miR-422a | −2.02 | −1.82 | 0.64 | 0.20 | 1.06 | 0.94 | 3.75E−06 |
| let-7i,miR-422a | −2.09 | −4.57 | 0.74 | −2.48 | 1.07 | 0.94 | 3.99E−06 |
| miR-340,miR-422a | −2.32 | −3.71 | 0.70 | −1.38 | 1.25 | 0.94 | 4.28E−06 |
| miR-143,miR-150 | −2.11 | 3.43 | 1.09 | 5.54 | 0.91 | 0.94 | 7.44E−06 |
| miR-15a,miR-378 | −1.61 | 3.12 | 0.70 | 4.73 | 0.82 | 0.94 | 9.88E−06 |
| miR-15b,miR-422a | −2.14 | −4.02 | 0.64 | −1.88 | 1.25 | 0.94 | 1.13E−05 |
| miR-27b,miR-92 | −2.18 | 7.68 | 0.77 | 9.86 | 1.27 | 0.94 | 1.66E−05 |
| miR-30e-3p,miR-422a | −1.83 | 1.28 | 0.83 | 3.10 | 1.08 | 0.94 | 4.76E−05 |
| miR-30b,miR-422a | −1.93 | −4.91 | 0.80 | −2.98 | 1.20 | 0.94 | 5.37E−05 |
| miR-142-3p,miR-92 | −2.25 | 2.26 | 0.87 | 4.51 | 1.44 | 0.94 | 5.77E−05 |
| miR-27a,miR-422a | −2.58 | −4.97 | 0.68 | −2.39 | 1.38 | 0.94 | 2.89E−06 |
| miR-142-5p,miR-342 | −1.93 | −1.26 | 0.91 | 0.67 | 0.86 | 0.94 | 4.69E−06 |
| miR-142-5p,miR-223 | −1.36 | 6.63 | 0.48 | 7.99 | 0.71 | 0.94 | 5.23E−06 |
| miR-27b,miR-378 | −1.91 | 2.12 | 0.77 | 4.03 | 1.02 | 0.94 | 1.15E−05 |
| miR-186,miR-27a | 1.30 | 1.01 | 0.43 | −0.29 | 0.75 | 0.94 | 1.35E−05 |
| miR-106b,miR-324-3p | −1.12 | −3.42 | 0.73 | −2.30 | 0.40 | 0.94 | 2.00E−05 |
| miR-34a,miR-518b | −2.55 | −3.39 | 1.40 | −0.84 | 1.21 | 0.94 | 2.14E−05 |
| miR-27a,miR-92 | −2.20 | 4.60 | 0.74 | 6.80 | 1.42 | 0.94 | 4.48E−05 |
| miR-30a-3p,miR-422a | −1.73 | 0.70 | 0.66 | 2.43 | 1.09 | 0.94 | 5.00E−05 |
| miR-181d,miR-29b | 2.55 | −2.09 | 1.08 | −4.63 | 0.95 | 0.93 | 5.26E−07 |
| miR-15b,miR-191 | −0.93 | 1.24 | 0.35 | 2.17 | 0.47 | 0.93 | 4.61E−06 |
| miR-192,miR-422a | −1.89 | −2.83 | 0.79 | −0.94 | 1.09 | 0.93 | 2.82E−05 |
| miR-422a,miR-576 | 2.39 | −1.56 | 0.78 | −3.95 | 1.64 | 0.93 | 8.46E−05 |
| miR-30c,miR-422a | −1.90 | −5.04 | 0.77 | −3.14 | 1.25 | 0.93 | 8.81E−05 |
| miR-142-3p,miR-145 | −1.76 | −6.14 | 0.57 | −4.38 | 0.92 | 0.93 | 4.05E−06 |
| miR-142-3p,miR-181d | −2.12 | −5.53 | 0.75 | −3.42 | 1.06 | 0.93 | 3.17E−06 |
| miR-181d,miR-27b | 2.09 | 0.11 | 0.84 | −1.98 | 1.00 | 0.93 | 3.56E−06 |
| miR-142-5p,miR-186 | −1.49 | 0.86 | 0.65 | 2.35 | 0.77 | 0.93 | 1.10E−05 |
| miR-150,miR-29c | 1.76 | −1.95 | 0.85 | −3.71 | 0.88 | 0.93 | 1.55E−05 |
| miR-200c,miR-422a | −2.20 | −0.58 | 1.17 | 1.62 | 1.04 | 0.93 | 1.71E−05 |
| miR-185,miR-92 | −1.81 | 6.44 | 0.69 | 8.25 | 1.07 | 0.93 | 2.49E−05 |
| miR-148a,miR-422a | −2.03 | −3.64 | 0.93 | −1.61 | 1.16 | 0.93 | 3.45E−05 |
| miR-34a,miR-422a | −2.77 | −0.32 | 1.74 | 2.46 | 1.23 | 0.93 | 3.79E−05 |
| miR-32,miR-422a | −2.56 | 1.56 | 1.20 | 4.12 | 1.51 | 0.93 | 5.27E−05 |
| miR-214,miR-566 | −2.28 | −0.09 | 1.19 | 2.19 | 1.29 | 0.93 | 5.85E−05 |
| miR-206,miR-422a | −2.31 | 0.68 | 1.17 | 2.99 | 1.33 | 0.93 | 6.05E−05 |
| miR-214,miR-518b | −2.84 | −3.36 | 1.54 | −0.52 | 1.65 | 0.93 | 8.68E−05 |
| miR-142-3p,miR-320 | −1.85 | 0.28 | 0.77 | 2.13 | 1.23 | 0.93 | 1.04E−04 |
| miR-331,miR-422a | −1.61 | −1.29 | 0.67 | 0.33 | 1.48 | 0.93 | 1.41E−04 |
| miR-26b,miR-422a | −1.86 | −6.33 | 0.76 | −4.48 | 1.07 | 0.92 | 2.36E−05 |
| miR-142-5p,miR-345 | −1.86 | −0.71 | 1.01 | 1.15 | 0.91 | 0.92 | 2.44E−05 |
| miR-27b,miR-324-3p | −1.55 | −0.58 | 0.80 | 0.97 | 0.86 | 0.92 | 5.10E−05 |
| miR-30a-5p,miR-30e-5p | 1.03 | −0.95 | 0.52 | −1.98 | 0.48 | 0.92 | 1.13E−05 |
| miR-29b,miR-92 | −2.78 | 9.83 | 1.08 | 12.60 | 1.56 | 0.92 | 1.64E−05 |
| miR-191,miR-27a | 1.38 | −0.29 | 0.71 | −1.66 | 0.67 | 0.92 | 1.72E−05 |
| miR-140,miR-181d | −1.75 | −1.54 | 0.74 | 0.22 | 1.04 | 0.92 | 3.67E−05 |
| miR-422a,miR-660 | 1.80 | 4.33 | 0.57 | 2.53 | 1.15 | 0.92 | 3.75E−05 |
| miR-126,miR-181a | −1.69 | −5.80 | 1.08 | −4.12 | 0.74 | 0.92 | 4.09E−05 |
| miR-126*,miR-378 | −1.52 | −2.26 | 0.58 | −0.74 | 0.97 | 0.92 | 5.24E−05 |
| miR-15a,miR-181d | −1.77 | 0.88 | 0.89 | 2.65 | 1.02 | 0.92 | 5.46E−05 |
| let-7f,miR-422a | −2.24 | −2.38 | 0.84 | −0.14 | 1.44 | 0.92 | 5.53E−05 |
| miR-181a,miR-27b | 1.91 | 1.00 | 1.12 | −0.92 | 1.01 | 0.92 | 6.84E−05 |
| miR-29b,miR-324-3p | −2.12 | 1.59 | 1.14 | 3.70 | 1.24 | 0.92 | 8.87E−05 |
| miR-132,miR-30e-5p | 1.37 | 4.22 | 0.92 | 2.85 | 0.66 | 0.92 | 9.53E−05 |
| miR-214,miR-422b | −2.22 | 0.40 | 0.91 | 2.61 | 1.48 | 0.92 | 1.07E−04 |
| miR-140,miR-378 | −1.59 | 0.70 | 0.75 | 2.29 | 1.03 | 0.92 | 1.17E−04 |
| miR-29b,miR-30a-5p | −1.83 | 6.52 | 0.79 | 8.35 | 1.22 | 0.92 | 1.18E−04 |
| let-7a,miR-422a | −1.87 | −4.21 | 0.60 | −2.34 | 1.57 | 0.92 | 1.70E−04 |
| miR-142-5p,miR-191 | −1.57 | 2.16 | 0.47 | 3.73 | 0.89 | 0.92 | 8.01E−06 |
| miR-24,miR-27b | 1.24 | −3.94 | 0.45 | −5.19 | 0.78 | 0.92 | 3.87E−05 |
| miR-126*,miR-181d | −1.69 | −4.50 | 0.67 | −2.81 | 0.98 | 0.92 | 2.63E−05 |
| miR-181d,miR-30e-5p | 1.88 | 3.46 | 0.92 | 1.59 | 1.02 | 0.92 | 3.03E−05 |
| miR-142-3p,miR-191 | −1.42 | −2.06 | 0.52 | −0.64 | 0.87 | 0.92 | 3.24E−05 |
| miR-181c,miR-29b | 2.34 | 1.31 | 1.43 | −1.03 | 1.09 | 0.92 | 3.99E−05 |
| miR-181d,miR-27a | 2.07 | 3.19 | 0.98 | 1.12 | 1.19 | 0.92 | 4.24E−05 |
| miR-148b,miR-378 | −1.46 | 2.14 | 0.69 | 3.61 | 0.84 | 0.92 | 4.39E−05 |

TABLE 15-continued microRNA biomarker pairs - benign lung and lung cancer patient sera.

| miRNA Biomarker Pair | Benign mean - Cancer mean | Benign mean | Benign SD | Cancer mean | Cancer SD | AUC ROC | Benign vs Cancer Assoc. |
|---|---|---|---|---|---|---|---|
| miR-15a,miR-320 | −1.51 | 6.69 | 0.74 | 8.20 | 0.89 | 0.92 | 6.22E−05 |
| miR-199a*,miR-422a | −2.05 | −4.20 | 0.81 | −2.15 | 1.32 | 0.92 | 6.35E−05 |
| miR-146a,miR-27a | 1.28 | −1.02 | 0.92 | −2.30 | 0.49 | 0.92 | 6.63E−05 |
| miR-142-5p,miR-181a | −2.12 | −2.20 | 1.02 | −0.08 | 1.27 | 0.92 | 6.83E−05 |
| miR-15a,miR-486 | −1.97 | 7.95 | 0.94 | 9.91 | 1.19 | 0.92 | 6.85E−05 |
| miR-27b,miR-342 | −1.70 | −0.06 | 0.81 | 1.64 | 1.03 | 0.92 | 7.00E−05 |
| miR-181a,miR-27a | 1.93 | 4.07 | 1.11 | 2.14 | 1.07 | 0.92 | 8.57E−05 |
| let-7g,miR-342 | −1.21 | −3.67 | 0.45 | −2.47 | 0.81 | 0.92 | 9.17E−05 |
| miR-29b,miR-345 | −2.02 | 2.90 | 0.98 | 4.92 | 1.27 | 0.92 | 1.00E−04 |
| let-7e,miR-422a | −1.98 | −5.35 | 0.65 | −3.37 | 1.47 | 0.92 | 1.91E−04 |
| miR-29b,miR-422b | −2.15 | 1.00 | 0.80 | 3.15 | 1.25 | 0.91 | 1.89E−05 |
| miR-142-3p,miR-202 | −1.70 | −6.03 | 0.93 | −4.33 | 0.82 | 0.91 | 2.31E−05 |
| miR-214,miR-422a | −3.10 | −0.29 | 1.16 | 2.81 | 1.86 | 0.91 | 2.84E−05 |
| miR-142-5p,miR-145 | −1.90 | −1.92 | 0.65 | −0.02 | 1.18 | 0.91 | 3.02E−05 |
| miR-422a,miR-497 | 1.95 | 0.38 | 0.91 | −1.57 | 1.11 | 0.91 | 3.66E−05 |
| miR-29b,miR-433 | −2.37 | −0.95 | 1.31 | 1.42 | 1.20 | 0.91 | 3.72E−05 |
| miR-140,miR-92 | −1.89 | 6.25 | 0.75 | 8.14 | 1.21 | 0.91 | 6.62E−05 |
| miR-142-5p,miR-92 | −2.40 | 6.47 | 0.93 | 8.87 | 1.55 | 0.91 | 6.67E−05 |
| miR-142-3p,miR-181b | −1.70 | −5.75 | 0.74 | −4.06 | 1.07 | 0.91 | 7.16E−05 |
| miR-30e-5p,miR-486 | −2.07 | 3.61 | 1.02 | 5.67 | 1.24 | 0.91 | 7.27E−05 |
| miR-196b,miR-422a | −2.13 | 0.90 | 0.95 | 3.04 | 1.37 | 0.91 | 9.10E−05 |
| miR-222,miR-29b | 1.83 | −4.92 | 0.83 | −6.75 | 1.18 | 0.91 | 1.01E−04 |
| miR-142-3p,miR-518b | −2.38 | −10.39 | 1.09 | −8.01 | 1.55 | 0.91 | 1.13E−04 |
| miR-29b,miR-30d | −1.93 | 5.34 | 0.85 | 7.27 | 1.30 | 0.91 | 1.37E−04 |
| miR-29b,miR-361 | −1.82 | 1.55 | 1.01 | 3.37 | 1.13 | 0.91 | 1.60E−04 |
| miR-342,miR-34a | 2.05 | −1.52 | 1.40 | −3.58 | 1.14 | 0.91 | 2.16E−04 |
| miR-106b,miR-181d | −1.62 | −2.95 | 1.31 | −1.33 | 0.94 | 0.91 | 2.45E−04 |
| miR-340,miR-92 | −1.95 | 5.86 | 0.84 | 7.81 | 1.34 | 0.91 | 1.59E−04 |
| miR-486,miR-7 | 1.41 | −8.20 | 0.66 | −9.61 | 0.96 | 0.91 | 1.82E−04 |
| miR-21,miR-422a | −1.95 | −7.30 | 0.73 | −5.35 | 1.15 | 0.91 | 2.33E−05 |
| miR-106b,miR-92 | −1.76 | 4.84 | 0.84 | 6.60 | 0.95 | 0.91 | 2.59E−05 |
| let-7i,miR-92 | −1.71 | 5.00 | 0.71 | 6.72 | 0.99 | 0.91 | 2.73E−05 |
| miR-101,miR-486 | −1.80 | 6.05 | 0.89 | 7.84 | 0.96 | 0.91 | 3.00E−05 |
| miR-181a,miR-29b | 2.16 | −1.41 | 1.11 | −3.57 | 1.13 | 0.91 | 3.14E−05 |
| miR-142-5p,miR-150 | −2.36 | 2.10 | 1.05 | 4.46 | 1.35 | 0.91 | 3.42E−05 |
| miR-142-3p,miR-342 | −1.79 | −5.48 | 0.47 | −3.69 | 1.17 | 0.91 | 3.57E−05 |
| miR-29b,miR-518b | −2.85 | −2.74 | 1.36 | 0.11 | 1.71 | 0.91 | 6.39E−05 |
| miR-142-5p,miR-181d | −2.26 | −1.32 | 1.23 | 0.94 | 1.28 | 0.91 | 7.39E−05 |
| miR-193b,miR-29b | 2.23 | −0.61 | 0.99 | −2.84 | 1.42 | 0.91 | 8.62E−05 |
| miR-146b,miR-422a | −1.63 | −4.11 | 0.45 | −2.48 | 1.17 | 0.91 | 9.89E−05 |
| miR-15b,miR-92 | −1.76 | 5.55 | 0.66 | 7.31 | 1.20 | 0.91 | 1.03E−04 |
| miR-142-5p,miR-23a | −1.26 | −0.60 | 0.81 | 0.66 | 0.65 | 0.91 | 1.10E−04 |
| miR-27a,miR-378 | −1.91 | −0.95 | 0.86 | 0.95 | 1.24 | 0.91 | 1.11E−04 |
| miR-197,miR-29b | 1.78 | −3.13 | 0.89 | −4.91 | 1.31 | 0.91 | 2.93E−04 |
| miR-342,miR-374 | 1.46 | 1.88 | 0.58 | 0.42 | 1.16 | 0.91 | 2.93E−04 |
| miR-422a,miR-487b | 1.83 | −1.05 | 0.92 | −2.88 | 1.32 | 0.91 | 2.93E−04 |
| miR-142-3p,miR-99b | −1.45 | −7.52 | 0.62 | −6.08 | 1.25 | 0.91 | 2.93E−04 |
| miR-29b,miR-320 | −2.31 | 7.94 | 1.09 | 10.24 | 1.66 | 0.91 | 2.93E−04 |
| miR-340,miR-378 | −1.65 | 0.31 | 0.82 | 1.96 | 1.22 | 0.91 | 2.93E−04 |
| miR-29b,miR-486 | −2.80 | 9.10 | 1.25 | 11.90 | 1.89 | 0.90 | 1.40E−04 |
| miR-23a,miR-422a | −1.52 | −2.50 | 0.55 | −0.98 | 1.17 | 0.90 | 3.13E−04 |
| miR-222,miR-27b | 1.24 | −2.70 | 0.88 | −3.95 | 0.89 | 0.90 | 3.20E−04 |
| miR-142-5p,miR-24 | −1.50 | 2.74 | 0.79 | 4.24 | 0.81 | 0.90 | 4.46E−05 |
| miR-148b,miR-181d | −1.63 | −0.09 | 0.83 | 1.54 | 0.93 | 0.90 | 5.60E−05 |
| miR-29b,miR-342 | −2.26 | 2.07 | 1.00 | 4.33 | 1.38 | 0.90 | 5.67E−05 |
| miR-152,miR-422a | −1.68 | −1.45 | 0.78 | 0.23 | 1.02 | 0.90 | 6.17E−05 |
| miR-7,miR-92 | −1.32 | 8.96 | 0.65 | 10.28 | 0.80 | 0.90 | 8.09E−05 |
| miR-210,miR-422a | −1.25 | −1.73 | 0.61 | −0.48 | 0.80 | 0.90 | 1.26E−04 |
| let-7c,miR-422a | −2.01 | −1.44 | 0.80 | 0.57 | 1.38 | 0.90 | 1.27E−04 |
| miR-27b,miR-518b | −2.37 | −4.97 | 1.30 | −2.60 | 1.49 | 0.90 | 1.66E−04 |
| miR-145,miR-374 | 1.43 | 2.54 | 0.67 | 1.12 | 0.96 | 0.90 | 1.70E−04 |
| miR-27a,miR-324-3p | −1.57 | −3.66 | 0.73 | −2.09 | 1.06 | 0.90 | 1.72E−04 |
| miR-140,miR-186 | −0.98 | 0.64 | 0.59 | 1.62 | 0.60 | 0.90 | 1.99E−04 |
| miR-185,miR-486 | −1.87 | 5.72 | 1.00 | 7.59 | 1.23 | 0.90 | 2.13E−04 |
| miR-422a,miR-496 | 2.64 | −1.66 | 1.16 | −4.30 | 1.93 | 0.90 | 2.83E−04 |
| miR-181a,miR-199a* | 1.40 | 3.30 | 0.75 | 1.90 | 0.99 | 0.90 | 3.49E−04 |
| miR-422a,miR-432 | 2.22 | 0.37 | 1.04 | −1.85 | 1.70 | 0.90 | 3.51E−04 |
| miR-181d,miR-23b | 1.40 | −2.13 | 0.50 | −3.53 | 0.92 | 0.90 | 6.23E−05 |
| miR-125b,miR-422a | −2.10 | −0.93 | 1.09 | 1.17 | 1.30 | 0.90 | 1.23E−04 |
| miR-145,miR-29b | 2.08 | −1.56 | 0.93 | −3.63 | 1.39 | 0.90 | 1.38E−04 |
| miR-142-5p,miR-146a | −1.47 | 2.90 | 1.12 | 4.37 | 0.71 | 0.90 | 2.51E−04 |
| miR-126,miR-320 | −1.57 | 0.89 | 0.84 | 2.46 | 1.10 | 0.90 | 3.57E−04 |
| miR-191,miR-374 | 1.09 | −1.54 | 0.53 | −2.63 | 0.59 | 0.90 | 2.81E−05 |

TABLE 15-continued microRNA biomarker pairs - benign lung and lung cancer patient sera.

| miRNA Biomarker Pair | Benign mean - Cancer mean | Benign mean | Benign SD | Cancer mean | Cancer SD | AUC ROC | Benign vs Cancer Assoc. |
|---|---|---|---|---|---|---|---|
| miR-126,miR-145 | −1.47 | −5.53 | 0.95 | −4.06 | 0.72 | 0.90 | 7.71E−05 |
| miR-150,miR-29b | 2.66 | −5.54 | 1.25 | −8.19 | 1.72 | 0.90 | 1.20E−04 |
| miR-133b,miR-422a | −2.16 | 0.37 | 1.13 | 2.53 | 1.34 | 0.90 | 1.22E−04 |
| miR-142-5p,miR-324-3p | −1.76 | −1.79 | 0.94 | −0.03 | 1.09 | 0.90 | 1.42E−04 |
| miR-27b,miR-345 | −1.69 | 0.49 | 1.14 | 2.18 | 0.88 | 0.90 | 1.50E−04 |
| miR-374,miR-378 | −1.62 | 0.30 | 0.60 | 1.92 | 1.17 | 0.90 | 1.73E−04 |
| let-7b,miR-422a | −1.88 | −5.06 | 0.82 | −3.18 | 1.31 | 0.90 | 1.75E−04 |
| miR-346,miR-432* | −1.63 | −2.73 | 1.11 | −1.09 | 0.91 | 0.90 | 2.34E−04 |
| miR-142-5p,miR-518b | −2.52 | −6.17 | 1.57 | −3.65 | 1.54 | 0.90 | 2.37E−04 |
| miR-142-3p,miR-328 | −1.56 | −5.46 | 0.71 | −3.90 | 1.14 | 0.90 | 3.07E−04 |
| miR-181a,miR-374 | 1.64 | 2.82 | 0.91 | 1.18 | 1.12 | 0.90 | 3.08E−04 |
| let-7g,miR-181d | −1.53 | −3.73 | 0.75 | −2.20 | 1.10 | 0.90 | 3.15E−04 |
| miR-106b,miR-378 | −1.46 | −0.71 | 1.09 | 0.75 | 0.81 | 0.90 | 3.79E−04 |
| miR-30a-5p,miR-422a | −1.36 | −6.19 | 0.55 | −4.83 | 1.11 | 0.90 | 4.17E−04 |
| miR-339,miR-422a | −1.67 | −0.98 | 0.67 | 0.69 | 1.30 | 0.90 | 4.18E−04 |
| let-7i,miR-378 | −1.42 | −0.55 | 0.87 | 0.87 | 0.96 | 0.90 | 4.18E−04 |
| miR-142-5p,miR-93 | −1.56 | 3.09 | 0.85 | 4.65 | 1.21 | 0.90 | 4.18E−04 |
| miR-224,miR-422a | −1.44 | 0.66 | 0.73 | 2.10 | 1.27 | 0.90 | 4.18E−04 |
| miR-30e-5p,miR-378 | −1.71 | −1.23 | 0.95 | 0.49 | 1.03 | 0.89 | 1.22E−04 |
| miR-576,miR-92 | −2.05 | 11.01 | 1.14 | 13.06 | 1.33 | 0.89 | 2.22E−04 |
| miR-142-5p,miR-423 | −1.56 | −2.81 | 0.88 | −1.25 | 1.19 | 0.89 | 4.54E−04 |
| miR-320,miR-660 | 1.03 | −3.27 | 0.53 | −4.29 | 0.88 | 0.89 | 4.55E−04 |
| miR-181a,miR-340 | 1.67 | 2.81 | 0.74 | 1.14 | 1.03 | 0.89 | 6.15E−05 |
| miR-23a,miR-27b | 1.05 | −0.60 | 0.62 | −1.65 | 0.59 | 0.89 | 1.12E−04 |
| miR-30a-5p,miR-92 | −0.98 | 3.38 | 0.56 | 4.36 | 0.58 | 0.89 | 1.30E−04 |
| miR-27a,miR-345 | −1.67 | −2.59 | 0.96 | −0.91 | 1.00 | 0.89 | 1.41E−04 |
| miR-29b,miR-382 | −2.17 | −0.25 | 1.35 | 1.92 | 1.24 | 0.89 | 1.55E−04 |
| miR-182,miR-422a | −1.65 | 1.67 | 1.10 | 3.32 | 0.92 | 0.89 | 1.94E−04 |
| miR-132,miR-27a | 1.57 | 3.95 | 1.04 | 2.38 | 0.89 | 0.89 | 2.18E−04 |
| miR-374,miR-92 | −1.92 | 5.85 | 0.79 | 7.77 | 1.39 | 0.89 | 2.19E−04 |
| miR-145,miR-340 | 1.45 | 2.53 | 0.71 | 1.08 | 1.00 | 0.89 | 2.33E−04 |
| miR-142-5p,miR-301 | −1.36 | −2.33 | 0.48 | −0.97 | 1.03 | 0.89 | 2.53E−04 |
| miR-185,miR-422a | −2.19 | −3.13 | 1.04 | −0.94 | 1.56 | 0.89 | 2.66E−04 |
| miR-132,miR-27b | 1.54 | 0.87 | 1.06 | −0.66 | 0.87 | 0.89 | 2.73E−04 |
| miR-126,miR-342 | −1.50 | −4.86 | 0.71 | −3.36 | 1.08 | 0.89 | 2.91E−04 |
| let-7i,miR-181d | −1.58 | −2.79 | 1.05 | −1.21 | 0.95 | 0.89 | 2.98E−04 |
| miR-15b,miR-181d | −1.63 | −2.24 | 0.96 | −0.61 | 1.08 | 0.89 | 3.21E−04 |
| miR-15b,miR-181a | −1.49 | −3.12 | 0.91 | −1.63 | 0.99 | 0.89 | 3.97E−04 |
| miR-197,miR-422a | −1.47 | −2.94 | 0.53 | −1.46 | 1.18 | 0.89 | 4.47E−04 |
| miR-142-3p,miR-486 | −2.31 | 1.54 | 1.28 | 3.84 | 1.66 | 0.89 | 4.62E−04 |
| miR-181a,miR-26a | 1.27 | 4.95 | 0.74 | 3.68 | 0.97 | 0.89 | 4.97E−04 |
| miR-130a,miR-320 | −1.20 | 2.78 | 0.57 | 3.98 | 0.97 | 0.89 | 4.98E−04 |
| miR-19a,miR-92 | −1.26 | 2.98 | 0.47 | 4.24 | 1.10 | 0.89 | 4.98E−04 |
| miR-143,miR-422a | −2.52 | −1.77 | 1.16 | 0.76 | 1.68 | 0.89 | 1.39E−04 |
| miR-191,miR-30b | 0.73 | −0.35 | 0.44 | −1.07 | 0.45 | 0.89 | 2.37E−04 |
| miR-126,miR-486 | −2.02 | 2.15 | 1.13 | 4.17 | 1.39 | 0.89 | 3.39E−04 |
| miR-422a,miR-98 | 2.06 | 0.35 | 0.77 | −1.71 | 1.67 | 0.89 | 5.23E−04 |
| miR-126*,miR-222 | −0.94 | −1.68 | 0.71 | −0.74 | 0.70 | 0.89 | 5.41E−04 |
| miR-191,miR-27b | 1.36 | −3.36 | 0.75 | −4.72 | 0.71 | 0.89 | 4.19E−05 |
| miR-181d,miR-340 | 1.81 | 1.93 | 0.86 | 0.11 | 1.07 | 0.89 | 5.66E−05 |
| miR-151,miR-27b | 1.09 | −0.79 | 0.49 | −1.88 | 0.71 | 0.89 | 9.90E−05 |
| miR-29c,miR-422a | −2.18 | −3.25 | 0.81 | −1.07 | 1.52 | 0.89 | 1.33E−04 |
| miR-21,miR-92 | −1.57 | 2.27 | 0.68 | 3.84 | 1.07 | 0.89 | 1.48E−04 |
| miR-29b,miR-326 | −2.36 | −2.27 | 1.32 | 0.09 | 1.45 | 0.89 | 1.56E−04 |
| miR-142-5p,miR-378 | −2.10 | 0.92 | 1.10 | 3.02 | 1.38 | 0.89 | 1.95E−04 |
| miR-181a,miR-26b | 1.20 | 5.43 | 0.61 | 4.24 | 0.80 | 0.89 | 2.06E−04 |
| miR-145,miR-27b | 1.68 | 0.72 | 1.05 | −0.96 | 1.00 | 0.89 | 2.13E−04 |
| miR-27b,miR-422b | −1.51 | −1.21 | 0.89 | 0.30 | 0.95 | 0.89 | 2.17E−04 |
| miR-186,miR-30e-5p | 1.10 | 1.28 | 0.79 | 0.18 | 0.57 | 0.89 | 2.21E−04 |
| miR-190,miR-422a | −1.61 | −0.06 | 0.86 | 1.54 | 1.14 | 0.89 | 3.79E−04 |
| miR-140,miR-222 | −1.03 | 1.28 | 0.63 | 2.31 | 0.73 | 0.89 | 5.68E−04 |
| miR-23b,miR-422a | −1.75 | 0.48 | 0.67 | 2.23 | 1.54 | 0.89 | 5.87E−04 |
| miR-181d,miR-496 | 2.13 | −3.44 | 1.14 | −5.57 | 1.67 | 0.89 | 5.91E−04 |
| miR-199a*,miR-92 | −1.67 | 5.37 | 0.90 | 7.04 | 1.35 | 0.89 | 5.91E−04 |
| miR-185,miR-324-3p | −1.17 | −1.82 | 0.73 | −0.64 | 0.87 | 0.89 | 5.92E−04 |
| miR-222,miR-422a | −1.26 | −4.60 | 0.78 | −3.34 | 1.02 | 0.89 | 5.92E−04 |
| miR-296,miR-422a | −1.45 | 0.19 | 0.37 | 1.65 | 1.35 | 0.89 | 5.92E−04 |
| miR-142-5p,miR-222 | −1.51 | 1.50 | 1.07 | 3.01 | 0.75 | 0.88 | 1.62E−04 |
| miR-24,miR-374 | 1.02 | −2.12 | 0.66 | −3.14 | 0.69 | 0.88 | 5.41E−04 |
| miR-125a,miR-142-3p | 1.44 | 5.58 | 0.66 | 4.14 | 1.22 | 0.88 | 6.43E−04 |
| miR-20a,miR-92 | −1.61 | 2.26 | 0.72 | 3.86 | 1.32 | 0.88 | 6.43E−04 |
| miR-27a,miR-93 | −1.37 | 1.21 | 0.63 | 2.58 | 1.22 | 0.88 | 6.43E−04 |
| miR-27a,miR-342 | −1.74 | −3.13 | 0.92 | −1.39 | 1.05 | 0.88 | 1.07E−04 |

TABLE 15-continued microRNA biomarker pairs - benign lung and lung cancer patient sera.

| miRNA Biomarker Pair | Benign mean - Cancer mean | Benign mean | Benign SD | Cancer mean | Cancer SD | AUC ROC | Benign vs Cancer Assoc. |
|---|---|---|---|---|---|---|---|
| miR-145,miR-27a | 1.71 | 3.79 | 0.98 | 2.08 | 1.06 | 0.88 | 1.78E−04 |
| miR-29b,miR-328 | −2.13 | 2.21 | 1.11 | 4.35 | 1.39 | 0.88 | 1.78E−04 |
| miR-29a,miR-422a | −2.26 | −5.00 | 0.77 | −2.74 | 1.67 | 0.88 | 1.93E−04 |
| miR-130a,miR-422a | −1.98 | −4.81 | 1.10 | −2.84 | 1.27 | 0.88 | 2.05E−04 |
| miR-18a,miR-422a | −1.66 | −2.52 | 0.63 | −0.86 | 1.21 | 0.88 | 2.08E−04 |
| miR-148b,miR-486 | −1.82 | 7.07 | 1.14 | 8.89 | 1.11 | 0.88 | 2.39E−04 |
| let-7f,miR-181d | −1.73 | −0.60 | 0.86 | 1.13 | 1.20 | 0.88 | 2.49E−04 |
| miR-214,miR-378 | −2.44 | 3.73 | 1.08 | 6.16 | 1.75 | 0.88 | 2.52E−04 |
| miR-126*,miR-181a | −1.54 | −5.38 | 1.06 | −3.84 | 0.90 | 0.88 | 2.98E−04 |
| miR-142-3p,miR-26b | −0.76 | −0.98 | 0.37 | −0.22 | 0.55 | 0.88 | 3.26E−04 |
| miR-126*,miR-24 | −0.92 | −0.44 | 0.52 | 0.49 | 0.63 | 0.88 | 3.42E−04 |
| let-7f,miR-181a | −1.59 | −1.48 | 0.70 | 0.11 | 1.19 | 0.88 | 3.44E−04 |
| miR-150,miR-27a | 2.17 | −0.23 | 1.16 | −2.40 | 1.52 | 0.88 | 3.58E−04 |
| miR-181d,miR-199a* | 1.54 | 2.42 | 0.75 | 0.88 | 1.12 | 0.88 | 3.63E−04 |
| miR-142-3p,miR-345 | −1.72 | −4.93 | 1.19 | −3.21 | 1.05 | 0.88 | 3.91E−04 |
| miR-378,miR-497 | 1.28 | −3.64 | 0.80 | −4.91 | 0.84 | 0.88 | 3.98E−04 |
| miR-181d,miR-497 | 1.44 | −1.40 | 0.62 | −2.84 | 1.11 | 0.88 | 4.16E−04 |
| miR-32,miR-486 | −2.52 | 10.43 | 1.32 | 12.94 | 1.84 | 0.88 | 4.60E−04 |
| miR-191,miR-340 | 1.12 | −1.55 | 0.59 | −2.67 | 0.83 | 0.88 | 5.18E−04 |
| miR-181d,miR-21 | 1.45 | 5.52 | 0.77 | 4.06 | 1.09 | 0.88 | 5.49E−04 |
| miR-126,miR-202 | −1.45 | −5.42 | 0.86 | −3.97 | 1.04 | 0.88 | 5.71E−04 |
| miR-142-3p,miR-26a | −0.70 | −1.46 | 0.17 | −0.76 | 0.60 | 0.88 | 6.00E−04 |
| miR-130b,miR-29b | 1.92 | −3.50 | 1.11 | −5.41 | 1.40 | 0.88 | 6.01E−04 |
| miR-148a,miR-181d | −1.52 | −1.86 | 0.97 | −0.34 | 1.09 | 0.88 | 7.00E−04 |
| miR-15b,miR-24 | −0.87 | 1.82 | 0.61 | 2.69 | 0.62 | 0.88 | 7.00E−04 |
| miR-20a,miR-93 | −0.75 | −1.13 | 0.36 | −0.37 | 0.75 | 0.88 | 7.00E−04 |
| miR-142-5p,miR-193b | −2.00 | −2.80 | 1.09 | −0.81 | 1.61 | 0.88 | 7.02E−04 |
| miR-148b,miR-30d | −0.90 | 3.19 | 0.55 | 4.09 | 0.70 | 0.88 | 7.02E−04 |
| miR-346,miR-518b | −1.97 | −2.83 | 1.17 | −0.86 | 1.51 | 0.88 | 7.02E−04 |
| miR-192,miR-92 | −1.51 | 6.74 | 0.69 | 8.25 | 1.07 | 0.88 | 2.30E−04 |
| miR-126*,miR-486 | −1.88 | 2.57 | 1.01 | 4.45 | 1.27 | 0.88 | 2.70E−04 |
| miR-194,miR-29b | 1.64 | 0.30 | 1.13 | −1.34 | 1.50 | 0.88 | 7.62E−04 |
| miR-146a,miR-29b | 1.78 | −6.36 | 1.28 | −8.14 | 0.84 | 0.88 | 1.39E−04 |
| miR-181d,miR-374 | 1.79 | 1.94 | 0.79 | 0.15 | 1.25 | 0.88 | 1.93E−04 |
| miR-378,miR-660 | 1.13 | 0.31 | 0.57 | −0.82 | 0.77 | 0.88 | 2.23E−04 |
| miR-29b,miR-566 | −2.28 | 0.49 | 1.32 | 2.78 | 1.49 | 0.88 | 2.69E−04 |
| miR-10a,miR-422a | −1.73 | −0.32 | 0.86 | 1.41 | 1.22 | 0.88 | 2.80E−04 |
| miR-148a,miR-345 | −1.12 | −1.26 | 0.73 | −0.13 | 0.68 | 0.88 | 2.83E−04 |
| miR-142-3p,miR-222 | −1.33 | −2.72 | 0.82 | −1.39 | 0.85 | 0.88 | 3.12E−04 |
| miR-101,miR-422a | −2.12 | −2.80 | 1.06 | −0.69 | 1.52 | 0.88 | 3.40E−04 |
| miR-422a,miR-638 | 1.82 | 2.13 | 1.20 | 0.31 | 1.12 | 0.88 | 3.52E−04 |
| miR-140,miR-150 | −1.85 | 1.88 | 1.01 | 3.73 | 1.30 | 0.88 | 3.81E−04 |
| miR-27b,miR-486 | −2.24 | 6.96 | 1.22 | 9.19 | 1.60 | 0.88 | 4.24E−04 |
| miR-27a,miR-486 | −2.26 | 3.88 | 1.20 | 6.14 | 1.65 | 0.88 | 4.43E−04 |
| miR-210,miR-29b | 1.90 | −2.04 | 1.03 | −3.93 | 1.36 | 0.88 | 4.44E−04 |
| miR-185,miR-25 | −0.74 | 2.18 | 0.45 | 2.92 | 0.51 | 0.88 | 4.54E−04 |
| miR-126,miR-181b | −1.41 | −5.14 | 0.59 | −3.73 | 1.10 | 0.88 | 4.54E−04 |
| miR-142-5p,miR-486 | −2.45 | 5.75 | 1.28 | 8.20 | 1.81 | 0.88 | 4.75E−04 |
| miR-145,miR-199a* | 1.18 | 3.02 | 0.63 | 1.84 | 0.87 | 0.88 | 5.03E−04 |
| miR-139,miR-422a | −1.77 | −0.25 | 0.94 | 1.51 | 1.30 | 0.88 | 5.08E−04 |
| let-7i,miR-324-3p | −1.08 | −3.26 | 0.69 | −2.18 | 0.73 | 0.88 | 5.50E−04 |
| miR-193b,miR-214 | 2.36 | −0.01 | 1.20 | −2.37 | 1.80 | 0.88 | 5.83E−04 |
| miR-340,miR-342 | −1.48 | −1.87 | 0.86 | −0.38 | 1.12 | 0.88 | 7.46E−04 |
| miR-15a,miR-210 | −1.04 | 0.83 | 0.59 | 1.87 | 0.80 | 0.88 | 8.13E−04 |
| miR-130b,miR-422a | −1.33 | −3.14 | 0.87 | −1.80 | 1.04 | 0.88 | 8.29E−04 |
| miR-27a,miR-30a-5p | −1.23 | 1.22 | 0.77 | 2.44 | 0.99 | 0.88 | 8.29E−04 |
| miR-16,miR-422a | −2.12 | −11.72 | 1.15 | −9.60 | 1.84 | 0.88 | 8.30E−04 |
| miR-19a,miR-422a | −1.64 | −6.59 | 0.81 | −4.95 | 1.42 | 0.88 | 8.30E−04 |
| miR-32,miR-92 | −2.29 | 11.04 | 1.43 | 13.33 | 1.72 | 0.88 | 8.30E−04 |
| miR-34a,miR-422b | −1.92 | 0.37 | 1.60 | 2.29 | 1.16 | 0.88 | 8.30E−04 |
| miR-15a,miR-181a | −1.63 | 0.00 | 1.14 | 1.63 | 0.98 | 0.87 | 3.99E−04 |
| miR-27a,miR-301 | −1.17 | −4.20 | 0.54 | −3.04 | 0.89 | 0.87 | 4.40E−04 |
| miR-15b,miR-378 | −1.47 | 0.00 | 0.81 | 1.46 | 1.08 | 0.87 | 5.26E−04 |
| miR-34a,miR-566 | −1.95 | −0.12 | 1.34 | 1.83 | 1.31 | 0.87 | 6.89E−04 |
| let-7f,miR-518b | −1.99 | −5.45 | 1.12 | −3.46 | 1.52 | 0.87 | 7.38E−04 |
| miR-126*,miR-320 | −1.42 | 1.32 | 0.82 | 2.74 | 1.08 | 0.87 | 7.97E−04 |
| miR-222,miR-30e-5p | 1.13 | 0.64 | 0.62 | −0.48 | 0.70 | 0.87 | 1.61E−04 |
| miR-433,miR-487b | 1.41 | 0.21 | 0.76 | −1.20 | 0.94 | 0.87 | 2.34E−04 |
| miR-186,miR-29b | 1.73 | −4.36 | 1.05 | −6.09 | 1.10 | 0.87 | 2.75E−04 |
| miR-27b,miR-326 | −1.54 | −4.50 | 0.89 | −2.97 | 1.01 | 0.87 | 2.79E−04 |
| miR-181d,miR-214 | 2.71 | −1.49 | 1.26 | −4.20 | 2.00 | 0.87 | 3.53E−04 |
| miR-17-5p,miR-27a | 1.20 | 1.60 | 0.52 | 0.39 | 0.93 | 0.87 | 4.28E−04 |
| let-7d,miR-422a | −1.76 | −2.94 | 0.73 | −1.18 | 1.39 | 0.87 | 4.84E−04 |

TABLE 15-continued microRNA biomarker pairs - benign lung and lung cancer patient sera.

| miRNA Biomarker Pair | Benign mean - Cancer mean | Benign mean | Benign SD | Cancer mean | Cancer SD | AUC ROC | Benign vs Cancer Assoc. |
|---|---|---|---|---|---|---|---|
| miR-27a,miR-518b | −2.33 | −8.04 | 1.36 | −5.71 | 1.68 | 0.87 | 5.44E−04 |
| miR-27b,miR-320 | −1.79 | 5.70 | 1.01 | 7.49 | 1.31 | 0.87 | 5.51E−04 |
| miR-27b,miR-301 | −1.17 | −1.13 | 0.74 | 0.04 | 0.83 | 0.87 | 6.40E−04 |
| miR-106b,miR-486 | −1.81 | 4.12 | 1.11 | 5.93 | 1.31 | 0.87 | 6.68E−04 |
| miR-22,miR-422a | −1.40 | −3.12 | 0.82 | −1.72 | 1.04 | 0.87 | 6.77E−04 |
| miR-143,miR-181d | −2.01 | 0.01 | 1.45 | 2.03 | 1.32 | 0.87 | 7.39E−04 |
| miR-181d,miR-576 | 2.13 | −2.75 | 1.35 | −4.88 | 1.75 | 0.87 | 9.79E−04 |
| miR-142-5p,miR-30a-5p | −1.42 | 3.09 | 0.93 | 4.51 | 1.07 | 0.87 | 9.80E−04 |
| miR-19b,miR-92 | −1.08 | 1.86 | 0.53 | 2.94 | 1.02 | 0.87 | 9.80E−04 |
| miR-214,miR-483 | −1.93 | −0.55 | 1.07 | 1.38 | 1.76 | 0.87 | 9.80E−04 |
| miR-361,miR-422a | −1.52 | −1.25 | 0.76 | 0.27 | 1.53 | 0.87 | 9.80E−04 |
| miR-181a,miR-30b | 1.28 | 4.01 | 0.71 | 2.73 | 0.78 | 0.87 | 1.44E−04 |
| miR-486,miR-576 | 2.15 | −10.17 | 1.36 | −12.32 | 1.35 | 0.87 | 3.08E−04 |
| miR-146a,miR-340 | 1.02 | −2.29 | 0.70 | −3.31 | 0.63 | 0.87 | 4.14E−04 |
| miR-10b,miR-181a | −1.41 | 0.11 | 0.87 | 1.52 | 0.98 | 0.87 | 5.35E−04 |
| miR-195,miR-92 | −1.76 | 3.50 | 0.80 | 5.26 | 1.44 | 0.87 | 7.73E−04 |
| miR-27a,miR-423 | −1.36 | −4.68 | 0.71 | −3.31 | 1.16 | 0.87 | 1.06E−03 |
| miR-32,miR-378 | −1.98 | 5.56 | 1.14 | 7.54 | 1.60 | 0.87 | 1.06E−03 |
| miR-140,miR-324-3p | −1.25 | −2.01 | 0.89 | −0.76 | 0.66 | 0.86 | 2.34E−04 |
| miR-132,miR-140 | 1.25 | 2.30 | 1.07 | 1.05 | 0.46 | 0.86 | 2.73E−04 |
| miR-125b,miR-145 | −1.22 | 0.25 | 0.96 | 1.47 | 0.63 | 0.86 | 3.65E−04 |
| let-7i,miR-191 | −0.89 | 0.69 | 0.38 | 1.57 | 0.69 | 0.86 | 4.60E−04 |
| let-7g,miR-150 | −1.63 | −0.31 | 0.68 | 1.32 | 1.30 | 0.86 | 5.51E−04 |
| miR-132,miR-142-5p | 1.76 | 2.08 | 1.40 | 0.32 | 0.97 | 0.86 | 5.54E−04 |
| miR-142-3p,miR-24 | −1.36 | −1.48 | 0.72 | −0.12 | 1.03 | 0.86 | 6.24E−04 |
| miR-145,miR-15b | 1.27 | 2.84 | 0.68 | 1.57 | 0.97 | 0.86 | 6.72E−04 |
| miR-15b,miR-486 | −1.82 | 4.83 | 1.11 | 6.65 | 1.34 | 0.86 | 7.28E−04 |
| miR-340,miR-518b | −2.08 | −6.78 | 1.14 | −4.70 | 1.61 | 0.86 | 7.77E−04 |
| miR-34a,miR-378 | −2.16 | 3.70 | 1.62 | 5.86 | 1.39 | 0.86 | 8.17E−04 |
| miR-10b,miR-422a | −2.07 | −0.79 | 1.08 | 1.28 | 1.66 | 0.86 | 9.05E−04 |
| miR-200c,miR-202 | −1.35 | 0.72 | 0.52 | 2.07 | 1.18 | 0.86 | 1.07E−03 |
| miR-126,miR-324-3p | −1.32 | −5.39 | 0.74 | −4.07 | 1.07 | 0.86 | 1.09E−03 |
| miR-143,miR-186 | −1.24 | 2.20 | 0.67 | 3.43 | 1.07 | 0.86 | 1.15E−03 |
| miR-181d,miR-29a | 1.75 | 3.22 | 1.03 | 1.47 | 1.45 | 0.86 | 1.15E−03 |
| miR-145a,miR-126 | 1.15 | 4.96 | 0.77 | 3.81 | 0.92 | 0.86 | 1.16E−03 |
| miR-126*,miR-422b | −1.19 | −5.59 | 0.69 | −4.40 | 0.98 | 0.86 | 1.16E−03 |
| miR-146b,miR-27b | 0.89 | −2.22 | 0.51 | −3.11 | 0.75 | 0.86 | 1.16E−03 |
| miR-148b,miR-210 | −0.97 | −0.23 | 0.52 | 0.74 | 0.87 | 0.86 | 1.16E−03 |
| miR-32,miR-320 | −1.89 | 9.16 | 0.90 | 11.05 | 1.81 | 0.86 | 1.16E−03 |
| miR-422a,miR-550 | 1.83 | −1.65 | 1.21 | −3.49 | 1.43 | 0.86 | 1.16E−03 |
| miR-486,miR-660 | 1.48 | −4.52 | 0.90 | −6.00 | 0.90 | 0.86 | 2.10E−04 |
| miR-142-3p,miR-422b | −1.62 | −6.63 | 0.77 | −5.01 | 1.17 | 0.86 | 3.09E−04 |
| miR-30d,miR-92 | −0.91 | 4.59 | 0.58 | 5.50 | 0.64 | 0.86 | 6.24E−04 |
| miR-140,miR-30a-5p | −0.91 | 2.87 | 0.47 | 3.78 | 0.73 | 0.86 | 8.56E−04 |
| miR-30e-5p,miR-422b | −1.45 | −4.56 | 0.93 | −3.10 | 1.08 | 0.86 | 8.94E−04 |
| miR-142-3p,miR-193b | −1.85 | −7.02 | 0.83 | −5.17 | 1.60 | 0.86 | 1.20E−03 |
| miR-24,miR-422a | −1.27 | −5.84 | 0.61 | −4.57 | 1.26 | 0.86 | 1.25E−03 |
| miR-320,miR-340 | 1.55 | −3.89 | 0.91 | −5.43 | 1.40 | 0.86 | 1.25E−03 |
| miR-140,miR-342 | −1.42 | −1.48 | 0.83 | −0.06 | 0.90 | 0.86 | 2.27E−04 |
| miR-126,miR-191 | −1.14 | −1.45 | 0.84 | −0.31 | 0.60 | 0.86 | 3.02E−04 |
| miR-126*,miR-191 | −0.99 | −1.02 | 0.76 | −0.03 | 0.52 | 0.86 | 3.80E−04 |
| miR-145,miR-26b | 0.98 | 5.16 | 0.58 | 4.17 | 0.68 | 0.86 | 4.15E−04 |
| miR-195,miR-486 | −1.82 | 2.78 | 0.77 | 4.60 | 1.41 | 0.86 | 4.23E−04 |
| miR-181a,miR-30c | 1.25 | 4.15 | 0.75 | 2.90 | 0.85 | 0.86 | 4.38E−04 |
| miR-145,miR-15a | 1.42 | −0.28 | 0.83 | −1.69 | 1.00 | 0.86 | 4.89E−04 |
| miR-145,miR-30c | 1.03 | 3.87 | 0.57 | 2.84 | 0.75 | 0.86 | 5.02E−04 |
| miR-125b,miR-181d | −1.58 | 0.85 | 1.19 | 2.44 | 0.94 | 0.86 | 5.61E−04 |
| miR-10a,miR-181d | −1.22 | 1.46 | 0.86 | 2.68 | 0.77 | 0.86 | 5.67E−04 |
| miR-181d,miR-200c | 1.65 | −1.24 | 1.01 | −2.89 | 1.17 | 0.86 | 5.91E−04 |
| let-7i,miR-181a | −1.44 | −3.67 | 0.92 | −2.23 | 1.02 | 0.86 | 6.99E−04 |
| miR-194,miR-422a | −1.46 | 0.60 | 1.13 | 2.06 | 0.90 | 0.86 | 7.72E−04 |
| miR-181c,miR-27b | 1.63 | 3.48 | 0.91 | 1.85 | 1.26 | 0.86 | 7.80E−04 |
| miR-30e-5p,miR-342 | −1.55 | −3.40 | 1.14 | −1.86 | 1.02 | 0.86 | 8.35E−04 |
| miR-142-3p,miR-425 | −1.25 | −6.75 | 0.93 | −5.50 | 0.82 | 0.86 | 8.45E−04 |
| let-7g,miR-191 | −0.84 | −0.25 | 0.58 | 0.59 | 0.58 | 0.86 | 8.47E−04 |
| miR-142-5p,miR-181b | −1.84 | −1.54 | 1.32 | 0.30 | 1.26 | 0.86 | 9.02E−04 |
| miR-145,miR-26a | 1.06 | 4.68 | 0.61 | 3.62 | 0.83 | 0.86 | 9.27E−04 |
| miR-155,miR-422a | −1.60 | −0.97 | 0.78 | 0.63 | 1.32 | 0.86 | 9.60E−04 |
| miR-346,miR-422a | −2.22 | 0.25 | 1.09 | 2.47 | 1.84 | 0.86 | 9.85E−04 |
| miR-22,miR-29b | 1.73 | −3.47 | 1.05 | −5.21 | 1.34 | 0.86 | 1.02E−03 |
| miR-148a,miR-222 | −0.80 | 0.96 | 0.53 | 1.76 | 0.60 | 0.86 | 1.05E−03 |
| miR-142-3p,miR-324-3p | −1.61 | −6.00 | 0.87 | −4.39 | 1.31 | 0.86 | 1.07E−03 |
| miR-320,miR-374 | 1.52 | −3.88 | 0.90 | −5.40 | 1.20 | 0.86 | 1.09E−03 |

TABLE 15-continued microRNA biomarker pairs - benign lung and lung cancer patient sera.

| miRNA Biomarker Pair | Benign mean - Cancer mean | Benign mean | Benign SD | Cancer mean | Cancer SD | AUC ROC | Benign vs Cancer Assoc. |
|---|---|---|---|---|---|---|---|
| miR-296,miR-29b | 1.67 | −0.07 | 0.81 | −1.74 | 1.41 | 0.86 | 1.09E−03 |
| miR-15b,miR-342 | −1.30 | −2.18 | 0.67 | −0.88 | 1.08 | 0.86 | 1.12E−03 |
| miR-32,miR-342 | −2.08 | 3.48 | 1.29 | 5.56 | 1.62 | 0.86 | 1.13E−03 |
| let-7c,miR-92 | −1.63 | 8.13 | 0.72 | 9.76 | 1.42 | 0.86 | 1.25E−03 |
| miR-346,miR-566 | −1.33 | 0.45 | 0.73 | 1.77 | 1.11 | 0.86 | 1.31E−03 |
| miR-422a,miR-425 | 1.18 | 0.57 | 0.95 | −0.61 | 0.78 | 0.86 | 1.33E−03 |
| let-7f,miR-342 | −1.40 | −0.54 | 0.80 | 0.86 | 1.29 | 0.86 | 1.36E−03 |
| miR-143,miR-223 | −1.11 | 7.96 | 0.44 | 9.07 | 1.03 | 0.86 | 1.36E−03 |
| miR-185,miR-186 | −0.90 | 0.83 | 0.56 | 1.74 | 0.76 | 0.86 | 1.36E−03 |
| miR-195,miR-422a | −2.14 | −6.07 | 1.32 | −3.93 | 1.82 | 0.86 | 1.36E−03 |
| miR-16,miR-92 | −1.74 | −2.15 | 0.62 | −0.41 | 1.47 | 0.86 | 7.20E−04 |
| miR-142-5p,miR-422b | −1.76 | −2.42 | 1.21 | −0.66 | 1.20 | 0.86 | 7.25E−04 |
| let-7b,miR-92 | −1.50 | 4.51 | 0.74 | 6.01 | 1.20 | 0.86 | 7.65E−04 |
| let-7e,miR-92 | −1.60 | 4.22 | 0.87 | 5.82 | 1.44 | 0.86 | 1.47E−03 |
| miR-27b,miR-296 | −1.10 | −2.09 | 0.44 | −0.99 | 1.01 | 0.86 | 1.47E−03 |
| miR-30d,miR-30e-5p | 1.10 | 0.26 | 0.72 | −0.83 | 0.64 | 0.85 | 2.38E−04 |
| miR-125a,miR-29b | 1.92 | −1.94 | 0.92 | −3.87 | 1.48 | 0.85 | 5.28E−04 |
| miR-202,miR-27b | 1.68 | 0.61 | 1.19 | −1.07 | 1.06 | 0.85 | 5.50E−04 |
| miR-143,miR-342 | −1.68 | 0.07 | 1.12 | 1.76 | 1.12 | 0.85 | 5.52E−04 |
| miR-140,miR-486 | −1.94 | 5.53 | 1.09 | 7.47 | 1.43 | 0.85 | 5.57E−04 |
| miR-202,miR-30e-5p | 1.47 | 3.96 | 0.87 | 2.49 | 1.06 | 0.85 | 5.68E−04 |
| miR-181b,miR-27b | 1.60 | 0.33 | 0.87 | −1.26 | 1.22 | 0.85 | 7.06E−04 |
| miR-155,miR-29b | 1.69 | −1.11 | 1.17 | −2.79 | 1.15 | 0.85 | 7.32E−04 |
| let-7f,miR-191 | −1.04 | 2.88 | 0.63 | 3.91 | 0.76 | 0.85 | 7.35E−04 |
| miR-126,miR-518b | −2.09 | −9.78 | 1.20 | −7.68 | 1.58 | 0.85 | 7.38E−04 |
| miR-150,miR-27b | 2.13 | −3.31 | 1.00 | −5.44 | 1.73 | 0.85 | 7.68E−04 |
| miR-191,miR-30c | 0.69 | −0.21 | 0.44 | −0.91 | 0.52 | 0.85 | 9.28E−04 |
| miR-196b,miR-342 | −1.29 | 2.74 | 0.88 | 4.04 | 0.94 | 0.85 | 1.02E−03 |
| miR-181d,miR-660 | 1.29 | 2.55 | 0.53 | 1.26 | 1.11 | 0.85 | 1.03E−03 |
| miR-148a,miR-92 | −1.65 | 5.93 | 0.88 | 7.58 | 1.36 | 0.85 | 1.11E−03 |
| miR-193b,miR-34a | 2.14 | 0.02 | 1.56 | −2.12 | 1.50 | 0.85 | 1.11E−03 |
| miR-496,miR-518b | −2.39 | −1.41 | 1.42 | 0.98 | 1.94 | 0.85 | 1.32E−03 |
| miR-23a,miR-29b | 1.55 | −2.78 | 0.96 | −4.33 | 1.24 | 0.85 | 1.33E−03 |
| miR-142-5p,miR-30d | −1.49 | 1.88 | 0.93 | 3.36 | 1.18 | 0.85 | 1.34E−03 |
| let-7f,miR-92 | −1.86 | 7.19 | 1.02 | 9.05 | 1.56 | 0.85 | 1.36E−03 |
| miR-140,miR-145 | −1.39 | −2.14 | 0.89 | −0.75 | 1.12 | 0.85 | 1.52E−03 |
| miR-106a,miR-92 | −1.23 | 3.06 | 0.66 | 4.28 | 1.10 | 0.85 | 1.59E−03 |
| miR-17-5p,miR-422a | −1.38 | −3.37 | 0.67 | −1.99 | 1.41 | 0.85 | 1.59E−03 |
| miR-210,miR-30e-5p | 1.14 | 3.51 | 0.71 | 2.37 | 0.96 | 0.85 | 1.59E−03 |
| miR-151,miR-422a | −1.46 | −2.68 | 0.73 | −1.22 | 1.29 | 0.85 | 1.59E−03 |
| miR-193b,miR-30e-5p | 1.61 | 4.94 | 1.05 | 3.34 | 1.50 | 0.85 | 1.59E−03 |
| miR-21,miR-486 | −1.62 | 1.55 | 1.10 | 3.17 | 1.36 | 0.85 | 1.59E−03 |
| miR-221,miR-422a | −1.58 | −4.60 | 0.85 | −3.02 | 1.52 | 0.85 | 1.59E−03 |
| miR-27b,miR-423 | −1.34 | −1.60 | 0.79 | −0.27 | 1.22 | 0.85 | 1.59E−03 |
| miR-21,miR-378 | −1.30 | −3.28 | 0.82 | −1.98 | 1.08 | 0.85 | 1.72E−03 |
| miR-106b,miR-150 | −1.72 | 0.47 | 1.00 | 2.19 | 1.50 | 0.85 | 1.72E−03 |
| miR-126,miR-150 | −1.92 | −1.50 | 0.84 | 0.42 | 1.80 | 0.85 | 1.72E−03 |
| miR-186,miR-27b | 1.25 | −2.07 | 0.68 | −3.32 | 0.82 | 0.85 | 2.24E−04 |
| miR-145,miR-30b | 1.06 | 3.73 | 0.64 | 2.67 | 0.70 | 0.85 | 3.39E−04 |
| miR-150,miR-30e-5p | 1.97 | 0.04 | 1.03 | −1.93 | 1.40 | 0.85 | 3.44E−04 |
| miR-126,miR-422b | −1.35 | −6.02 | 0.62 | −4.67 | 1.01 | 0.85 | 3.99E−04 |
| miR-142-3p,miR-146a | −1.33 | −1.32 | 0.81 | 0.01 | 0.97 | 0.85 | 7.42E−04 |
| miR-29a,miR-342 | −1.42 | −3.16 | 0.93 | −1.74 | 1.01 | 0.85 | 7.53E−04 |
| miR-20a,miR-486 | −1.67 | 1.54 | 0.98 | 3.21 | 1.27 | 0.85 | 7.84E−04 |
| miR-140,miR-24 | −0.99 | 2.52 | 0.60 | 3.51 | 0.74 | 0.85 | 8.03E−04 |
| miR-15a,miR-191 | −1.08 | 4.36 | 0.71 | 5.44 | 0.78 | 0.85 | 8.29E−04 |
| miR-374,miR-518b | −2.05 | −6.79 | 1.15 | −4.74 | 1.62 | 0.85 | 9.49E−04 |
| miR-21,miR-345 | −1.07 | −4.91 | 0.73 | −3.85 | 0.76 | 0.85 | 9.58E−04 |
| miR-139,miR-181d | −1.25 | 1.53 | 0.92 | 2.78 | 0.86 | 0.85 | 9.92E−04 |
| miR-125b,miR-150 | −1.68 | 4.27 | 1.04 | 5.95 | 1.30 | 0.85 | 1.08E−03 |
| miR-126*,miR-342 | −1.36 | −4.44 | 0.76 | −3.08 | 1.09 | 0.85 | 1.10E−03 |
| let-7c,miR-181d | −1.50 | 0.34 | 1.01 | 1.84 | 1.11 | 0.85 | 1.10E−03 |
| miR-193b,miR-27b | 1.80 | 1.60 | 1.12 | −0.21 | 1.41 | 0.85 | 1.16E−03 |
| miR-30b,miR-92 | −1.55 | 4.66 | 0.96 | 6.22 | 1.22 | 0.85 | 1.16E−03 |
| miR-181a,miR-30e-5p | 1.73 | 4.34 | 1.46 | 2.61 | 1.08 | 0.85 | 1.29E−03 |
| miR-17-5p,miR-29b | 1.70 | −3.74 | 1.26 | −5.44 | 1.22 | 0.85 | 1.30E−03 |
| miR-140,miR-202 | −1.38 | −2.03 | 0.89 | −0.66 | 1.08 | 0.85 | 1.36E−03 |
| miR-142-3p,miR-301 | −1.21 | −6.55 | 0.76 | −5.33 | 0.98 | 0.85 | 1.44E−03 |
| miR-181b,miR-27a | 1.65 | 3.41 | 1.08 | 1.76 | 1.33 | 0.85 | 1.67E−03 |
| miR-142-5p,miR-181c | −1.75 | −4.60 | 1.17 | −2.85 | 1.43 | 0.85 | 1.86E−03 |
| miR-148b,miR-320 | −1.31 | 5.76 | 0.80 | 7.07 | 1.15 | 0.85 | 1.87E−03 |
| let-7f,miR-145 | −1.37 | −1.20 | 0.81 | 0.17 | 1.22 | 0.85 | 1.87E−03 |
| miR-126*,miR-296 | −0.74 | −6.47 | 0.29 | −5.73 | 0.81 | 0.85 | 1.87E−03 |

TABLE 15-continued microRNA biomarker pairs - benign lung and lung cancer patient sera.

| miRNA Biomarker Pair | Benign mean - Cancer mean | Benign mean | Benign SD | Cancer mean | Cancer SD | AUC ROC | Benign vs Cancer Assoc. |
|---|---|---|---|---|---|---|---|
| miR-181d,miR-339 | 1.15 | −0.81 | 0.76 | −1.96 | 1.07 | 0.85 | 1.87E-03 |
| miR-20a,miR-422a | −1.94 | −7.31 | 0.98 | −5.37 | 1.81 | 0.85 | 1.87E-03 |
| miR-26a,miR-92 | −1.55 | 3.72 | 0.91 | 5.27 | 1.37 | 0.85 | 1.87E-03 |
| miR-432,miR-92 | −1.85 | 9.20 | 1.20 | 11.05 | 1.55 | 0.85 | 1.87E-03 |
| miR-487b,miR-92 | −1.84 | 10.59 | 1.11 | 12.43 | 1.77 | 0.85 | 1.87E-03 |
| let-7g,miR-92 | −1.67 | 4.06 | 0.80 | 5.73 | 1.40 | 0.85 | 1.07E-03 |
| miR-497,miR-518b | −1.70 | −3.45 | 0.77 | −1.75 | 1.46 | 0.85 | 1.13E-03 |
| miR-301,miR-340 | 0.91 | 2.94 | 0.44 | 2.03 | 0.87 | 0.85 | 2.02E-03 |
| miR-27b,miR-30a-5p | −1.23 | 4.29 | 0.74 | 5.52 | 0.90 | 0.84 | 6.98E-04 |
| miR-34a,miR-433 | −1.92 | −1.52 | 1.36 | 0.40 | 1.28 | 0.84 | 7.42E-04 |
| miR-17-5p,miR-27b | 1.17 | −1.48 | 0.58 | −2.65 | 0.94 | 0.84 | 7.66E-04 |
| miR-10b,miR-181d | −1.55 | 1.00 | 0.97 | 2.55 | 1.19 | 0.84 | 1.01E-03 |
| miR-27a,miR-422b | −1.59 | −4.29 | 1.06 | −2.69 | 1.19 | 0.84 | 1.07E-03 |
| miR-148b,miR-191 | −0.94 | 3.43 | 0.73 | 4.37 | 0.63 | 0.84 | 1.13E-03 |
| miR-181d,miR-34a | 2.21 | −1.47 | 1.58 | −3.68 | 1.60 | 0.84 | 1.19E-03 |
| miR-29b,miR-301 | −1.69 | 1.25 | 1.17 | 2.94 | 1.25 | 0.84 | 1.19E-03 |
| let-7e,miR-181d | −1.47 | −3.57 | 0.82 | −2.10 | 1.20 | 0.84 | 1.22E-03 |
| miR-191,miR-26a | 0.72 | 0.60 | 0.53 | −0.13 | 0.52 | 0.84 | 1.30E-03 |
| miR-142-5p,miR-328 | −1.71 | −1.24 | 1.14 | 0.47 | 1.32 | 0.84 | 1.38E-03 |
| miR-143,miR-92 | −2.15 | 7.80 | 1.23 | 9.95 | 1.82 | 0.84 | 1.61E-03 |
| miR-142-5p,miR-197 | −1.30 | −0.16 | 0.92 | 1.14 | 1.00 | 0.84 | 1.64E-03 |
| let-7c,miR-486 | −1.69 | 7.41 | 0.96 | 9.10 | 1.47 | 0.84 | 1.85E-03 |
| let-7c,miR-150 | −1.59 | 3.76 | 0.97 | 5.36 | 1.35 | 0.84 | 1.90E-03 |
| miR-27a,miR-30d | −1.29 | 0.01 | 0.71 | 1.30 | 1.15 | 0.84 | 1.98E-03 |
| miR-30b,miR-378 | −1.26 | −0.89 | 0.84 | 0.37 | 1.04 | 0.84 | 2.02E-03 |
| miR-181b,miR-200c | 1.28 | −0.97 | 0.79 | −2.25 | 1.10 | 0.84 | 2.11E-03 |
| miR-29c,miR-92 | −1.80 | 6.32 | 0.78 | 8.12 | 1.69 | 0.84 | 2.13E-03 |
| miR-30e-5p,miR-320 | −1.61 | 2.35 | 1.24 | 3.96 | 1.23 | 0.84 | 2.14E-03 |
| miR-186,miR-29c | 0.89 | −0.71 | 0.44 | −1.60 | 0.83 | 0.84 | 2.18E-03 |
| miR-193a,miR-29b | 1.30 | 1.57 | 0.54 | 0.27 | 1.32 | 0.84 | 2.18E-03 |
| miR-142-3p,miR-197 | −1.16 | −4.38 | 0.66 | −3.22 | 1.19 | 0.84 | 2.18E-03 |
| miR-27b,miR-361 | −1.06 | −0.65 | 0.74 | 0.41 | 0.99 | 0.84 | 2.18E-03 |
| miR-28,miR-422a | −1.72 | 0.32 | 0.82 | 2.04 | 1.69 | 0.84 | 2.18E-03 |
| let-7g,miR-378 | −1.37 | −1.49 | 0.59 | −0.12 | 1.31 | 0.84 | 2.18E-03 |
| miR-125b,miR-92 | −1.72 | 8.64 | 1.28 | 10.36 | 1.47 | 0.84 | 2.18E-03 |
| miR-140,miR-181b | −1.33 | −1.76 | 0.97 | −0.43 | 1.09 | 0.84 | 2.18E-03 |
| miR-142-3p,miR-181c | −1.59 | −8.81 | 0.89 | −7.21 | 1.45 | 0.84 | 2.18E-03 |
| miR-19a,miR-486 | −1.32 | 2.26 | 0.76 | 3.58 | 1.18 | 0.84 | 2.18E-03 |
| miR-26a,miR-342 | −1.09 | −4.01 | 0.58 | −2.93 | 0.99 | 0.84 | 2.18E-03 |
| miR-26b,miR-378 | −1.18 | −2.32 | 0.84 | −1.14 | 1.08 | 0.84 | 2.18E-03 |
| miR-30b,miR-342 | −1.09 | −3.07 | 0.66 | −1.98 | 1.00 | 0.84 | 2.18E-03 |
| miR-30d,miR-422a | −1.29 | −4.98 | 0.56 | −3.69 | 1.33 | 0.84 | 2.18E-03 |
| miR-331,miR-92 | −1.25 | 8.27 | 0.54 | 9.52 | 1.25 | 0.84 | 2.18E-03 |
| miR-376a,miR-422a | −1.94 | 1.11 | 1.34 | 3.05 | 1.71 | 0.84 | 2.18E-03 |
| miR-24,miR-29b | 1.72 | −6.30 | 1.00 | −8.02 | 1.30 | 0.84 | 7.91E-04 |
| miR-26a,miR-518b | −1.68 | −8.93 | 1.04 | −7.25 | 1.43 | 0.84 | 1.95E-03 |
| miR-126,miR-99b | −1.13 | −6.88 | 0.83 | −5.75 | 0.97 | 0.84 | 2.35E-03 |
| miR-142-5p,miR-202 | −1.85 | −1.81 | 1.36 | 0.04 | 1.08 | 0.84 | 4.28E-04 |
| miR-27b,miR-433 | −1.63 | −3.10 | 1.20 | −1.47 | 0.99 | 0.84 | 5.25E-04 |
| let-7i,miR-486 | −1.77 | 4.28 | 1.09 | 6.05 | 1.27 | 0.84 | 6.39E-04 |
| miR-16,miR-486 | −1.80 | −2.87 | 0.88 | −1.07 | 1.42 | 0.84 | 6.99E-04 |
| miR-29b,miR-331 | −1.70 | 1.58 | 1.02 | 3.28 | 1.27 | 0.84 | 7.68E-04 |
| miR-15a,miR-202 | −1.35 | 0.38 | 0.99 | 1.74 | 0.88 | 0.84 | 7.78E-04 |
| miR-27b,miR-328 | −1.53 | −0.04 | 1.00 | 1.49 | 1.10 | 0.84 | 8.21E-04 |
| miR-126,miR-24 | −1.07 | −0.87 | 0.63 | 0.20 | 0.81 | 0.84 | 8.50E-04 |
| miR-328,miR-34a | 1.83 | −1.54 | 1.24 | −3.38 | 1.31 | 0.84 | 8.93E-04 |
| miR-142-3p,miR-566 | −1.74 | −7.11 | 1.18 | −5.38 | 1.24 | 0.84 | 9.17E-04 |
| miR-29b,miR-324-5p | −1.77 | 0.43 | 0.96 | 2.20 | 1.42 | 0.84 | 9.66E-04 |
| miR-222,miR-27a | 1.26 | 0.37 | 0.90 | −0.89 | 0.92 | 0.84 | 1.17E-03 |
| miR-142-5p,miR-326 | −1.82 | −5.73 | 1.44 | −3.91 | 1.20 | 0.84 | 1.19E-03 |
| miR-142-3p,miR-150 | −2.21 | −2.11 | 0.90 | 0.10 | 1.95 | 0.84 | 1.19E-03 |
| miR-181d,miR-26b | 1.34 | 4.55 | 0.97 | 3.22 | 0.96 | 0.84 | 1.22E-03 |
| miR-27a,miR-328 | −1.51 | −3.11 | 1.08 | −1.60 | 1.12 | 0.84 | 1.36E-03 |
| miR-151,miR-27a | 1.12 | 2.29 | 0.66 | 1.17 | 0.92 | 0.84 | 1.37E-03 |
| miR-142-5p,miR-320 | −2.00 | 4.49 | 1.23 | 6.49 | 1.61 | 0.84 | 1.39E-03 |
| miR-214,miR-92 | −2.78 | 9.28 | 1.53 | 12.06 | 2.35 | 0.84 | 1.45E-03 |
| miR-29c,miR-342 | −1.34 | −1.41 | 0.99 | −0.07 | 1.00 | 0.84 | 1.67E-03 |
| miR-210,miR-27b | 1.30 | 0.16 | 0.93 | −1.14 | 1.00 | 0.84 | 1.69E-03 |
| miR-181d,miR-29c | 1.67 | 1.47 | 1.04 | −0.20 | 1.40 | 0.84 | 1.87E-03 |
| miR-126*,miR-186 | −0.91 | −2.31 | 0.69 | −1.40 | 0.70 | 0.84 | 1.99E-03 |
| miR-150,miR-214 | 2.68 | −4.91 | 1.17 | −7.59 | 2.50 | 0.84 | 2.06E-03 |
| miR-214,miR-328 | −2.03 | 1.57 | 1.54 | 3.60 | 1.56 | 0.84 | 2.07E-03 |
| miR-214,miR-324-3p | −2.11 | 1.02 | 1.23 | 3.13 | 1.85 | 0.84 | 2.12E-03 |

TABLE 15-continued microRNA biomarker pairs - benign lung and lung cancer patient sera.

| miRNA Biomarker Pair | Benign mean - Cancer mean | Benign mean | Benign SD | Cancer mean | Cancer SD | AUC ROC | Benign vs Cancer Assoc. |
|---|---|---|---|---|---|---|---|
| miR-15a,miR-181b | −1.35 | 0.66 | 0.96 | 2.01 | 1.10 | 0.84 | 2.13E−03 |
| miR-152,miR-181d | −1.17 | 0.33 | 0.85 | 1.50 | 0.95 | 0.84 | 2.39E−03 |
| miR-32,miR-518b | −2.48 | −1.43 | 1.48 | 1.05 | 2.21 | 0.84 | 2.46E−03 |
| miR-342,miR-576 | 1.51 | −3.51 | 1.01 | −5.02 | 1.30 | 0.84 | 2.53E−03 |
| miR-16,miR-93 | −0.91 | −5.54 | 0.72 | −4.63 | 0.73 | 0.84 | 2.54E−03 |
| miR-181d,miR-30a-3p | 1.36 | −2.34 | 0.82 | −3.70 | 1.34 | 0.84 | 2.54E−03 |
| miR-185,miR-345 | −1.28 | −0.75 | 0.93 | 0.54 | 1.07 | 0.84 | 2.54E−03 |
| miR-378,miR-422a | −0.67 | −4.02 | 0.35 | −3.34 | 0.67 | 0.84 | 2.54E−03 |
| let-7a,miR-518b | −1.62 | −7.28 | 1.02 | −5.66 | 1.55 | 0.84 | 2.55E−03 |
| let-7f,miR-328 | −1.17 | −0.52 | 0.81 | 0.65 | 1.08 | 0.84 | 2.55E−03 |
| miR-146a,miR-422a | −1.30 | −5.99 | 0.77 | −4.69 | 1.25 | 0.84 | 2.55E−03 |
| miR-148a,miR-518b | −1.78 | −6.71 | 1.34 | −4.93 | 1.44 | 0.84 | 2.55E−03 |
| miR-15a,miR-328 | −1.22 | 0.96 | 0.85 | 2.18 | 1.04 | 0.84 | 2.55E−03 |
| miR-197,miR-27a | 1.11 | 2.03 | 0.71 | 0.92 | 1.04 | 0.84 | 2.55E−03 |
| miR-27a,miR-361 | −1.07 | −3.73 | 0.70 | −2.66 | 0.99 | 0.84 | 2.55E−03 |
| miR-181d,miR-26a | 1.42 | 4.07 | 0.76 | 2.66 | 1.10 | 0.84 | 7.63E−04 |
| miR-126,miR-132 | −1.33 | −5.68 | 1.04 | −4.36 | 0.90 | 0.84 | 1.25E−03 |
| miR-374,miR-486 | −1.98 | 5.13 | 1.26 | 7.11 | 1.54 | 0.84 | 1.26E−03 |
| miR-224,miR-92 | −1.18 | 10.05 | 0.64 | 11.23 | 1.10 | 0.84 | 2.75E−03 |
| miR-143,miR-145 | −1.65 | −0.59 | 0.97 | 1.06 | 1.13 | 0.83 | 3.86E−04 |
| miR-181d,miR-30b | 1.42 | 3.13 | 0.97 | 1.71 | 0.95 | 0.83 | 6.41E−04 |
| miR-340,miR-345 | −1.42 | −1.32 | 0.89 | 0.09 | 1.00 | 0.83 | 6.54E−04 |
| miR-126,miR-345 | −1.43 | −4.32 | 1.09 | −2.89 | 0.92 | 0.83 | 8.68E−04 |
| miR-126*,miR-145 | −1.33 | −5.10 | 0.95 | −3.77 | 0.91 | 0.83 | 9.06E−04 |
| miR-126,miR-222 | −1.06 | −2.11 | 0.72 | −1.05 | 0.79 | 0.83 | 1.16E−03 |
| miR-29b,miR-99b | −1.85 | 0.05 | 0.96 | 1.90 | 1.56 | 0.83 | 1.24E−03 |
| let-7a,miR-181d | −1.36 | −2.43 | 0.69 | −1.07 | 1.16 | 0.83 | 1.29E−03 |
| let-7f,miR-378 | −1.57 | 1.64 | 0.84 | 3.20 | 1.33 | 0.83 | 1.41E−03 |
| miR-139,miR-29b | 1.32 | −0.58 | 0.94 | −1.90 | 1.00 | 0.83 | 1.48E−03 |
| miR-27a,miR-320 | −1.81 | 2.62 | 1.14 | 4.43 | 1.47 | 0.83 | 1.60E−03 |
| miR-130b,miR-142-3p | 1.30 | 4.18 | 0.87 | 2.88 | 1.03 | 0.83 | 1.67E−03 |
| miR-210,miR-92 | −0.87 | 7.84 | 0.54 | 8.71 | 0.73 | 0.83 | 1.82E−03 |
| miR-30c,miR-92 | −1.52 | 4.53 | 0.96 | 6.05 | 1.27 | 0.83 | 1.83E−03 |
| miR-32,miR-433 | −1.79 | 0.23 | 1.24 | 2.01 | 1.44 | 0.83 | 1.92E−03 |
| miR-340,miR-486 | −2.00 | 5.14 | 1.28 | 7.15 | 1.68 | 0.83 | 1.97E−03 |
| let-7i,miR-145 | −1.22 | −3.39 | 0.62 | −2.17 | 1.11 | 0.83 | 2.00E−03 |
| miR-148b,miR-181a | −1.15 | −0.67 | 0.93 | 0.49 | 0.85 | 0.83 | 2.06E−03 |
| let-7b,miR-324-3p | −0.86 | −3.75 | 0.44 | −2.89 | 0.80 | 0.83 | 2.41E−03 |
| miR-29b,miR-423 | −1.80 | 0.68 | 1.33 | 2.48 | 1.49 | 0.83 | 2.69E−03 |
| miR-30c,miR-378 | −1.23 | −1.03 | 0.79 | 0.20 | 1.09 | 0.83 | 2.80E−03 |
| miR-19b,miR-27a | 1.13 | −2.74 | 0.63 | −3.86 | 1.06 | 0.83 | 2.96E−03 |
| miR-126,miR-186 | −1.06 | −2.74 | 0.79 | −1.69 | 0.90 | 0.83 | 2.97E−03 |
| miR-214,miR-605 | −1.70 | −0.78 | 1.31 | 0.93 | 1.46 | 0.83 | 2.97E−03 |
| miR-301,miR-422a | −1.42 | −0.77 | 0.90 | 0.65 | 1.34 | 0.83 | 2.97E−03 |
| miR-496,miR-92 | −2.26 | 11.23 | 1.57 | 13.49 | 2.13 | 0.83 | 2.97E−03 |
| miR-15a,miR-324-3p | −1.27 | 0.41 | 0.90 | 1.68 | 0.91 | 0.83 | 1.11E−03 |
| miR-126*,miR-345 | −1.29 | −3.89 | 1.02 | −2.60 | 0.85 | 0.83 | 1.15E−03 |
| miR-200c,miR-518b | −1.93 | −3.63 | 1.37 | −1.70 | 1.41 | 0.83 | 1.25E−03 |
| miR-26a,miR-378 | −1.25 | −1.84 | 0.65 | −0.58 | 1.09 | 0.83 | 1.58E−03 |
| miR-192,miR-324-3p | −0.87 | −1.52 | 0.61 | −0.65 | 0.68 | 0.83 | 1.62E−03 |
| miR-142-3p,miR-210 | −1.38 | −5.58 | 0.85 | −4.20 | 1.19 | 0.83 | 2.15E−03 |
| miR-29a,miR-92 | −1.88 | 4.57 | 0.77 | 6.45 | 1.79 | 0.83 | 2.18E−03 |
| miR-125a,miR-374 | 1.11 | 1.98 | 0.63 | 0.87 | 1.14 | 0.83 | 3.19E−03 |
| miR-126*,miR-181b | −1.26 | −4.71 | 0.70 | −3.45 | 1.25 | 0.83 | 3.20E−03 |
| miR-26b,miR-342 | −1.00 | −4.49 | 0.74 | −3.50 | 0.87 | 0.83 | 3.20E−03 |
| miR-422a,miR-525 | 1.83 | −2.67 | 1.28 | −4.50 | 1.28 | 0.83 | 9.28E−04 |
| miR-142-5p,miR-361 | −1.26 | −1.85 | 1.02 | −0.60 | 0.80 | 0.83 | 1.14E−03 |
| miR-140,miR-422b | −1.28 | −2.64 | 0.82 | −1.35 | 0.99 | 0.83 | 1.17E−03 |
| miR-24,miR-340 | 1.05 | −2.13 | 0.42 | −3.18 | 0.93 | 0.83 | 1.17E−03 |
| miR-145,miR-30e-5p | 1.52 | 4.07 | 1.08 | 2.55 | 1.12 | 0.83 | 1.28E−03 |
| miR-27b,miR-30d | −1.29 | 3.08 | 0.70 | 4.38 | 1.08 | 0.83 | 1.31E−03 |
| miR-181b,miR-30e-5p | 1.45 | 3.68 | 0.94 | 2.23 | 1.14 | 0.83 | 1.34E−03 |
| miR-193a,miR-422a | −1.74 | 1.89 | 0.82 | 3.62 | 1.51 | 0.83 | 1.37E−03 |
| miR-148b,miR-326 | −1.24 | −4.49 | 0.96 | −3.24 | 0.88 | 0.83 | 1.47E−03 |
| miR-151,miR-340 | 0.86 | 1.02 | 0.40 | 0.16 | 0.77 | 0.83 | 1.50E−03 |
| miR-320,miR-34a | 2.08 | −7.28 | 1.46 | −9.36 | 1.62 | 0.83 | 1.66E−03 |
| miR-106b,miR-145 | −1.26 | −3.55 | 0.82 | −2.29 | 1.03 | 0.83 | 1.67E−03 |
| miR-199a*,miR-378 | −1.38 | −0.18 | 0.79 | 1.19 | 1.18 | 0.83 | 1.78E−03 |
| miR-126*,miR-518b | −1.95 | −9.35 | 1.27 | −7.40 | 1.63 | 0.83 | 2.06E−03 |
| miR-126,miR-146a | −1.04 | −0.71 | 0.79 | 0.33 | 0.80 | 0.83 | 2.09E−03 |
| miR-142-3p,miR-382 | −1.57 | −7.71 | 1.30 | −6.14 | 1.13 | 0.83 | 2.15E−03 |
| miR-181d,miR-185 | 1.68 | 1.35 | 1.33 | −0.33 | 1.27 | 0.83 | 2.20E−03 |
| miR-130a,miR-92 | −1.60 | 4.76 | 1.30 | 6.36 | 1.19 | 0.83 | 2.32E−03 |

TABLE 15-continued microRNA biomarker pairs - benign lung and lung cancer patient sera.

| miRNA Biomarker Pair | Benign mean - Cancer mean | Benign mean | Benign SD | Cancer mean | Cancer SD | AUC ROC | Benign vs Cancer Assoc. |
|---|---|---|---|---|---|---|---|
| miR-15b,miR-324-3p | -1.12 | -2.71 | 0.79 | -1.58 | 0.94 | 0.83 | 2.44E-03 |
| miR-106b,miR-191 | -0.93 | 0.53 | 0.59 | 1.46 | 0.82 | 0.83 | 2.77E-03 |
| miR-142-3p,miR-190 | -1.02 | -7.25 | 0.64 | -6.23 | 0.92 | 0.83 | 2.92E-03 |
| miR-126*,miR-150 | -1.78 | -1.08 | 0.89 | 0.70 | 1.72 | 0.83 | 3.14E-03 |
| miR-145,miR-496 | 1.77 | -2.84 | 1.17 | -4.61 | 1.59 | 0.83 | 3.17E-03 |
| miR-202,miR-374 | 1.39 | 2.43 | 0.94 | 1.04 | 1.26 | 0.83 | 3.39E-03 |
| miR-27b,miR-93 | -1.34 | 4.29 | 0.89 | 5.63 | 1.21 | 0.83 | 3.40E-03 |
| miR-155,miR-27b | 1.12 | 0.92 | 0.80 | -0.20 | 0.99 | 0.83 | 3.44E-03 |
| miR-143,miR-486 | -2.20 | 7.08 | 1.42 | 9.29 | 2.04 | 0.83 | 3.45E-03 |
| miR-148a,miR-378 | -1.36 | 0.38 | 1.02 | 1.73 | 1.17 | 0.83 | 3.45E-03 |
| miR-150,miR-374 | 1.88 | -1.48 | 0.99 | -3.36 | 1.83 | 0.83 | 3.45E-03 |
| miR-181b,miR-374 | 1.36 | 2.16 | 0.67 | 0.79 | 1.36 | 0.83 | 3.45E-03 |
| miR-222,miR-340 | 1.05 | -0.89 | 0.67 | -1.94 | 0.99 | 0.83 | 3.45E-03 |
| miR-320,miR-576 | 1.68 | -8.98 | 0.99 | -10.65 | 1.59 | 0.83 | 3.45E-03 |
| miR-126*,miR-324-3p | -1.18 | -4.96 | 0.68 | -3.78 | 0.96 | 0.83 | 1.19E-03 |
| miR-143,miR-518b | -2.28 | -4.84 | 1.74 | -2.56 | 1.66 | 0.83 | 1.67E-03 |
| miR-223,miR-27a | 1.17 | -4.76 | 0.64 | -5.93 | 1.06 | 0.83 | 2.20E-03 |
| miR-29b,miR-638 | -1.39 | 2.34 | 1.08 | 3.73 | 1.09 | 0.83 | 2.52E-03 |
| miR-26b,miR-518b | -1.61 | -9.41 | 1.25 | -7.80 | 1.32 | 0.83 | 3.04E-03 |
| miR-186,miR-422a | -1.29 | -3.96 | 0.74 | -2.68 | 1.21 | 0.83 | 3.26E-03 |
| miR-19b,miR-422a | -1.45 | -7.71 | 0.75 | -6.25 | 1.42 | 0.83 | 3.50E-03 |
| miR-193b,miR-27a | 1.80 | 4.67 | 1.15 | 2.87 | 1.75 | 0.83 | 3.70E-03 |
| miR-181d,miR-30c | 1.39 | 3.26 | 0.93 | 1.87 | 1.03 | 0.82 | 1.05E-03 |
| miR-143,miR-181a | -1.87 | -0.87 | 1.40 | 1.00 | 1.28 | 0.82 | 1.09E-03 |
| miR-143,miR-345 | -1.62 | 0.62 | 1.12 | 2.23 | 1.20 | 0.82 | 1.27E-03 |
| miR-186,miR-29a | 0.98 | 1.04 | 0.39 | 0.07 | 0.89 | 0.82 | 1.57E-03 |
| miR-142-5p,miR-17-5p | -1.40 | 0.27 | 0.74 | 1.67 | 1.21 | 0.82 | 1.59E-03 |
| miR-15a,miR-345 | -1.38 | 1.48 | 1.17 | 2.86 | 0.90 | 0.82 | 1.62E-03 |
| miR-30e-5p,miR-518b | -2.14 | -8.31 | 1.64 | -6.18 | 1.58 | 0.82 | 1.74E-03 |
| miR-29b,miR-335 | -1.56 | 2.64 | 1.05 | 4.20 | 1.26 | 0.82 | 1.81E-03 |
| miR-202,miR-27a | 1.68 | 3.69 | 1.28 | 2.01 | 1.26 | 0.82 | 1.87E-03 |
| miR-193b,miR-200c | 1.42 | 0.28 | 1.05 | -1.14 | 1.11 | 0.82 | 1.98E-03 |
| miR-145,miR-34a | 1.81 | -0.86 | 1.44 | -2.67 | 1.34 | 0.82 | 2.03E-03 |
| miR-148b,miR-30a-5p | -0.81 | 4.35 | 0.63 | 5.16 | 0.62 | 0.82 | 2.08E-03 |
| miR-142-5p,miR-324-5p | -1.18 | -2.87 | 0.83 | -1.69 | 0.96 | 0.82 | 2.15E-03 |
| miR-142-5p,miR-19b | -1.32 | 4.61 | 0.89 | 5.93 | 1.12 | 0.82 | 2.48E-03 |
| miR-200c,miR-92 | -1.82 | 8.99 | 1.40 | 10.81 | 1.44 | 0.82 | 2.53E-03 |
| miR-142-3p,miR-30b | -0.70 | -2.41 | 0.32 | -1.71 | 0.67 | 0.82 | 2.54E-03 |
| miR-378,miR-496 | 1.97 | -5.68 | 1.12 | -7.64 | 1.79 | 0.82 | 2.56E-03 |
| miR-324-3p,miR-340 | 1.31 | 2.39 | 0.94 | 1.09 | 1.08 | 0.82 | 2.57E-03 |
| miR-142-5p,miR-210 | -1.52 | -1.37 | 1.05 | 0.16 | 1.29 | 0.82 | 2.57E-03 |
| miR-23a,miR-340 | 0.81 | 1.21 | 0.59 | 0.40 | 0.67 | 0.82 | 2.75E-03 |
| miR-26b,miR-92 | -1.48 | 3.24 | 0.91 | 4.72 | 1.34 | 0.82 | 2.83E-03 |
| miR-150,miR-15b | 1.72 | -1.18 | 0.91 | -2.91 | 1.63 | 0.82 | 2.84E-03 |
| miR-422b,miR-576 | 1.68 | -1.80 | 0.75 | -3.48 | 1.66 | 0.82 | 3.08E-03 |
| miR-155,miR-181d | -1.09 | 0.81 | 0.84 | 1.90 | 0.91 | 0.82 | 3.27E-03 |
| miR-101,miR-324-3p | -1.10 | -1.49 | 0.82 | -0.39 | 0.96 | 0.82 | 3.68E-03 |
| miR-181a,miR-98 | 1.41 | -0.55 | 0.90 | -1.96 | 1.31 | 0.82 | 3.72E-03 |
| miR-142-3p,miR-22 | -1.20 | -4.20 | 0.81 | -3.00 | 1.10 | 0.82 | 3.72E-03 |
| miR-132,miR-214 | 2.21 | -0.73 | 1.38 | -2.94 | 2.09 | 0.82 | 3.86E-03 |
| let-7e,miR-486 | -1.66 | 3.50 | 1.24 | 5.16 | 1.46 | 0.82 | 3.89E-03 |
| miR-126,miR-328 | -1.27 | -4.84 | 0.95 | -3.57 | 1.13 | 0.82 | 3.98E-03 |
| miR-126,miR-30a-5p | -0.99 | -0.52 | 0.59 | 0.47 | 0.98 | 0.82 | 3.99E-03 |
| miR-106a,miR-422a | -1.61 | -6.51 | 0.83 | -4.91 | 1.64 | 0.82 | 4.00E-03 |
| miR-210,miR-27a | 1.33 | 3.24 | 0.88 | 1.91 | 1.30 | 0.82 | 4.00E-03 |
| miR-30c,miR-342 | -1.06 | -3.20 | 0.60 | -2.14 | 1.08 | 0.82 | 4.00E-03 |
| miR-15b,miR-320 | -1.37 | 3.57 | 0.91 | 4.94 | 1.12 | 0.82 | 1.98E-03 |
| miR-15b,miR-17-5p | -0.76 | -0.65 | 0.56 | 0.12 | 0.60 | 0.82 | 1.99E-03 |
| miR-106b,miR-342 | -1.29 | -2.89 | 0.99 | -1.60 | 1.01 | 0.82 | 2.23E-03 |
| miR-15b,miR-518b | -1.89 | -7.09 | 1.39 | -5.20 | 1.52 | 0.82 | 2.30E-03 |
| miR-200c,miR-378 | -1.46 | 3.51 | 1.11 | 4.96 | 0.97 | 0.82 | 1.04E-03 |
| miR-150,miR-34a | 2.38 | -4.89 | 1.81 | -7.27 | 1.64 | 0.82 | 1.22E-03 |
| miR-181d,miR-432 | 1.71 | -1.41 | 1.03 | -3.12 | 1.37 | 0.82 | 1.27E-03 |
| miR-140,miR-181a | -1.61 | -2.42 | 1.31 | -0.81 | 1.06 | 0.82 | 1.30E-03 |
| miR-142-3p,miR-433 | -1.69 | -8.52 | 1.00 | -6.83 | 1.40 | 0.82 | 1.46E-03 |
| miR-148b,miR-24 | -0.84 | 4.01 | 0.47 | 4.85 | 0.75 | 0.82 | 2.12E-03 |
| miR-132,miR-142-3p | 1.61 | 6.29 | 1.34 | 4.68 | 1.17 | 0.82 | 2.22E-03 |
| miR-133b,miR-145 | -1.29 | 1.55 | 1.05 | 2.84 | 0.96 | 0.82 | 2.28E-03 |
| miR-15a,miR-342 | -1.45 | 0.94 | 0.76 | 2.38 | 1.33 | 0.82 | 2.32E-03 |
| miR-324-3p,miR-374 | 1.28 | 2.41 | 0.68 | 1.13 | 1.17 | 0.82 | 2.35E-03 |
| miR-200c,miR-422b | -1.27 | 0.04 | 0.84 | 1.31 | 1.08 | 0.82 | 2.36E-03 |
| let-7g,miR-518b | -1.80 | -8.58 | 1.23 | -6.79 | 1.51 | 0.82 | 2.36E-03 |
| miR-339,miR-92 | -1.29 | 8.60 | 0.78 | 9.88 | 1.14 | 0.82 | 2.49E-03 |

TABLE 15-continued microRNA biomarker pairs - benign lung and lung cancer patient sera.

| miRNA Biomarker Pair | Benign mean - Cancer mean | Benign mean | Benign SD | Cancer mean | Cancer SD | AUC ROC | Benign vs Cancer Assoc. |
|---|---|---|---|---|---|---|---|
| miR-133b,miR-518b | −1.91 | −2.70 | 1.38 | −0.79 | 1.58 | 0.82 | 2.53E−03 |
| let-7b,miR-486 | −1.56 | 3.79 | 1.09 | 5.35 | 1.33 | 0.82 | 2.67E−03 |
| miR-29a,miR-345 | −1.35 | −2.62 | 0.85 | −1.27 | 1.20 | 0.82 | 2.70E−03 |
| miR-133b,miR-181d | −1.65 | 2.15 | 1.18 | 3.80 | 1.40 | 0.82 | 2.90E−03 |
| miR-142-5p,miR-335 | −1.36 | −1.04 | 1.09 | 0.31 | 1.07 | 0.82 | 2.91E−03 |
| miR-192,miR-486 | −1.57 | 6.02 | 0.95 | 7.59 | 1.43 | 0.82 | 2.92E−03 |
| miR-185,miR-19b | −0.74 | 4.58 | 0.52 | 5.31 | 0.63 | 0.82 | 2.93E−03 |
| let-7i,miR-320 | −1.32 | 3.02 | 1.01 | 4.34 | 1.09 | 0.82 | 3.14E−03 |
| miR-214,miR-320 | −2.25 | 7.30 | 1.48 | 9.55 | 2.03 | 0.82 | 3.24E−03 |
| miR-328,miR-374 | 1.23 | 1.86 | 0.86 | 0.63 | 1.08 | 0.82 | 3.24E−03 |
| miR-191,miR-26b | 0.60 | 1.08 | 0.40 | 0.48 | 0.54 | 0.82 | 3.52E−03 |
| let-7i,miR-181c | −1.20 | −6.20 | 0.79 | −5.00 | 1.10 | 0.82 | 3.59E−03 |
| miR-29b,miR-93 | −1.81 | 6.56 | 1.38 | 8.37 | 1.55 | 0.82 | 3.59E−03 |
| miR-222,miR-374 | 1.04 | −0.88 | 0.80 | −1.92 | 0.89 | 0.82 | 3.66E−03 |
| miR-126,miR-433 | −1.40 | −7.91 | 1.02 | −6.51 | 1.27 | 0.82 | 4.19E−03 |
| miR-142-3p,miR-151 | −1.17 | −4.63 | 0.60 | −3.46 | 1.24 | 0.82 | 4.62E−03 |
| miR-30a-3p,miR-378 | −1.15 | 4.62 | 0.62 | 5.78 | 1.18 | 0.82 | 4.63E−03 |
| miR-15a,miR-30a-5p | −0.93 | 5.29 | 0.65 | 6.22 | 0.81 | 0.82 | 3.03E−03 |
| miR-410,miR-422a | −2.01 | −0.02 | 1.36 | 2.00 | 1.82 | 0.82 | 3.53E−03 |
| miR-142-3p,miR-30c | −0.73 | −2.27 | 0.26 | −1.54 | 0.68 | 0.81 | 1.61E−03 |
| miR-140,miR-518b | −2.02 | −6.39 | 1.26 | −4.38 | 1.65 | 0.81 | 1.62E−03 |
| miR-146b,miR-181d | −1.12 | −2.33 | 0.66 | −1.21 | 0.95 | 0.81 | 1.68E−03 |
| miR-134,miR-29b | 1.91 | 0.50 | 1.56 | −1.41 | 1.34 | 0.81 | 1.79E−03 |
| miR-142-5p,miR-194 | −1.31 | −3.70 | 0.92 | −2.39 | 1.06 | 0.81 | 2.04E−03 |
| miR-18a,miR-27b | 0.93 | −0.62 | 0.50 | −1.55 | 0.83 | 0.81 | 2.07E−03 |
| miR-142-3p,miR-186 | −1.34 | −3.35 | 0.90 | −2.01 | 1.11 | 0.81 | 2.10E−03 |
| miR-148b,miR-342 | −1.37 | −0.02 | 0.90 | 1.35 | 1.17 | 0.81 | 2.36E−03 |
| let-7e,miR-518b | −1.73 | −8.42 | 1.18 | −6.69 | 1.47 | 0.81 | 2.46E−03 |
| miR-142-5p,miR-339 | −1.11 | −2.12 | 0.88 | −1.02 | 0.87 | 0.81 | 2.60E−03 |
| miR-150,miR-576 | 1.76 | −6.91 | 1.35 | −8.66 | 1.41 | 0.81 | 2.61E−03 |
| miR-181d,miR-98 | 1.55 | −1.43 | 0.81 | −2.98 | 1.45 | 0.81 | 2.67E−03 |
| miR-145,miR-576 | 1.81 | −2.18 | 1.32 | −3.98 | 1.50 | 0.81 | 2.72E−03 |
| let-7i,miR-342 | −1.25 | −2.73 | 0.84 | −1.48 | 1.09 | 0.81 | 2.80E−03 |
| miR-29c,miR-345 | −1.27 | −0.86 | 0.87 | 0.40 | 1.10 | 0.81 | 2.86E−03 |
| let-7g,miR-181a | −1.39 | −4.61 | 1.06 | −3.22 | 1.14 | 0.81 | 2.91E−03 |
| miR-181d,miR-192 | 1.38 | 1.05 | 1.12 | −0.33 | 1.09 | 0.81 | 2.98E−03 |
| miR-150,miR-32 | 2.52 | −6.66 | 1.48 | −9.18 | 2.34 | 0.81 | 3.05E−03 |
| miR-143,miR-378 | −1.85 | 2.25 | 1.35 | 4.10 | 1.59 | 0.81 | 3.17E−03 |
| let-7g,miR-486 | −1.73 | 3.34 | 1.24 | 5.06 | 1.51 | 0.81 | 3.39E−03 |
| let-7f,miR-320 | −1.47 | 5.21 | 0.90 | 6.68 | 1.37 | 0.81 | 3.40E−03 |
| miR-15a,miR-422b | −1.30 | −0.22 | 0.95 | 1.08 | 1.13 | 0.81 | 3.42E−03 |
| miR-15a,miR-30d | −1.00 | 4.08 | 0.67 | 5.07 | 0.91 | 0.81 | 3.65E−03 |
| miR-125b,miR-378 | −1.42 | 3.09 | 1.09 | 4.51 | 1.22 | 0.81 | 3.71E−03 |
| miR-142-3p,miR-23a | −1.11 | −4.82 | 0.76 | −3.71 | 1.02 | 0.81 | 3.94E−03 |
| miR-29c,miR-324-3p | −1.16 | −1.94 | 0.74 | −0.78 | 1.10 | 0.81 | 4.09E−03 |
| miR-29b,miR-339 | −1.42 | 1.33 | 1.03 | 2.75 | 1.28 | 0.81 | 4.13E−03 |
| let-7g,miR-324-3p | −1.03 | −4.20 | 0.69 | −3.17 | 0.98 | 0.81 | 4.63E−03 |
| miR-19b,miR-27b | 1.11 | −5.81 | 0.73 | −6.92 | 1.08 | 0.81 | 4.99E−03 |
| let-7e,miR-378 | −1.31 | −1.34 | 0.72 | −0.03 | 1.36 | 0.81 | 5.34E−03 |
| miR-378,miR-432 | 1.55 | −3.65 | 1.00 | −5.20 | 1.54 | 0.81 | 5.35E−03 |
| let-7b,miR-181d | −1.37 | −3.28 | 1.14 | −1.91 | 0.96 | 0.81 | 1.91E−03 |
| miR-24,miR-30e-5p | 1.11 | −0.60 | 0.91 | −1.71 | 0.85 | 0.81 | 2.65E−03 |
| miR-365,miR-422a | −1.54 | −1.25 | 1.07 | 0.29 | 1.32 | 0.81 | 2.80E−03 |
| miR-320,miR-98 | 1.28 | −7.24 | 0.71 | −8.53 | 1.34 | 0.81 | 5.73E−03 |
| miR-181d,miR-638 | 1.31 | 0.35 | 1.08 | −0.96 | 0.87 | 0.81 | 1.44E−03 |
| miR-15a,miR-518b | −2.04 | −3.97 | 1.43 | −1.94 | 1.57 | 0.81 | 1.58E−03 |
| miR-106b,miR-181a | −1.48 | −3.83 | 1.25 | −2.35 | 1.02 | 0.81 | 1.93E−03 |
| miR-181a,miR-576 | 1.83 | −2.35 | 1.49 | −4.18 | 1.35 | 0.81 | 2.20E−03 |
| miR-199a*,miR-518b | −1.80 | −7.27 | 1.07 | −5.47 | 1.58 | 0.81 | 2.23E−03 |
| miR-181a,miR-214 | 2.53 | −0.61 | 1.86 | −3.14 | 2.03 | 0.81 | 2.35E−03 |
| let-7a,miR-181a | −1.22 | −3.31 | 0.84 | −2.09 | 1.02 | 0.81 | 2.37E−03 |
| miR-125b,miR-342 | −1.25 | 0.91 | 0.99 | 2.17 | 0.97 | 0.81 | 2.47E−03 |
| miR-181b,miR-340 | 1.39 | 2.14 | 1.03 | 0.75 | 1.20 | 0.81 | 3.33E−03 |
| miR-186,miR-340 | 1.04 | −0.26 | 0.69 | −1.29 | 0.95 | 0.81 | 3.57E−03 |
| miR-422a,miR-7 | 1.63 | 0.55 | 1.07 | −1.08 | 1.50 | 0.81 | 3.58E−03 |
| miR-29b,miR-365 | −1.51 | 1.55 | 1.00 | 3.06 | 1.38 | 0.81 | 3.58E−03 |
| miR-142-3p,miR-30a-5p | −1.27 | −1.13 | 0.70 | 0.15 | 1.24 | 0.81 | 3.71E−03 |
| miR-30c,miR-518b | −1.65 | −8.12 | 1.24 | −6.47 | 1.44 | 0.81 | 3.74E−03 |
| miR-150,miR-185 | 1.77 | −2.07 | 1.17 | −3.84 | 1.65 | 0.81 | 3.93E−03 |
| let-7e,miR-320 | −1.20 | 2.24 | 0.73 | 3.44 | 1.16 | 0.81 | 4.05E−03 |
| let-7b,miR-150 | −1.46 | 0.14 | 0.90 | 1.60 | 1.40 | 0.81 | 4.06E−03 |
| miR-142-3p,miR-30d | −1.34 | −2.34 | 0.68 | −1.00 | 1.36 | 0.81 | 4.26E−03 |
| miR-126,miR-193b | −1.56 | −6.41 | 0.81 | −4.84 | 1.60 | 0.81 | 4.80E−03 |

TABLE 15-continued microRNA biomarker pairs - benign lung and lung cancer patient sera.

| miRNA Biomarker Pair | Benign mean - Cancer mean | Benign mean | Benign SD | Cancer mean | Cancer SD | AUC ROC | Benign vs Cancer Assoc. |
|---|---|---|---|---|---|---|---|
| miR-202,miR-576 | 1.83 | −2.26 | 1.07 | −4.09 | 1.88 | 0.81 | 5.53E−03 |
| miR-18a,miR-92 | −1.28 | 7.05 | 0.73 | 8.33 | 1.18 | 0.80 | 2.81E−03 |
| miR-214,miR-342 | −2.19 | 1.55 | 1.04 | 3.74 | 2.14 | 0.80 | 3.05E−03 |
| miR-126*,miR-30a-5p | −0.84 | −0.09 | 0.53 | 0.75 | 0.80 | 0.80 | 3.88E−03 |
| miR-133b,miR-378 | −1.49 | 4.39 | 1.06 | 5.87 | 1.26 | 0.80 | 2.79E−03 |
| miR-126*,miR-146a | −0.89 | −0.28 | 0.72 | 0.61 | 0.70 | 0.80 | 2.81E−03 |
| miR-422a,miR-422b | 0.94 | 0.68 | 0.63 | −0.25 | 0.83 | 0.80 | 2.99E−03 |
| miR-30b,miR-518b | −1.68 | −7.98 | 1.25 | −6.30 | 1.43 | 0.80 | 3.22E−03 |
| miR-148b,miR-181b | −1.27 | −0.40 | 0.94 | 0.87 | 1.10 | 0.80 | 3.34E−03 |
| miR-221,miR-27b | 0.93 | −2.71 | 0.72 | −3.64 | 0.79 | 0.80 | 3.45E−03 |
| miR-142-5p,miR-26b | −0.93 | 3.23 | 0.62 | 4.16 | 0.84 | 0.80 | 3.50E−03 |
| miR-142-5p,miR-151 | −1.31 | −0.42 | 0.76 | 0.90 | 1.27 | 0.80 | 3.90E−03 |
| let-7d,miR-142-3p | 0.87 | 4.38 | 0.26 | 3.51 | 0.93 | 0.80 | 4.56E−03 |
| miR-328,miR-340 | 1.26 | 1.85 | 0.82 | 0.59 | 1.24 | 0.80 | 5.31E−03 |
| miR-296,miR-92 | −1.08 | 9.76 | 0.64 | 10.84 | 1.10 | 0.80 | 5.60E−03 |
| miR-140,miR-23a | −0.75 | −0.82 | 0.38 | −0.07 | 0.79 | 0.80 | 5.74E−03 |
| miR-142-3p,miR-331 | −0.99 | −6.00 | 0.58 | −5.01 | 1.02 | 0.80 | 5.84E−03 |
| miR-181b,miR-214 | 2.25 | −1.27 | 0.85 | −3.52 | 2.12 | 0.80 | 1.92E−03 |
| miR-326,miR-340 | 1.35 | 6.32 | 1.04 | 4.97 | 1.16 | 0.80 | 3.67E−03 |
| let-7e,miR-191 | −0.77 | −0.10 | 0.60 | 0.68 | 0.62 | 0.80 | 2.59E−03 |
| miR-30b,miR-320 | −1.16 | 2.68 | 0.84 | 3.84 | 1.02 | 0.80 | 3.64E−03 |
| miR-145,miR-214 | 2.31 | −0.89 | 1.47 | −3.20 | 2.17 | 0.80 | 3.85E−03 |
| miR-140,miR-320 | −1.49 | 4.27 | 1.04 | 5.76 | 1.37 | 0.80 | 4.15E−03 |
| miR-496,miR-566 | −1.75 | 1.86 | 1.17 | 3.61 | 1.66 | 0.80 | 4.64E−03 |
| miR-23b,miR-92 | −1.50 | 9.89 | 0.98 | 11.39 | 1.45 | 0.80 | 4.65E−03 |

The prevalence of serum biomarkers in paired analysis from Table 15 are shown in Table 16.

TABLE 16

Prevalence of serum biomarkers in pairs

| miRNA | Paired Appearances |
|---|---|
| miR-422a | 55 |
| miR-29b | 25 |
| miR-92 | 19 |
| miR-142-5p | 17 |
| miR-142-3p | 14 |
| miR-181d | 14 |
| miR-27b | 12 |
| miR-378 | 12 |
| miR-27a | 11 |
| miR-30e-5p | 9 |
| miR-181a | 8 |
| miR-126 | 7 |
| miR-342 | 7 |
| miR-140 | 6 |
| miR-15a | 6 |
| miR-324-3p | 6 |
| miR-374 | 6 |
| miR-486 | 6 |
| miR-518b | 6 |
| miR-106b | 5 |
| miR-145 | 5 |
| miR-150 | 5 |
| miR-191 | 5 |
| miR-345 | 5 |
| miR-126* | 4 |
| miR-148b | 4 |
| miR-214 | 4 |
| miR-320 | 4 |
| let-7g | 3 |
| let-7i | 3 |
| miR-146a | 3 |
| miR-15b | 3 |
| miR-185 | 3 |
| miR-186 | 3 |
| miR-23a | 3 |
| miR-24 | 3 |
| miR-30a-5p | 3 |
| miR-340 | 3 |
| miR-34a | 3 |
| miR-101 | 2 |
| miR-132 | 2 |
| miR-181b | 2 |
| miR-199a* | 2 |
| miR-202 | 2 |
| miR-222 | 2 |
| miR-422b | 2 |
| miR-660 | 2 |
| miR-7 | 2 |
| miR-93 | 2 |

The data in Tables 15 and 16 show miRNAs and miRNA biomarker pairs that can distinguish patients with benign conditions of the lung from patients with lung cancer in serum samples, irrespective of patient sex or cancer type. These miRNAs are useful for diagnosis of lung cancer. The serum samples from cancer patients were from patients with early stage I through stage III lung cancer. These results show that miRNAs are suited to detect lung cancer at an early stage and are effective for screening patients and distinguishing patients with benign lung conditions from those with lung cancer.

Example 3

Differentially Expressed miRNAs in Serum from Male and Female Lung Cancer Patients While the serum miRNAs in Tables 15 and 16 are able to distinguish patients with benign lung conditions from patients with lung cancers, further analysis of the data from Example 2 revealed that certain miRNAs pairs were better for distinguishing those patient groups within a specific sex. In particular, a number of miRNA pairs had an AUC ROC of 1.00 (Table 17). These pairs showed a significant improvement of the ROC AUC when distinguishing female patients with benign lung conditions from female lung cancer patients. Similarly, an improvement in AUC was also observed for specific miRNA pairs when distinguishing male patients with benign lung conditions from male patients with lung cancers (Table 18). The miRNAs and miRNA pairs in Tables 17 and 18 are useful for diagnosing lung cancer in female and male patients respectively. These miRNAs can be used in combinations of two or more.

TABLE 17 microRNAs pairs that are differentially expressed in serum of female patients with benign lung conditions as compared to female lung cancer patients.

| miRNA Biomarker Pair | Benign mean − Cancer mean | Benign mean | Benign SD | Cancer mean | Cancer SD | AUC ROC | Female Benign vs Female Cancer Assoc. |
|---|---|---|---|---|---|---|---|
| miR-15a,miR-422a | −2.47 | −0.93 | 0.69 | 1.53 | 0.25 | 1.00 | 1.26E−06 |
| miR-181d,miR-27b | 2.42 | 0.41 | 0.67 | −2.01 | 0.39 | 1.00 | 2.81E−06 |
| miR-27b,miR-422a | −2.83 | −1.85 | 0.42 | 0.98 | 0.85 | 1.00 | 4.16E−06 |
| miR-15b,miR-191 | −1.27 | 1.22 | 0.35 | 2.49 | 0.25 | 1.00 | 4.79E−06 |
| miR-181d,miR-29b | 3.10 | −1.87 | 0.63 | −4.97 | 0.87 | 1.00 | 6.28E−06 |
| miR-142-3p,miR-422a | −2.76 | −7.16 | 0.58 | −4.40 | 0.84 | 1.00 | 1.13E−05 |
| miR-23a,miR-27a | 1.30 | 2.53 | 0.40 | 1.24 | 0.27 | 1.00 | 1.22E−05 |
| miR-222,miR-27a | 1.94 | 0.69 | 0.54 | −1.25 | 0.50 | 1.00 | 1.54E−05 |
| miR-126,miR-422a | −2.50 | −6.52 | 0.30 | −4.03 | 0.92 | 1.00 | 1.91E−05 |
| miR-142-5p,miR-145 | −2.27 | −2.07 | 0.59 | 0.20 | 0.67 | 1.00 | 2.04E−05 |
| miR-142-3p,miR-145 | −1.85 | −6.12 | 0.64 | −4.27 | 0.39 | 1.00 | 2.61E−05 |
| miR-143,miR-223 | −1.58 | 7.88 | 0.50 | 9.46 | 0.41 | 1.00 | 2.93E−05 |
| miR-324-5p,miR-422a | −1.64 | −0.12 | 0.59 | 1.53 | 0.33 | 1.00 | 3.27E−05 |
| miR-30e-5p,miR-422a | −2.59 | −5.10 | 0.83 | −2.51 | 0.68 | 1.00 | 3.40E−05 |
| miR-27a,miR-422a | −3.08 | −4.90 | 0.86 | −1.82 | 0.94 | 1.00 | 3.56E−05 |
| miR-126*,miR-222 | −1.39 | −1.95 | 0.33 | −0.56 | 0.48 | 1.00 | 4.02E−05 |
| miR-140,miR-422a | −2.63 | −3.25 | 0.70 | −0.62 | 0.86 | 1.00 | 4.13E−05 |
| miR-101,miR-92 | −2.39 | 6.57 | 0.86 | 8.97 | 0.54 | 1.00 | 4.24E−05 |
| miR-202,miR-29b | 3.08 | −1.42 | 0.55 | −4.50 | 1.18 | 1.00 | 4.36E−05 |
| miR-29b,miR-422a | −3.40 | 0.62 | 0.81 | 4.02 | 1.21 | 1.00 | 4.83E−05 |
| miR-30e-5p,miR-324-3p | −1.38 | −3.89 | 0.39 | −2.51 | 0.46 | 1.00 | 5.23E−05 |
| miR-181b,miR-29b | 3.29 | −1.41 | 0.56 | −4.71 | 1.32 | 1.00 | 5.65E−05 |
| miR-142-5p,miR-181a | −2.69 | −2.70 | 1.05 | −0.01 | 0.56 | 1.00 | 6.22E−05 |
| miR-126*,miR-422a | −2.52 | −6.16 | 0.37 | −3.64 | 1.06 | 1.00 | 6.52E−05 |
| miR-195,miR-93 | −1.23 | −0.12 | 0.48 | 1.11 | 0.27 | 1.00 | 7.27E−05 |
| miR-140,miR-222 | −1.49 | 0.96 | 0.54 | 2.46 | 0.41 | 1.00 | 7.76E−05 |
| miR-126,miR-181d | −2.00 | −5.08 | 0.47 | −3.08 | 0.78 | 1.00 | 8.18E−05 |
| miR-142-5p,miR-422a | −3.17 | −3.11 | 1.24 | 0.07 | 0.74 | 1.00 | 8.18E−05 |
| miR-24,miR-27a | 1.45 | −0.82 | 0.47 | −2.27 | 0.48 | 1.00 | 9.51E−05 |
| miR-27a,miR-361 | −1.91 | −3.91 | 0.58 | −2.00 | 0.68 | 1.00 | 1.03E−04 |
| miR-346,miR-518b | −3.12 | −3.23 | 1.35 | −0.11 | 0.61 | 1.00 | 1.18E−04 |
| miR-222,miR-27b | 1.69 | −2.36 | 0.17 | −4.05 | 0.78 | 1.00 | 1.21E−04 |
| miR-15b,miR-181a | −2.08 | −3.58 | 0.87 | −1.50 | 0.47 | 1.00 | 1.24E−04 |
| miR-142-5p,miR-191 | −1.88 | 2.10 | 0.57 | 3.97 | 0.69 | 1.00 | 1.25E−04 |
| miR-433,miR-487b | 1.86 | 0.03 | 0.80 | −1.83 | 0.39 | 1.00 | 1.28E−04 |
| miR-29b,miR-518b | −3.68 | −3.01 | 1.17 | 0.67 | 1.34 | 1.00 | 1.40E−04 |
| miR-106b,miR-422a | −2.78 | −4.93 | 1.21 | −2.15 | 0.61 | 1.00 | 1.50E−04 |
| miR-21,miR-422a | −1.98 | −7.01 | 0.73 | −5.03 | 0.64 | 1.00 | 1.52E−04 |
| miR-15b,miR-422a | −2.56 | −3.99 | 0.77 | −1.42 | 0.98 | 1.00 | 1.53E−04 |
| miR-181a,miR-27a | 2.60 | 4.49 | 1.22 | 1.90 | 0.35 | 1.00 | 1.58E−04 |
| miR-142-5p,miR-345 | −2.27 | −1.00 | 0.82 | 1.27 | 0.75 | 1.00 | 1.61E−04 |
| miR-32,miR-422a | −2.32 | 1.49 | 1.06 | 3.81 | 0.45 | 1.00 | 1.73E−04 |
| miR-30e-5p,miR-92 | −2.12 | 4.44 | 0.61 | 6.56 | 0.86 | 1.00 | 1.93E−04 |
| miR-148b,miR-422a | −2.37 | −1.65 | 0.91 | 0.73 | 0.77 | 1.00 | 2.02E−04 |
| miR-192,miR-422a | −2.57 | −2.91 | 0.89 | −0.34 | 0.94 | 1.00 | 2.02E−04 |
| let-7i,miR-422a | −2.32 | −4.52 | 0.97 | −2.20 | 0.66 | 1.00 | 2.10E−04 |
| miR-19b,miR-486 | −1.55 | 1.22 | 0.67 | 2.77 | 0.42 | 1.00 | 2.16E−04 |
| miR-15a,miR-181d | −1.97 | 0.51 | 0.87 | 2.48 | 0.51 | 1.00 | 2.30E−04 |
| miR-142-3p,miR-26a | −0.97 | −1.55 | 0.16 | −0.58 | 0.47 | 1.00 | 2.36E−04 |
| miR-142-3p,miR-181a | −2.28 | −6.76 | 1.00 | −4.48 | 0.62 | 1.00 | 2.44E−04 |
| miR-29b,miR-378 | −2.72 | 4.28 | 0.58 | 7.00 | 1.34 | 1.00 | 3.51E−04 |
| miR-15a,miR-181b | −1.93 | 0.29 | 0.95 | 2.22 | 0.42 | 1.00 | 3.58E−04 |
| miR-142-3p,miR-342 | −1.82 | −5.31 | 0.53 | −3.49 | 0.83 | 1.00 | 3.83E−04 |
| miR-195,miR-20b | −0.89 | −2.27 | 0.37 | −1.39 | 0.32 | 1.00 | 4.08E−04 |
| miR-145,miR-27a | 2.17 | 3.86 | 0.99 | 1.69 | 0.67 | 1.00 | 4.11E−04 |
| miR-374,miR-422a | −2.43 | −3.55 | 0.58 | −1.11 | 1.20 | 1.00 | 4.24E−04 |
| miR-27b,miR-361 | −1.64 | −0.86 | 0.55 | 0.77 | 0.71 | 1.00 | 4.32E−04 |
| miR-142-3p,miR-518b | −3.02 | −10.77 | 1.19 | −7.75 | 1.17 | 1.00 | 4.33E−04 |
| miR-140,miR-181d | −2.13 | −1.81 | 0.85 | 0.33 | 0.82 | 1.00 | 4.67E−04 |
| miR-27b,miR-326 | −2.07 | −4.77 | 0.93 | −2.70 | 0.67 | 1.00 | 4.73E−04 |
| miR-139,miR-422a | −1.96 | 0.11 | 0.79 | 2.07 | 0.76 | 1.00 | 4.75E−04 |

TABLE 17-continued microRNAs pairs that are differentially expressed in serum of female patients with benign lung conditions as compared to female lung cancer patients.

| miRNA Biomarker Pair | Benign mean – Cancer mean | Benign mean | Benign SD | Cancer mean | Cancer SD | AUC ROC | Female Benign vs Female Cancer Assoc. |
|---|---|---|---|---|---|---|---|
| let-7g,miR-422a | −2.29 | −5.45 | 0.45 | −3.16 | 1.21 | 1.00 | 5.12E−04 |
| miR-140,miR-345 | −1.73 | −1.14 | 0.78 | 0.58 | 0.59 | 1.00 | 5.44E−04 |
| miR-148b,miR-326 | −1.80 | −4.71 | 0.87 | −2.91 | 0.59 | 1.00 | 7.05E−04 |
| miR-20a,miR-92 | −2.00 | 2.04 | 0.64 | 4.05 | 1.01 | 1.00 | 7.88E−04 |
| miR-133b,miR-181b | −1.98 | 1.60 | 0.75 | 3.58 | 0.93 | 1.00 | 8.83E−04 |
| miR-132,miR-30e-5p | 1.50 | 4.32 | 0.72 | 2.82 | 0.56 | 1.00 | 9.62E−04 |
| miR-19b,miR-92 | −1.73 | 1.67 | 0.55 | 3.40 | 0.91 | 1.00 | 9.98E−04 |
| miR-181a,miR-30c | 1.67 | 4.48 | 0.84 | 2.81 | 0.59 | 1.00 | 1.02E−03 |
| miR-197,miR-422a | −1.61 | −2.91 | 0.70 | −1.30 | 0.70 | 1.00 | 1.06E−03 |
| miR-142-5p,miR-222 | −1.98 | 1.10 | 1.07 | 3.08 | 0.59 | 1.00 | 1.06E−03 |
| miR-148a,miR-422a | −1.90 | −3.26 | 0.97 | −1.36 | 0.66 | 1.00 | 1.07E−03 |
| let-7g,miR-181d | −1.79 | −4.01 | 0.66 | −2.22 | 0.89 | 1.00 | 1.09E−03 |
| miR-197,miR-29b | 2.09 | −3.24 | 0.50 | −5.33 | 1.20 | 1.00 | 1.09E−03 |
| miR-331,miR-422a | −2.05 | −1.27 | 0.76 | 0.78 | 1.03 | 1.00 | 1.17E−03 |
| miR-15a,miR-181a | −1.98 | −0.53 | 1.10 | 1.46 | 0.59 | 1.00 | 1.22E−03 |
| miR-339,miR-422a | −1.86 | −0.80 | 0.70 | 1.06 | 0.94 | 1.00 | 1.24E−03 |
| miR-181b,miR-215 | 2.65 | −2.89 | 1.09 | −5.54 | 1.29 | 1.00 | 1.33E−03 |
| miR-145,miR-374 | 1.52 | 2.51 | 0.71 | 0.98 | 0.67 | 1.00 | 1.33E−03 |
| miR-206,miR-518b | −3.45 | −3.25 | 1.79 | 0.20 | 1.29 | 1.00 | 1.35E−03 |
| miR-106b,miR-486 | −2.13 | 4.17 | 1.00 | 6.29 | 0.94 | 1.00 | 1.47E−03 |
| miR-126*,miR-181a | −2.04 | −5.76 | 1.23 | −3.72 | 0.49 | 1.00 | 1.53E−03 |
| miR-422a,miR-576 | 2.97 | −1.39 | 0.74 | −4.35 | 1.78 | 1.00 | 1.54E−03 |
| miR-17-5p,miR-422a | −1.93 | −3.45 | 0.62 | −1.52 | 1.09 | 1.00 | 1.56E−03 |
| miR-106b,miR-345 | −1.88 | −2.82 | 1.11 | −0.94 | 0.59 | 1.00 | 1.75E−03 |
| miR-126,miR-342 | −1.56 | −4.68 | 0.82 | −3.12 | 0.66 | 1.00 | 1.75E−03 |
| miR-139,miR-181d | −1.46 | 1.56 | 0.90 | 3.02 | 0.50 | 1.00 | 1.75E−03 |
| miR-140,miR-30a-5p | −1.19 | 2.79 | 0.55 | 3.98 | 0.79 | 1.00 | 1.75E−03 |
| miR-142-3p,miR-26b | −0.87 | −1.04 | 0.46 | −0.17 | 0.36 | 1.00 | 1.75E−03 |
| miR-142-3p,miR-361 | −1.59 | −6.17 | 1.14 | −4.58 | 0.50 | 1.00 | 1.75E−03 |
| miR-19a,miR-92 | −1.47 | 2.86 | 0.48 | 4.33 | 0.97 | 1.00 | 1.75E−03 |
| miR-222,miR-422a | −1.21 | −4.21 | 0.43 | −3.01 | 0.71 | 1.00 | 1.75E−03 |
| miR-296,miR-422a | −1.64 | 0.25 | 0.27 | 1.88 | 1.45 | 1.00 | 1.75E−03 |
| miR-29b,miR-382 | −2.62 | 0.02 | 1.24 | 2.63 | 1.30 | 1.00 | 1.75E−03 |

TABLE 18 microRNA pairs that are differentially expressed in serum of male patients with benign lung conditions as compared to male lung cancer patients.

| miRNA Biomarker Pair | Benign mean – Cancer mean | Benign mean | Benign SD | Cancer mean | Cancer SD | AUC ROC | Male Benign vs Male Cancer Assoc. |
|---|---|---|---|---|---|---|---|
| miR-185,miR-93 | −1.02 | 3.02 | 0.52 | 4.04 | 0.35 | 1.00 | 8.52E−04 |
| miR-30e-5p,miR-433 | −1.46 | −6.82 | 0.91 | −5.36 | 0.41 | 1.00 | 1.16E−03 |
| miR-126,miR-378 | −1.74 | −2.73 | 0.81 | −0.99 | 0.80 | 1.00 | 2.19E−03 |
| miR-342,miR-497 | 1.51 | −0.74 | 0.16 | −2.24 | 1.24 | 1.00 | 2.67E−03 |
| let-7f,miR-342 | −1.61 | −1.09 | 0.22 | 0.52 | 1.47 | 1.00 | 2.70E−03 |
| miR-142-5p,miR-422a | −2.46 | −3.09 | 0.19 | −0.63 | 1.61 | 1.00 | 2.70E−03 |
| miR-145,miR-200c | 1.86 | −0.20 | 0.55 | −2.06 | 1.03 | 1.00 | 2.70E−03 |
| miR-148a,miR-19b | −1.60 | 3.30 | 0.99 | 4.90 | 0.65 | 1.00 | 2.70E−03 |
| miR-191,miR-340 | 1.42 | −1.26 | 0.39 | −2.68 | 0.84 | 1.00 | 2.70E−03 |
| miR-200b,miR-422a | −1.87 | 1.76 | 0.60 | 3.63 | 1.33 | 1.00 | 2.70E−03 |
| miR-340,miR-378 | −2.00 | 0.15 | 0.41 | 2.14 | 1.43 | 1.00 | 2.70E−03 |

Example 4 miRNA Markers that Distinguish Lung Cancer from Cancer-Free Subjects with or without Benign Conditions In an additional study, serum miRNAs that distinguish lung cancer patients from cancer free human subjects with or without benign conditions are identified. Serum samples were obtained from patients with benign conditions, normal patients, and lung cancer patients (Table 19). All procedures and data analysis were performed as described above.

TABLE 19

Histopathological and patient information for lung cancer and benign specimens.

| Sample ID | Age | Sex | Cancer Status | Diagnosis | Cell Type |
|---|---|---|---|---|---|
| 1 | 59 | F | Other | Benign | NA |
| 2 | 60 | F | Other | Benign | NA |
| 3 | 64 | F | Other | Benign | NA |
| 4 | 69 | F | Other | Benign | NA |
| 5 | 71 | F | Other | Benign | NA |
| 6 | 73 | F | Other | Benign | NA |
| 7 | 77 | F | Other | Benign | NA |
| 8 | 56 | M | Other | Benign | NA |
| 9 | 58 | M | Other | Benign | NA |
| 10 | 60 | M | Other | Benign | NA |
| 11 | 69 | M | Other | Benign | NA |
| 12 | 71 | M | Other | Benign | NA |
| 13 | 59 | F | Cancer | Cancer | ADCA |
| 14 | 64 | F | Cancer | Cancer | ADCA |
| 15 | 66 | F | Cancer | Cancer | ADCA |
| 15 | 66 | F | Cancer | Cancer | ADCA |
| 16 | 66 | F | Cancer | Cancer | SCC |
| 17 | 72 | F | Cancer | Cancer | SCC |
| 18 | 73 | F | Cancer | Cancer | SCC |
| 19 | 73 | F | Cancer | Cancer | SCC |
| 20 | 56 | M | Cancer | Cancer | SCC |
| 20 | 56 | M | Cancer | Cancer | SCC |
| 21 | 60 | M | Cancer | Cancer | ADCA |
| 21 | 60 | M | Cancer | Cancer | ADCA |
| 22 | 63 | M | Cancer | Cancer | ADCA |
| 23 | 66 | M | Cancer | Cancer | SCC |
| 24 | 69 | M | Cancer | Cancer | ADCA |
| 25 | 69 | M | Cancer | Cancer | SCC |
| 26 | 69 | M | Cancer | Cancer | SCC |
| 27 | 71 | M | Cancer | Cancer | SCC |
| 28 | 72 | M | Cancer | Cancer | ADCA |
| 29 | 79 | M | Cancer | Cancer | ADCA |
| 30 | 67 | M | Cancer | Cancer | ADCA |
| 31 | 82 | F | Cancer | Cancer | SCC |
| 32 | 77 | M | Cancer | Cancer | ADCA |
| 33 | 41 | M | Other | Normal | NA |
| 34 | 40 | F | Other | Normal | NA |
| 35 | 66 | F | Other | Normal | NA |
| 36 | 65 | F | Other | Normal | NA |
| 37 | 20 | F | Other | Normal | NA |
| 38 | 41 | M | Other | Normal | NA |
| 39 | 37 | M | Other | Normal | NA |
| 40 | 50 | M | Other | Normal | NA |
| 41 | 47 | F | Other | Normal | NA |
| 42 | 50 | F | Other | Normal | NA |
| 43 | 51 | F | Other | Normal | NA |
| 44 | 70 | F | Other | Normal | NA |
| 45 | 55 | F | Other | Normal | NA |
| 46 | 69 | M | Other | Normal | NA |
| 47 | 61 | M | Other | Normal | NA |
| 48 | 60 | M | Other | Normal | NA |
| 49 | 58 | M | Other | Normal | NA |
| 50 | 53 | M | Other | Normal | NA |
| 51 | 75 | M | Other | Normal | NA |
| 52 | 55 | M | Other | Normal | NA |

Table 20 provides differential expression data for miRNAs in the form of average dCt values for cancer and other samples (other=benign and normal). Table 21 shows differentially expressed miRNA biomarker pairs that distinguish samples from lung cancer patients from normal patients and patients with benign tumors. Such miRNA and biomarker pairs can be used for screening and diagnosis of lung cancer.

TABLE 20

Expression of miRNAs in serum from patients with lung cancer or from patients with benign or normal conditions. Other = benign and normal cases.

| miRNA | cancer dCT | Cancer SD | Other dCT | Other SD | Cancer – Other ddCT | ttest p-value |
|---|---|---|---|---|---|---|
| miR-15b | −0.523 | 0.624 | −1.867 | 1.032 | 1.344 | 2.45E−09 |
| miR-30a-5p | −3.139 | 0.571 | −1.901 | 1.010 | −1.239 | 3.11E−09 |
| miR-346 | 4.384 | 1.995 | 1.228 | 2.523 | 3.156 | 3.98E−08 |
| let-7g | −2.051 | 0.650 | −3.095 | 0.948 | 1.044 | 1.47E−07 |
| let-7a | −0.898 | 0.756 | −2.176 | 1.131 | 1.278 | 5.14E−07 |
| let-7f | 0.878 | 0.944 | −0.601 | 1.303 | 1.479 | 1.09E−06 |
| miR-93 | −7.708 | 0.932 | −6.577 | 1.416 | −1.131 | 1.59E−06 |
| miR-214 | 3.494 | 1.727 | 1.205 | 2.038 | 2.289 | 1.92E−06 |
| miR-15a | 2.777 | 0.898 | 1.659 | 1.028 | 1.118 | 2.81E−06 |
| let-7d | 0.782 | 0.890 | −0.266 | 0.969 | 1.049 | 4.26E−06 |
| miR-142-3p | −3.320 | 0.843 | −4.174 | 0.978 | 0.853 | 6.67E−06 |
| miR-605 | 3.922 | 2.437 | 0.776 | 2.956 | 3.146 | 9.81E−06 |
| miR-483 | 3.478 | 1.463 | 1.494 | 1.903 | 1.983 | 1.11E−05 |
| miR-374 | −0.243 | 0.834 | −1.170 | 0.919 | 0.927 | 1.56E−05 |
| miR-150 | −3.282 | 1.435 | −1.928 | 1.409 | −1.354 | 1.59E−05 |
| miR-486 | −6.137 | 1.241 | −4.782 | 1.564 | −1.354 | 1.89E−05 |
| miR-181d | 0.507 | 1.026 | 1.643 | 1.140 | −1.135 | 3.24E−05 |
| miR-21 | −3.900 | 0.608 | −3.082 | 0.991 | −0.817 | 7.43E−05 |
| miR-320 | −4.331 | 1.237 | −3.075 | 1.461 | −1.255 | 8.98E−05 |
| miR-345 | 0.133 | 0.638 | 0.895 | 0.809 | −0.762 | 9.71E−05 |
| miR-30d | −1.569 | 1.155 | −0.241 | 1.437 | −1.328 | 1.02E−04 |
| miR-145 | 1.626 | 1.094 | 0.029 | 1.717 | 1.597 | 1.37E−04 |
| miR-365 | 1.679 | 1.098 | 2.738 | 1.175 | −1.059 | 1.89E−04 |
| miR-99a | 3.577 | 1.230 | 2.575 | 1.118 | 1.001 | 2.29E−04 |
| miR-23a | 0.873 | 0.545 | 1.546 | 0.757 | −0.672 | 2.41E−04 |
| miR-133b | 3.006 | 1.601 | 1.125 | 2.129 | 1.881 | 2.86E−04 |
| miR-566 | 3.050 | 1.587 | 1.437 | 1.844 | 1.613 | 3.30E−04 |
| miR-26b | −3.142 | 0.637 | −3.772 | 0.878 | 0.629 | 3.50E−04 |
| miR-22 | 0.286 | 0.976 | 1.237 | 1.089 | −0.951 | 3.86E−04 |
| miR-30c | −1.646 | 0.588 | −2.129 | 0.652 | 0.483 | 6.45E−04 |
| miR-190 | 2.962 | 1.061 | 2.004 | 1.171 | 0.958 | 7.39E−04 |
| miR-485-3p | 4.321 | 1.402 | 3.158 | 1.442 | 1.164 | 1.05E−03 |
| miR-206 | 4.582 | 1.381 | 3.498 | 1.396 | 1.084 | 1.18E−03 |
| miR-181b | 0.709 | 1.054 | 1.514 | 1.011 | −0.804 | 1.24E−03 |
| miR-19b | −4.720 | 0.805 | −4.070 | 1.050 | −0.650 | 1.52E−03 |
| miR-148a | −0.268 | 0.761 | 0.443 | 0.917 | −0.710 | 1.62E−03 |
| let-7b | −1.755 | 0.708 | −2.322 | 0.807 | 0.566 | 1.79E−03 |
| miR-29a | −1.448 | 1.083 | −0.491 | 1.275 | −0.957 | 1.95E−03 |
| miR-103 | 0.010 | 1.025 | −0.952 | 1.274 | 0.961 | 2.05E−03 |
| miR-30b | −1.462 | 0.546 | −1.898 | 0.637 | 0.436 | 2.18E−03 |
| miR-496 | 6.002 | 1.586 | 4.850 | 1.558 | 1.152 | 2.30E−03 |
| miR-182 | 3.886 | 1.377 | 2.482 | 1.831 | 1.404 | 2.47E−03 |
| miR-186 | −0.683 | 0.639 | −0.181 | 0.683 | −0.502 | 2.47E−03 |
| miR-99b | 2.233 | 1.366 | 3.268 | 1.408 | −1.035 | 2.82E−03 |
| miR-125b | 2.544 | 0.949 | 3.321 | 1.082 | −0.777 | 2.95E−03 |
| miR-26a | −3.017 | 0.883 | −3.703 | 1.076 | 0.685 | 3.37E−03 |
| miR-339 | 2.286 | 0.654 | 2.973 | 0.975 | −0.686 | 3.42E−03 |
| miR-342 | 0.460 | 0.887 | 1.055 | 0.843 | −0.595 | 4.51E−03 |
| miR-146a | −3.761 | 1.010 | −3.126 | 1.055 | −0.635 | 4.56E−03 |
| miR-328 | 0.971 | 0.871 | 0.142 | 1.182 | 0.829 | 4.84E−03 |
| miR-335 | 0.655 | 0.783 | 1.269 | 0.877 | −0.613 | 4.94E−03 |
| miR-106b | −1.435 | 0.656 | −1.944 | 0.797 | 0.508 | 6.12E−03 |
| miR-326 | 5.137 | 1.046 | 5.869 | 1.199 | −0.732 | 6.28E−03 |
| miR-17-5p | −0.410 | 0.910 | −0.955 | 0.830 | 0.545 | 6.80E−03 |
| miR-29c | −0.087 | 1.212 | 0.875 | 1.407 | −0.961 | 6.85E−03 |
| miR-133a | 2.968 | 2.760 | 4.572 | 2.392 | −1.605 | 7.58E−03 |
| miR-146b | −1.593 | 1.008 | −1.052 | 0.868 | −0.542 | 8.03E−03 |
| miR-181a | 1.149 | 0.818 | 1.705 | 0.854 | −0.556 | 8.94E−03 |
| miR-10b | 2.422 | 1.089 | 3.088 | 1.046 | −0.666 | 9.43E−03 |
| miR-19a | −2.693 | 1.102 | −1.781 | 1.478 | −0.912 | 1.02E−02 |
| miR-130b | −0.325 | 0.766 | 0.163 | 0.768 | −0.488 | 1.03E−02 |
| miR-410 | 3.440 | 1.646 | 2.508 | 1.434 | 0.932 | 1.07E−02 |
| miR-126 | −3.241 | 0.733 | −3.653 | 0.830 | 0.411 | 1.17E−02 |
| miR-422a | 2.734 | 1.662 | 3.572 | 1.377 | −0.839 | 1.43E−02 |

TABLE 20-continued

Expression of miRNAs in serum from patients with lung cancer or from patients with benign or normal conditions. Other = benign and normal cases.

| miRNA | cancer dCT | Cancer SD | Other dCT | Other SD | Cancer − Other ddCT | ttest p-value |
|---|---|---|---|---|---|---|
| miR-425 | 1.878 | 0.795 | 2.375 | 0.812 | −0.497 | 1.49E−02 |
| miR-151 | 0.360 | 0.773 | 0.797 | 0.717 | −0.436 | 1.52E−02 |
| miR-20a | −3.836 | 1.304 | −4.484 | 1.271 | 0.648 | 1.72E−02 |
| miR-660 | −0.907 | 0.835 | −0.409 | 0.849 | −0.498 | 1.76E−02 |
| miR-497 | 3.057 | 0.925 | 3.687 | 1.097 | −0.630 | 1.92E−02 |
| miR-100 | 2.862 | 1.415 | 3.688 | 1.429 | −0.826 | 1.98E−02 |
| miR-194 | 3.243 | 0.960 | 2.533 | 1.236 | 0.710 | 2.10E−02 |
| miR-30e-5p | −0.729 | 1.007 | 0.056 | 1.367 | −0.785 | 2.15E−02 |
| miR-210 | 1.024 | 0.850 | 1.462 | 0.773 | −0.438 | 2.41E−02 |
| miR-423 | 2.172 | 0.924 | 1.547 | 1.119 | 0.625 | 2.59E−02 |
| miR-204 | 5.281 | 1.609 | 4.442 | 1.566 | 0.838 | 2.92E−02 |
| miR-9* | 2.947 | 1.060 | 3.492 | 1.027 | −0.545 | 3.09E−02 |
| miR-25 | −2.165 | 1.097 | −1.600 | 1.111 | −0.565 | 3.40E−02 |
| miR-301 | 2.140 | 0.717 | 1.711 | 0.824 | 0.430 | 3.56E−02 |
| miR-502 | 4.651 | 1.659 | 5.422 | 1.511 | −0.772 | 3.70E−02 |
| miR-518b | 4.924 | 1.447 | 3.973 | 1.855 | 0.951 | 4.13E−02 |
| miR-125a | 0.901 | 1.248 | 1.533 | 1.226 | −0.631 | 4.33E−02 |
| miR-223 | −5.788 | 1.381 | −5.053 | 1.652 | −0.735 | 4.44E−02 |
| miR-134 | 3.501 | 1.357 | 2.828 | 1.340 | 0.674 | 4.72E−02 |
| miR-132 | 1.518 | 0.796 | 1.957 | 0.894 | −0.439 | 5.03E−02 |
| miR-24 | −3.178 | 0.614 | −2.922 | 0.708 | −0.257 | 6.34E−02 |
| miR-361 | 1.789 | 0.961 | 2.155 | 0.796 | −0.366 | 6.61E−02 |
| miR-28 | 3.299 | 0.980 | 2.869 | 0.949 | 0.431 | 6.67E−02 |
| miR-185 | 1.585 | 1.359 | 2.330 | 1.626 | −0.745 | 7.50E−02 |
| miR-432 | 3.290 | 1.405 | 2.728 | 1.224 | 0.562 | 7.60E−02 |
| miR-192 | 0.357 | 0.940 | 0.725 | 0.828 | −0.368 | 7.93E−02 |
| let-7c | 1.936 | 0.836 | 1.595 | 0.774 | 0.341 | 7.93E−02 |
| miR-296 | 4.006 | 1.424 | 3.484 | 1.208 | 0.522 | 7.99E−02 |
| miR-152 | 2.617 | 1.223 | 3.180 | 1.315 | −0.563 | 8.79E−02 |
| miR-139 | 3.347 | 0.883 | 3.737 | 0.963 | −0.390 | 9.01E−02 |
| miR-191 | −1.679 | 1.115 | −1.199 | 1.230 | −0.480 | 1.16E−01 |
| miR-30e-3p | 4.375 | 1.159 | 3.924 | 1.219 | 0.451 | 1.27E−01 |
| miR-30a-3p | 3.592 | 1.065 | 3.996 | 1.087 | −0.404 | 1.28E−01 |
| miR-32 | 3.558 | 2.615 | 2.639 | 2.302 | 0.919 | 1.29E−01 |
| miR-16 | −7.960 | 1.397 | −8.410 | 1.700 | 0.450 | 1.50E−01 |
| miR-10a | 3.135 | 1.137 | 3.562 | 1.214 | −0.427 | 1.57E−01 |
| miR-505 | 3.804 | 0.899 | 3.471 | 1.002 | 0.332 | 1.73E−01 |
| miR-143 | 3.697 | 1.939 | 3.076 | 1.787 | 0.620 | 1.82E−01 |
| miR-148b | 1.275 | 0.877 | 1.522 | 0.717 | −0.247 | 1.82E−01 |
| miR-324-5p | 3.015 | 0.871 | 3.256 | 0.779 | −0.241 | 1.95E−01 |
| miR-222 | −1.220 | 0.858 | −0.993 | 0.743 | −0.227 | 2.09E−01 |
| miR-200c | 2.177 | 2.198 | 2.817 | 2.051 | −0.640 | 2.26E−01 |
| miR-324-3p | 2.038 | 1.273 | 2.413 | 1.213 | −0.375 | 2.28E−01 |
| miR-126* | −2.694 | 0.451 | −2.813 | 0.555 | 0.119 | 2.33E−01 |
| miR-638 | 2.384 | 1.822 | 1.926 | 1.546 | 0.458 | 2.51E−01 |
| miR-181c | 4.089 | 1.069 | 3.769 | 1.175 | 0.319 | 2.69E−01 |
| miR-7 | 2.534 | 1.084 | 2.255 | 1.024 | 0.279 | 2.89E−01 |
| miR-378 | 1.215 | 3.252 | 1.976 | 2.796 | −0.760 | 2.91E−01 |
| let-7e | 1.287 | 3.313 | 0.605 | 2.787 | 0.682 | 3.37E−01 |
| miR-340 | 2.165 | 2.654 | 2.808 | 2.604 | −0.643 | 3.51E−01 |
| miR-140 | 0.181 | 0.659 | 0.064 | 0.580 | 0.118 | 4.27E−01 |
| miR-382 | 3.241 | 1.348 | 3.495 | 1.295 | −0.254 | 4.35E−01 |
| miR-422b | 1.176 | 1.174 | 0.932 | 1.293 | 0.244 | 4.65E−01 |
| miR-98 | 5.914 | 0.927 | 6.143 | 1.263 | −0.229 | 4.77E−01 |
| miR-155 | 1.620 | 1.136 | 1.778 | 0.950 | −0.158 | 5.16E−01 |
| miR-197 | 0.073 | 0.927 | 0.215 | 0.872 | −0.142 | 5.23E−01 |
| miR-23b | 3.618 | 1.178 | 3.797 | 1.124 | −0.179 | 5.25E−01 |
| miR-106a | −2.070 | 1.499 | −2.262 | 1.314 | 0.192 | 5.44E−01 |
| miR-18a | 1.848 | 1.364 | 1.668 | 1.160 | 0.180 | 5.46E−01 |
| miR-34a | 3.868 | 1.378 | 4.067 | 1.386 | −0.199 | 5.69E−01 |
| miR-195 | −1.630 | 1.559 | −1.825 | 1.430 | 0.195 | 5.81E−01 |
| miR-202 | 2.694 | 2.197 | 2.941 | 1.719 | −0.247 | 5.81E−01 |
| miR-20b | −0.425 | 1.325 | −0.575 | 1.142 | 0.150 | 6.01E−01 |
| miR-376a | 4.192 | 1.482 | 4.363 | 1.353 | −0.172 | 6.15E−01 |
| miR-142-5p | 0.923 | 0.932 | 1.036 | 0.948 | −0.114 | 6.41E−01 |
| miR-92 | 4.110 | 3.501 | 4.401 | 2.527 | −0.291 | 6.62E−01 |
| miR-127 | 3.641 | 1.726 | 3.819 | 1.636 | −0.178 | 6.73E−01 |
| miR-27a | −0.307 | 0.859 | −0.182 | 1.170 | −0.126 | 6.74E−01 |
| miR-199a* | −0.915 | 0.770 | −0.977 | 0.656 | 0.062 | 6.96E−01 |
| miR-550 | 4.637 | 1.079 | 4.559 | 1.015 | 0.078 | 7.43E−01 |
| miR-101 | −0.181 | 1.511 | −0.133 | 1.343 | −0.048 | 8.89E−01 |
| let-7i | −0.730 | 0.653 | −0.709 | 0.754 | −0.020 | 9.14E−01 |
| miR-501 | 4.581 | 1.674 | 4.548 | 1.542 | 0.033 | 9.32E−01 |
| miR-130a | −1.039 | 0.940 | −1.020 | 0.944 | −0.019 | 9.36E−01 |
| miR-27b | 2.845 | 1.229 | 2.820 | 1.405 | 0.025 | 9.45E−01 |
| miR-584 | 3.214 | 1.501 | 3.226 | 1.529 | −0.012 | 9.76E−01 |
| miR-433 | 3.993 | 1.531 | 3.992 | 1.332 | 0.001 | 9.97E−01 |
| miR-221 | −1.894 | 1.070 | −1.894 | 1.014 | −0.001 | 9.98E−01 |

TABLE 21

Differentially expressed miRNA biomarker pairs that distinguish lung cancer patients from normal patients with no lung tumors and patients with benign lung tumors. Other = benign and normal cases.

| miRNA Biomarker Pair | Cancer mean − Other mean | Cancer mean | Cancer SD | Other mean | Other SD | AUC ROC | Other vs Cancer Assoc. |
|---|---|---|---|---|---|---|---|
| miR-15a,miR-92 | 2.31 | 10.55 | 1.17 | 8.24 | 0.77 | 0.96 | 1.83E−13 |
| miR-15b,miR-92 | 2.47 | 7.22 | 1.25 | 4.75 | 0.93 | 0.95 | 8.99E−13 |
| miR-214,miR-422b | 2.09 | 2.40 | 1.18 | 0.31 | 0.72 | 0.95 | 4.61E−12 |
| miR-15b,miR-24 | 1.59 | 2.67 | 0.63 | 1.09 | 0.77 | 0.95 | 7.90E−13 |
| miR-146a,miR-15b | −1.99 | −3.27 | 1.09 | −1.29 | 0.93 | 0.94 | 6.21E−11 |
| let-7g,miR-150 | 2.41 | 1.28 | 1.23 | −1.14 | 1.04 | 0.93 | 5.66E−12 |
| miR-142-3p,miR-92 | 2.07 | 4.46 | 1.28 | 2.39 | 0.74 | 0.93 | 5.38E−11 |
| miR-346,miR-422b | 2.94 | 3.28 | 2.00 | 0.34 | 0.84 | 0.93 | 1.48E−10 |
| let-7a,miR-92 | 2.42 | 6.85 | 1.35 | 4.43 | 1.00 | 0.93 | 2.10E−11 |
| let-7f,miR-146a | 2.15 | 4.69 | 1.02 | 2.54 | 1.10 | 0.92 | 2.23E−11 |
| miR-106b,miR-92 | 1.65 | 6.30 | 0.91 | 4.66 | 0.71 | 0.92 | 2.70E−11 |
| let-7g,miR-342 | 1.65 | −2.48 | 1.00 | −4.13 | 0.92 | 0.92 | 3.57E−09 |
| let-7a,miR-181a | 1.82 | −2.03 | 1.00 | −3.85 | 0.81 | 0.92 | 3.34E−10 |
| let-7d,miR-92 | 2.27 | 8.57 | 1.47 | 6.30 | 0.77 | 0.92 | 1.14E−10 |
| miR-15b,miR-181a | 1.87 | −1.66 | 1.11 | −3.53 | 0.82 | 0.92 | 1.50E−10 |
| let-7f,miR-92 | 2.64 | 8.64 | 1.46 | 6.00 | 1.24 | 0.92 | 9.94E−11 |
| let-7g,miR-92 | 2.18 | 5.69 | 1.28 | 3.52 | 0.87 | 0.92 | 4.53E−11 |
| let-7b,miR-92 | 1.72 | 5.99 | 1.04 | 4.27 | 0.70 | 0.92 | 1.05E−10 |

TABLE 21-continued

Differentially expressed miRNA biomarker pairs that distinguish lung cancer patients from normal patients with no lung tumors and patients with benign lung tumors. Other = benign and normal cases.

| miRNA Biomarker Pair | Cancer mean – Other mean | Cancer mean | Cancer SD | Other mean | Other SD | AUC ROC | Other vs Cancer Assoc. |
|---|---|---|---|---|---|---|---|
| let-7g,miR-146a | 1.70 | 1.75 | 0.93 | 0.05 | 0.88 | 0.91 | 2.78E−10 |
| miR-142-3p,miR-181a | 1.47 | −4.42 | 0.89 | −5.89 | 0.79 | 0.91 | 2.36E−09 |
| miR-181d,miR-346 | −4.22 | −3.91 | 2.07 | 0.31 | 2.29 | 0.91 | 1.11E−10 |
| miR-126,miR-92 | 1.59 | 4.52 | 1.06 | 2.92 | 0.77 | 0.91 | 3.38E−09 |
| miR-150,miR-15b | −2.70 | −2.80 | 1.68 | −0.10 | 1.25 | 0.91 | 6.51E−10 |
| let-7f,miR-181a | 2.04 | −0.24 | 1.27 | −2.28 | 0.86 | 0.91 | 2.84E−10 |
| miR-15b,miR-342 | 1.94 | −0.95 | 1.26 | −2.89 | 1.04 | 0.91 | 6.17E−09 |
| miR-7,miR-92 | 1.39 | 10.26 | 0.83 | 8.88 | 0.64 | 0.91 | 2.65E−10 |
| miR-181b,miR-346 | −3.93 | −3.72 | 2.27 | 0.21 | 1.95 | 0.91 | 4.07E−10 |
| miR-181b,miR-214 | −3.06 | −2.82 | 1.76 | 0.24 | 1.56 | 0.91 | 5.08E−10 |
| miR-15a,miR-425 | 1.57 | 0.87 | 1.10 | −0.71 | 0.87 | 0.90 | 2.72E−08 |
| miR-146a,miR-374 | −1.61 | −3.57 | 1.09 | −1.96 | 0.80 | 0.90 | 6.42E−09 |
| miR-146b,miR-374 | −1.49 | −1.38 | 1.09 | 0.11 | 0.76 | 0.90 | 3.15E−08 |
| miR-181a,miR-346 | −3.69 | −3.28 | 2.29 | 0.41 | 1.78 | 0.90 | 9.09E−10 |
| miR-150,miR-214 | −3.66 | −6.84 | 2.25 | −3.19 | 1.83 | 0.90 | 1.34E−09 |
| miR-214,miR-92 | 3.46 | 11.29 | 2.00 | 7.84 | 1.95 | 0.90 | 2.12E−09 |
| miR-142-3p,miR-30a-5p | 2.03 | −0.18 | 1.17 | −2.21 | 1.01 | 0.90 | 4.42E−10 |
| miR-346,miR-92 | 4.29 | 12.16 | 2.62 | 7.87 | 2.15 | 0.90 | 1.13E−09 |
| miR-374,miR-92 | 2.09 | 7.51 | 1.40 | 5.42 | 0.88 | 0.90 | 1.16E−09 |
| miR-346,miR-422a | 3.97 | 1.70 | 2.12 | −2.27 | 2.22 | 0.90 | 6.06E−10 |
| miR-150,miR-346 | −4.53 | −7.75 | 2.83 | −3.22 | 2.16 | 0.89 | 9.72E−10 |
| miR-15b,miR-335 | 1.85 | −1.20 | 0.73 | −3.05 | 1.29 | 0.89 | 1.80E−09 |
| miR-342,miR-346 | −3.76 | −3.99 | 2.40 | −0.23 | 1.87 | 0.89 | 2.05E−09 |
| miR-146a,miR-15a | −1.83 | −6.60 | 1.37 | −4.78 | 0.86 | 0.89 | 2.54E−09 |
| miR-181d,miR-214 | −3.34 | −2.99 | 1.94 | 0.34 | 1.91 | 0.89 | 2.74E−09 |
| let-7b,miR-150 | 1.95 | 1.57 | 1.26 | −0.38 | 1.00 | 0.89 | 3.83E−09 |
| miR-190,miR-92 | 2.06 | 10.69 | 1.23 | 8.63 | 1.15 | 0.89 | 2.93E−09 |
| miR-181d,miR-98 | −2.11 | −3.08 | 1.59 | −0.97 | 0.92 | 0.89 | 1.44E−08 |
| let-7a,miR-150 | 2.66 | 2.44 | 1.76 | −0.22 | 1.32 | 0.89 | 4.15E−09 |
| miR-214,miR-425 | 2.81 | 1.70 | 1.44 | −1.11 | 1.76 | 0.89 | 2.46E−09 |
| miR-142-3p,miR-181d | 2.00 | −3.79 | 1.32 | −5.79 | 1.35 | 0.89 | 9.09E−08 |
| miR-214,miR-342 | 2.89 | 3.08 | 1.88 | 0.19 | 1.57 | 0.89 | 7.89E−09 |
| miR-142-3p,miR-425 | 1.37 | −5.19 | 0.91 | −6.56 | 0.73 | 0.89 | 7.70E−09 |
| let-7g,miR-181d | 2.11 | −2.56 | 1.35 | −4.67 | 1.41 | 0.89 | 7.42E−08 |
| miR-30c,miR-92 | 1.67 | 6.11 | 1.10 | 4.45 | 0.89 | 0.89 | 7.84E−09 |
| let-7a,miR-181d | 2.35 | −1.40 | 1.53 | −3.75 | 1.68 | 0.89 | 1.18E−07 |
| miR-130b,miR-15a | −1.56 | −3.10 | 1.04 | −1.55 | 0.91 | 0.88 | 2.52E−08 |
| miR-142-3p,miR-345 | 1.57 | −3.45 | 1.05 | −5.02 | 0.86 | 0.88 | 1.42E−08 |
| miR-15a,miR-181d | 2.23 | 2.30 | 1.46 | 0.06 | 1.58 | 0.88 | 1.22E−07 |
| let-7f,miR-150 | 2.87 | 4.22 | 1.90 | 1.35 | 1.49 | 0.88 | 6.69E−09 |
| miR-15b,miR-345 | 1.97 | −0.69 | 1.01 | −2.66 | 1.21 | 0.88 | 1.56E−09 |
| miR-346,miR-518b | 2.13 | −0.60 | 1.64 | −2.72 | 0.89 | 0.88 | 1.99E−08 |
| miR-24,miR-374 | −1.21 | −2.97 | 0.77 | −1.76 | 0.69 | 0.88 | 1.22E−08 |
| let-7f,miR-342 | 2.11 | 0.47 | 1.42 | −1.64 | 1.19 | 0.88 | 1.96E−08 |
| let-7g,miR-345 | 1.68 | −2.22 | 0.97 | −3.90 | 1.13 | 0.88 | 2.61E−08 |
| miR-15a,miR-181a | 1.71 | 1.67 | 1.23 | −0.04 | 0.90 | 0.88 | 3.07E−08 |
| miR-15a,miR-30a-5p | 2.27 | 5.91 | 0.97 | 3.64 | 1.44 | 0.88 | 4.23E−10 |
| let-7d,miR-486 | 2.41 | 6.96 | 1.31 | 4.55 | 1.52 | 0.88 | 5.15E−09 |
| miR-146a,miR-214 | −2.91 | −7.28 | 1.56 | −4.37 | 1.81 | 0.88 | 3.27E−09 |
| miR-15a,miR-345 | 1.81 | 2.64 | 1.07 | 0.83 | 1.04 | 0.88 | 4.06E−09 |
| miR-15b,miR-93 | 1.46 | 3.22 | 1.06 | 1.76 | 0.72 | 0.88 | 2.05E−08 |
| miR-15b,miR-181d | 2.40 | −1.03 | 1.52 | −3.43 | 1.59 | 0.88 | 5.80E−08 |
| miR-146b,miR-214 | −2.86 | −5.16 | 1.48 | −2.31 | 1.76 | 0.88 | 2.02E−09 |
| miR-15a,miR-210 | 1.52 | 1.76 | 1.12 | 0.24 | 0.89 | 0.88 | 1.06E−07 |
| miR-142-3p,miR-99b | 1.36 | −6.25 | 1.23 | −7.60 | 1.05 | 0.88 | 2.18E−07 |
| miR-346,miR-486 | 4.43 | 10.55 | 2.60 | 6.12 | 2.78 | 0.88 | 1.18E−08 |
| let-7a,miR-342 | 1.89 | −1.32 | 1.27 | −3.21 | 1.03 | 0.88 | 1.33E−08 |
| miR-181a,miR-214 | −2.80 | −2.36 | 1.79 | 0.44 | 1.67 | 0.88 | 1.72E−08 |
| let-7f,miR-24 | 1.75 | 4.09 | 0.98 | 2.34 | 1.05 | 0.87 | 3.00E−09 |
| let-7g,miR-24 | 1.29 | 1.14 | 0.85 | −0.15 | 0.70 | 0.87 | 7.88E−09 |
| miR-214,miR-375 | 4.29 | 0.81 | 2.70 | −3.48 | 2.67 | 0.87 | 2.30E−08 |
| let-7g,miR-181b | 1.81 | −2.75 | 1.30 | −4.56 | 1.10 | 0.87 | 1.03E−07 |
| miR-142-3p,miR-146a | 1.59 | 0.51 | 1.15 | −1.07 | 0.68 | 0.87 | 6.05E−09 |
| miR-15b,miR-326 | 2.00 | −5.65 | 1.09 | −7.65 | 1.40 | 0.87 | 2.43E−08 |
| miR-130b,miR-142-3p | −1.32 | 2.99 | 0.95 | 4.30 | 0.65 | 0.87 | 1.86E−08 |
| let-7g,miR-181a | 1.58 | −3.19 | 1.16 | −4.76 | 1.13 | 0.87 | 3.08E−08 |
| miR-335,miR-374 | −1.47 | 0.91 | 0.76 | 2.38 | 1.03 | 0.87 | 1.71E−08 |
| miR-130b,miR-15b | −1.72 | 0.23 | 1.00 | 1.95 | 1.15 | 0.87 | 2.62E−08 |
| let-7d,miR-150 | 2.51 | 4.15 | 2.02 | 1.65 | 1.13 | 0.87 | 6.84E−08 |
| miR-181d,miR-193a | −2.40 | −4.89 | 1.42 | −2.48 | 1.58 | 0.87 | 2.23E−08 |
| miR-142-3p,miR-342 | 1.54 | −3.71 | 1.13 | −5.25 | 0.77 | 0.87 | 2.53E−08 |

TABLE 21-continued

Differentially expressed miRNA biomarker pairs that distinguish lung cancer patients from normal patients with no lung tumors and patients with benign lung tumors. Other = benign and normal cases.

| miRNA Biomarker Pair | Cancer mean − Other mean | Cancer mean | Cancer SD | Other mean | Other SD | AUC ROC | Other vs Cancer Assoc. |
|---|---|---|---|---|---|---|---|
| miR-15b,miR-30a-5p | 2.43 | 2.58 | 0.88 | 0.15 | 1.70 | 0.87 | 9.93E−10 |
| let-7i,miR-30a-5p | 1.16 | 2.40 | 0.70 | 1.24 | 0.83 | 0.87 | 8.47E−08 |
| let-7f,miR-181d | 2.56 | 0.39 | 1.69 | −2.18 | 1.72 | 0.87 | 1.05E−07 |
| miR-151,miR-15b | −1.75 | 0.87 | 0.95 | 2.62 | 1.30 | 0.87 | 6.22E−08 |
| miR-17-5p,miR-92 | 1.59 | 7.28 | 1.23 | 5.69 | 0.85 | 0.87 | 9.94E−08 |
| miR-106b,miR-150 | 1.88 | 1.89 | 1.35 | 0.00 | 1.04 | 0.87 | 3.93E−08 |
| miR-125a,miR-214 | −2.87 | −2.62 | 1.85 | 0.25 | 1.89 | 0.87 | 6.22E−08 |
| miR-132,miR-15b | −1.80 | 2.01 | 0.98 | 3.80 | 1.26 | 0.87 | 2.71E−08 |
| miR-320,miR-346 | −4.27 | −8.72 | 2.21 | −4.44 | 2.94 | 0.87 | 1.16E−08 |
| miR-146a,miR-26a | −1.36 | −0.78 | 0.79 | 0.57 | 0.90 | 0.87 | 2.52E−08 |
| miR-132,miR-214 | −2.74 | −2.03 | 1.91 | 0.72 | 1.63 | 0.87 | 5.53E−08 |
| miR-181d,miR-496 | −2.25 | −5.45 | 1.78 | −3.20 | 1.33 | 0.86 | 3.26E−07 |
| miR-15b,miR-19b | 1.99 | 4.23 | 1.07 | 2.24 | 1.31 | 0.86 | 8.91E−09 |
| miR-20a,miR-92 | 1.73 | 3.88 | 1.54 | 2.15 | 0.84 | 0.86 | 5.61E−07 |
| miR-301,miR-92 | 1.54 | 9.86 | 1.13 | 8.32 | 0.90 | 0.86 | 9.60E−08 |
| miR-143,miR-223 | 1.48 | 9.70 | 1.09 | 8.22 | 1.02 | 0.86 | 5.36E−07 |
| miR-320,miR-496 | −2.43 | −10.38 | 1.64 | −7.95 | 1.79 | 0.86 | 4.11E−07 |
| miR-142-3p,miR-150 | 2.30 | 0.04 | 1.85 | −2.26 | 0.78 | 0.86 | 1.68E−08 |
| miR-26b,miR-92 | 1.78 | 4.60 | 1.26 | 2.82 | 1.09 | 0.86 | 1.01E−07 |
| miR-15a,miR-326 | 1.85 | −2.32 | 1.39 | −4.17 | 1.14 | 0.86 | 2.28E−07 |
| miR-181a,miR-190 | −1.46 | −1.81 | 1.14 | −0.35 | 0.93 | 0.86 | 4.85E−07 |
| miR-126*,miR-30a-5p | 1.27 | 0.42 | 0.79 | −0.85 | 0.86 | 0.86 | 6.46E−08 |
| miR-29b,miR-375 | 2.56 | 1.87 | 2.41 | −0.69 | 1.57 | 0.86 | 7.76E−07 |
| miR-486,miR-98 | −2.26 | −9.73 | 1.69 | −7.48 | 1.35 | 0.86 | 1.60E−07 |
| miR-150,miR-374 | −2.32 | −3.10 | 1.87 | −0.77 | 1.12 | 0.86 | 9.90E−08 |
| miR-155,miR-214 | −2.48 | −1.96 | 1.81 | 0.52 | 1.41 | 0.86 | 7.40E−08 |
| miR-181b,miR-496 | −2.07 | −5.37 | 1.51 | −3.30 | 1.18 | 0.86 | 7.05E−08 |
| miR-150,miR-30c | −1.90 | −1.70 | 1.62 | 0.21 | 0.89 | 0.86 | 2.24E−07 |
| miR-30b,miR-92 | 1.62 | 6.30 | 1.11 | 4.68 | 1.05 | 0.86 | 1.10E−07 |
| miR-142-3p,miR-181b | 1.70 | −3.98 | 1.24 | −5.68 | 1.13 | 0.86 | 2.83E−07 |
| let-7g,miR-30a-5p | 2.14 | 1.05 | 0.91 | −1.09 | 1.57 | 0.86 | 8.39E−09 |
| miR-103,miR-92 | 2.02 | 7.72 | 1.39 | 5.69 | 1.31 | 0.86 | 1.15E−07 |
| miR-181b,miR-26b | −1.41 | 3.85 | 1.12 | 5.26 | 0.84 | 0.86 | 3.73E−07 |
| miR-181d,miR-30b | −1.55 | 1.96 | 1.19 | 3.50 | 0.98 | 0.86 | 4.14E−07 |
| miR-422a,miR-566 | −2.48 | −0.37 | 1.37 | 2.11 | 1.85 | 0.86 | 7.14E−08 |
| let-7f,miR-181b | 2.27 | 0.20 | 1.61 | −2.07 | 1.40 | 0.86 | 1.03E−07 |
| miR-422a,miR-605 | −4.03 | −1.30 | 2.39 | 2.73 | 2.81 | 0.85 | 5.42E−08 |
| miR-15b,miR-210 | 1.69 | −1.57 | 1.23 | −3.25 | 1.12 | 0.85 | 3.32E−07 |
| miR-126,miR-150 | 1.83 | 0.10 | 1.62 | −1.73 | 0.76 | 0.85 | 2.76E−07 |
| let-7d,miR-181d | 2.20 | 0.32 | 1.57 | −1.88 | 1.48 | 0.85 | 2.83E−07 |
| miR-181d,miR-26b | −1.70 | 3.66 | 1.19 | 5.36 | 1.09 | 0.85 | 1.23E−07 |
| let-7f,miR-326 | 2.20 | −4.23 | 1.37 | −6.43 | 1.47 | 0.85 | 5.55E−08 |
| let-7f,miR-345 | 2.14 | 0.73 | 1.33 | −1.41 | 1.49 | 0.85 | 8.61E−08 |
| let-7d,miR-181a | 1.67 | −0.31 | 1.45 | −1.98 | 0.73 | 0.85 | 2.09E−07 |
| miR-214,miR-99b | 2.68 | 0.53 | 1.87 | −2.15 | 1.80 | 0.85 | 2.18E−07 |
| miR-106a,miR-486 | 1.50 | 4.07 | 1.16 | 2.57 | 0.93 | 0.85 | 3.34E−07 |
| miR-214,miR-365 | 3.34 | 1.89 | 2.00 | −1.45 | 2.42 | 0.85 | 1.04E−07 |
| miR-15b,miR-181b | 2.10 | −1.22 | 1.51 | −3.33 | 1.31 | 0.85 | 1.39E−07 |
| miR-214,miR-326 | 2.90 | −1.65 | 1.98 | −4.55 | 1.88 | 0.85 | 1.10E−07 |
| miR-140,miR-150 | 1.59 | 3.54 | 1.27 | 1.96 | 0.82 | 0.85 | 1.37E−07 |
| miR-181d,miR-432 | −1.78 | −2.87 | 1.57 | −1.09 | 0.87 | 0.85 | 4.64E−07 |
| miR-15a,miR-335 | 1.68 | 2.12 | 1.07 | 0.44 | 1.19 | 0.85 | 1.42E−07 |
| miR-140,miR-30a-5p | 1.31 | 3.32 | 0.86 | 2.01 | 0.89 | 0.85 | 1.09E−07 |
| miR-15a,miR-181b | 1.94 | 2.11 | 1.43 | 0.17 | 1.33 | 0.85 | 4.93E−07 |
| miR-26a,miR-92 | 1.84 | 4.73 | 1.33 | 2.89 | 1.16 | 0.85 | 1.77E−07 |
| miR-142-3p,miR-24 | 1.18 | −0.09 | 0.99 | −1.27 | 0.58 | 0.85 | 2.10E−07 |
| miR-151,miR-374 | −1.37 | 0.58 | 1.08 | 1.95 | 0.98 | 0.85 | 1.43E−06 |
| miR-181d,miR-374 | −2.02 | 0.74 | 1.66 | 2.76 | 1.45 | 0.85 | 1.43E−06 |
| miR-142-3p,miR-22 | 1.71 | −3.63 | 1.20 | −5.34 | 1.14 | 0.85 | 2.25E−07 |
| miR-320,miR-98 | −2.13 | −7.88 | 1.45 | −5.75 | 1.43 | 0.85 | 1.51E−07 |
| miR-150,miR-15a | −2.54 | −6.13 | 1.97 | −3.59 | 1.15 | 0.85 | 3.28E−08 |
| miR-125a,miR-98 | −1.61 | −2.67 | 1.49 | −1.06 | 1.00 | 0.85 | 1.53E−06 |
| miR-486,miR-496 | −2.62 | −12.25 | 1.95 | −9.63 | 1.77 | 0.85 | 4.71E−07 |
| miR-142-3p,miR-146b | 1.47 | −1.67 | 1.18 | −3.14 | 0.67 | 0.85 | 6.87E−08 |
| miR-194,miR-92 | 1.86 | 10.98 | 1.30 | 9.12 | 1.34 | 0.85 | 4.70E−07 |
| miR-98,miR-99b | 1.55 | 0.69 | 1.37 | −0.86 | 0.84 | 0.85 | 8.26E−07 |
| miR-193a,miR-92 | 2.34 | 12.98 | 1.63 | 10.64 | 1.70 | 0.85 | 4.79E−07 |
| miR-142-3p,miR-486 | 2.20 | 2.85 | 1.76 | 0.65 | 1.35 | 0.85 | 4.71E−07 |
| miR-132,miR-15a | −1.63 | −1.32 | 1.10 | 0.31 | 1.17 | 0.85 | 3.08E−07 |
| miR-126,miR-146a | 1.11 | 0.57 | 0.82 | −0.54 | 0.62 | 0.85 | 7.03E−08 |
| miR-181d,miR-206 | −2.14 | −4.07 | 1.48 | −1.93 | 1.56 | 0.85 | 4.55E−07 |

TABLE 21-continued

Differentially expressed miRNA biomarker pairs that distinguish lung cancer patients from normal patients with no lung tumors and patients with benign lung tumors. Other = benign and normal cases.

| miRNA Biomarker Pair | Cancer mean − Other mean | Cancer mean | Cancer SD | Other mean | Other SD | AUC ROC | Other vs Cancer Assoc. |
|---|---|---|---|---|---|---|---|
| miR-142-3p,miR-99a | 1.96 | −5.49 | 1.40 | −7.45 | 1.30 | 0.85 | 2.32E−07 |
| miR-181a,miR-30c | −1.07 | 2.76 | 0.79 | 3.83 | 0.60 | 0.85 | 8.83E−08 |
| miR-15a,miR-486 | 2.44 | 8.94 | 1.68 | 6.50 | 1.57 | 0.85 | 1.04E−07 |
| miR-210,miR-214 | −2.63 | −2.47 | 1.92 | 0.17 | 1.70 | 0.85 | 2.29E−07 |
| miR-181a,miR-374 | −1.49 | 1.37 | 1.23 | 2.86 | 0.79 | 0.85 | 2.69E−07 |
| miR-30a-5p,miR-374 | −2.05 | −2.87 | 1.17 | −0.82 | 1.41 | 0.85 | 2.94E−08 |
| miR-133b,miR-92 | 3.05 | 10.78 | 1.91 | 7.73 | 2.31 | 0.85 | 2.91E−07 |
| miR-214,miR-99a | 3.38 | 1.38 | 2.22 | −2.00 | 2.41 | 0.85 | 2.06E−07 |
| miR-15a,miR-24 | 1.42 | 6.00 | 1.16 | 4.58 | 0.79 | 0.84 | 2.95E−07 |
| let-7f,miR-335 | 2.01 | 0.21 | 0.92 | −1.80 | 1.56 | 0.84 | 3.63E−08 |
| miR-15b,miR-99b | 1.79 | −3.49 | 1.28 | −5.28 | 1.37 | 0.84 | 1.11E−06 |
| let-7c,miR-181d | 1.51 | 1.47 | 1.17 | −0.04 | 1.01 | 0.84 | 7.45E−07 |
| let-7a,miR-125a | 1.87 | −1.78 | 1.36 | −3.65 | 1.61 | 0.84 | 2.36E−06 |
| miR-342,miR-374 | −1.56 | 0.66 | 1.37 | 2.22 | 0.79 | 0.84 | 5.64E−07 |
| miR-374,miR-425 | 1.37 | −2.16 | 1.03 | −3.53 | 0.83 | 0.84 | 1.93E−07 |
| let-7g,miR-132 | 1.50 | −3.54 | 0.88 | −5.04 | 1.12 | 0.84 | 1.19E−07 |
| let-7f,miR-125a | 2.08 | 0.00 | 1.59 | −2.08 | 1.70 | 0.84 | 2.61E−06 |
| miR-214,miR-345 | 2.97 | 3.40 | 1.86 | 0.42 | 2.05 | 0.84 | 8.39E−08 |
| miR-126,miR-181d | 1.52 | −3.74 | 1.39 | −5.26 | 1.34 | 0.84 | 2.61E−06 |
| let-7d,miR-320 | 2.25 | 5.12 | 1.24 | 2.87 | 1.65 | 0.84 | 5.38E−08 |
| let-7f,miR-221 | 1.48 | 2.80 | 0.94 | 1.31 | 1.07 | 0.84 | 1.72E−07 |
| miR-142-3p,miR-186 | 1.40 | −2.59 | 1.14 | −3.99 | 0.84 | 0.84 | 5.42E−07 |
| miR-422a,miR-496 | −2.30 | −3.54 | 1.85 | −1.24 | 1.14 | 0.84 | 1.14E−07 |
| miR-197,miR-214 | −2.38 | −3.43 | 1.85 | −1.05 | 1.65 | 0.84 | 9.62E−07 |
| miR-181a,miR-26b | −1.14 | 4.32 | 0.97 | 5.46 | 0.59 | 0.84 | 3.96E−07 |
| miR-193a,miR-422a | 2.24 | 2.77 | 1.70 | 0.53 | 1.47 | 0.84 | 4.19E−07 |
| miR-15a,miR-342 | 1.78 | 2.38 | 1.40 | 0.60 | 1.08 | 0.84 | 3.58E−07 |
| miR-92,miR-98 | −2.03 | −11.15 | 1.74 | −9.12 | 1.09 | 0.84 | 4.90E−07 |
| miR-181d,miR-505 | −1.43 | −3.26 | 1.19 | −1.83 | 1.19 | 0.84 | 2.97E−06 |
| miR-181a,miR-26a | −1.24 | 4.15 | 1.03 | 5.39 | 0.66 | 0.84 | 3.65E−07 |
| miR-133b,miR-150 | 3.28 | 6.36 | 2.14 | 3.08 | 2.40 | 0.84 | 2.67E−07 |
| miR-126*,miR-92 | 1.31 | 5.06 | 1.02 | 3.76 | 0.93 | 0.84 | 1.39E−06 |
| miR-142-3p,miR-210 | 1.28 | −4.33 | 1.07 | −5.61 | 0.73 | 0.84 | 5.10E−07 |
| miR-181d,miR-30c | −1.60 | 2.14 | 1.34 | 3.73 | 1.19 | 0.84 | 3.50E−06 |
| miR-214,miR-24 | 2.56 | 6.74 | 1.81 | 4.17 | 1.75 | 0.84 | 2.78E−07 |
| miR-181a,miR-30b | −1.02 | 2.58 | 0.77 | 3.60 | 0.72 | 0.84 | 9.02E−07 |
| miR-24,miR-30c | −0.78 | −1.57 | 0.59 | −0.78 | 0.59 | 0.84 | 1.72E−06 |
| miR-410,miR-92 | 2.07 | 11.20 | 1.82 | 9.13 | 1.24 | 0.84 | 1.47E−06 |
| miR-142-3p,miR-335 | 1.44 | −3.96 | 1.07 | −5.41 | 0.96 | 0.84 | 3.63E−07 |
| miR-130b,miR-374 | −1.34 | −0.07 | 1.07 | 1.27 | 0.92 | 0.84 | 1.16E−06 |
| miR-15b,miR-301 | 0.93 | −2.64 | 0.65 | −3.57 | 0.69 | 0.84 | 6.30E−07 |
| miR-142-3p,miR-19b | 1.59 | 1.47 | 1.36 | −0.12 | 0.97 | 0.84 | 1.25E−06 |
| miR-181b,miR-206 | −1.85 | −3.88 | 1.47 | −2.03 | 1.31 | 0.84 | 1.55E−06 |
| miR-150,miR-30b | −1.85 | −1.88 | 1.66 | −0.03 | 1.00 | 0.83 | 1.11E−06 |
| miR-30c,miR-342 | 1.14 | −2.06 | 1.02 | −3.20 | 0.62 | 0.83 | 1.14E−06 |
| miR-496,miR-99a | 2.27 | 3.81 | 1.64 | 1.54 | 1.71 | 0.83 | 1.07E−06 |
| miR-142-3p,miR-23a | 1.53 | −4.17 | 1.06 | −5.70 | 1.14 | 0.83 | 6.18E−07 |
| miR-181a,miR-98 | −1.53 | −2.40 | 1.42 | −0.87 | 0.82 | 0.83 | 1.67E−06 |
| miR-550,miR-92 | 1.41 | 12.45 | 1.15 | 11.04 | 1.00 | 0.83 | 2.02E−06 |
| let-7c,miR-92 | 1.58 | 9.72 | 1.28 | 8.14 | 1.05 | 0.83 | 1.16E−06 |
| miR-206,miR-92 | 2.21 | 12.32 | 1.78 | 10.11 | 1.43 | 0.83 | 7.83E−07 |
| miR-142-5p,miR-30a-5p | 1.06 | 4.05 | 1.04 | 2.99 | 0.66 | 0.83 | 4.83E−06 |
| miR-150,miR-206 | −2.45 | −7.91 | 2.09 | −5.46 | 1.17 | 0.83 | 2.57E−07 |
| let-7d,miR-342 | 1.74 | 0.40 | 1.54 | −1.35 | 0.95 | 0.83 | 9.01E−07 |
| miR-214,miR-423 | 1.77 | 1.42 | 1.43 | −0.35 | 1.22 | 0.83 | 1.45E−06 |
| miR-150,miR-26a | −2.07 | −0.31 | 1.80 | 1.76 | 1.22 | 0.83 | 1.17E−06 |
| miR-150,miR-193a | −2.56 | −8.56 | 2.16 | −6.00 | 1.69 | 0.83 | 1.72E−06 |
| miR-181d,miR-30e-3p | −1.45 | −3.82 | 1.24 | −2.38 | 1.02 | 0.83 | 3.50E−06 |
| miR-103,miR-181a | 1.42 | −1.16 | 1.14 | −2.59 | 0.95 | 0.83 | 9.87E−07 |
| miR-150,miR-26b | −1.98 | −0.15 | 1.75 | 1.83 | 1.08 | 0.83 | 8.95E−07 |
| miR-125a,miR-15b | −1.94 | 1.40 | 1.52 | 3.33 | 1.65 | 0.83 | 5.85E−06 |
| miR-142-3p,miR-324-5p | 1.15 | −6.29 | 1.19 | −7.44 | 0.70 | 0.83 | 5.85E−06 |
| miR-27b,miR-30d | 1.26 | 4.38 | 1.02 | 3.11 | 0.76 | 0.83 | 4.81E−07 |
| miR-214,miR-335 | 2.84 | 2.87 | 1.82 | 0.04 | 2.29 | 0.83 | 8.02E−07 |
| miR-142-3p,miR-151 | 1.35 | −3.63 | 1.20 | −4.98 | 0.85 | 0.83 | 2.35E−06 |
| let-7c,miR-150 | 1.81 | 5.30 | 1.48 | 3.49 | 1.16 | 0.83 | 9.35E−07 |
| miR-151,miR-15a | −1.59 | −2.46 | 1.19 | −0.87 | 1.22 | 0.83 | 1.87E−06 |
| miR-496,miR-92 | 2.29 | 13.67 | 1.79 | 11.38 | 1.70 | 0.83 | 1.88E−06 |
| miR-150,miR-98 | −2.37 | −6.87 | 2.28 | −4.50 | 1.05 | 0.83 | 1.40E−06 |
| miR-26b,miR-342 | 1.24 | −3.58 | 1.06 | −4.82 | 0.83 | 0.83 | 2.11E−06 |
| miR-320,miR-638 | −1.81 | −6.77 | 1.39 | −4.96 | 1.33 | 0.83 | 1.60E−06 |

TABLE 21-continued

Differentially expressed miRNA biomarker pairs that distinguish lung cancer patients from normal patients with no lung tumors and patients with benign lung tumors. Other = benign and normal cases.

| miRNA Biomarker Pair | Cancer mean – Other mean | Cancer mean | Cancer SD | Other mean | Other SD | AUC ROC | Other vs Cancer Assoc. |
|---|---|---|---|---|---|---|---|
| miR-29b,miR-30a-5p | 1.44 | 7.79 | 1.35 | 6.35 | 0.87 | 0.83 | 4.08E−06 |
| let-7b,miR-181d | 1.64 | −2.26 | 1.25 | −3.91 | 1.43 | 0.82 | 7.09E−06 |
| miR-346,miR-566 | 1.49 | 1.33 | 1.39 | −0.16 | 0.88 | 0.82 | 3.34E−06 |
| miR-106b,miR-19b | 1.17 | 3.31 | 0.75 | 2.14 | 1.03 | 0.82 | 2.46E−06 |
| let-7g,miR-93 | 1.17 | 1.69 | 1.04 | 0.52 | 0.74 | 0.82 | 2.64E−06 |
| miR-133b,miR-422b | 1.60 | 1.80 | 1.36 | 0.20 | 0.99 | 0.82 | 1.28E−06 |
| miR-326,miR-374 | −1.60 | 5.36 | 1.20 | 6.96 | 1.22 | 0.82 | 1.80E−06 |
| miR-326,miR-496 | −1.96 | −0.95 | 1.70 | 1.01 | 1.32 | 0.82 | 2.86E−06 |
| miR-422a,miR-98 | −1.82 | −0.85 | 1.85 | 0.97 | 1.07 | 0.82 | 9.09E−06 |
| miR-181b,miR-374 | −1.72 | 0.93 | 1.55 | 2.65 | 1.15 | 0.82 | 4.21E−06 |
| miR-106b,miR-345 | 1.15 | −1.61 | 0.79 | −2.76 | 1.02 | 0.82 | 3.99E−06 |
| miR-193a,miR-486 | 2.56 | 11.44 | 1.86 | 8.88 | 2.02 | 0.82 | 1.89E−06 |
| miR-496,miR-99b | 1.71 | 3.12 | 1.29 | 1.41 | 1.25 | 0.82 | 1.14E−06 |
| miR-150,miR-7 | −1.65 | −5.87 | 1.42 | −4.22 | 1.19 | 0.82 | 4.37E−06 |
| miR-422a,miR-638 | −1.50 | 0.25 | 1.35 | 1.75 | 1.02 | 0.82 | 4.43E−06 |
| miR-346,miR-483 | 1.31 | 0.99 | 1.26 | −0.32 | 0.67 | 0.82 | 2.39E−06 |
| miR-181b,miR-505 | −1.17 | −3.11 | 1.20 | −1.93 | 0.92 | 0.82 | 1.06E−05 |
| miR-151,miR-214 | −2.71 | −3.17 | 1.95 | −0.47 | 2.03 | 0.82 | 9.45E−07 |
| miR-181d,miR-190 | −1.99 | −2.44 | 1.48 | −0.45 | 1.77 | 0.82 | 8.13E−06 |
| miR-16,miR-92 | 1.64 | −0.20 | 1.75 | −1.84 | 0.72 | 0.82 | 6.96E−06 |
| miR-150,miR-496 | −2.59 | −9.32 | 2.43 | −6.73 | 1.29 | 0.82 | 1.46E−06 |
| miR-140,miR-92 | 1.35 | 7.96 | 1.18 | 6.61 | 0.85 | 0.82 | 1.89E−06 |
| miR-181d,miR-638 | −1.73 | −1.96 | 1.48 | −0.23 | 1.18 | 0.82 | 2.71E−06 |
| let-7c,miR-30a-5p | 1.54 | 5.08 | 1.06 | 3.54 | 1.29 | 0.82 | 2.34E−06 |
| miR-125a,miR-26b | −1.23 | 4.03 | 1.19 | 5.27 | 1.20 | 0.82 | 1.28E−05 |
| miR-125a,miR-496 | −1.83 | −5.12 | 1.45 | −3.30 | 1.49 | 0.82 | 5.42E−06 |
| let-7g,miR-151 | 1.46 | −2.40 | 1.19 | −3.86 | 1.22 | 0.82 | 8.95E−06 |
| miR-374,miR-99b | 1.40 | −3.20 | 1.32 | −4.60 | 1.05 | 0.82 | 1.36E−05 |
| miR-126*,miR-181d | 1.24 | −3.19 | 1.24 | −4.43 | 0.90 | 0.82 | 1.36E−05 |
| miR-126,miR-181a | 0.99 | −4.36 | 0.79 | −5.36 | 0.87 | 0.82 | 1.09E−05 |
| miR-18a,miR-486 | 1.51 | 8.00 | 1.33 | 6.49 | 1.04 | 0.82 | 3.70E−06 |
| miR-199a*,miR-92 | 1.34 | 6.88 | 1.27 | 5.55 | 0.77 | 0.81 | 3.58E−06 |
| miR-214,miR-361 | 2.58 | 1.73 | 2.03 | −0.85 | 1.95 | 0.81 | 2.41E−06 |
| miR-190,miR-326 | 1.70 | −2.18 | 1.43 | −3.88 | 1.43 | 0.81 | 1.21E−05 |
| miR-181d,miR-28 | −1.43 | −2.76 | 1.31 | −1.33 | 1.11 | 0.81 | 1.39E−05 |
| miR-150,miR-505 | −1.76 | −7.12 | 1.68 | −5.36 | 1.27 | 0.81 | 1.35E−05 |
| miR-150,miR-29b | −1.78 | −8.06 | 1.69 | −6.28 | 1.23 | 0.81 | 9.87E−06 |
| miR-345,miR-374 | −1.59 | 0.40 | 1.24 | 1.99 | 1.21 | 0.81 | 2.42E−06 |
| let-7b,miR-345 | 1.22 | −1.92 | 0.98 | −3.14 | 0.96 | 0.81 | 4.65E−06 |
| miR-30b,miR-99b | 1.05 | −4.41 | 0.93 | −5.47 | 0.93 | 0.81 | 1.73E−05 |
| miR-125a,miR-374 | −1.56 | 1.11 | 1.48 | 2.66 | 1.35 | 0.81 | 1.73E−05 |
| miR-486,miR-638 | −1.93 | −8.60 | 1.65 | −6.67 | 1.47 | 0.81 | 6.21E−06 |
| let-7i,miR-92 | 1.20 | 7.04 | 1.08 | 5.84 | 0.98 | 0.81 | 1.69E−05 |
| miR-15a,miR-361 | 1.43 | 0.98 | 1.22 | −0.45 | 1.08 | 0.81 | 5.69E−06 |
| miR-15b,miR-197 | 1.44 | −0.60 | 1.33 | −2.03 | 1.35 | 0.81 | 1.95E−05 |
| miR-296,miR-486 | 1.82 | 10.15 | 1.39 | 8.32 | 1.27 | 0.81 | 8.33E−07 |
| miR-181d,miR-410 | −2.03 | −2.95 | 2.05 | −0.92 | 1.62 | 0.81 | 1.96E−05 |
| miR-432,miR-92 | 1.80 | 11.07 | 1.52 | 9.27 | 1.43 | 0.81 | 7.88E−06 |
| miR-125a,miR-142-3p | −1.49 | 4.20 | 1.42 | 5.69 | 1.36 | 0.81 | 2.01E−05 |
| miR-15a,miR-324-5p | 1.39 | −0.20 | 1.24 | −1.59 | 1.04 | 0.81 | 8.48E−06 |
| miR-181d,miR-296 | −1.62 | −3.51 | 1.56 | −1.89 | 0.96 | 0.81 | 5.33E−06 |
| miR-195,miR-486 | 1.60 | 4.56 | 1.44 | 2.96 | 0.89 | 0.81 | 1.28E−06 |
| miR-143,miR-486 | 2.11 | 9.98 | 1.87 | 7.86 | 1.59 | 0.81 | 7.80E−06 |
| miR-26b,miR-99b | 1.14 | −6.12 | 1.08 | −7.26 | 0.89 | 0.81 | 2.14E−05 |
| miR-181d,miR-204 | −1.93 | −4.79 | 1.57 | −2.85 | 1.58 | 0.81 | 6.80E−05 |
| miR-30b,miR-342 | 1.09 | −1.88 | 1.01 | −2.97 | 0.72 | 0.81 | 5.72E−06 |
| miR-342,miR-98 | −1.72 | −3.17 | 1.75 | −1.45 | 0.74 | 0.81 | 3.20E−06 |
| miR-15b,miR-17-5p | 0.88 | −0.06 | 0.86 | −0.94 | 0.57 | 0.81 | 1.08E−05 |
| miR-27a,miR-30a-5p | 1.07 | 2.83 | 1.05 | 1.76 | 1.09 | 0.81 | 2.34E−05 |
| miR-126,miR-146b | 0.99 | −1.62 | 0.92 | −2.61 | 0.61 | 0.81 | 3.43E−06 |
| miR-150,miR-576 | −1.53 | −8.60 | 1.37 | −7.07 | 1.09 | 0.81 | 6.06E−06 |
| miR-26a,miR-342 | 1.31 | −3.44 | 1.17 | −4.75 | 0.84 | 0.81 | 3.22E−06 |
| let-7i,miR-486 | 1.34 | 5.43 | 1.23 | 4.09 | 0.95 | 0.81 | 7.84E−06 |
| miR-140,miR-345 | 0.85 | 0.05 | 0.86 | −0.81 | 0.72 | 0.81 | 2.48E−05 |
| miR-181b,miR-26a | −1.47 | 3.71 | 1.32 | 5.18 | 1.05 | 0.81 | 6.81E−06 |
| miR-20b,miR-486 | 1.43 | 5.70 | 1.33 | 4.27 | 0.96 | 0.81 | 6.13E−06 |
| miR-130b,miR-496 | −1.91 | −6.59 | 1.63 | −4.68 | 1.52 | 0.81 | 8.73E−06 |
| miR-106b,miR-181d | 1.58 | −1.95 | 1.36 | −3.53 | 1.66 | 0.80 | 2.80E−05 |
| miR-150,miR-296 | −1.92 | −7.34 | 1.85 | −5.42 | 1.13 | 0.80 | 4.78E−06 |
| miR-150,miR-550 | −1.61 | −8.03 | 1.56 | −6.42 | 1.08 | 0.80 | 9.82E−06 |
| miR-214,miR-382 | 2.41 | 0.18 | 2.21 | −2.23 | 1.91 | 0.80 | 1.68E−05 |

TABLE 21-continued

Differentially expressed miRNA biomarker pairs that distinguish lung cancer patients from normal patients with no lung tumors and patients with benign lung tumors. Other = benign and normal cases.

| miRNA Biomarker Pair | Cancer mean − Other mean | Cancer mean | Cancer SD | Other mean | Other SD | AUC ROC | Other vs Cancer Assoc. |
|---|---|---|---|---|---|---|---|
| miR-143,miR-320 | 1.95 | 8.14 | 1.76 | 6.18 | 1.37 | 0.80 | 5.87E−06 |
| let-7e,miR-378 | 1.38 | 0.02 | 1.24 | −1.36 | 1.01 | 0.80 | 7.54E−06 |
| miR-30c,miR-99b | 1.09 | −4.59 | 1.05 | −5.69 | 0.93 | 0.80 | 3.24E−05 |
| miR-361,miR-374 | −1.21 | 2.05 | 1.26 | 3.27 | 0.99 | 0.80 | 3.34E−05 |
| miR-181a,miR-193a | −1.77 | −4.15 | 1.48 | −2.38 | 1.53 | 0.80 | 1.48E−05 |
| miR-206,miR-486 | 2.35 | 10.71 | 2.15 | 8.36 | 1.74 | 0.80 | 1.01E−05 |
| miR-326,miR-410 | −1.62 | 1.65 | 1.33 | 3.26 | 1.24 | 0.80 | 4.30E−06 |
| miR-24,miR-26b | −0.87 | −0.03 | 0.76 | 0.84 | 0.70 | 0.80 | 1.19E−05 |
| miR-142-3p,miR-326 | 1.33 | −8.41 | 1.37 | −9.74 | 1.93 | 0.80 | 3.75E−05 |
| miR-181b,miR-30b | −1.25 | 2.15 | 1.18 | 3.40 | 0.78 | 0.80 | 5.09E−06 |
| miR-214,miR-93 | 2.44 | 7.28 | 2.22 | 4.84 | 1.86 | 0.80 | 1.17E−05 |
| miR-132,miR-142-3p | −1.39 | 4.77 | 1.24 | 6.16 | 1.02 | 0.80 | 7.03E−06 |
| miR-16,miR-486 | 1.77 | −1.81 | 1.73 | −3.58 | 1.23 | 0.80 | 1.33E−05 |
| miR-126,miR-342 | 1.06 | −3.66 | 1.02 | −4.72 | 0.72 | 0.80 | 9.88E−06 |
| miR-181a,miR-496 | −1.77 | −4.87 | 1.53 | −3.10 | 1.52 | 0.80 | 1.75E−05 |
| miR-28,miR-92 | 1.56 | 11.03 | 1.37 | 9.47 | 1.29 | 0.80 | 1.54E−05 |
| miR-30c,miR-345 | 1.17 | −1.80 | 0.87 | −2.97 | 1.10 | 0.80 | 1.34E−05 |
| miR-505,miR-92 | 1.53 | 11.54 | 1.30 | 10.01 | 1.30 | 0.80 | 1.50E−05 |
| let-7b,miR-342 | 1.19 | −2.18 | 0.97 | −3.37 | 1.02 | 0.80 | 1.10E−05 |
| let-7c,miR-181b | 1.21 | 1.28 | 1.17 | 0.07 | 0.85 | 0.80 | 1.32E−05 |

Table 22 shows miRNAs that can be used in combination with other miRNA biomarkers to characterize lung disease, as well as the prevalence of those biomarkers in pairs from Table 21.

TABLE 22

Prevalence of serum biomarkers in paired analysis of cancer vs. (normal and benign) patients.

| miRNA | Paired Appearances |
|---|---|
| miR-92 | 29 |
| miR-214 | 22 |
| miR-142-3p | 21 |
| miR-181d | 21 |
| miR-15b | 20 |
| miR-15a | 17 |
| miR-150 | 16 |
| miR-181a | 15 |
| let-7f | 13 |
| miR-374 | 13 |
| let-7g | 11 |
| miR-346 | 11 |
| miR-181b | 10 |
| miR-146a | 9 |
| miR-342 | 9 |
| miR-24 | 8 |
| miR-30a-5p | 8 |
| miR-486 | 7 |
| let-7a | 6 |
| let-7d | 6 |
| miR-345 | 6 |
| miR-98 | 6 |
| miR-30c | 5 |
| miR-335 | 5 |
| miR-422a | 5 |
| miR-125a | 4 |
| miR-126 | 4 |
| miR-130b | 4 |
| miR-132 | 4 |
| miR-210 | 4 |
| miR-26b | 4 |
| miR-320 | 4 |
| miR-326 | 4 |
| miR-425 | 4 |
| miR-496 | 4 |
| miR-99b | 4 |
| miR-146b | 3 |
| miR-193a | 3 |
| miR-26a | 3 |
| miR-30b | 3 |
| let-7b | 2 |
| miR-106b | 2 |
| miR-126* | 2 |
| miR-133b | 2 |
| miR-140 | 2 |
| miR-151 | 2 |
| miR-190 | 2 |
| miR-301 | 2 |
| miR-375 | 2 |
| miR-422b | 2 |
| miR-99a | 2 |

Example 5

Lung Cancer Classifier Development

An initial training set of 14 miRNAs were selected from pairs in Table 15 to further verify their diagnostic potential. These miRNAs were shown above to have diagnostic potential for distinguishing patients with benign lung conditions from patients with lung cancer, as evidenced by the high AUC ROC scores for miRNA biomarker pairs that include these miRNAs. From a group of 20 benign lung samples and 34 lung cancer samples (Table 23), a set of training samples (12 benign, 16 lung cancer) was chosen from patients that were age and sex matched. qRT-PCR was performed as described above in Example 2.

TABLE 23

Histopathological and patient information for lung cancer and benign specimens.

| Sample ID | Age | Sex | Cell Type | AJCC Stage | Smoking History | Diagnosis |
|---|---|---|---|---|---|---|
| 1 | 59 | F | Lymphoplasmacytic | NA | no | Benign |
| 2 | 60 | F | Granuloma | NA | yes | Benign |
| 3 | 64 | F | Granuloma | NA | yes | Benign |
| 4 | 69 | F | Hamartoma | NA | yes | Benign |
| 5 | 71 | F | Granuloma | NA | yes | Benign |
| 6 | 73 | F | Granuloma | NA | yes | Benign |
| 7 | 77 | F | Hamartoma | NA | yes | Benign |
| 8 | 56 | M | No Malignancy | NA | yes | Benign |
| 10 | 60 | M | Necrotizing Granuloma | NA | yes | Benign |
| 11 | 69 | M | Granulomas | NA | yes | Benign |
| 12 | 71 | M | Infarct | NA | yes | Benign |
| 13 | 59 | F | ADCA | IB | yes | LC |
| 14 | 64 | F | ADCA | IA | yes | LC |
| 15 | 66 | F | ADCA | IB | yes | LC |
| 16 | 66 | F | SCC | IIB | yes | LC |
| 17 | 72 | F | SCC | IB | yes | LC |
| 18 | 73 | F | SCC | IIB | yes | LC |
| 19 | 73 | F | SCC | IIIA | yes | LC |
| 20 | 56 | M | SCC | IIB | yes | LC |
| 21 | 60 | M | ADCA | IB | yes | LC |
| 22 | 63 | M | ADCA | IIIA | yes | LC |
| 23 | 66 | M | SCC | IB | yes | LC |
| 24 | 69 | M | ADCA | IIIA | yes | LC |
| 25 | 69 | M | SCC | IB | yes | LC |
| 26 | 69 | M | SCC | IIB | yes | LC |
| 27 | 71 | M | SCC | IIB | yes | LC |
| 28 | 72 | M | ADCA | IB | yes | LC |
| 29 | 79 | M | ADCA | IIIA | yes | LC |
| 30 | 67 | M | ADCA | IA | yes | LC |
| 31 | 82 | F | SCC | IIB | yes | LC |
| 32 | 77 | M | ADCA | IIIA | yes | LC |
| 53 | 70 | F | SCC | IB | yes | LC |
| 54 | 49 | M | Granuloma | NA | yes | Benign |
| 55 | 75 | F | Large | IIIA | yes | LC |
| 56 | 80 | M | ADCA | IB | yes | LC |
| 57 | 35 | F | Granuloma | NA | no | Benign |
| 58 | NA | F | Granuloma | NA | yes | Benign |
| 59 | 52 | M | Granuloma | NA | no | Benign |
| 60 | 74 | M | SCC | IIB | yes | LC |
| 61 | 65 | F | Adenosquamous | IIB | yes | LC |
| 62 | 77 | M | SCC | IIB | yes | LC |
| 63 | 51 | M | Granuloma | NA | yes | Benign |
| 64 | 55 | M | NSCLC | IB | yes | LC |
| 65 | 47 | F | Harmatoma | NA | yes | Benign |
| 66 | 80 | F | Spindle Cell ADCA | IIIA | yes | LC |
| 67 | 45 | F | Granuloma | NA | yes | Benign |
| 68 | 54 | F | NSCLC | IB | yes | LC |
| 69 | 46 | F | Pleomorphic Carcinoma | IB | yes | LC |
| 70 | 68 | M | Large | IB | yes | LC |
| 71 | 87 | M | SCC | IB | yes | LC |
| 72 | 87 | M | SCC | IB | yes | LC |
| 73 | 80 | M | ADCA | IA | yes | LC |
| 74 | 40 | F | Hamartoma | NA | yes | Benign |

Figure 3:
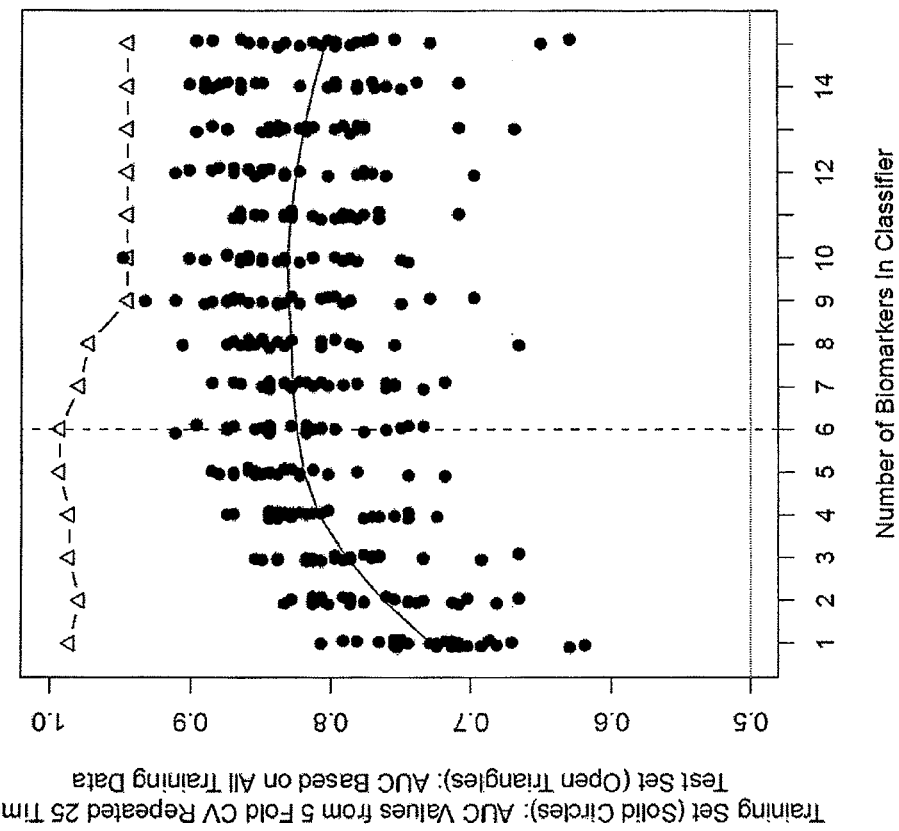
FIG. 3 shows the distribution of area under the curve (AUC) values for the Linear Discriminate Analysis (LDA) classifier as a function of the number of biomarkers, as described in Example 5. This procedure determines the optimal number of biomarkers to use for the classifier. Solid black circles represent results from the training set; Open triangles represent results from the test set. The vertical dashed line is where performance levels off. The maximum mean AUC is where the number of features=9.

To verify a subset of the 14 miRNAs in the training set, a separate test sample set was selected from Table 23 that was composed of 8 benign and 18 LuCa samples. miRNA biomarker selection and classifier evaluation was generated by performing 25 repetitions of 5-fold cross validation on the training samples, and measuring the AUC ROC values as a function of the number of miRNA biomarkers (features). A range of biomarkers was used in order to determine the optimal number of features for classification. Five-fold cross-validation is a process where the training set is subdivided into an 80% sample set and a 20% sample set, and feature selection and classifier training is performed on the 80% training samples. Performance is measured by classifying the remaining 20% samples not used for feature selection and classifier training. This process was repeated 5 times so that all samples were in the 20% test set once and only once. One iteration of 5-fold cross-validation produced a single AUC value. Five-fold cross-validation was repeated 25 times in order to achieve a better sampling of combinations of 80% and 20% sets, and to identify an empirical distribution of AUC values for a given number of biomarkers in the classifier. Top biomarkers according to a simple Welch's t-test were used as inputs into a Linear Discriminate Analysis (LDA) classifier for training. Biomarkers were defined as pairs of miRNAs (differential expression of two miRNAs), where the expression value of one miRNA is subtracted from the expression value of another miRNA. All possible pairs were investigated. FIG. 3 shows the distribution of AUC values for the LDA classifier as a function of the number of biomarkers. This procedure determines the optimal number of biomarkers to use for the classifier, and performance expectations moving forward. A classifier of 6 differentially expressed miRNA pairs (miR-142-5p and miR181d; miR-142-3p and miR181d; miR-142-3p and miR-422a; miR-142-5p and miR-422a; miR-92 and miR-27b; miR-24 and miR-27a) was identified as the optimal classifier for diagnosis of lung cancer in this experiment. This classifier is marked by the vertical dotted line in FIG. 3. A cutoff for the LDA classifier was set so that the continuous valued classification probabilities were converted into calls diagnosing patients as having lung cancer (classifier-positive) or benign (classifier-negative) tumors. For simplicity, a cutpoint of 0.5 was chosen as the threshold. This value produced a near maximum of sensitivity and specificity. Performance estimates of training and test data using a cutoff of 0.5 of the LDA classifier trained on six biomarker pairs is provided in FIG. 4. The sensitivity (SENS), specificity (SPEC), negative predictive value (NPV) and positive predictive value (PPV) are as indicated.

Any of the six pairs identified as part of the classifier in this experiment may be used to diagnose lung cancer. Predictive accuracy may increase with the use of more than one pair from the optimal classifier set.

Example 6 qRT-PCR for Evaluation of microRNA Expression in Human Lung Cancer Patient Plasma RNA To identify miRNA biomarkers for lung cancer in human plasma, qRT-PCR was used to compare levels of miRNAs present in the plasma of patients with lung cancer (n=14) to the levels in patents without lung cancer (n=12). Patient information and lung cancer pathology information are shown in Table 24.

TABLE 24

Human Lung Cancer and Normal Patient Information and Tumor Pathology.
TNM stage (Sobin and Wittekind, 2002)

| Age | Sex | Tumor Location | Cell & Tumor Characteristics | TNM Stage | AJCC Stage |
|---|---|---|---|---|---|
| 66 | M | upper lobe left lung | ADCA | NA | NA |
| 48 | M | lower lobe left lung | BA | NA | NA |
| 72 | M | upper lobe right lung | SCC | T3NxM0 | NA |
| 66 | M | left lung | SCC | T3NxM0 | NA |
| 54 | M | lower lobe right lung | SCC | NA | IIIB |
| 69 | M | upper lobe left lung | UC | NA | IIIA |

TABLE 24-continued

Human Lung Cancer and Normal Patient Information and Tumor Pathology.
TNM stage (Sobin and Wittekind, 2002)

| Age | Sex | Tumor Location | Cell & Tumor Characteristics | TNM Stage | AJCC Stage |
|---|---|---|---|---|---|
| 52 | M | lower lobe left lung | SCC | NA | IIIA |
| 54 | F | left lung | ADCA | NA | IV |
| 49 | F | left lung | SCC | T4N1M0 | III |
| 67 | M | upper lobe right lung | SCC | T3N1M0 | III |
| 59 | F | right lung | SCC | T3N2M0 | III |
| 51 | M | left lung | SCC | T4N2M0 | III |
| 44 | M | right lung | SCC | T4NXM0 | III |
| 52 | M | upper lobe left lung | SCC | T3N1M0 | III |
| Normal Patients | | | | | |
| 39 | F | — | Normal | — | — |
| 44 | M | — | Normal | — | — |
| 58 | F | — | Normal | — | — |
| 59 | F | — | Normal | — | — |
| 61 | M | — | Normal | — | — |
| 52 | M | — | Normal | — | — |
| 59 | M | — | Normal | — | — |
| 57 | F | — | Normal | — | — |
| 59 | F | — | Normal | — | — |
| 56 | M | — | Normal | — | — |
| 52 | F | — | Normal | — | — |
| 62 | F | — | Normal | — | — |

For plasma preparation, whole blood (10 ml) was collected from each donor into a BD Vacutainer® K2EDTA tube (Becton, Dickinson and Company; Franklin Lakes, N.J., USA). Tubes were inverted 8-10 times immediately after blood collection and then centrifuged for 10 minutes at 2,000×g within two hours of collection. Plasma was transferred to a new tube using a serological pipette and frozen at −80° C. until it was subjected to RNA isolation.

Plasma RNA was purified using the organic extraction of the mirVana PARIS™ Kit (Part No. AM1556; Applied Biosystems/Ambion; Austin, Tex., USA), with the following modifications. After thawing plasma on ice, an equal volume of 2× denaturing solution from the mirVana PARIS™ Kit was added and the mixture was incubated on ice for five minutes. An equal volume of acid phenol:chloroform was added, then the mixture was vortexed for one minute, and incubated on ice for five minutes. Tubes were centrifuged at 13,000×g for 15 minutes at 4° C., and the aqueous phase was removed to a fresh tube. Glycogen (5 mg/ml), 3M NaOAc (1/10 volume), and 100% ethanol (1.5 volume)I were added to the samples. Samples were mixed by inversion and incubated at room temperature. Lysate/ethanol mixtures were passed through a mirVana PARIS™ filter cartridge, and filters were washed once with 650 µl of Wash 1 buffer and twice with 650 µl of Wash 2/3 buffer. RNA was eluted with nuclease free water (50 µl, heated to 95° C.), by centrifugation at 10,000×g for 1 minute.

qRT-PCR reactions were performed using TaqMan® MicroRNA Assays (Applied Biosystems; Foster City, Calif., USA) specific for each individual miRNA. Reverse transcription reactions were assembled on ice prior to the addition of RNA template (Table 25). Next, 0.25 µl of plasma RNA template per reaction was added and mixed. RT reactions were incubated in a 384-well GeneAmp® PCR System 9700 (Applied Biosystems) at 16° C. for 30 minutes, then at 42° C. for 30 minutes, then at 85° C. for 5 minutes, and then were frozen in a −20° C. freezer.

TABLE 25

Reverse transcription reaction components.

| Component | µl per 10 µl rxn | Final Concentration |
|---|---|---|
| Nuclease-free water | 5.85 | — |
| 10X RT Buffer (Asuragen, Inc.) | 1.0 | 1X |
| dNTP mix (100 mM), (Ambion, Inc.; Austin, TX USA) | 0.1 | 1 mM each |
| 1.25 X RT Primer (Applied Biosystems, Inc., Foster City, CA, USA) | 2.0 | 0.25X |
| RNasin ® Ribonuclease Inhibitor (20 U/µl, Promega, Corp. Madison, WI, USA; cat. no. N2115) | 0.13 | 0.26 U/µl |
| Multiscribe ™ Recombinant Moloney Murine Leukemia Virus Reverse Transcriptase (MMLV-RT) (50 U/µl, Applied Biosystems, Inc., Foster City, CA, USA; part no. 4311235) | 0.67 | 3.35 U/µl |
| Human Plasma RNA | 0.25 | — |

PCR components were assembled on ice prior to the addition of the cDNA from the RT reactions (Table 26). PCRs were incubated in an ABI PRISM™ 7900HT Fast Real-Time PCR system (Applied Biosystems) at 95° C. for 1 minute, then for 50 cycles at 95° C. for 5 seconds, and then at 60° C. for 30 seconds. Initial data analysis was done using the 7500 Fast System SDS V2.3 software (Applied Biosystems).

TABLE 26

Real-time PCR components.

| Component | µl per 15 µl rxn | Final Concentration |
|---|---|---|
| Nuclease-free water | 6.1 | — |
| MgCl$_2$ (50 mM) | 1.5 | 5 mM |
| 10X Platinum PCR Buffer, Minus Mg (Invitrogen; cat. no. 53286 | 1.5 | 1X |
| dNTP mix (2.5 mM each) (Ambion, Inc.; Austin, TX USA) | 1.5 | 0.25 mM each |
| 3X TaqMan Assay Buffer | 2.0 | 0.4X |
| 50X ROX Internal marker | 0.3 | 1X |
| Platinum ® Taq DNA Polymerase (5 U/µl) (Invitrogen Corp., Carlsbad, CA, USA; SKU#, 10966-083) | 0.1 | 0.033 U/µl |
| cDNA from RT reaction | 2.0 | |

The qRT-PCR data were initially assessed for outliers. All miRNAs in a given sample with raw Ct values of 50 were eliminated from further analysis. All data from samples with fewer than 150 miRNAs that had raw Ct values less than 50 were eliminated. The average raw Ct for 50 miRNAs that were detected in each plasma sample was calculated for each individual sample. The average Ct for a given sample was subtracted from the raw Ct values for each miRNA in the corresponding sample to produce a dCt for each miRNA that was detected. These normalized measures were used to identify miRNAs that were present at significantly different levels in the plasma samples from normal donors and lung cancer patients.

The average dCt values for each miRNA in the normal donor and lung cancer patient samples were calculated. The average dCt values for the lung cancer patient samples were subtracted from the average dCt values for the normal donors to determine the variance in the levels of the various miRNAs between the two patient sets. The student t-test was then used to evaluate the capacity of the various miRNAs to distinguish the plasmas of lung cancer patients and normal donors.

Table 27 provides differential expression data for miRNAs in the form of average dCt values for cancer and normal samples. In addition, ddCt values represent the difference in expression between cancer and normal samples.

TABLE 27 miRNA Biomarkers Differentially Expressed Between Plasma Samples of Lung Cancer Patients and Plasma Samples of Normal Patients.

| miRNA | Cancer Average dCt | Cancer SD | Normal Average dCt | Normal SD | ddCt (Cancer − Normal) | t-test |
|---|---|---|---|---|---|---|
| miR-499 | 14.92 | 2.91 | 20.32 | 1.75 | −5.40 | 9.72E−03 |
| miR-498 | 15.86 | 3.34 | 20.61 | 3.92 | −4.75 | 7.34E−03 |
| miR-205 | 6.94 | 2.61 | 11.69 | 2.60 | −4.75 | 2.73E−04 |
| miR-122a | 9.05 | 1.47 | 13.44 | 3.32 | −4.39 | 2.20E−03 |
| miR-519c | 12.89 | 18.06 | 16.50 | 5.51 | −3.61 | 6.26E−01 |
| miR-515-5p | 15.34 | 5.81 | 18.90 | 6.53 | −3.56 | 3.97E−01 |
| miR-215 | 7.22 | 2.05 | 10.52 | 1.85 | −3.30 | 2.36E−04 |
| miR-449 | 11.00 | 2.12 | 14.02 | 3.43 | −3.02 | 5.19E−02 |
| miR-200a* | 11.13 | 3.52 | 13.92 | 4.29 | −2.80 | 8.63E−02 |
| miR-375 | 5.91 | 2.96 | 8.68 | 0.91 | −2.78 | 4.27E−03 |
| miR-515-3p | 11.23 | 2.15 | 14.00 | 2.25 | −2.77 | 5.46E−02 |
| miR-206 | 8.08 | 1.86 | 10.84 | 2.82 | −2.76 | 9.56E−03 |
| miR-448 | 16.67 | 2.38 | 19.41 | 4.33 | −2.74 | 1.11E−01 |
| miR-520d | 12.17 | 4.82 | 14.81 | 5.14 | −2.65 | 2.51E−01 |
| miR-7 | 6.35 | 1.20 | 8.99 | 1.85 | −2.65 | 7.93E−04 |
| miR-129 | 12.94 | 1.93 | 15.48 | 2.58 | −2.54 | 1.10E−02 |
| miR-218 | 9.78 | 1.57 | 12.22 | 2.96 | −2.44 | 2.08E−01 |
| miR-192 | 2.79 | 0.98 | 5.17 | 2.12 | −2.38 | 2.79E−03 |
| miR-302a* | 13.71 | 2.80 | 15.99 | 4.94 | −2.27 | 2.14E−01 |
| miR-451 | −3.87 | 1.07 | −1.64 | 1.66 | −2.23 | 8.05E−04 |
| miR-517* | 16.16 | 4.45 | 18.27 | 4.16 | −2.11 | 3.63E−01 |
| miR-95 | 9.36 | 1.38 | 11.46 | 2.27 | −2.10 | 3.19E−02 |
| miR-520h | 13.40 | 4.22 | 15.48 | 6.16 | −2.08 | 4.39E−01 |
| miR-525 | 9.01 | 2.08 | 11.07 | 4.14 | −2.06 | 1.38E−01 |
| miR-367 | 16.65 | 2.60 | 18.65 | 2.02 | −2.00 | 4.60E−01 |
| miR-124a | 14.03 | 6.20 | 16.01 | 4.05 | −1.98 | 6.14E−01 |
| miR-16 | −5.75 | 1.12 | −3.84 | 1.81 | −1.91 | 5.26E−03 |
| miR-9* | 9.48 | 1.24 | 11.38 | 3.72 | −1.90 | 1.35E−01 |
| miR-31 | 8.14 | 1.22 | 10.02 | 2.12 | −1.87 | 1.51E−02 |
| miR-136 | 14.00 | 2.43 | 15.80 | 3.08 | −1.81 | 1.78E−01 |
| miR-32 | 4.58 | 1.60 | 6.34 | 4.03 | −1.76 | 1.96E−01 |
| miR-200a | 9.04 | 1.83 | 10.80 | 1.92 | −1.76 | 3.61E−02 |
| miR-512-5p | 11.10 | 1.00 | 12.84 | 3.23 | −1.75 | 9.53E−02 |
| miR-125b | 5.99 | 0.95 | 7.73 | 1.46 | −1.74 | 3.67E−03 |
| miR-514 | 15.39 | 3.68 | 17.12 | 2.55 | −1.73 | 2.23E−01 |
| miR-30e-5p | 1.54 | 1.10 | 3.21 | 3.04 | −1.67 | 9.36E−02 |
| miR-483 | 8.17 | 2.23 | 9.84 | 3.68 | −1.66 | 1.90E−01 |
| miR-383 | 9.65 | 1.07 | 11.28 | 3.06 | −1.63 | 1.01E−01 |
| miR-216 | 11.93 | 4.12 | 13.52 | 3.84 | −1.59 | 3.27E−01 |
| miR-195 | 0.82 | 1.27 | 2.41 | 2.57 | −1.59 | 6.89E−02 |
| miR-137 | 10.44 | 1.48 | 12.03 | 2.63 | −1.59 | 8.01E−02 |
| miR-138 | 10.95 | 2.24 | 12.53 | 2.96 | −1.59 | 1.54E−01 |
| miR-18b | 10.90 | 1.61 | 12.44 | 2.89 | −1.54 | 1.26E−01 |
| miR-501 | 8.64 | 3.37 | 10.16 | 2.16 | −1.51 | 3.32E−01 |
| miR-101 | 1.01 | 1.10 | 2.49 | 0.97 | −1.48 | 1.64E−03 |
| miR-373* | 11.57 | 2.36 | 13.04 | 3.78 | −1.48 | 2.58E−01 |
| miR-183 | 10.45 | 2.07 | 11.92 | 1.47 | −1.47 | 6.55E−02 |
| miR-365 | 6.16 | 1.15 | 7.60 | 2.13 | −1.44 | 7.52E−02 |
| miR-141 | 7.46 | 2.24 | 8.89 | 1.86 | −1.43 | 8.79E−02 |
| miR-193a | 8.84 | 1.17 | 10.27 | 1.80 | −1.43 | 2.98E−02 |
| miR-182* | 13.84 | 3.72 | 15.25 | 5.66 | −1.41 | 6.75E−01 |
| miR-96 | 9.46 | 2.57 | 10.76 | 1.81 | −1.30 | 2.15E−01 |
| miR-453 | 11.17 | 2.33 | 12.41 | 4.18 | −1.24 | 3.75E−01 |
| miR-10b | 5.29 | 2.50 | 6.53 | 1.54 | −1.24 | 1.37E−01 |
| miR-486 | −3.17 | 1.13 | −1.94 | 1.88 | −1.23 | 6.36E−02 |
| miR-29c | 0.92 | 0.88 | 2.15 | 0.73 | −1.22 | 7.09E−04 |
| miR-217 | 15.57 | 4.55 | 16.72 | 3.56 | −1.15 | 6.68E−01 |
| miR-497 | 7.92 | 1.99 | 9.06 | 1.71 | −1.14 | 1.95E−01 |
| miR-346 | 12.04 | 2.82 | 13.17 | 2.40 | −1.13 | 3.55E−01 |
| miR-489 | 12.77 | 2.64 | 13.88 | 1.93 | −1.12 | 2.26E−01 |
| miR-429 | 10.14 | 3.78 | 11.18 | 2.95 | −1.04 | 4.69E−01 |
| miR-200c | 5.05 | 1.39 | 6.05 | 0.60 | −1.00 | 2.56E−01 |
| miR-197 | −0.44 | 1.09 | 0.52 | 2.67 | −0.96 | 2.64E−01 |
| miR-185 | 5.80 | 1.87 | 6.74 | 2.43 | −0.95 | 2.91E−01 |
| miR-296 | 7.12 | 1.00 | 8.05 | 0.89 | −0.93 | 1.91E−02 |
| miR-214 | 5.36 | 1.21 | 6.29 | 3.10 | −0.93 | 3.45E−01 |
| miR-299-3p | 12.86 | 3.54 | 13.76 | 3.65 | −0.90 | 6.14E−01 |
| miR-29a | 0.90 | 1.03 | 1.78 | 0.82 | −0.88 | 2.32E−02 |
| miR-520a* | 16.86 | 4.44 | 17.73 | 4.79 | −0.87 | 7.99E−01 |
| miR-526a | 14.96 | 2.77 | 15.82 | 5.53 | −0.86 | 7.32E−01 |
| miR-507 | 15.97 | 3.63 | 16.83 | 4.64 | −0.85 | 6.12E−01 |
| miR-432* | 10.52 | 1.19 | 11.35 | 2.83 | −0.83 | 3.77E−01 |
| miR-128a | 9.94 | 0.81 | 10.77 | 0.91 | −0.83 | 1.02E−01 |
| miR-193b | 9.82 | 1.68 | 10.63 | 2.24 | −0.82 | 3.12E−01 |
| miR-372 | 13.70 | 2.33 | 14.51 | 3.70 | −0.81 | 5.80E−01 |
| miR-516-3p | 7.97 | 1.33 | 8.78 | 2.77 | −0.81 | 3.70E−01 |
| miR-378 | 8.98 | 1.43 | 9.76 | 0.71 | −0.79 | 1.39E−01 |
| miR-520d* | 14.84 | 2.95 | 15.62 | 5.39 | −0.78 | 7.48E−01 |
| miR-100 | 6.13 | 0.94 | 6.90 | 1.53 | −0.76 | 1.50E−01 |
| miR-184 | 13.58 | 3.37 | 14.32 | 3.39 | −0.75 | 5.94E−01 |
| miR-20b | 1.68 | 1.07 | 2.41 | 1.49 | −0.74 | 1.83E−01 |
| miR-188 | 6.45 | 1.25 | 7.19 | 3.10 | −0.74 | 4.54E−01 |
| miR-150 | 1.22 | 1.15 | 1.94 | 1.08 | −0.72 | 1.11E−01 |
| miR-19a | −0.82 | 0.83 | −0.10 | 1.45 | −0.71 | 1.50E−01 |
| miR-25 | −0.33 | 1.19 | 0.38 | 0.44 | −0.71 | 5.58E−02 |
| miR-19b | −2.17 | 0.73 | −1.47 | 1.17 | −0.70 | 8.97E−02 |
| miR-92 | −4.42 | 1.03 | −3.78 | 2.21 | −0.64 | 3.73E−01 |
| miR-376a* | 9.47 | 1.78 | 10.08 | 1.35 | −0.60 | 4.21E−01 |
| miR-135b | 12.67 | 3.43 | 13.22 | 2.27 | −0.55 | 7.05E−01 |
| miR-202 | 7.26 | 2.04 | 7.80 | 3.64 | −0.54 | 6.55E−01 |
| miR-452 | 7.16 | 1.51 | 7.68 | 2.21 | −0.53 | 4.95E−01 |
| miR-10a | 5.83 | 1.03 | 6.34 | 1.48 | −0.51 | 3.32E−01 |
| miR-93 | −0.50 | 0.62 | −0.03 | 0.26 | −0.46 | 2.02E−02 |
| let-7f | 2.49 | 1.80 | 2.95 | 3.35 | −0.46 | 6.78E−01 |
| miR-148a | 3.19 | 0.63 | 3.64 | 0.92 | −0.45 | 1.69E−01 |
| miR-203 | 11.63 | 4.32 | 12.07 | 3.30 | −0.45 | 7.69E−01 |
| miR-299-5p | 10.67 | 1.50 | 11.10 | 2.82 | −0.44 | 6.67E−01 |
| miR-20a | −1.34 | 1.00 | −0.93 | 1.68 | −0.41 | 4.64E−01 |
| miR-182 | 5.87 | 2.36 | 6.28 | 1.17 | −0.41 | 5.80E−01 |
| miR-520c | 12.30 | 1.81 | 12.69 | 2.42 | −0.38 | 6.84E−01 |
| miR-511 | 9.88 | 2.11 | 10.26 | 1.72 | −0.38 | 6.19E−01 |
| miR-510 | 13.51 | 2.81 | 13.84 | 2.54 | −0.33 | 7.54E−01 |
| let-7c | 3.31 | 0.97 | 3.64 | 0.96 | −0.33 | 3.91E−01 |
| miR-18a* | 6.06 | 1.15 | 6.39 | 1.32 | −0.33 | 5.17E−01 |
| miR-139 | 5.96 | 0.74 | 6.27 | 0.56 | −0.31 | 2.41E−01 |
| miR-204 | 8.90 | 0.92 | 9.19 | 1.09 | −0.30 | 4.69E−01 |
| miR-527 | 13.03 | 3.34 | 13.32 | 5.13 | −0.29 | 8.89E−01 |
| miR-190 | 5.55 | 1.41 | 5.82 | 0.92 | −0.27 | 5.60E−01 |
| miR-99a | 6.83 | 1.37 | 7.10 | 1.91 | −0.27 | 6.90E−01 |
| miR-30a-3p | 5.81 | 0.59 | 6.07 | 1.18 | −0.26 | 5.07E−01 |
| miR-518d | 10.54 | 1.76 | 10.78 | 3.73 | −0.25 | 8.38E−01 |
| miR-17-5p | 0.76 | 0.67 | 1.00 | 1.22 | −0.24 | 5.59E−01 |
| miR-517a | 15.36 | 2.77 | 15.58 | 3.38 | −0.22 | 9.06E−01 |
| miR-210 | 3.64 | 0.95 | 3.85 | 1.99 | −0.21 | 7.45E−01 |
| miR-520a | 15.16 | 2.80 | 15.35 | 4.92 | −0.20 | 9.13E−01 |
| miR-500 | 9.79 | 2.41 | 9.98 | 1.05 | −0.19 | 8.33E−01 |
| miR-422a | 6.48 | 1.31 | 6.64 | 2.63 | −0.16 | 8.50E−01 |
| miR-208 | 17.02 | 2.56 | 17.16 | 2.34 | −0.15 | 9.07E−01 |
| miR-302a | 16.05 | 5.66 | 16.18 | 4.20 | −0.13 | 9.69E−01 |
| miR-520g | 14.64 | 4.07 | 14.75 | 4.42 | −0.12 | 9.56E−01 |
| miR-196b | 6.83 | 1.13 | 6.95 | 1.56 | −0.11 | 8.44E−01 |
| miR-526b* | 15.90 | 3.56 | 16.01 | 4.78 | −0.11 | 9.50E−01 |
| miR-142-3p | −1.22 | 0.68 | −1.15 | 1.53 | −0.07 | 8.81E−01 |
| miR-199b | 8.18 | 1.48 | 8.24 | 1.63 | −0.05 | 9.33E−01 |
| miR-34c | 6.72 | 0.70 | 6.76 | 1.18 | −0.04 | 9.14E−01 |
| miR-517c | 10.66 | 3.19 | 10.68 | 2.12 | −0.01 | 9.91E−01 |
| let-7b | 0.52 | 1.61 | 0.53 | 1.10 | −0.01 | 9.83E−01 |
| miR-329 | 10.61 | 1.42 | 10.60 | 2.16 | 0.01 | 9.95E−01 |
| miR-381 | 10.99 | 1.65 | 10.98 | 2.78 | 0.01 | 9.91E−01 |
| miR-106b | 0.39 | 0.69 | 0.38 | 1.15 | 0.01 | 9.69E−01 |
| miR-424 | 8.65 | 1.22 | 8.62 | 0.84 | 0.03 | 9.42E−01 |
| miR-148b | 3.79 | 0.60 | 3.74 | 1.73 | 0.05 | 9.32E−01 |
| miR-126 | 0.28 | 1.13 | 0.23 | 1.43 | 0.05 | 9.28E−01 |
| miR-132 | 4.66 | 0.82 | 4.61 | 1.00 | 0.05 | 8.86E−01 |
| let-7a | 1.49 | 1.01 | 1.43 | 1.77 | 0.06 | 9.24E−01 |
| miR-345 | 4.05 | 0.50 | 3.99 | 0.93 | 0.06 | 8.41E−01 |
| miR-374 | 1.95 | 0.87 | 1.88 | 0.85 | 0.07 | 8.35E−01 |
| miR-450 | 10.64 | 2.91 | 10.56 | 0.71 | 0.07 | 9.48E−01 |
| miR-325 | 19.66 | 1.84 | 19.58 | 4.95 | 0.08 | 9.69E−01 |
| miR-17-3p | 6.86 | 0.83 | 6.77 | 1.49 | 0.09 | 8.53E−01 |
| let-7i | 0.86 | 1.02 | 0.76 | 2.26 | 0.09 | 8.96E−01 |
| miR-181b | 2.68 | 0.72 | 2.57 | 1.76 | 0.11 | 8.39E−01 |

TABLE 27-continued miRNA Biomarkers Differentially Expressed Between Plasma Samples of Lung Cancer Patients and Plasma Samples of Normal Patients.

| miRNA | Cancer Average dCt | Cancer SD | Normal Average dCt | Normal SD | ddCt (Cancer − Normal) | t-test |
|---|---|---|---|---|---|---|
| miR-30a-5p | −0.25 | 0.85 | −0.37 | 1.28 | 0.11 | 7.95E−01 |
| miR-18a | 6.16 | 0.84 | 6.04 | 0.99 | 0.12 | 7.44E−01 |
| miR-106a | 2.33 | 0.67 | 2.20 | 0.87 | 0.13 | 6.89E−01 |
| miR-146b | 1.05 | 0.51 | 0.92 | 0.97 | 0.13 | 6.80E−01 |
| miR-147 | 18.12 | 3.46 | 17.97 | 3.45 | 0.15 | 9.32E−01 |
| miR-103 | 1.82 | 0.85 | 1.68 | 1.53 | 0.15 | 7.69E−01 |
| miR-30d | 1.15 | 0.66 | 1.00 | 0.55 | 0.15 | 5.24E−01 |
| miR-422b | 3.51 | 0.94 | 3.34 | 2.86 | 0.17 | 8.44E−01 |
| miR-135a | 8.57 | 0.90 | 8.40 | 0.66 | 0.18 | 6.18E−01 |
| miR-196a | 7.99 | 1.57 | 7.81 | 1.63 | 0.18 | 7.74E−01 |
| miR-335 | 5.14 | 1.40 | 4.94 | 2.42 | 0.20 | 8.00E−01 |
| miR-21 | −1.38 | 0.83 | −1.62 | 1.13 | 0.23 | 5.57E−01 |
| miR-23a | 1.42 | 0.49 | 1.18 | 0.34 | 0.24 | 1.49E−01 |
| miR-130b | 1.75 | 0.97 | 1.50 | 0.95 | 0.25 | 5.20E−01 |
| let-7d | 3.78 | 1.40 | 3.53 | 1.28 | 0.25 | 6.40E−01 |
| miR-495 | 7.86 | 0.75 | 7.60 | 1.01 | 0.25 | 5.03E−01 |
| miR-26b | −0.46 | 1.24 | −0.71 | 1.60 | 0.26 | 6.55E−01 |
| miR-15b | 1.33 | 1.27 | 1.04 | 1.61 | 0.29 | 6.16E−01 |
| miR-130a | 1.54 | 1.30 | 1.19 | 0.85 | 0.35 | 4.25E−01 |
| let-7e | 7.16 | 2.12 | 6.82 | 1.95 | 0.35 | 6.75E−01 |
| miR-30c | 1.32 | 0.88 | 0.97 | 1.85 | 0.35 | 5.60E−01 |
| miR-34b | 17.45 | 3.79 | 17.08 | 2.65 | 0.36 | 8.59E−01 |
| miR-377 | 12.83 | 3.23 | 12.46 | 2.43 | 0.37 | 7.57E−01 |
| miR-140 | 3.21 | 0.98 | 2.85 | 0.87 | 0.37 | 3.18E−01 |
| miR-520b | 17.47 | 1.67 | 17.10 | 2.22 | 0.37 | 7.38E−01 |
| let-7g | 0.06 | 0.86 | −0.31 | 0.93 | 0.38 | 2.97E−01 |
| miR-542-3p | 11.03 | 2.43 | 10.65 | 0.81 | 0.38 | 5.88E−01 |
| miR-98 | 5.72 | 1.04 | 5.33 | 1.55 | 0.39 | 4.82E−01 |
| miR-502 | 7.79 | 0.82 | 7.39 | 3.28 | 0.40 | 6.90E−01 |
| miR-199a* | 1.46 | 0.68 | 1.06 | 0.65 | 0.40 | 1.45E−01 |
| miR-503 | 12.38 | 2.88 | 11.98 | 2.20 | 0.41 | 7.23E−01 |
| miR-23b | 3.86 | 0.63 | 3.44 | 0.61 | 0.43 | 9.05E−02 |
| miR-320 | 0.90 | 1.29 | 0.47 | 2.35 | 0.43 | 5.77E−01 |
| miR-212 | 8.16 | 1.12 | 7.68 | 3.05 | 0.48 | 6.16E−01 |
| miR-518c* | 11.99 | 3.66 | 11.49 | 4.28 | 0.50 | 7.62E−01 |
| miR-26a | −1.95 | 0.77 | −2.45 | 0.70 | 0.51 | 9.24E−02 |
| miR-152 | 4.37 | 0.54 | 3.86 | 0.70 | 0.52 | 5.05E−02 |
| miR-142-5p | 2.40 | 0.86 | 1.89 | 0.79 | 0.52 | 1.23E−01 |
| miR-154* | 10.20 | 1.53 | 9.67 | 1.19 | 0.54 | 4.24E−01 |
| miR-505 | 4.37 | 0.60 | 3.82 | 0.50 | 0.56 | 1.67E−02 |
| miR-105 | 14.01 | 4.11 | 13.45 | 3.41 | 0.56 | 7.54E−01 |
| miR-223 | −2.23 | 0.60 | −2.80 | 0.91 | 0.57 | 8.13E−02 |
| miR-432 | 4.51 | 1.22 | 3.93 | 1.05 | 0.58 | 2.02E−01 |
| miR-324-3p | 4.32 | 0.63 | 3.69 | 0.87 | 0.64 | 4.85E−02 |
| miR-24 | −0.27 | 0.95 | −0.91 | 1.27 | 0.64 | 1.70E−01 |
| miR-28 | 5.44 | 0.86 | 4.80 | 0.93 | 0.64 | 8.36E−02 |
| miR-149 | 13.18 | 3.27 | 12.49 | 1.73 | 0.69 | 5.19E−01 |
| miR-219 | 12.63 | 3.46 | 11.93 | 2.22 | 0.70 | 5.73E−01 |
| miR-433 | 5.73 | 1.05 | 5.03 | 1.23 | 0.70 | 1.36E−01 |
| miR-221 | −0.28 | 0.70 | −1.00 | 0.61 | 0.71 | 1.06E−02 |
| nniR-146a | −0.57 | 0.63 | −1.31 | 0.52 | 0.74 | 3.13E−03 |
| miR-133b | 4.68 | 0.77 | 3.94 | 1.17 | 0.75 | 7.52E−01 |
| miR-181d | 2.19 | 0.65 | 1.43 | 1.34 | 0.76 | 9.40E−02 |
| miR-224 | 8.03 | 1.59 | 7.25 | 0.91 | 0.78 | 1.60E−01 |
| miR-181c | 4.54 | 0.62 | 3.74 | 0.65 | 0.80 | 4.14E−03 |
| miR-485-5p | 8.02 | 1.05 | 7.22 | 1.45 | 0.80 | 1.28E−01 |
| miR-423 | 3.83 | 0.52 | 3.01 | 0.99 | 0.81 | 2.10E−02 |
| miR-376b | 10.41 | 3.28 | 9.60 | 2.69 | 0.82 | 5.88E−01 |
| miR-504 | 19.43 | 1.91 | 18.60 | 2.06 | 0.83 | 4.61E−01 |
| miR-29b | 5.46 | 1.80 | 4.63 | 1.73 | 0.83 | 2.42E−01 |
| miR-1 | 9.49 | 3.81 | 8.65 | 4.25 | 0.84 | 6.15E−01 |
| miR-425 | 4.92 | 0.67 | 4.08 | 1.23 | 0.84 | 4.98E−02 |
| miR-15a | 4.65 | 0.96 | 3.80 | 1.19 | 0.85 | 6.09E−02 |
| miR-107 | 7.16 | 1.11 | 6.30 | 1.18 | 0.85 | 7.14E−02 |
| miR-133a | 7.24 | 1.34 | 6.38 | 0.89 | 0.86 | 6.48E−02 |
| miR-382 | 4.69 | 1.32 | 3.83 | 1.96 | 0.86 | 2.13E−01 |
| miR-508 | 14.81 | 3.67 | 13.95 | 3.85 | 0.86 | 5.98E−01 |
| miR-324-5p | 5.01 | 0.95 | 4.14 | 0.90 | 0.86 | 2.60E−02 |
| miR-493-3p | 8.94 | 1.71 | 8.07 | 1.98 | 0.87 | 2.48E−01 |
| miR-376a | 4.01 | 1.41 | 3.14 | 2.40 | 0.87 | 2.84E−01 |
| miR-27a | 2.75 | 1.51 | 1.87 | 0.48 | 0.88 | 5.53E−02 |
| miR-361 | 4.39 | 1.31 | 3.50 | 2.49 | 0.89 | 2.84E−01 |
| miR-342 | 3.18 | 0.65 | 2.28 | 0.61 | 0.90 | 1.32E−03 |
| miR-496 | 8.29 | 1.45 | 7.39 | 1.38 | 0.90 | 1.17E−01 |
| miR-199a | 7.65 | 1.23 | 6.73 | 0.66 | 0.92 | 2.44E−02 |
| miR-30b | 0.74 | 0.95 | −0.20 | 0.86 | 0.94 | 1.41E−02 |
| miR-509 | 10.99 | 2.32 | 10.04 | 4.06 | 0.95 | 4.85E−01 |
| miR-518c | 15.52 | 3.23 | 14.57 | 4.89 | 0.96 | 6.15E−01 |
| miR-211 | 12.00 | 3.08 | 11.04 | 1.44 | 0.96 | 3.44E−01 |
| miR-125a | 4.10 | 0.70 | 3.10 | 0.87 | 1.00 | 4.54E−03 |
| miR-186 | 1.05 | 0.58 | 0.05 | 0.98 | 1.00 | 6.49E−03 |
| miR-30e-3p | 6.03 | 1.04 | 5.01 | 1.43 | 1.02 | 5.33E−02 |
| miR-155 | 4.43 | 0.81 | 3.40 | 1.57 | 1.03 | 5.71E−02 |
| miR-369-3p | 10.05 | 2.75 | 9.02 | 1.04 | 1.03 | 2.30E−01 |
| miR-380-3p | 12.73 | 3.70 | 11.69 | 1.09 | 1.03 | 4.40E−01 |
| miR-338 | 6.79 | 1.62 | 5.74 | 2.90 | 1.04 | 2.85E−01 |
| miR-340 | 7.19 | 1.35 | 6.14 | 1.76 | 1.05 | 1.41E−01 |
| miR-323 | 7.40 | 0.94 | 6.35 | 1.24 | 1.05 | 2.63E−02 |
| miR-379 | 7.43 | 1.40 | 6.36 | 1.64 | 1.07 | 9.03E−02 |
| miR-523 | 18.31 | 3.96 | 17.23 | 4.04 | 1.07 | 6.07E−01 |
| miR-494 | 9.67 | 2.01 | 8.60 | 1.36 | 1.07 | 1.30E−01 |
| miR-488 | 19.32 | 2.87 | 18.24 | 4.26 | 1.08 | 6.58E−01 |
| miR-127 | 3.79 | 1.01 | 2.69 | 0.92 | 1.09 | 8.18E−03 |
| miR-362 | 7.75 | 1.81 | 6.65 | 1.72 | 1.10 | 1.25E−01 |
| miR-380-5p | 13.64 | 3.87 | 12.53 | 1.05 | 1.11 | 4.85E−01 |
| miR-330 | 9.99 | 1.07 | 8.87 | 0.90 | 1.12 | 7.91E−03 |
| miR-485-3p | 6.78 | 2.34 | 5.64 | 1.14 | 1.14 | 1.22E−01 |
| miR-331 | 5.30 | 1.42 | 4.15 | 1.47 | 1.15 | 6.07E−02 |
| miR-525* | 14.27 | 2.93 | 13.11 | 4.19 | 1.16 | 4.31E−01 |
| miR-181a | 3.11 | 0.79 | 1.95 | 1.75 | 1.16 | 5.19E−02 |
| miR-518a | 14.18 | 3.31 | 13.01 | 1.66 | 1.17 | 5.60E−01 |
| miR-27b | 3.70 | 1.38 | 2.54 | 0.65 | 1.17 | 1.12E−02 |
| miR-518e | 12.68 | 3.06 | 11.52 | 4.33 | 1.17 | 4.69E−01 |
| miR-328 | 4.46 | 0.72 | 3.28 | 1.14 | 1.18 | 6.03E−03 |
| miR-301 | 4.31 | 0.89 | 3.13 | 0.74 | 1.18 | 1.11E−03 |
| miR-198 | 12.16 | 2.90 | 10.95 | 3.57 | 1.20 | 3.60E−01 |
| miR-145 | 3.96 | 0.93 | 2.76 | 1.53 | 1.21 | 2.88E−02 |
| miR-412 | 15.14 | 2.67 | 13.93 | 4.58 | 1.22 | 5.36E−01 |
| miR-213 | 8.89 | 0.92 | 7.65 | 1.69 | 1.24 | 3.91E−02 |
| miR-33 | 11.04 | 3.12 | 9.78 | 1.64 | 1.26 | 2.34E−01 |
| miR-191 | 0.70 | 0.70 | −0.56 | 0.43 | 1.26 | 1.12E−05 |
| miR-520e | 15.89 | 2.25 | 14.62 | 3.13 | 1.26 | 3.72E−01 |
| miR-153 | 13.74 | 4.11 | 12.47 | 3.04 | 1.27 | 4.48E−01 |
| miR-143 | 10.70 | 4.07 | 9.42 | 0.87 | 1.28 | 2.71E−01 |
| miR-519d | 10.08 | 2.32 | 8.80 | 3.83 | 1.28 | 3.30E−01 |
| miR-99b | 5.41 | 0.78 | 4.12 | 1.13 | 1.28 | 3.61E−03 |
| miR-134 | 4.75 | 1.57 | 3.44 | 2.56 | 1.30 | 1.44E−01 |
| miR-154 | 10.45 | 2.99 | 9.13 | 1.36 | 1.32 | 1.86E−01 |
| miR-518b | 11.66 | 2.69 | 10.32 | 3.41 | 1.35 | 2.88E−01 |
| miR-410 | 4.99 | 1.38 | 3.63 | 2.02 | 1.36 | 6.32E−02 |
| miR-339 | 5.00 | 0.99 | 3.61 | 0.65 | 1.38 | 3.07E−04 |
| miR-151 | 2.06 | 0.85 | 0.67 | 2.01 | 1.39 | 4.25E−02 |
| miR-34a | 9.63 | 2.42 | 8.16 | 4.89 | 1.47 | 3.59E−01 |
| miR-187 | 11.03 | 3.50 | 9.47 | 1.39 | 1.56 | 1.44E−01 |
| miR-518f | 16.54 | 3.42 | 14.96 | 4.52 | 1.59 | 3.44E−01 |
| miR-302b* | 16.36 | 4.66 | 14.77 | 10.39 | 1.60 | 8.65E−01 |
| miR-222 | 1.40 | 0.80 | −0.26 | 1.26 | 1.66 | 9.65E−04 |
| miR-491 | 6.15 | 1.30 | 4.47 | 2.74 | 1.68 | 7.14E−02 |
| miR-302d | 17.55 | 3.40 | 15.83 | 3.69 | 1.72 | 3.64E−01 |
| miR-370 | 8.23 | 2.20 | 6.49 | 1.59 | 1.74 | 2.85E−02 |
| miR-368 | 12.18 | 3.72 | 10.42 | 2.36 | 1.75 | 2.66E−01 |
| miR-490 | 12.44 | 2.92 | 10.69 | 3.28 | 1.75 | 1.67E−01 |
| miR-189 | 16.98 | 4.15 | 15.22 | 4.24 | 1.76 | 4.19E−01 |
| miR-526b | 18.30 | 4.33 | 16.52 | 3.99 | 1.78 | 4.25E−01 |
| miR-539 | 7.73 | 2.58 | 5.93 | 1.09 | 1.81 | 3.51E−02 |
| miR-493 | 10.90 | 3.44 | 9.10 | 1.50 | 1.81 | 1.20E−01 |
| miR-487b | 7.48 | 3.19 | 5.64 | 1.79 | 1.85 | 7.84E−02 |
| miR-126* | 0.06 | 3.20 | −1.89 | 1.08 | 1.95 | 4.74E−02 |
| miR-371 | 17.55 | 3.02 | 15.56 | 3.01 | 2.00 | 1.52E−01 |
| miR-369-5p | 11.37 | 4.74 | 9.29 | 0.69 | 2.08 | 3.84E−01 |
| miR-455 | 14.46 | 3.74 | 12.38 | 2.70 | 2.08 | 1.66E−01 |
| miR-337 | 15.71 | 4.66 | 13.59 | 1.81 | 2.12 | 3.79E−01 |
| miR-128b | 14.50 | 3.21 | 12.30 | 1.98 | 2.21 | 4.63E−02 |
| miR-326 | 7.41 | 0.88 | 5.16 | 1.36 | 2.25 | 1.09E−04 |
| miR-373 | 16.08 | 4.49 | 13.83 | 3.98 | 2.25 | 2.17E−01 |
| miR-487a | 11.12 | 4.01 | 8.85 | 1.94 | 2.27 | 1.27E−01 |

TABLE 27-continued miRNA Biomarkers Differentially Expressed Between Plasma Samples of Lung Cancer Patients and Plasma Samples of Normal Patients.

| miRNA | Cancer Average dCt | Cancer SD | Normal Average dCt | Normal SD | ddCt (Cancer − Normal) | t-test |
|---|---|---|---|---|---|---|
| miR-452* | 12.84 | 4.18 | 10.47 | 1.24 | 2.37 | 1.59E−01 |
| miR-9 | 11.88 | 4.01 | 9.44 | 0.82 | 2.44 | 7.45E−02 |
| miR-409-5p | 12.34 | 4.03 | 9.87 | 1.51 | 2.47 | 1.99E−01 |
| miR-519e | 12.44 | 2.93 | 9.89 | 3.03 | 2.56 | 4.33E−02 |
| miR-542-5p | 15.61 | 4.73 | 12.74 | 1.91 | 2.87 | 1.18E−01 |
| miR-517b | 17.60 | 4.35 | 14.57 | 5.50 | 3.03 | 3.87E−01 |
| miR-520f | 16.59 | 4.22 | 13.21 | 4.64 | 3.38 | 9.69E−02 |
| miR-22 | 8.62 | 2.78 | 5.17 | 2.12 | 3.44 | 1.55E−03 |

Example 7

QRT-PCR for Evaluation of MicroRNA Expression in Human Lung Cancer Patient Plasma RNA A second set of plasma samples, isolated from a distinct set of lung cancer and normal patients (Table 28), was used to perform an additional comparison of miRNAs expressed in lung cancer and normal patients. In Table 28, TNM (tumor, node, metastasis) stage is described in Sobin and Wittekind, N.J.: John Wiley & Sons, 2002. The following abbreviations are used in Table 28: adenocarcinoma (ADCA); bronchoalveolar (BA), squamous cell carcinoma (SCC), and not available (NA).

TABLE 28

Human Lung Cancer and Normal Patient Information and Tumor Pathology . . .

| Age | Sex | Cell & Tumor Characteristics | TNM Stage |
|---|---|---|---|
| Lung Cancer Patients | | | |
| 70 | F | upper lobe of left lung, ADCA | NA |
| 66 | M | upper lobe of left lung, ADCA | NA |
| 48 | M | lower lobe of left lung, BA | NA |
| 69 | M | Lower lobe of left lung, SCC | NA |
| 66 | F | Upper lobe of right lung, SCC | NA |
| 72 | M | Upper lobe of right lung, SCC | T3NxM0 |
| 66 | M | Left lung, SCC | T3NxM0 |
| 46 | M | Left lung, SCC | T3NxM0 |
| 62 | M | Right lung, SCC | T2NxM0 |
| Normal Patients | | | |
| 40 | F | Normal | — |
| 41 | F | Normal | — |
| 59 | F | Normal | — |
| 56 | M | Normal | — |
| 52 | F | Normal | — |
| 37 | M | Normal | — |
| 34 | M | Normal | — |

To assess the expression of miRNAs, real-time RT-PCR detection with TaqMan® Micro RNA Assays (Applied Biosystems, Foster City, Calif., USA) was used to screen RNA isolated from seven normal human plasma and nine lung cancer patient plasma samples.

Plasma RNA was isolated as described above in Example 6. qRT-PCR reactions were performed using TaqMan® MicroRNA Assays (Applied Biosystems; Foster City, Calif., USA) specific for each individual miRNA. Reverse transcription reactions were assembled on ice prior to the addition of RNA template (Table 29). Next, 0.25 µl of plasma RNA template per reaction was added and mixed. RT reactions were incubated in a 384-well GeneAmp® PCR System 9700 (Applied Biosystems) at 16° C. for 30 minutes, then at 42° C. for 30 minutes, then at 85° C. for 5 minutes, and then were frozen in a −20° C. freezer.

TABLE 29

Reverse transcription reaction components.

| Component | µl per 10 µl rxn | Final Concentration |
|---|---|---|
| Nuclease-free water | 5.6 | |
| 10× Reverse Transcription Buffer (Ambion, Inc., Austin, TX, USA) | 1.0 | 1X |
| dNTP mix (2.5 mM each) (Ambion, Inc. Austin, TX, USA) | 1.0 | 0.25 mM each |
| 1.25X RT Primer (Applied Biosystems) | 2.0 | 0.25X |
| RNasin ® Ribonuclease Inhibitor (40 U/µl, Promega, Corp. Madison, WI, USA; cat. no. N2115) | 0.1 | 0.4 U/µl |
| Moloney Murine Leukemia Virus Reverse Transcriptase (MMLV-RT) (200 U/µl) (Invitrogen) | 0.05 | 1 U/µl |
| Human Plasma RNA | 0.25 | — |

PCR components were assembled on ice prior to the addition of the cDNA from the RT reactions (Table 30). PCRs were incubated in an ABI PRISM™ 7900HT Fast Real-Time PCR system (Applied Biosystems) at 95° C. for 1 minute, then for 50 cycles at 95° C. for 5 seconds and then at 60° C. for 30 seconds. Initial data analysis was done using the 7500 Fast System SDS V2.3 software (Applied Biosystems).

TABLE 30

Real-time PCR components

| Component | µl per 15 µl rxn | Final Concentration |
|---|---|---|
| Nuclease-free water | 6.1 | — |
| MgCl$_2$ (50 mM) | 1.5 | 5 mM |
| 10X Platinum PCR Buffer, Minus Mg (Invitrogen Corp., Carlsbad, CA, USA) | 1.5 | 1X |
| dNTP mix (2.5 mM each) (Ambion) | 1.5 | 0.25 mM each |
| 3X TaqMan Assay (Applied Biosystems) | 2.0 | 0.4X |
| 50X ROX Internal marker | 0.3 | 1X |
| Platinum ® Taq DNA Polymerase (5 U/µl) (Invitrogen) | 0.1 | 0.033 U/µl |
| cDNA from RT reaction | 2.0 | |

The qRT-PCR data were initially assessed for outliers. All miRNAs in a given sample with raw Ct values of 50 were eliminated from further analysis. All data from samples with fewer than 150 miRNAs that had raw Ct values less than 50 were eliminated. The average raw Ct for 50 miRNAs that were detected in each plasma sample was calculated for each individual sample. The average Ct for a given sample was subtracted from the raw Ct values for each miRNA in the corresponding sample to produce a dCt for each miRNA that was detected. These normalized measures were used to identify miRNAs that were present at significantly different levels in the plasma samples from normal donors and lung cancer patients.

The average dCt values for each miRNA in the normal donor and lung cancer patient samples were calculated. The average dCt values for the lung cancer patient samples were subtracted from the average dCt values for the normal donors to determine the variance in the levels of the various miRNAs between the two patient sets. The student t-test was then used to evaluate the capacity of the various miRNAs to distinguish the plasmas of lung cancer patients and normal donors.

Table 31 provides dCt values for normal and cancer patients, as well as ddCt values for cancer vs normal samples for each miRNA.

TABLE 31 miRNA Biomarkers Differentially Expressed Between Plasma Samples of Lung Cancer Patients and Plasma Samples of Normal Patients.

| miRNA | Normal Average | Normal SD | Cancer Average | Cancer SD | Cancer – Normal | p-value Cancer – Normal |
|---|---|---|---|---|---|---|
| miR-369-5p | 6.85 | 0.42 | 10.19 | 1.67 | -6.85 | 2.10E-01 |
| miR-218 | 12.91 | 5.50 | 6.75 | 1.67 | -6.16 | 1.02E-01 |
| miR-489 | 12.17 | 0.91 | 6.84 | 0.53 | -5.34 | 1.43E-03 |
| miR-455 | 14.66 | 1.48 | 9.71 | 4.67 | -4.96 | 1.54E-01 |
| miR-511 | 9.32 | 2.05 | 4.74 | 0.49 | -4.58 | 7.65E-03 |
| miR-507 | 15.24 | 3.54 | 11.04 | 1.82 | -4.20 | 4.08E-02 |
| miR-516-3p | 10.45 | 3.30 | 6.57 | 2.14 | -3.88 | 4.48E-02 |
| miR-448 | 16.11 | 3.36 | 12.34 | 2.25 | -3.77 | 6.14E-02 |
| miR-483 | 8.13 | 2.26 | 4.42 | 1.88 | -3.71 | 1.34E-02 |
| miR-122a | 9.90 | 2.79 | 6.41 | 4.58 | -3.49 | 2.21E-01 |
| miR-383 | 10.16 | 2.98 | 6.94 | 1.41 | -3.22 | 5.05E-02 |
| miR-206 | 8.53 | 2.95 | 5.36 | 2.41 | -3.18 | 7.67E-02 |
| miR-34c | 12.19 | 2.27 | 9.07 | 4.52 | -3.11 | 1.55E-01 |
| miR-375 | 5.04 | 1.54 | 2.14 | 2.43 | -2.90 | 2.90E-02 |
| miR-514 | 13.85 | 3.16 | 11.10 | 2.79 | -2.75 | 1.51E-01 |
| miR-452* | 7.01 | 1.39 | 4.32 | 0.44 | -2.70 | 1.27E-02 |
| miR-302b* | 15.04 | 5.63 | 12.35 | 1.98 | -2.70 | 4.04E-01 |
| miR-527 | 12.54 | 3.69 | 10.04 | 1.43 | -2.50 | 3.25E-01 |
| miR-340 | 2.28 | 0.47 | 4.64 | 0.86 | -2.28 | 1.35E-01 |
| miR-134 | 1.76 | 0.89 | -0.34 | 0.72 | -2.10 | 3.11E-03 |
| miR-429 | 6.95 | 0.83 | 4.96 | 1.57 | -1.99 | 2.06E-02 |
| miR-31 | 6.99 | 1.52 | 5.01 | 1.96 | -1.98 | 9.24E-02 |
| miR-200c | 2.49 | 1.02 | 0.51 | 0.37 | -1.98 | 1.47E-03 |
| miR-33 | 9.07 | 2.12 | 7.17 | 2.10 | -1.90 | 1.85E-01 |
| miR-152 | 1.53 | 1.25 | -0.30 | 0.37 | -1.83 | 1.03E-02 |
| miR-518b | 8.88 | 2.90 | 7.06 | 2.03 | -1.82 | 2.57E-01 |
| miR-452 | 7.83 | 1.23 | 6.13 | 1.72 | -1.70 | 8.72E-02 |
| miR-146a | -4.76 | 1.25 | -6.39 | 0.44 | -1.63 | 2.02E-02 |
| miR-155 | -0.43 | 1.13 | -2.02 | 0.10 | -1.59 | 2.32E-02 |
| miR-10b | 4.69 | 1.64 | 3.11 | 0.93 | -1.58 | 1.15E-01 |
| miR-34a | 10.13 | 2.33 | 8.56 | 2.13 | -1.56 | 2.63E-01 |
| miR-210 | 2.13 | 0.79 | 0.60 | 1.52 | -1.52 | 4.55E-02 |
| miR-213 | 6.79 | 0.84 | 5.30 | 1.29 | -1.49 | 7.16E-02 |
| miR-346 | 9.17 | 2.33 | 7.72 | 4.58 | -1.45 | 4.86E-01 |
| miR-362 | 3.67 | 0.66 | 2.30 | 0.81 | -1.37 | 8.91E-03 |
| miR-214 | 5.14 | 2.14 | 3.79 | 1.63 | -1.34 | 2.68E-01 |
| miR-422a | 5.79 | 0.87 | 4.49 | 1.28 | -1.31 | 5.97E-02 |
| miR-181a | 2.43 | 1.16 | 1.20 | 0.82 | -1.23 | 6.97E-02 |
| miR-127 | 1.77 | 1.96 | 0.55 | 1.59 | -1.22 | 2.78E-01 |
| miR-520d | 14.69 | 3.20 | 13.48 | 3.92 | -1.21 | 6.49E-01 |
| miR-135a | 6.23 | 0.86 | 5.02 | 0.62 | -1.21 | 6.96E-02 |
| miR-191 | -3.94 | 1.09 | -5.15 | 0.46 | -1.21 | 4.41E-02 |
| miR-432 | 0.02 | 1.02 | -1.18 | 1.11 | -1.20 | 9.43E-02 |
| miR-449 | 7.47 | 1.38 | 6.27 | 2.05 | -1.20 | 3.26E-01 |
| miR-328 | 0.58 | 0.80 | -0.60 | 0.49 | -1.19 | 1.52E-02 |
| miR-486 | -5.54 | 2.54 | -6.70 | 0.92 | -1.16 | 3.55E-01 |
| miR-149 | 10.20 | 3.16 | 9.07 | 2.96 | -1.13 | 6.00E-01 |
| miR-150 | -2.32 | 1.89 | -3.44 | 1.25 | -1.12 | 2.77E-01 |
| miR-197 | -0.34 | 0.93 | -1.46 | 0.81 | -1.12 | 5.62E-02 |
| miR-146b | -2.33 | 0.62 | -3.37 | 0.77 | -1.04 | 2.67E-02 |
| miR-30a-3p | 3.14 | 0.69 | 2.11 | 1.16 | -1.03 | 8.18E-02 |
| miR-181b | 1.52 | 0.45 | 0.50 | 1.15 | -1.02 | 5.56E-02 |
| miR-425 | 1.78 | 0.70 | 0.79 | 0.67 | -1.00 | 3.33E-02 |
| miR-376a | 2.69 | 1.08 | 1.70 | 0.60 | -0.99 | 9.58E-02 |
| miR-382 | 2.21 | 1.45 | 1.29 | 0.69 | -0.91 | 2.23E-01 |
| miR-223 | -7.86 | 1.23 | -8.73 | 0.72 | -0.87 | 1.91E-01 |
| miR-99b | 2.34 | 1.27 | 1.48 | 0.78 | -0.86 | 2.55E-01 |
| miR-28 | 1.11 | 1.32 | 0.29 | 0.34 | -0.82 | 2.10E-01 |
| miR-497 | 5.55 | 0.77 | 4.74 | 0.71 | -0.82 | 1.28E-01 |
| miR-142-5p | 0.49 | 2.86 | -0.32 | 0.72 | -0.81 | 5.54E-01 |
| miR-186 | -1.82 | 0.85 | -2.60 | 0.64 | -0.78 | 1.16E-01 |
| miR-369-3p | 8.03 | 1.05 | 7.27 | 1.98 | -0.76 | 4.60E-01 |
| miR-92 | -6.18 | 1.79 | -6.94 | 1.09 | -0.76 | 4.67E-01 |
| miR-224 | 3.33 | 0.97 | 2.58 | 1.24 | -0.75 | 2.87E-01 |
| miR-100 | 4.75 | 0.33 | 4.00 | 1.20 | -0.75 | 1.44E-01 |
| miR-106b | -1.13 | 0.59 | -1.85 | 0.90 | -0.72 | 1.21E-01 |
| miR-183 | 6.87 | 2.37 | 6.16 | 1.37 | -0.71 | 5.62E-01 |
| miR-24 | -5.08 | 1.13 | -5.77 | 1.13 | -0.70 | 3.17E-01 |
| miR-203 | 8.21 | 0.74 | 7.51 | 2.59 | -0.69 | 5.42E-01 |
| miR-99a | 5.24 | 0.93 | 4.56 | 0.49 | -0.68 | 2.16E-01 |
| miR-7 | 4.02 | 1.35 | 3.38 | 1.46 | -0.64 | 4.79E-01 |
| miR-17-5p | -1.80 | 0.63 | -2.42 | 0.79 | -0.62 | 1.60E-01 |
| miR-342 | -0.72 | 0.82 | -1.34 | 0.43 | -0.62 | 1.58E-01 |
| miR-129 | 13.07 | 2.15 | 12.45 | 1.91 | -0.62 | 6.98E-01 |
| miR-330 | 5.38 | 0.79 | 4.78 | 1.60 | -0.59 | 4.10E-01 |
| miR-324-3p | 0.45 | 1.02 | -0.14 | 0.31 | -0.59 | 2.41E-01 |
| miR-301 | 0.88 | 0.46 | 0.29 | 0.74 | -0.58 | 1.43E-01 |
| miR-132 | 1.77 | 0.61 | 1.20 | 0.97 | -0.57 | 2.38E-01 |
| miR-211 | 8.81 | 1.68 | 8.25 | 2.49 | -0.56 | 6.63E-01 |
| miR-30a-5p | -2.45 | 0.36 | -2.98 | 0.32 | -0.54 | 2.34E-02 |
| miR-18b | 9.78 | 0.54 | 9.25 | 3.12 | -0.53 | 7.09E-01 |
| miR-324-5p | 2.09 | 1.01 | 1.56 | 0.85 | -0.53 | 3.65E-01 |
| let-7c | -0.48 | 1.01 | -1.00 | 0.41 | -0.52 | 3.04E-01 |
| miR-190 | 3.86 | 0.80 | 3.36 | 0.40 | -0.51 | 2.23E-01 |
| miR-196b | 2.60 | 1.05 | 2.11 | 0.73 | -0.50 | 3.82E-01 |
| miR-133b | 1.01 | 1.20 | 0.52 | 0.53 | -0.49 | 4.21E-01 |
| miR-181c | 5.55 | 0.88 | 5.09 | 0.60 | -0.47 | 3.29E-01 |
| miR-501 | 5.00 | 1.36 | 4.53 | 1.84 | -0.47 | 6.40E-01 |
| miR-370 | 3.92 | 0.84 | 3.47 | 0.88 | -0.45 | 3.89E-01 |
| miR-19b | -5.57 | 1.30 | -6.01 | 1.38 | -0.44 | 5.86E-01 |
| miR-10a | 3.84 | 0.62 | 3.41 | 1.53 | -0.44 | 5.10E-01 |
| miR-222 | -2.92 | 0.90 | -3.34 | 0.82 | -0.42 | 4.27E-01 |
| miR-26b | -4.90 | 0.72 | -5.24 | 0.51 | -0.34 | 3.97E-01 |
| miR-345 | 0.92 | 1.01 | 0.60 | 0.78 | -0.33 | 5.90E-01 |
| miR-19a | -3.23 | 1.52 | -3.53 | 1.57 | -0.30 | 7.49E-01 |
| miR-192 | 0.86 | 1.43 | 0.61 | 0.99 | -0.25 | 7.46E-01 |
| miR-148a | 2.33 | 0.50 | 2.09 | 0.41 | -0.24 | 4.32E-01 |
| miR-296 | 4.41 | 1.53 | 4.17 | 0.62 | -0.24 | 7.51E-01 |
| miR-193a | 9.83 | 2.32 | 9.62 | 4.57 | -0.21 | 9.19E-01 |
| miR-21 | -2.95 | 0.50 | -3.12 | 0.07 | -0.18 | 4.58E-01 |
| miR-422b | 3.22 | 0.91 | 3.07 | 1.32 | -0.14 | 8.25E-01 |
| miR-18a* | 3.09 | 1.61 | 2.96 | 1.66 | -0.14 | 8.89E-01 |
| miR-30c | -3.19 | 0.47 | -3.32 | 1.17 | -0.13 | 7.89E-01 |
| miR-126* | -3.91 | 1.02 | -4.02 | 0.52 | -0.12 | 8.18E-01 |
| miR-125b | 3.64 | 0.79 | 3.53 | 1.16 | -0.11 | 8.52E-01 |
| miR-105 | 12.26 | 1.93 | 12.16 | 5.18 | -0.11 | 9.64E-01 |
| miR-140 | -1.34 | 0.99 | -1.44 | 0.90 | -0.10 | 8.62E-01 |
| miR-107 | 3.93 | 0.64 | 3.85 | 0.86 | -0.08 | 8.62E-01 |
| miR-500 | 7.31 | 2.33 | 7.23 | 3.62 | -0.08 | 9.65E-01 |
| miR-93 | -4.61 | 0.86 | -4.68 | 0.53 | -0.07 | 8.88E-01 |
| miR-20b | -1.78 | 1.20 | -1.85 | 0.85 | -0.07 | 9.15E-01 |
| miR-126 | -4.72 | 0.86 | -4.78 | 0.89 | -0.06 | 9.03E-01 |
| miR-151 | -0.51 | 0.79 | -0.54 | 2.53 | -0.03 | 9.75E-01 |
| miR-361 | 3.00 | 1.22 | 2.97 | 1.41 | -0.02 | 9.75E-01 |
| miR-30d | -1.94 | 0.82 | -1.93 | 0.31 | 0.01 | 9.87E-01 |
| miR-320 | -2.50 | 1.07 | -2.49 | 1.09 | 0.02 | 9.81E-01 |
| miR-202 | 8.25 | 3.09 | 8.27 | 3.94 | 0.02 | 9.92E-01 |
| miR-20a | -5.91 | 1.13 | -5.88 | 1.36 | 0.03 | 9.64E-01 |
| miR-26a | -6.16 | 0.87 | -6.12 | 0.72 | 0.04 | 9.38E-01 |
| miR-98 | 1.66 | 1.15 | 1.73 | 0.64 | 0.06 | 9.24E-01 |
| miR-18a | 2.64 | 0.70 | 2.74 | 0.46 | 0.09 | 8.00E-01 |
| miR-188 | 7.41 | 1.66 | 7.51 | 1.88 | 0.10 | 9.28E-01 |
| miR-505 | 2.80 | 0.39 | 2.92 | 1.00 | 0.11 | 8.00E-01 |
| miR-30e-5p | 1.32 | 1.47 | 1.48 | 0.98 | 0.16 | 8.37E-01 |
| miR-194 | 4.30 | 0.93 | 4.47 | 1.36 | 0.17 | 8.07E-01 |
| miR-365 | 3.91 | 1.26 | 4.09 | 1.29 | 0.18 | 8.31E-01 |
| miR-423 | 2.31 | 1.08 | 2.55 | 0.66 | 0.24 | 6.72E-01 |
| miR-331 | -0.10 | 0.70 | 0.15 | 1.85 | 0.25 | 7.48E-01 |
| miR-30e-3p | 1.76 | 0.63 | 2.02 | 1.26 | 0.25 | 6.55E-01 |
| miR-130b | 0.91 | 0.77 | 1.16 | 0.46 | 0.25 | 5.72E-01 |
| miR-29c | 0.90 | 1.10 | 1.16 | 0.74 | 0.26 | 6.58E-01 |
| miR-433 | 2.89 | 1.05 | 3.19 | 2.46 | 0.30 | 7.78E-01 |
| miR-145 | 1.87 | 0.73 | 2.17 | 2.45 | 0.30 | 7.63E-01 |
| miR-142-3p | -4.16 | 0.78 | -3.85 | 0.87 | 0.31 | 5.37E-01 |
| miR-374 | -2.07 | 0.51 | -1.76 | 1.15 | 0.31 | 5.33E-01 |
| miR-9* | 5.91 | 0.33 | 6.23 | 0.52 | 0.31 | 2.74E-01 |
| miR-25 | -0.93 | 1.05 | -0.58 | 0.54 | 0.35 | 5.12E-01 |
| miR-410 | 3.42 | 2.92 | 3.78 | 2.10 | 0.36 | 8.18E-01 |

TABLE 31-continued miRNA Biomarkers Differentially Expressed Between Plasma Samples of Lung Cancer Patients and Plasma Samples of Normal Patients.

| miRNA | Normal Average | Normal SD | Cancer Average | Cancer SD | Cancer – Normal | p-value Cancer – Normal |
|---|---|---|---|---|---|---|
| let-7f | −1.12 | 0.55 | −0.73 | 0.97 | 0.39 | 4.00E−01 |
| miR-485-3p | 2.40 | 1.40 | 2.82 | 1.59 | 0.43 | 6.33E−01 |
| miR-485-5p | 4.80 | 0.82 | 5.24 | 0.99 | 0.44 | 4.51E−01 |
| let-7a | −2.14 | 0.91 | −1.65 | 0.71 | 0.49 | 3.39E−01 |
| miR-29a | −0.12 | 0.68 | 0.38 | 0.78 | 0.50 | 2.68E−01 |
| miR-453 | 13.41 | 3.43 | 13.93 | 2.98 | 0.53 | 8.04E−01 |
| miR-30b | −3.88 | 0.51 | −3.35 | 1.07 | 0.53 | 2.74E−01 |
| miR-125a | 0.10 | 1.19 | 0.65 | 0.45 | 0.55 | 3.53E−01 |
| miR-432* | 10.92 | 1.99 | 11.48 | 5.95 | 0.56 | 8.47E−01 |
| miR-103 | −1.67 | 0.97 | −1.08 | 0.23 | 0.59 | 2.71E−01 |
| miR-16 | −9.07 | 1.52 | −8.44 | 1.42 | 0.63 | 4.82E−01 |
| miR-379 | 6.37 | 3.12 | 7.01 | 4.44 | 0.64 | 7.83E−01 |
| miR-215 | 6.65 | 1.41 | 7.30 | 6.01 | 0.65 | 7.84E−01 |
| miR-22 | 2.52 | 0.76 | 3.19 | 0.57 | 0.67 | 1.30E−01 |
| miR-335 | 0.72 | 0.68 | 1.46 | 0.91 | 0.74 | 1.35E−01 |
| miR-490 | 9.31 | 1.44 | 10.05 | 1.56 | 0.74 | 4.34E−01 |
| miR-181d | 0.68 | 1.25 | 1.47 | 1.84 | 0.79 | 3.97E−01 |
| miR-15a | 0.92 | 0.78 | 1.72 | 0.60 | 0.80 | 8.48E−02 |
| miR-185 | 4.09 | 1.53 | 4.90 | 0.58 | 0.81 | 2.90E−01 |
| miR-27b | 1.86 | 1.51 | 2.79 | 0.74 | 0.93 | 2.36E−01 |
| miR-339 | 1.73 | 0.61 | 2.66 | 1.03 | 0.93 | 7.71E−02 |
| miR-23a | 1.66 | 0.75 | 2.60 | 0.84 | 0.95 | 6.77E−02 |
| miR-15b | −1.55 | 0.50 | −0.60 | 1.04 | 0.95 | 5.97E−02 |
| miR-493-3p | 6.38 | 1.09 | 7.35 | 2.74 | 0.97 | 4.11E−01 |
| miR-148b | 2.29 | 0.96 | 3.27 | 0.56 | 0.98 | 9.89E−02 |
| let-7i | −0.94 | 0.97 | 0.08 | 1.19 | 1.03 | 1.31E−01 |
| miR-377 | 11.85 | 2.75 | 12.88 | 2.85 | 1.03 | 5.44E−01 |
| let-7g | −2.13 | 0.52 | −1.07 | 0.78 | 1.06 | 1.76E−02 |
| miR-27a | 0.11 | 1.17 | 1.18 | 0.85 | 1.08 | 1.10E−01 |
| miR-130a | −0.14 | 1.58 | 0.96 | 1.22 | 1.10 | 2.26E−01 |
| miR-182 | 2.05 | 2.15 | 3.15 | 1.19 | 1.10 | 3.77E−01 |
| miR-196a | 5.16 | 1.43 | 6.29 | 1.66 | 1.13 | 2.33E−01 |
| miR-326 | 5.04 | 0.75 | 6.19 | 1.43 | 1.15 | 9.74E−02 |
| let-7d | 0.36 | 1.07 | 1.55 | 0.68 | 1.19 | 5.48E−01 |
| miR-323 | 5.47 | 1.14 | 6.70 | 1.09 | 1.23 | 1.15E−01 |
| let-7b | −3.10 | 1.27 | −1.85 | 3.05 | 1.25 | 3.48E−01 |
| miR-23b | 2.86 | 1.15 | 4.12 | 1.02 | 1.26 | 7.88E−02 |
| miR-106a | −1.31 | 0.69 | −0.04 | 0.68 | 1.27 | 1.60E−02 |
| let-7e | 5.75 | 0.69 | 7.02 | 2.16 | 1.27 | 1.73E−01 |
| miR-451 | −4.08 | 2.18 | −2.78 | 1.15 | 1.31 | 2.54E−01 |
| miR-212 | 5.96 | 1.34 | 7.27 | 3.00 | 1.31 | 3.27E−01 |
| miR-101 | 0.47 | 1.34 | 1.86 | 0.38 | 1.39 | 7.90E−02 |
| miR-496 | 7.36 | 0.64 | 8.77 | 3.00 | 1.41 | 2.47E−01 |
| miR-17-3p | 5.27 | 0.87 | 6.69 | 4.64 | 1.42 | 4.40E−01 |
| miR-221 | −2.94 | 1.90 | −1.51 | 1.24 | 1.43 | 1.73E−01 |
| miR-1 | 3.09 | 2.05 | 4.64 | 4.56 | 1.55 | 4.39E−01 |
| miR-491 | 4.46 | 0.49 | 6.05 | 5.13 | 1.59 | 4.64E−01 |
| miR-32 | 1.95 | 1.13 | 3.55 | 1.47 | 1.60 | 7.20E−02 |
| miR-502 | 6.90 | 1.61 | 8.66 | 2.23 | 1.76 | 1.41E−01 |
| miR-136 | 12.12 | 2.23 | 13.90 | 1.98 | 1.78 | 2.19E−01 |
| miR-199a* | −2.10 | 0.91 | −0.14 | 1.13 | 1.96 | 7.48E−03 |
| miR-204 | 5.99 | 1.29 | 8.02 | 2.36 | 2.03 | 8.27E−02 |
| miR-539 | 1.85 | 0.62 | 3.93 | 1.95 | 2.08 | 2.29E−02 |
| miR-198 | 9.75 | 2.43 | 11.97 | 1.74 | 2.22 | 2.07E−01 |
| miR-29b | 4.50 | 0.61 | 6.79 | 4.32 | 2.28 | 1.86E−01 |
| miR-139 | 4.52 | 1.27 | 6.81 | 4.87 | 2.30 | 2.91E−01 |
| miR-199a | 4.90 | 1.50 | 7.44 | 2.03 | 2.54 | 3.11E−02 |
| miR-195 | −1.55 | 1.46 | 1.00 | 1.84 | 2.55 | 2.27E−02 |
| miR-378 | 5.92 | 0.88 | 8.54 | 4.88 | 2.62 | 1.84E−01 |
| miR-133a | 4.04 | 1.21 | 6.77 | 3.37 | 2.73 | 9.58E−02 |
| miR-493 | 6.03 | 0.50 | 8.91 | 3.06 | 2.88 | 4.81E−02 |
| miR-199b | 7.40 | 3.00 | 10.32 | 4.75 | 2.92 | 2.64E−01 |
| miR-487b | 2.88 | 1.44 | 5.84 | 2.27 | 2.95 | 3.48E−02 |
| miR-518d | 12.26 | 2.54 | 15.45 | 4.24 | 3.19 | 1.71E−01 |
| miR-494 | 5.25 | 0.65 | 9.43 | 4.10 | 4.18 | 3.49E−02 |
| miR-519d | 10.41 | 3.51 | 15.51 | 2.22 | 5.10 | 5.16E−02 |
| miR-542-3p | 9.78 | 1.61 | 17.13 | 0.94 | 7.35 | 3.14E−03 |

Example 8

Combinations of miRNAs that Distinguish Plasma from Lung Cancer Patients and Plasma from Normal Patients The un-normalized qRT-PCR data, generated as described in Example 6, were used to calculate dCt values for each pair of miRNAs that was quantified. The dCt results for the various miRNA pairs in the lung cancer and normal donor plasma samples were analyzed using Receiver-Operator Characteristic (ROC) analysis to determine which miRNA pairs have the capacity to distinguish plasma samples from lung cancer patients and those from normal patients. One miRNA pair (let-7c:miR-326) accurately classified the 14 lung cancer patient samples and 12 normal donor samples that were analyzed (Table 32). Twenty additional miRNA pairs accurately classified all but one of the 26 samples (ROC AUC >0.98) and 221 miRNA pairs had an ROC AUC score of at least 0.93 (Table 32). 166 independent miRNAs were included at least once in the 221 miRNA pairs of Table 32 (Table 33). Numerous miRNAs were used in multiple biomarkers pairs, indicating the strength of their variable levels in the plasmas of lung cancer patients and normal donors.

TABLE 32

Biomarker pairs that can be used to identify plasma from lung cancer patients.

| miRNA Biomarker Pair | Cancer – Normal | Cancer mean | Cancer SD | Normal mean | Normal SD | AUC. ROC | Normal vs Cancer Assoc |
|---|---|---|---|---|---|---|---|
| let-7c,miR-326 | −2.581 | −4.107 | 1.227 | −1.526 | 0.977 | 1.000 | 3.76E−06 |
| miR-326,miR-7 | 3.787 | 1.066 | 1.573 | −2.721 | 1.292 | 0.994 | 5.72E−07 |
| miR-206,miR-491 | −4.433 | 1.933 | 2.352 | 6.366 | 0.706 | 0.994 | 5.58E−06 |
| miR-339,miR-375 | 4.387 | −0.555 | 2.34 | −4.942 | 1.279 | 0.994 | 5.77E−06 |
| miR-30a-3p,miR-326 | −2.505 | −1.602 | 0.847 | 0.903 | 0.825 | 0.988 | 8.26E−08 |
| miR-151,miR-206 | 4.145 | −6.025 | 1.923 | −10.17 | 1.055 | 0.988 | 8.06E−07 |
| miR-10b,miR-30b | −2.478 | 4.175 | 1.094 | 6.654 | 0.711 | 0.988 | 5.06E−07 |
| miR-330,miR-375 | 3.556 | 4.056 | 1.129 | 0.5 | 1.444 | 0.988 | 8.51E−07 |
| miR-134,miR-206 | 4.061 | −3.335 | 2.143 | −7.395 | 1.012 | 0.988 | 4.50E−06 |
| miR-432*,miR-491 | −2.755 | 4.087 | 1.122 | 6.842 | 1.093 | 0.988 | 1.66E−06 |
| miR-181d,miR-375 | 3.773 | −3.266 | 1.845 | −7.039 | 1.514 | 0.988 | 6.74E−06 |
| miR-191,miR-200c | 2.258 | −4.345 | 1.38 | −6.603 | 0.576 | 0.988 | 2.71E−05 |
| miR-23a,miR-326 | −2.005 | −5.99 | 0.67 | −3.985 | 1.377 | 0.988 | 3.27E−04 |

TABLE 32-continued

Biomarker pairs that can be used to identify plasma from lung cancer patients.

| miRNA Biomarker Pair | Cancer – Normal | Cancer mean | Cancer SD | Normal mean | Normal SD | AUC. ROC | Normal vs Cancer Assoc |
|---|---|---|---|---|---|---|---|
| miR-181a,miR-218 | 3.525 | −6.162 | 1.367 | −9.687 | 1.232 | 0.982 | 3.87E−07 |
| miR-151,miR-218 | 3.852 | −7.152 | 1.693 | −11.004 | 1.214 | 0.982 | 6.72E−07 |
| miR-491,miR-512-5p | 3.294 | −4.693 | 1.361 | −7.987 | 1.384 | 0.982 | 3.08E−06 |
| miR-326,miR-375 | 4.862 | 1.86 | 2.118 | −3.003 | 1.751 | 0.982 | 1.27E−06 |
| miR-200c,miR-326 | −3.247 | −2.363 | 1.432 | 0.884 | 1.301 | 0.982 | 3.03E−06 |
| miR-20b,miR-30b | −1.7 | 0.935 | 0.791 | 2.635 | 0.818 | 0.982 | 1.88E−05 |
| miR-491,miR-516-3p | 2.483 | −1.823 | 1.497 | −4.306 | 0.743 | 0.982 | 2.50E−05 |
| miR-125b,miR-146a | −2.414 | 6.68 | 1.271 | 9.094 | 1.453 | 0.982 | 1.87E−04 |
| miR-16,miR-487b | −3.219 | −12.463 | 1.565 | −9.244 | 0.902 | 0.976 | 1.70E−06 |
| miR-326,miR-345 | 2.189 | 3.358 | 1.025 | 1.17 | 0.62 | 0.976 | 1.06E−06 |
| miR-140,miR-192 | 2.354 | 0.428 | 1.127 | −1.926 | 0.75 | 0.976 | 1.88E−06 |
| miR-383,miR-491 | −3.309 | 3.498 | 1.557 | 6.808 | 1.042 | 0.976 | 1.47E−06 |
| miR-339,miR-7 | 3.405 | −1.35 | 1.636 | −4.756 | 1.201 | 0.976 | 2.90E−06 |
| miR-375,miR-99b | −4.127 | 0.126 | 2.101 | 4.253 | 1.365 | 0.976 | 4.27E−06 |
| miR-199a,miR-375 | 3.998 | 2.022 | 2.221 | −1.976 | 1.361 | 0.976 | 1.22E−05 |
| miR-206,miR-376a | −3.632 | 4.069 | 2.158 | 7.701 | 1.13 | 0.976 | 2.22E−05 |
| miR-375,miR-505 | −3.565 | 1.066 | 2.078 | 4.63 | 1.299 | 0.976 | 2.40E−05 |
| miR-200c,miR-301 | −2.181 | 0.736 | 1.467 | 2.917 | 0.943 | 0.976 | 1.44E−04 |
| miR-451,miR-487b | −3.483 | −10.526 | 1.419 | −7.043 | 1.167 | 0.970 | 4.25E−07 |
| miR-218,miR-326 | −4.775 | 1.758 | 2.029 | 6.533 | 1.644 | 0.970 | 7.52E−07 |
| miR-206,miR-213 | −3.739 | −0.548 | 1.432 | 3.191 | 1.495 | 0.970 | 1.28E−06 |
| miR-206,miR-422b | −2.932 | 4.567 | 1.453 | 7.499 | 0.656 | 0.970 | 1.94E−06 |
| miR-192,miR-326 | −3.958 | −4.625 | 1.422 | −0.667 | 1.79 | 0.970 | 4.07E−06 |
| miR-205,miR-326 | −5.331 | −0.247 | 2.68 | 5.084 | 1.383 | 0.970 | 2.42E−06 |
| miR-218,miR-491 | −4 | 3.237 | 1.991 | 7.237 | 1.131 | 0.970 | 2.33E−06 |
| miR-206,miR-361 | −3.644 | 3.694 | 1.846 | 7.338 | 0.941 | 0.970 | 2.68E−06 |
| miR-206,miR-410 | −4.117 | 3.088 | 2.074 | 7.205 | 1.201 | 0.970 | 2.83E−06 |
| miR-30a-3p,miR-99b | −1.539 | 0.404 | 0.676 | 1.943 | 0.541 | 0.970 | 1.17E−06 |
| miR-151,miR-383 | 3.021 | −7.591 | 1.125 | −10.612 | 1.322 | 0.970 | 3.05E−06 |
| miR-218,miR-338 | −3.544 | 2.533 | 1.997 | 6.076 | 0.871 | 0.970 | 1.03E−05 |
| miR-212,miR-512-5p | 2.338 | −2.562 | 0.818 | −4.899 | 1.165 | 0.970 | 1.20E−05 |
| miR-375,miR-496 | −3.513 | −2.507 | 1.622 | 1.006 | 1.35 | 0.970 | 3.20E−06 |
| miR-125b,miR-326 | −3.819 | −1.454 | 1.395 | 2.364 | 1.993 | 0.970 | 2.14E−06 |
| miR-375,miR-433 | −3.899 | −0.297 | 2.138 | 3.602 | 1.456 | 0.970 | 1.38E−05 |
| miR-361,miR-432* | 2.177 | −5.657 | 0.981 | −7.833 | 0.996 | 0.970 | 1.04E−05 |
| miR-142-5p,miR-375 | 3.709 | −3.011 | 1.817 | −6.72 | 1.587 | 0.970 | 1.03E−05 |
| miR-126*,miR-192 | 3.618 | −2.726 | 3.7 | −6.344 | 1.554 | 0.970 | 3.71E−04 |
| miR-192,miR-339 | −3.212 | −2.209 | 1.267 | 1.003 | 1.199 | 0.964 | 7.76E−07 |
| miR-192,miR-196b | −1.673 | −3.784 | 0.693 | −2.111 | 0.672 | 0.964 | 2.03E−06 |
| miR-7,miR-99b | −3.219 | 0.94 | 1.324 | 4.16 | 1.244 | 0.964 | 1.39E−06 |
| miR-213,miR-31 | 2.851 | 0.485 | 1.097 | −2.366 | 1.357 | 0.964 | 8.52E−06 |
| miR-16,miR-30b | −2.854 | −6.488 | 1.137 | −3.634 | 1.28 | 0.964 | 5.02E−06 |
| miR-137,miR-151 | −2.98 | 8.385 | 1.354 | 11.365 | 1.186 | 0.964 | 3.56E−06 |
| miR-218,miR-361 | −3.403 | 4.699 | 1.854 | 8.102 | 1.133 | 0.964 | 9.35E−06 |
| miR-190,miR-326 | −2.875 | −2.216 | 1.149 | 0.659 | 1.439 | 0.964 | 1.60E−05 |
| miR-204,miR-375 | 3.036 | 2.9 | 1.546 | −0.136 | 1.093 | 0.964 | 5.75E−06 |
| miR-10b,miR-191 | −2.706 | 4.092 | 0.827 | 6.797 | 1.602 | 0.964 | 7.67E−05 |
| let-7i,miR-206 | 2.852 | −7.226 | 1.658 | −10.078 | 0.941 | 0.964 | 1.89E−05 |
| miR-200c,miR-339 | −2.38 | 0.054 | 1.598 | 2.433 | 0.562 | 0.964 | 7.64E−05 |
| miR-16,miR-191 | −3.172 | −6.452 | 0.997 | −3.28 | 2.171 | 0.964 | 3.14E−04 |
| miR-15a,miR-375 | 3.933 | −0.809 | 2.627 | −4.741 | 1.514 | 0.964 | 1.04E−04 |
| miR-17-5p,miR-30b | −1.179 | 0.021 | 0.599 | 1.2 | 0.724 | 0.964 | 1.98E−04 |
| miR-206,miR-212 | −3.234 | −0.074 | 1.284 | 3.161 | 0.855 | 0.958 | 9.84E−08 |
| miR-192,miR-30b | −2.691 | 2.046 | 1.119 | 4.738 | 0.968 | 0.958 | 8.39E−07 |
| miR-148b,miR-192 | 2.441 | 1.001 | 1.169 | −1.44 | 0.8 | 0.958 | 2.08E−06 |
| miR-16,miR-24 | −2.548 | −5.478 | 1.194 | −2.93 | 0.86 | 0.958 | 1.84E−06 |
| miR-206,miR-320 | −3.19 | 7.179 | 1.448 | 10.369 | 1.082 | 0.958 | 1.33E−06 |
| miR-326,miR-34c | 2.292 | 0.694 | 1.193 | −1.598 | 0.666 | 0.958 | 4.24E−06 |
| miR-191,miR-7 | 3.012 | −5.642 | 1.176 | −8.654 | 1.338 | 0.958 | 4.22E−06 |
| miR-218,miR-410 | −3.67 | 4.367 | 1.98 | 8.037 | 0.979 | 0.958 | 6.12E−06 |
| miR-181a,miR-206 | 3.917 | −4.968 | 1.895 | −8.886 | 1.362 | 0.958 | 2.92E−06 |
| miR-206,miR-370 | −3.847 | 0.507 | 1.493 | 4.354 | 1.829 | 0.958 | 8.63E−06 |
| miR-222,miR-30a-3p | 1.917 | −4.407 | 0.844 | −6.324 | 0.879 | 0.958 | 9.47E−06 |
| miR-326,miR-423 | 1.435 | 3.585 | 0.787 | 2.15 | 0.45 | 0.958 | 8.83E−06 |
| miR-137,miR-491 | −3.268 | 4.292 | 1.736 | 7.56 | 1.117 | 0.958 | 7.53E−06 |
| miR-192,miR-342 | −2.906 | −0.395 | 1.167 | 2.511 | 1.525 | 0.958 | 2.65E−05 |
| miR-206,miR-382 | −3.617 | 3.394 | 1.975 | 7.011 | 1.325 | 0.958 | 1.25E−05 |
| miR-375,miR-423 | −3.732 | 1.792 | 2.137 | 5.525 | 1.133 | 0.958 | 1.41E−05 |
| miR-17-5p,miR-487b | −1.765 | −5.972 | 0.75 | −4.206 | 0.929 | 0.958 | 3.09E−05 |
| miR-326,miR-511 | 3.331 | −1.766 | 1.725 | −5.097 | 1.433 | 0.958 | 1.60E−05 |
| miR-155,miR-218 | 3.407 | −4.95 | 1.869 | −8.357 | 1.487 | 0.958 | 2.72E−05 |
| miR-502,miR-512-5p | 2.078 | −3.048 | 0.794 | −5.126 | 1.254 | 0.958 | 1.02E−04 |
| miR-326,miR-451 | 4.483 | 11.283 | 1.583 | 6.801 | 2.924 | 0.958 | 2.66E−04 |
| miR-192,miR-324-3p | −2.747 | −1.537 | 0.913 | 1.211 | 1.871 | 0.958 | 3.03E−04 |

TABLE 32-continued

Biomarker pairs that can be used to identify plasma from lung cancer patients.

| miRNA Biomarker Pair | Cancer − Normal | Cancer mean | Cancer SD | Normal mean | Normal SD | AUC. ROC | Normal vs Cancer Assoc |
|---|---|---|---|---|---|---|---|
| miR-200c,miR-222 | −2.659 | 3.647 | 1.719 | 6.306 | 1.268 | 0.958 | 1.44E−04 |
| miR-191,miR-19b | 1.962 | 2.879 | 0.738 | 0.916 | 1.513 | 0.958 | 9.08E−04 |
| miR-125b,miR-30d | −1.858 | 4.974 | 0.794 | 6.832 | 1.528 | 0.958 | 1.60E−03 |
| miR-126*,miR-375 | 4.818 | −5.343 | 4.264 | −10.161 | 1.649 | 0.958 | 1.12E−03 |
| miR-17-3p,miR-326 | −2.159 | −0.548 | 1.082 | 1.611 | 0.426 | 0.952 | 2.36E−06 |
| miR-31,miR-326 | −4.124 | 0.729 | 1.784 | 4.853 | 1.56 | 0.952 | 1.69E−06 |
| miR-151,miR-31 | 3.261 | −6.084 | 1.107 | −9.346 | 1.535 | 0.952 | 5.98E−06 |
| miR-192,miR-487b | −3.021 | −3.844 | 1.462 | −0.824 | 1.091 | 0.952 | 3.49E−06 |
| miR-21,miR-326 | −2.015 | −8.794 | 1.076 | −6.779 | 0.525 | 0.952 | 5.34E−06 |
| miR-30a-5p,miR-326 | −2.135 | −7.665 | 1.208 | −5.53 | 0.488 | 0.952 | 1.07E−05 |
| miR-323,miR-375 | 3.637 | 1.676 | 1.891 | −1.962 | 1.188 | 0.952 | 5.25E−06 |
| miR-212,miR-383 | 2.111 | −1.492 | 1.042 | −3.603 | 0.83 | 0.952 | 6.46E−06 |
| miR-152,miR-29c | 1.741 | 3.447 | 0.87 | 1.707 | 0.667 | 0.952 | 6.28E−06 |
| miR-206,miR-338 | −3.801 | 1.295 | 2.033 | 5.095 | 1.204 | 0.952 | 6.79E−06 |
| miR-218,miR-222 | −3.952 | 7.905 | 1.771 | 11.856 | 1.9 | 0.952 | 1.57E−05 |
| miR-192,miR-221 | −2.621 | 3.067 | 1.408 | 5.689 | 0.997 | 0.952 | 1.21E−05 |
| miR-132,miR-326 | −2.197 | −2.749 | 1.28 | −0.552 | 0.603 | 0.952 | 1.60E−05 |
| miR-375,miR-485-5p | −3.762 | −2.511 | 1.824 | 1.251 | 1.579 | 0.952 | 8.36E−06 |
| miR-197,miR-491 | −2.634 | −6.586 | 1.654 | −3.951 | 0.759 | 0.952 | 3.87E−05 |
| miR-132,miR-375 | 3.015 | −0.961 | 1.801 | −3.975 | 1.139 | 0.952 | 3.37E−05 |
| miR-21,miR-375 | 3.281 | −6.749 | 1.711 | −10.03 | 1.547 | 0.952 | 3.00E−05 |
| miR-181c,miR-200c | 1.796 | −0.508 | 1.234 | −2.304 | 0.667 | 0.952 | 1.28E−04 |
| miR-30a-3p,miR-375 | 2.73 | 0.305 | 1.903 | −2.425 | 1.032 | 0.952 | 1.51E−04 |
| miR-16,miR-20a | −1.497 | −4.405 | 1.106 | −2.908 | 0.53 | 0.952 | 2.39E−04 |
| miR-191,miR-93 | 1.725 | 1.202 | 0.903 | −0.523 | 0.551 | 0.946 | 5.38E−06 |
| miR-181a,miR-210 | 1.367 | −0.524 | 0.594 | −1.891 | 0.61 | 0.946 | 6.88E−06 |
| miR-210,miR-218 | 2.356 | −5.643 | 1.168 | −7.998 | 0.935 | 0.946 | 7.11E−06 |
| miR-410,miR-432* | 2.392 | −5.266 | 1.175 | −7.658 | 0.97 | 0.946 | 7.44E−06 |
| miR-191,miR-451 | 3.494 | 4.575 | 1.087 | 1.082 | 2.035 | 0.946 | 6.46E−05 |
| miR-181c,miR-192 | 2.86 | 1.754 | 1.253 | −1.106 | 1.432 | 0.946 | 2.10E−05 |
| miR-134,miR-137 | 2.895 | −5.694 | 1.532 | −8.59 | 1.216 | 0.946 | 1.66E−05 |
| miR-186,miR-29c | 2.228 | 0.124 | 1.076 | −2.104 | 1.171 | 0.946 | 4.64E−05 |
| miR-146a,miR-192 | 2.468 | −3.358 | 1.432 | −5.826 | 1.126 | 0.946 | 5.23E−05 |
| miR-181a,miR-29c | 2.384 | 2.189 | 0.914 | −0.195 | 1.856 | 0.946 | 9.90E−04 |
| miR-100,miR-326 | −3.014 | −1.279 | 1.351 | 1.735 | 1.035 | 0.946 | 1.25E−06 |
| miR-218,miR-422b | −2.534 | 5.705 | 1.053 | 8.238 | 1.145 | 0.946 | 6.35E−06 |
| miR-192,miR-223 | −2.369 | 5.019 | 0.972 | 7.388 | 1.024 | 0.946 | 3.92E−06 |
| miR-30b,miR-451 | 3.176 | 4.612 | 1.301 | 1.436 | 1.403 | 0.946 | 4.81E−06 |
| miR-31,miR-410 | −3.234 | 3.147 | 1.637 | 6.381 | 1.198 | 0.946 | 6.09E−06 |
| miR-106b,miR-326 | −2.235 | −7.022 | 1.197 | −4.787 | 0.743 | 0.946 | 7.70E−06 |
| miR-29c,miR-326 | −3.474 | −6.488 | 1.435 | −3.013 | 1.686 | 0.946 | 1.27E−05 |
| miR-10b,miR-487b | −2.797 | −1.88 | 1.302 | 0.917 | 1.22 | 0.946 | 8.40E−06 |
| miR-10b,miR-28 | −2.3 | −0.739 | 1.226 | 1.561 | 0.788 | 0.946 | 7.86E−06 |
| miR-205,miR-331 | −5.304 | 1.401 | 3.03 | 6.705 | 1.702 | 0.946 | 1.48E−05 |
| let-7c,miR-222 | −1.993 | 1.903 | 1.136 | 3.896 | 0.738 | 0.946 | 2.00E−05 |
| miR-218,miR-29b | −2.835 | 4.347 | 1.61 | 7.182 | 1.007 | 0.946 | 1.71E−05 |
| miR-31,miR-362 | −2.627 | 0.743 | 1.423 | 3.37 | 1.125 | 0.946 | 2.24E−05 |
| miR-106b,miR-186 | −0.988 | −0.658 | 0.548 | 0.33 | 0.429 | 0.946 | 2.89E−05 |
| miR-215,miR-342 | −3.483 | 4.038 | 2.027 | 7.522 | 1.365 | 0.946 | 2.90E−05 |
| miR-192,miR-505 | −2.494 | −1.587 | 1.236 | 0.907 | 1.301 | 0.946 | 4.84E−05 |
| miR-125b,miR-30e-3p | −2.56 | 0.175 | 1.35 | 2.735 | 1.244 | 0.946 | 3.94E−05 |
| miR-375,miR-491 | −4.588 | −0.668 | 2.409 | 3.92 | 2.334 | 0.946 | 5.27E−05 |
| miR-324-5p,miR-375 | 3.852 | −0.507 | 2.448 | −4.36 | 1.44 | 0.946 | 6.05E−05 |
| miR-101,miR-326 | −3.63 | −6.399 | 1.624 | −2.768 | 2.237 | 0.946 | 1.53E−04 |
| miR-29c,miR-99b | −2.508 | −4.481 | 1.264 | −1.973 | 1.444 | 0.946 | 1.15E−04 |
| miR-375,miR-379 | −3.982 | −2.067 | 2.425 | 1.915 | 1.784 | 0.946 | 7.08E−05 |
| miR-206,miR-326 | −5.008 | 0.67 | 2.306 | 5.677 | 1.724 | 0.940 | 1.67E−06 |
| miR-181a,miR-31 | 3.034 | −5.027 | 1.277 | −8.061 | 1.332 | 0.940 | 5.11E−06 |
| miR-10a,miR-222 | −2.167 | 4.428 | 1.018 | 6.594 | 0.809 | 0.940 | 3.13E−06 |
| miR-218,miR-376a | −3.22 | 5.238 | 1.627 | 8.459 | 0.999 | 0.940 | 3.32E−06 |
| miR-145,miR-218 | 3.629 | −5.391 | 1.582 | −9.02 | 1.532 | 0.940 | 4.30E−06 |
| miR-24,miR-451 | 2.87 | 3.601 | 1.31 | 0.731 | 1.126 | 0.940 | 3.36E−06 |
| miR-375,miR-485-3p | −3.365 | −0.624 | 1.221 | 2.741 | 1.579 | 0.940 | 6.38E−06 |
| miR-218,miR-99b | −3.663 | 3.97 | 1.668 | 7.633 | 1.624 | 0.940 | 8.40E−06 |
| miR-326,miR-486 | 3.481 | 10.585 | 1.765 | 7.104 | 1.296 | 0.940 | 6.30E−06 |
| miR-137,miR-181a | −2.752 | 7.328 | 1.273 | 10.08 | 1.21 | 0.940 | 8.55E−06 |
| let-7c,miR-99b | −1.615 | −2.1 | 0.74 | −0.485 | 0.77 | 0.940 | 1.62E−05 |
| miR-155,miR-31 | 2.902 | −3.715 | 1.284 | −6.617 | 1.473 | 0.940 | 2.47E−05 |
| miR-192,miR-28 | −2.482 | −2.65 | 1.412 | −0.168 | 0.932 | 0.940 | 2.03E−05 |
| miR-15b,miR-16 | 2.205 | 7.077 | 1.373 | 4.872 | 0.629 | 0.940 | 3.50E−05 |
| miR-197,miR-410 | −2.319 | −5.43 | 1.288 | −3.112 | 0.883 | 0.940 | 1.68E−05 |
| miR-134,miR-218 | 3.661 | −4.613 | 2.302 | −8.275 | 1.111 | 0.940 | 4.05E−05 |
| miR-100,miR-181a | −1.924 | 3.02 | 0.886 | 4.943 | 1.015 | 0.940 | 4.01E−05 |
| miR-101,miR-191 | −2.697 | 0.309 | 1.415 | 3.006 | 1.265 | 0.940 | 3.00E−05 |

TABLE 32-continued

Biomarker pairs that can be used to identify plasma from lung cancer patients.

| miRNA Biomarker Pair | Cancer − Normal | Cancer mean | Cancer SD | Normal mean | Normal SD | AUC. ROC | Normal vs Cancer Assoc |
|---|---|---|---|---|---|---|---|
| miR-19a,miR-24 | −1.35 | −0.546 | 0.796 | 0.804 | 0.512 | 0.940 | 3.00E−05 |
| miR-29a,miR-326 | −3.128 | −6.507 | 1.551 | −3.379 | 1.528 | 0.940 | 2.89E−05 |
| let-7i,miR-151 | −1.293 | −1.201 | 0.745 | 0.092 | 0.498 | 0.940 | 2.49E−05 |
| miR-151,miR-197 | 2.346 | 2.493 | 1.179 | 0.147 | 1.148 | 0.940 | 3.14E−05 |
| miR-383,miR-410 | −2.994 | 4.654 | 1.535 | 7.647 | 1.457 | 0.940 | 3.37E−05 |
| miR-146b,miR-192 | 2.059 | −1.737 | 1.197 | −3.795 | 0.911 | 0.940 | 4.61E−05 |
| miR-215,miR-324-3p | −3.278 | 2.896 | 1.712 | 6.174 | 1.654 | 0.940 | 4.84E−05 |
| miR-361,miR-383 | 2.52 | −5.26 | 1.328 | −7.78 | 1.254 | 0.940 | 4.62E−05 |
| miR-192,miR-328 | −3.071 | −1.678 | 1.334 | 1.393 | 1.842 | 0.940 | 1.14E−04 |
| miR-213,miR-215 | 3.466 | 1.635 | 2.076 | −1.831 | 1.549 | 0.940 | 6.12E−05 |
| miR-21,miR-222 | −1.427 | −2.784 | 0.916 | −1.358 | 0.617 | 0.940 | 9.66E−05 |
| miR-196b,miR-326 | −1.71 | −0.879 | 1.088 | 0.831 | 0.754 | 0.940 | 9.57E−05 |
| miR-200c,miR-342 | −1.898 | 1.868 | 1.236 | 3.765 | 0.816 | 0.940 | 1.08E−04 |
| miR-133a,miR-375 | 3.537 | 1.484 | 2.141 | −2.053 | 1.794 | 0.940 | 1.20E−04 |
| miR-342,miR-451 | 3.133 | 7.053 | 1.352 | 3.92 | 2.104 | 0.940 | 3.12E−04 |
| miR-205,miR-362 | −3.553 | −0.331 | 2.377 | 3.222 | 1.574 | 0.940 | 1.47E−04 |
| miR-186,miR-200c | 2.001 | −4.001 | 1.403 | −6.002 | 0.877 | 0.940 | 2.13E−04 |
| miR-107,miR-375 | 3.558 | 1.632 | 2.537 | −1.926 | 1.628 | 0.940 | 2.72E−04 |
| miR-200c,miR-328 | −2.178 | 0.584 | 1.518 | 2.762 | 1.185 | 0.940 | 4.09E−04 |
| miR-19b,miR-326 | −2.951 | −9.587 | 1.206 | −6.635 | 2.482 | 0.940 | 1.84E−03 |
| miR-16,miR-331 | −2.948 | −11.052 | 1.597 | −8.104 | 0.861 | 0.935 | 6.96E−06 |
| miR-223,miR-451 | 2.801 | 1.638 | 0.975 | −1.163 | 1.402 | 0.935 | 1.26E−05 |
| miR-31,miR-99b | −3.157 | 2.735 | 1.402 | 5.893 | 1.388 | 0.935 | 6.80E−06 |
| miR-375,miR-487b | −3.972 | −0.895 | 1.313 | 3.076 | 2.14 | 0.935 | 2.81E−05 |
| miR-186,miR-205 | 4.5 | −5.765 | 2.4 | −10.265 | 1.736 | 0.935 | 1.20E−05 |
| miR-206,miR-485-5p | −3.558 | 0.058 | 1.661 | 3.616 | 1.615 | 0.935 | 1.17E−05 |
| miR-222,miR-31 | 3.536 | −6.738 | 1.694 | −10.274 | 1.586 | 0.935 | 1.24E−05 |
| miR-151,miR-92 | 2.026 | 6.479 | 1.107 | 4.454 | 0.743 | 0.935 | 1.26E−05 |
| miR-10a,miR-328 | −1.686 | 1.366 | 0.789 | 3.051 | 0.835 | 0.935 | 2.45E−05 |
| miR-195,miR-487b | −2.601 | −5.908 | 1.358 | −3.307 | 1.115 | 0.935 | 1.67E−05 |
| miR-191,miR-29c | 2.485 | −0.22 | 1.431 | −2.705 | 0.879 | 0.935 | 1.96E−05 |
| miR-205,miR-99b | −4.371 | 1.446 | 2.398 | 5.817 | 1.755 | 0.935 | 1.84E−05 |
| miR-206,miR-222 | −4.419 | 6.679 | 2.341 | 11.099 | 1.927 | 0.935 | 2.07E−05 |
| miR-181d,miR-206 | 3.513 | −5.896 | 1.726 | −9.409 | 1.651 | 0.935 | 2.05E−05 |
| miR-218,miR-370 | −3.394 | 1.72 | 1.799 | 5.113 | 1.461 | 0.935 | 1.93E−05 |
| miR-218,miR-493-3p | −2.778 | 0.871 | 1.528 | 3.649 | 1.216 | 0.935 | 1.95E−05 |
| miR-137,miR-410 | −2.952 | 5.448 | 1.531 | 8.4 | 1.279 | 0.935 | 1.69E−05 |
| miR-195,miR-331 | −2.462 | −4.488 | 1.411 | −2.026 | 1.03 | 0.935 | 3.22E−05 |
| miR-192,miR-301 | −3.203 | −1.527 | 1.557 | 1.676 | 1.584 | 0.935 | 2.88E−05 |
| miR-339,miR-451 | 3.615 | 8.867 | 1.329 | 5.252 | 2.141 | 0.935 | 8.19E−05 |
| miR-19b,miR-451 | 1.531 | 1.697 | 0.544 | 0.165 | 0.93 | 0.935 | 1.03E−04 |
| miR-19a,miR-451 | 1.52 | 3.055 | 0.686 | 1.535 | 0.798 | 0.935 | 3.59E−05 |
| miR-326,miR-512-5p | 4.016 | −3.435 | 1.559 | −7.451 | 2.353 | 0.935 | 7.74E−05 |
| miR-196b,miR-375 | 3.076 | 0.915 | 1.564 | −2.161 | 1.465 | 0.935 | 2.76E−05 |
| miR-181d,miR-31 | 2.63 | −5.955 | 1.059 | −8.585 | 1.562 | 0.935 | 9.28E−05 |
| miR-192,miR-222 | −3.205 | 1.384 | 1.586 | 4.589 | 1.66 | 0.935 | 4.56E−05 |
| miR-192,miR-199a* | −2.229 | 1.356 | 1.29 | 3.585 | 0.922 | 0.935 | 3.35E−05 |
| miR-326,miR-93 | 2.714 | 7.909 | 1.289 | 5.195 | 1.551 15b3 | | 8.99E−05 |
| miR-140,miR-16 | 2.281 | 8.962 | 1.26 | 6.682 | 1.151 | 0.935 | 6.63E−05 |
| miR-218,miR-485-5p | −3.228 | 1.313 | 1.954 | 4.541 | 1.459 | 0.935 | 6.98E−05 |
| miR-20b,miR-24 | −1.444 | 1.945 | 0.93 | 3.39 | 0.586 | 0.935 | 8.30E−05 |
| miR-212,miR-218 | 2.772 | −1.331 | 1.693 | −4.103 | 1.284 | 0.935 | 8.33E−05 |
| miR-326,miR-452 | 2.775 | 0.254 | 1.849 | −2.521 | 1.06 | 0.935 | 9.99E−05 |
| miR-155,miR-375 | 3.651 | −0.926 | 2.112 | −4.577 | 2.093 | 0.935 | 1.92E−04 |
| miR-16,miR-326 | −4.161 | −13.16 | 1.529 | −8.999 | 3.11 | 0.935 | 6.99E−04 |
| miR-10b,miR-140 | −1.946 | 1.556 | 1.151 | 3.502 | 1.143 | 0.935 | 2.49E−04 |
| miR-30e-5p,miR-326 | −3.92 | −5.871 | 1.737 | −1.951 | 2.924 | 0.935 | 7.73E−04 |
| miR-106b,miR-151 | −1.372 | −1.666 | 0.644 | −0.294 | 1.029 | 0.935 | 8.49E−04 |
| miR-19a,miR-326 | −2.963 | −8.228 | 1.155 | −5.265 | 2.766 | 0.935 | 3.73E−03 |
| miR-142-5p,miR-326 | −1.734 | −5.011 | 0.588 | −3.277 | 1.806 | 0.935 | 7.19E−03 |
| miR-192,miR-23b | −2.347 | −1.078 | 1.249 | 1.269 | 0.812 | 0.929 | 7.97E−06 |
| miR-206,miR-502 | −3.155 | 0.295 | 1.473 | 3.45 | 1.348 | 0.929 | 7.32E−06 |
| miR-31,miR-491 | −3.549 | 1.992 | 1.585 | 5.541 | 1.728 | 0.929 | 1.73E−05 |
| miR-218,miR-30e-3p | −3.216 | 3.476 | 1.363 | 6.692 | 1.647 | 0.929 | 2.35E−05 |
| miR-140,miR-451 | 2.602 | 7.086 | 1.09 | 4.483 | 1.326 | 0.929 | 2.17E−05 |
| miR-100,miR-222 | −2.426 | 4.731 | 1.35 | 7.156 | 0.899 | 0.929 | 1.57E−05 |
| miR-101,miR-223 | −1.999 | 3.246 | 1.154 | 5.245 | 0.802 | 0.929 | 2.90E−05 |
| miR-142-5p,miR-192 | 2.449 | −0.385 | 1.386 | −2.834 | 0.997 | 0.929 | 2.58E−05 |
| miR-139,miR-326 | −2.501 | −1.393 | 1.065 | 1.108 | 1.365 | 0.929 | 4.43E−05 |
| miR-146a,miR-29c | 1.968 | −1.496 | 1.171 | −3.463 | 0.734 | 0.929 | 3.13E−05 |
| miR-192,miR-26a | −2.301 | 4.736 | 1.342 | 7.037 | 0.878 | 0.929 | 2.73E−05 |
| miR-107,miR-192 | 2.499 | 4.37 | 1.293 | 1.871 | 1.162 | 0.929 | 2.60E−05 |
| miR-181b,miR-326 | −2.137 | −4.73 | 1.212 | −2.593 | 0.92 | 0.929 | 3.31E−05 |
| miR-134,miR-432* | 2.471 | −5.438 | 1.402 | −7.909 | 1.143 | 0.929 | 4.75E−05 |

TABLE 32-continued

Biomarker pairs that can be used to identify plasma from lung cancer patients.

| miRNA Biomarker Pair | Cancer − Normal | Cancer mean | Cancer SD | Normal mean | Normal SD | AUC. ROC | Normal vs Cancer Assoc |
|---|---|---|---|---|---|---|---|
| miR-205,miR-491 | −3.969 | 0.959 | 2.2 | 4.928 | 2.007 | 0.929 | 6.83E−05 |
| miR-213,miR-486 | 2.406 | 11.996 | 1.486 | 9.59 | 1.033 | 0.929 | 6.77E−05 |
| miR-137,miR-376a | −2.466 | 6.429 | 1.378 | 8.895 | 1.249 | 0.929 | 7.22E−05 |
| miR-31,miR-423 | −2.688 | 4.314 | 1.33 | 7.002 | 1.571 | 0.929 | 0.000122073 |
| miR-324-5p,miR-7 | 3.016 | −1.338 | 1.805 | −4.355 | 1.419 | 0.929 | 7.64E−05 |
| miR-486,miR-99b | −2.515 | −8.578 | 1.503 | −6.063 | 1.237 | 0.929 | 9.41E−05 |
| miR-218,miR-320 | −2.867 | 8.191 | 1.85 | 11.059 | 1.253 | 0.929 | 0.000104295 |
| miR-200c,miR-330 | −1.822 | −4.65 | 1.246 | −2.828 | 0.706 | 0.929 | 0.000130877 |
| miR-326,miR-505 | 1.692 | 3.039 | 0.894 | 1.347 | 0.984 | 0.929 | 0.000146787 |
| miR-146a,miR-190 | 1.507 | −5.628 | 0.904 | −7.135 | 0.771 | 0.929 | 0.000118807 |
| miR-193a,miR-205 | 2.861 | 1.862 | 2.048 | −0.998 | 1.07 | 0.929 | 0.000189991 |
| miR-181a,miR-30e-5p | 2.829 | 1.572 | 1.16 | −1.257 | 2.96 | 0.929 | 0.007701382 |
| miR-101,miR-126* | −3.391 | 0.952 | 3.488 | 4.343 | 1.882 | 0.929 | 0.005004755 |
| miR-125a,miR-192 | 2.927 | 1.308 | 1.296 | −1.618 | 1.468 | 0.929 | 2.21E−05 |
| miR-181d,miR-218 | 3.27 | −7.032 | 1.533 | −10.302 | 1.608 | 0.929 | 2.33E−05 |
| miR-152,miR-192 | 2.554 | 1.585 | 1.188 | −0.969 | 1.229 | 0.929 | 1.87E−05 |
| miR-151,miR-181b | 1.275 | −0.625 | 0.593 | −1.9 | 0.71 | 0.929 | 6.69E−05 |
| miR-151,miR-210 | 1.595 | −1.581 | 0.889 | −3.176 | 0.717 | 0.929 | 3.60E−05 |
| miR-125a,miR-375 | 3.797 | −1.21 | 1.887 | −5.007 | 2.063 | 0.929 | 6.81E−05 |
| miR-152,miR-375 | 3.688 | −0.839 | 2.167 | −4.527 | 1.849 | 0.929 | 9.32E−05 |
| miR-148b,miR-375 | 3.548 | −1.445 | 2.338 | −4.994 | 1.958 | 0.929 | 0.000309212 |
| miR-126*,miR-218 | 4.372 | −9.198 | 3.315 | −13.57 | 2.107 | 0.929 | 0.000499998 |
| miR-10a,miR-375 | 2.646 | 0.396 | 1.888 | −2.25 | 1.407 | 0.929 | 0.000437429 |
| miR-10a,miR-326 | −2.755 | −1.582 | 1.273 | 1.173 | 1.089 | 0.923 | 3.89E−06 |
| miR-206,miR-422a | −2.597 | 1.603 | 1.579 | 4.2 | 0.517 | 0.923 | 2.60E−05 |
| miR-29c,miR-342 | −2.125 | −2.257 | 0.993 | −0.132 | 1.043 | 0.923 | 2.25E−05 |
| miR-181a,miR-383 | 2.794 | −6.534 | 1.032 | −9.328 | 1.574 | 0.923 | 4.92E−05 |
| miR-383,miR-422b | −1.808 | 6.133 | 0.704 | 7.941 | 0.999 | 0.923 | 4.27E−05 |
| miR-31,miR-370 | −3.194 | 0.335 | 1.751 | 3.529 | 1.445 | 0.923 | 3.27E−05 |
| miR-215,miR-326 | −4.157 | −0.192 | 2.214 | 3.964 | 1.874 | 0.923 | 2.60E−05 |
| miR-31,miR-485-5p | −2.674 | 0.117 | 1.188 | 2.791 | 1.412 | 0.923 | 3.61E−05 |
| miR-301,miR-375 | 4.116 | −0.969 | 2.065 | −5.085 | 2.058 | 0.923 | 3.67E−05 |
| miR-181c,miR-375 | 3.806 | −0.799 | 1.882 | −4.605 | 1.943 | 0.923 | 4.03E−05 |
| miR-31,miR-328 | −3.054 | 3.676 | 1.547 | 6.731 | 1.591 | 0.923 | 5.26E−05 |
| miR-181c,miR-29c | 2.023 | 3.617 | 1.155 | 1.593 | 0.871 | 0.923 | 3.51E−05 |
| miR-15b,miR-451 | 2.526 | 5.2 | 1.44 | 2.674 | 1.152 | 0.923 | 4.57E−05 |
| miR-151,miR-486 | 2.619 | 5.229 | 1.453 | 2.611 | 1.164 | 0.923 | 3.27E−05 |
| miR-328,miR-375 | 3.944 | −0.83 | 2.069 | −4.774 | 2.001 | 0.923 | 5.15E−05 |
| miR-190,miR-191 | −1.848 | 4.53 | 1.03 | 6.378 | 0.876 | 0.923 | 4.81E−05 |
| miR-101,miR-27a | −2.24 | −1.737 | 1.432 | 0.503 | 0.869 | 0.923 | 6.95E−05 |
| miR-145,miR-206 | 3.964 | −4.119 | 2.347 | −8.082 | 1.759 | 0.923 | 5.43E−05 |
| miR-218,miR-423 | −3.125 | 5.534 | 1.432 | 8.659 | 1.84 | 0.923 | 0.000106511 |
| miR-222,miR-29c | 2.886 | 0.478 | 1.409 | −2.408 | 1.619 | 0.923 | 8.32E−05 |
| miR-192,miR-99b | −3.208 | −2.619 | 1.437 | 0.589 | 1.892 | 0.923 | 0.000103222 |
| miR-151,miR-516-3p | 2.195 | −5.916 | 1.207 | −8.111 | 1.069 | 0.923 | 5.14E−05 |
| miR-30d,miR-326 | −2.095 | −6.262 | 1.048 | −4.167 | 1.152 | 0.923 | 7.70E−05 |
| miR-330,miR-7 | 2.752 | 3.542 | 1.489 | 0.79 | 1.385 | 0.923 | 5.79E−05 |
| miR-222,miR-486 | 2.893 | 4.575 | 1.712 | 1.682 | 1.277 | 0.923 | 5.27E−05 |
| miR-127,miR-375 | 4.026 | −1.329 | 2.107 | −5.355 | 2.136 | 0.923 | 7.05E−05 |
| miR-342,miR-375 | 3.749 | −2.063 | 1.733 | −5.812 | 2.143 | 0.923 | 8.35E−05 |
| miR-101,miR-152 | −1.93 | −3.358 | 1.118 | −1.429 | 0.96 | 0.923 | 8.18E−05 |
| miR-101,miR-27b | −2.523 | −2.69 | 1.365 | −0.168 | 1.345 | 0.923 | 8.59E−05 |
| miR-218,miR-433 | −3.174 | 3.518 | 1.711 | 6.691 | 1.747 | 0.923 | 0.000105844 |
| miR-192,miR-330 | −2.827 | −7.014 | 1.517 | −4.187 | 1.513 | 0.923 | 8.44E−05 |
| miR-10b,miR-340 | −2.212 | −2.485 | 1.287 | −0.273 | 1.109 | 0.923 | 8.74E−05 |
| miR-145,miR-375 | 3.794 | −1.357 | 1.909 | −5.151 | 2.155 | 0.923 | 0.000102562 |
| miR-206,miR-328 | −3.938 | 3.617 | 2.349 | 7.556 | 1.945 | 0.923 | 9.47E−05 |
| miR-206,miR-362 | −3.489 | 0.705 | 2.113 | 4.194 | 1.582 | 0.923 | 7.12E−05 |
| miR-192,miR-423 | −2.756 | −1.04 | 1.21 | 1.716 | 1.82 | 0.923 | 0.000275531 |
| miR-151,miR-452 | 1.912 | −5.102 | 1.386 | −7.014 | 0.545 | 0.923 | 0.000173117 |
| miR-148a,miR-148b | −0.854 | −0.6 | 0.471 | 0.254 | 0.489 | 0.923 | 0.00015307 |
| miR-215,miR-323 | −3.348 | 0.04 | 2.186 | 3.387 | 1.463 | 0.923 | 0.000115248 |
| miR-34c,miR-375 | 3.116 | 1.559 | 2.075 | −1.556 | 1.288 | 0.923 | 0.000117925 |
| miR-324-3p,miR-375 | 3.594 | −0.985 | 2.145 | −4.579 | 1.931 | 0.923 | 0.000151045 |
| miR-335,miR-451 | 2.786 | 9.015 | 1.809 | 6.229 | 1.381 | 0.923 | 0.000174237 |
| miR-125b,miR-342 | −2.362 | 2.865 | 1.159 | 5.227 | 1.575 | 0.923 | 0.000356556 |
| miR-190,miR-99b | −1.829 | −0.13 | 0.914 | 1.699 | 1.205 | 0.923 | 0.000335029 |
| miR-145,miR-192 | 3.033 | 1.177 | 1.511 | −1.856 | 2.059 | 0.923 | 0.00042416 |
| miR-10b,miR-342 | −2.489 | 1.61 | 1.25 | 4.099 | 1.669 | 0.923 | 0.00038973 |
| miR-222,miR-375 | 4.413 | −3.601 | 2.351 | −8.014 | 2.929 | 0.923 | 0.000411581 |
| miR-27b,miR-375 | 4.227 | −1.437 | 2.894 | −5.663 | 2.24 | 0.923 | 0.000328816 |
| miR-423,miR-486 | 2.046 | 6.999 | 1.224 | 4.954 | 1.273 | 0.923 | 0.000378623 |
| miR-199b,miR-215 | 3.254 | 1.169 | 2.444 | −2.085 | 1.495 | 0.923 | 0.000415598 |
| miR-151,miR-375 | 4.072 | −2.997 | 2.144 | −7.069 | 2.945 | 0.923 | 0.000763553 |

TABLE 32-continued

Biomarker pairs that can be used to identify plasma from lung cancer patients.

| miRNA Biomarker Pair | Cancer − Normal | Cancer mean | Cancer SD | Normal mean | Normal SD | AUC. ROC | Normal vs Cancer Assoc |
|---|---|---|---|---|---|---|---|
| miR-181d,miR-486 | 1.987 | 5.359 | 1.326 | 3.372 | 1.245 | 0.923 | 0.000628771 |
| miR-191,miR-375 | 4.016 | −4.431 | 2.375 | −8.447 | 2.932 | 0.923 | 0.001046642 |
| miR-146a,miR-200c | 1.74 | −5.62 | 1.544 | −7.361 | 0.591 | 0.923 | 0.001134329 |
| miR-23a,miR-375 | 3.246 | −3.679 | 1.948 | −6.926 | 2.409 | 0.923 | 0.001202938 |
| miR-140,miR-375 | 3.331 | −2.242 | 2.407 | −5.572 | 2.026 | 0.923 | 0.000807039 |
| miR-213,miR-29c | 2.389 | 7.889 | 1.137 | 5.5 | 1.986 | 0.923 | 0.001863408 |
| miR-18a,miR-326 | −2.062 | −1.256 | 0.943 | 0.806 | 1.935 | 0.923 | 0.00412067 |
| let-7b,miR-99b | −1.295 | −4.889 | 1.828 | −3.594 | 0.388 | 0.923 | 0.021340617 |

TABLE 33

Biomarkers that can be used in combination to identify plasma from lung cancer patients, and the prevalence of each miRNA.

| Biomarker | No. Used |
|---|---|
| miR-10b | 65 |
| miR-192 | 62 |
| miR-206 | 61 |
| miR-101 | 58 |
| miR-205 | 52 |
| miR-16 | 50 |
| miR-151 | 44 |
| miR-137 | 43 |
| miR-215 | 43 |
| miR-181a | 42 |
| miR-218 | 42 |
| miR-126* | 41 |
| miR-125b | 39 |
| miR-326 | 39 |
| miR-100 | 38 |
| miR-31 | 36 |
| miR-197 | 35 |
| miR-222 | 34 |
| miR-191 | 32 |
| miR-200c | 32 |
| miR-186 | 31 |
| miR-145 | 30 |
| miR-155 | 30 |
| miR-29c | 30 |
| let-7c | 28 |
| miR-181c | 27 |
| miR-125a | 26 |
| miR-134 | 25 |
| miR-181d | 25 |
| let-7b | 24 |
| miR-127 | 24 |
| miR-146a | 24 |
| miR-139 | 23 |
| miR-152 | 23 |
| miR-190 | 23 |
| miR-30e-5p | 23 |
| miR-106b | 22 |
| miR-10a | 22 |
| miR-132 | 21 |
| miR-148a | 21 |
| miR-213 | 21 |
| miR-29a | 21 |
| miR-375 | 21 |
| miR-133b | 19 |
| miR-15a | 18 |
| miR-107 | 17 |
| miR-148b | 17 |
| miR-19a | 17 |
| miR-106a | 15 |
| miR-130a | 15 |
| miR-17-3p | 15 |
| miR-18a* | 15 |
| miR-195 | 15 |
| miR-20b | 15 |
| miR-301 | 15 |
| miR-339 | 15 |
| miR-410 | 15 |
| miR-188 | 14 |
| miR-193a | 14 |
| let-7g | 13 |
| let-7i | 13 |
| miR-140 | 13 |
| miR-181b | 13 |
| miR-25 | 13 |
| miR-328 | 13 |
| miR-133a | 12 |
| miR-150 | 12 |
| miR-17-5p | 12 |
| miR-21 | 12 |
| miR-214 | 12 |
| miR-370 | 12 |
| miR-383 | 12 |
| miR-130b | 11 |
| miR-199a | 11 |
| miR-212 | 11 |
| miR-221 | 11 |
| miR-27b | 11 |
| miR-30e-3p | 11 |
| miR-338 | 11 |
| miR-361 | 11 |
| miR-141 | 10 |
| miR-142-5p | 10 |
| miR-30a-3p | 10 |
| miR-30a-5p | 10 |
| miR-451 | 10 |
| miR-142-3p | 9 |
| miR-146b | 9 |
| miR-15b | 9 |
| miR-18a | 9 |
| miR-210 | 9 |
| miR-296 | 9 |
| miR-323 | 9 |
| miR-362 | 9 |
| let-7a | 8 |
| miR-196b | 8 |
| miR-223 | 8 |
| miR-29b | 8 |
| miR-324-5p | 8 |
| miR-376a | 8 |
| miR-379 | 8 |
| miR-491 | 8 |
| let-7d | 7 |
| miR-126 | 7 |
| miR-182 | 7 |
| miR-185 | 7 |
| miR-204 | 7 |

TABLE 33-continued

Biomarkers that can be used in combination to identify plasma from lung cancer patients, and the prevalence of each miRNA.

| Biomarker | No. Used |
|---|---|
| miR-23a | 7 |
| miR-27a | 7 |
| miR-324-3p | 7 |
| miR-342 | 7 |
| miR-34c | 7 |
| miR-382 | 7 |
| miR-425 | 7 |
| miR-432* | 7 |
| miR-103 | 6 |
| miR-193b | 6 |
| miR-196a | 6 |
| nniR-199a* | 6 |
| miR-199b | 6 |
| miR-28 | 6 |
| miR-30d | 6 |
| miR-330 | 6 |
| miR-423 | 6 |
| miR-433 | 6 |
| miR-485-5p | 6 |
| miR-20a | 5 |
| miR-23b | 5 |
| miR-26a | 5 |
| miR-30b | 5 |
| miR-30c | 5 |
| miR-320 | 5 |
| miR-345 | 5 |
| miR-422b | 5 |
| miR-335 | 4 |
| miR-365 | 4 |
| miR-486 | 4 |
| miR-24 | 3 |
| miR-26b | 3 |
| miR-331 | 3 |
| miR-340 | 3 |
| miR-34a | 3 |
| miR-374 | 3 |
| miR-452 | 3 |
| miR-483 | 3 |
| miR-512-5p | 3 |
| let-7e | 2 |
| miR-32 | 2 |
| miR-422a | 2 |
| miR-424 | 2 |
| miR-432 | 2 |
| miR-485-3p | 2 |
| miR-487b | 2 |
| miR-496 | 2 |
| miR-505 | 2 |
| miR-7 | 2 |
| miR-202 | 1 |
| miR-369-3p | 1 |
| miR-495 | 1 |
| miR-502 | 1 |
| miR-511 | 1 |
| miR-516-3p | 1 |
| miR-517c | 1 |
| miR-92 | 1 |
| miR-93 | 1 |
| miR-99a | 1 |
| miR-99b | 1 |

Example 9

QRT-PCR for Evaluation of MicroRNA Expression in Human Lung Cancer Patient Serum RNA To further assess the selectivity and sensitivity of certain miRNAs and combinations of miRNA, an additional set of serum samples, isolated from a distinct set of lung cancer patients and normal subjects (Table 34), was used to compare miRNAs expressed in serum from lung cancer patients and normal subjects. Histopathological analyses of lung lobe sections from cancer patients and normal subjects were performed by a board certified pathologist to determine a pathological diagnosis.

TABLE 34

Histopathological and patient information for serum samples.

| Sample ID | Sex | Diagnosis | Cell type |
|---|---|---|---|
| 1 | M | Cancer | ADCA |
| 2 | M | Cancer | ADCA |
| 3 | M | Cancer | ADCA |
| 4 | M | Cancer | SCCA |
| 5 | M | Cancer | SCCA |
| 6 | F | Cancer | ADCA |
| 7 | F | Cancer | SCCA |
| 8 | M | Cancer | SCCA |
| 9 | M | Cancer | ADCA |
| 10 | F | Cancer | ADCA |
| 11 | M | Cancer | ADCA |
| 12 | F | Cancer | ADCA |
| 13 | F | Cancer | ADCA |
| 14 | M | Cancer | ADCA |
| 15 | F | Cancer | SCCA |
| 16 | F | Cancer | ADCA |
| 17 | M | Cancer | SCCA |
| 18 | M | Cancer | ADCA |
| 19 | M | Cancer | ADCA |
| 20 | M | Cancer | SCCA |
| 21 | F | Cancer | ADCA |
| 22 | F | Cancer | ADCA |
| 23 | F | Cancer | ADCA |
| 24 | F | Cancer | SCCA |
| 25 | F | Cancer | SCCA |
| 26 | M | Cancer | SCCA |
| 27 | M | Cancer | ADCA |
| 28 | M | Cancer | ADCA |
| 29 | M | Cancer | SCCA |
| 30 | M | Cancer | ADCA |
| 31 | F | Normal | Normal |
| 32 | F | Normal | Normal |
| 33 | F | Normal | Normal |
| 34 | M | Normal | Normal |
| 35 | F | Normal | Normal |
| 36 | M | Normal | Normal |
| 37 | M | Normal | Normal |
| 38 | M | Normal | Normal |
| 39 | M | Normal | Normal |
| 40 | M | Normal | Normal |
| 41 | M | Normal | Normal |
| 42 | M | Normal | Normal |
| 43 | M | Normal | Normal |
| 44 | F | Normal | Normal |
| 45 | M | Normal | Normal |
| 46 | F | Normal | Normal |
| 47 | F | Normal | Normal |
| 48 | F | Normal | Normal |
| 49 | F | Normal | Normal |
| 50 | M | Normal | Normal |

ADCA, adenocarcinoma;
SCCA, squamous cell carcinoma.

First, the expression of 180 miRNAs in serum RNA was evaluated from the 30 lung cancer patients and 20 normal subjects (Table 34). Blood collection, serum RNA extraction, and qRT-PCR were performed as described in Example 2 above. Table 35 shows the mean dCt and ddCt values following PCR amplification of miRNAs from the serum samples. dCt values were calculated as the difference between the Ct of a specific miRNA and the mean Ct for the top 50 expressed miRNAs as a normalizer. The miRNAs are arranged in increasing t-test p-value.

TABLE 35

Expression of miRNAs in serum from patients having lung cancer and from normal subjects.

| miRNA ID | Cancer mean dCt | Cancer SD | Normal mean dCt | Normal SD | Cancer − Normal ddCt | ttest p-value |
|---|---|---|---|---|---|---|
| miR-15b | 0.86 | 0.36 | −1.47 | 0.42 | 2.33 | 5.19E−25 |
| miR-340 | 1.22 | 0.77 | 5.44 | 0.93 | −4.22 | 6.49E−21 |
| let-7e | −0.72 | 0.93 | 3.50 | 1.01 | −4.22 | 6.11E−20 |
| miR-103 | 1.78 | 0.58 | −0.79 | 0.60 | 2.57 | 7.76E−20 |
| let-7f | 2.19 | 0.79 | −0.52 | 0.38 | 2.71 | 6.24E−19 |
| miR-605 | 8.11 | 2.13 | 0.34 | 1.70 | 7.77 | 3.58E−18 |
| miR-346 | 7.64 | 2.02 | 1.27 | 1.27 | 6.37 | 1.66E−16 |
| miR-214 | 6.95 | 1.75 | 1.38 | 1.32 | 5.57 | 3.52E−16 |
| miR-378 | 0.74 | 0.66 | 4.36 | 1.31 | −3.63 | 3.58E−16 |
| miR-182 | 6.21 | 1.19 | 2.34 | 0.88 | 3.87 | 6.00E−16 |
| miR-190 | 4.88 | 0.79 | 2.42 | 0.64 | 2.46 | 1.46E−15 |
| miR-422b | 3.23 | 0.58 | 1.01 | 0.84 | 2.22 | 8.17E−15 |
| miR-185 | 1.31 | 1.24 | 4.78 | 0.80 | −3.47 | 3.32E−14 |
| miR-133b | 5.18 | 1.59 | 0.63 | 1.30 | 4.55 | 3.33E−14 |
| miR-26a | −1.26 | 0.73 | −3.17 | 0.48 | 1.91 | 9.23E−14 |
| miR-142-3p | −1.29 | 0.76 | −3.27 | 0.50 | 1.98 | 1.09E−13 |
| let-7a | 0.28 | 0.86 | −1.93 | 0.57 | 2.21 | 2.08E−13 |
| miR-30e-5p | −0.31 | 0.76 | 2.29 | 1.00 | −2.60 | 1.63E−12 |
| miR-145 | 2.52 | 0.72 | −0.09 | 1.25 | 2.61 | 1.90E−12 |
| miR-106a | −2.64 | 0.95 | −0.69 | 0.22 | −1.95 | 6.28E−12 |
| miR-30c | −0.20 | 0.45 | −1.20 | 0.34 | 1.00 | 3.61E−11 |
| miR-15a | 3.93 | 0.65 | 2.37 | 0.65 | 1.56 | 6.88E−11 |
| miR-374 | 0.99 | 0.67 | −0.53 | 0.59 | 1.53 | 7.83E−11 |
| miR-483 | 6.70 | 2.16 | 1.98 | 1.72 | 4.72 | 1.17E−10 |
| let-7g | −1.19 | 0.56 | −2.49 | 0.55 | 1.31 | 1.34E−10 |
| miR-23a | 1.45 | 0.63 | 3.16 | 0.83 | −1.71 | 2.48E−10 |
| miR-26b | −1.19 | 0.69 | −2.96 | 0.84 | 1.77 | 3.34E−10 |
| miR-143 | 2.10 | 1.22 | 4.93 | 1.30 | −2.83 | 4.12E−10 |
| miR-133a | 3.55 | 1.64 | 6.80 | 1.12 | −3.25 | 5.67E−10 |
| miR-22 | 1.25 | 0.86 | 3.32 | 1.04 | −2.07 | 6.67E−10 |
| miR-18c | 6.22 | 0.86 | 4.09 | 1.11 | 2.13 | 8.03E−10 |
| miR-320 | −2.99 | 0.85 | −1.24 | 0.72 | −1.75 | 1.13E−09 |
| miR-134 | 5.75 | 1.29 | 3.22 | 0.84 | 2.53 | 1.24E−09 |
| miR-193b | 3.97 | 1.30 | 6.97 | 1.19 | −3.00 | 1.29E−09 |
| miR-18a | 1.52 | 0.83 | 3.90 | 1.42 | −2.38 | 1.33E−09 |
| miR-126 | −1.65 | 0.54 | −2.92 | 0.63 | 1.27 | 1.64E−09 |
| miR-223 | −5.87 | 1.30 | −1.41 | 2.61 | −4.45 | 2.11E−09 |
| miR-204 | 7.43 | 1.45 | 4.85 | 0.99 | 2.58 | 2.07E−08 |
| miR-195 | −2.13 | 1.14 | −0.11 | 0.88 | −2.02 | 2.11E−08 |
| miR-19a | −2.61 | 1.03 | 0.43 | 2.08 | −3.04 | 2.86E−08 |
| miR-200c | 6.01 | 1.37 | 2.92 | 1.27 | 3.09 | 3.22E−08 |
| miR-152 | 3.23 | 0.74 | 5.15 | 1.34 | −1.91 | 8.04E−08 |
| miR-566 | 5.71 | 1.59 | 2.35 | 2.00 | 3.36 | 1.12E−07 |
| miR-30a-5p | −1.39 | 0.61 | −0.41 | 0.42 | −0.97 | 1.13E−07 |
| miR-410 | 6.06 | 2.14 | 3.01 | 0.66 | 3.04 | 1.64E−07 |
| miR-146a | −1.25 | 0.70 | −2.34 | 0.54 | 1.10 | 2.94E−07 |
| miR-485-3p | 5.75 | 1.47 | 3.76 | 0.71 | 1.99 | 1.03E−06 |
| miR-328 | 2.44 | 0.66 | 0.90 | 1.30 | 1.53 | 1.37E−06 |
| miR-30d | −0.33 | 0.74 | 1.58 | 1.61 | −1.91 | 1.60E−06 |
| let-7d | 1.55 | 0.89 | 0.33 | 0.58 | 1.23 | 1.89E−06 |
| miR-27b | 2.59 | 0.77 | 4.30 | 1.35 | −1.72 | 2.32E−06 |
| miR-155 | 3.79 | 0.97 | 2.49 | 0.65 | 1.31 | 3.15E−06 |
| miR-432 | 6.23 | 2.00 | 3.54 | 1.00 | 2.69 | 4.44E−06 |
| miR-301 | 3.23 | 0.68 | 2.20 | 0.74 | 1.03 | 5.96E−06 |
| miR-28 | 5.03 | 1.04 | 3.53 | 0.93 | 1.50 | 8.10E−06 |
| miR-502 | 5.08 | 1.49 | 6.97 | 0.70 | −1.89 | 8.46E−06 |
| miR-487b | 5.90 | 1.32 | 4.04 | 1.20 | 1.87 | 8.86E−06 |
| miR-191 | −1.02 | 0.55 | 0.12 | 1.00 | −1.14 | 1.03E−05 |
| miR-29a | 0.03 | 0.82 | 1.59 | 1.45 | −1.56 | 1.26E−05 |
| miR-193a | 6.44 | 1.12 | 4.34 | 1.67 | 2.10 | 1.75E−05 |
| miR-486 | −4.64 | 1.27 | −2.80 | 1.33 | −1.84 | 1.91E−05 |
| miR-186 | 0.31 | 0.88 | 1.31 | 0.37 | −0.99 | 1.93E−05 |
| miR-221 | −0.20 | 0.80 | −1.27 | 0.81 | 1.07 | 3.08E−05 |
| miR-505 | 5.85 | 1.08 | 4.47 | 0.93 | 1.38 | 4.43E−05 |
| miR-181a | 3.61 | 0.76 | 2.75 | 0.50 | 0.86 | 4.82E−05 |
| miR-550 | 6.58 | 0.93 | 5.53 | 0.58 | 1.06 | 5.94E−05 |
| miR-21 | −2.15 | 0.42 | −1.60 | 0.52 | −0.56 | 1.28E−04 |
| let-7i | −0.11 | 0.57 | 0.80 | 0.95 | −0.90 | 1.45E−04 |
| miR-496 | 7.89 | 1.83 | 5.81 | 1.44 | 2.08 | 1.54E−04 |
| miR-192 | 1.18 | 0.97 | 2.17 | 0.57 | −0.99 | 1.58E−04 |
| miR-30e-3p | −9.07 | 13.86 | 4.59 | 1.37 | −13.66 | 3.22E−04 |
| miR-101 | 1.64 | 0.93 | 0.55 | 1.10 | 1.09 | 4.95E−04 |
| miR-222 | −0.42 | 0.35 | 0.11 | 0.65 | −0.52 | 5.66E−04 |
| miR-206 | 5.76 | 1.59 | 4.25 | 1.19 | 1.52 | 6.69E−04 |
| miR-516-3p | 5.66 | 2.70 | 3.31 | 1.24 | 2.35 | 6.76E−04 |
| miR-34a | 3.01 | 2.87 | 5.43 | 1.08 | −2.42 | 7.69E−04 |
| miR-365 | 2.88 | 1.22 | 4.01 | 0.88 | −1.13 | 8.64E−04 |
| miR-17-5p | 0.32 | 0.68 | −0.27 | 0.38 | 0.59 | 9.61E−04 |
| miR-98 | 4.62 | 1.06 | 3.55 | 0.95 | 1.07 | 1.00E−03 |
| miR-339 | 3.67 | 0.96 | 4.74 | 1.01 | −1.07 | 1.25E−03 |
| miR-433 | 6.13 | 1.50 | 4.66 | 1.14 | 1.47 | 1.34E−03 |
| miR-338 | 5.53 | 1.12 | 6.56 | 0.83 | −1.03 | 1.46E−03 |
| miR-20b | −0.39 | 1.13 | 0.89 | 1.57 | −1.28 | 1.60E−03 |
| miR-125b | 4.03 | 1.29 | 5.10 | 0.84 | −1.08 | 2.11E−03 |
| miR-150 | 0.07 | 1.23 | −0.91 | 0.69 | 0.98 | 2.20E−03 |
| miR-19b | −3.47 | 0.94 | −2.62 | 0.82 | −0.84 | 2.35E−03 |
| miR-148a | 1.29 | 0.56 | 1.85 | 0.68 | −0.56 | 2.65E−03 |
| miR-27a | 0.61 | 1.07 | 1.48 | 0.64 | −0.87 | 3.08E−03 |
| miR-324-5p | 4.08 | 0.86 | 4.82 | 0.76 | −0.74 | 3.73E−03 |
| miR-148b | 3.13 | 0.53 | 2.71 | 0.41 | 0.42 | 4.73E−03 |
| miR-18b | 3.11 | 0.80 | 2.35 | 0.96 | 0.76 | 4.88E−03 |
| miR-525 | 6.48 | 2.16 | 4.92 | 1.12 | 1.56 | 5.42E−03 |
| miR-130b | 1.69 | 0.66 | 1.18 | 0.51 | 0.51 | 5.49E−03 |
| miR-106b | −0.55 | 0.74 | −1.13 | 0.63 | 0.58 | 6.17E−03 |
| miR-342 | 2.52 | 0.68 | 1.96 | 0.70 | 0.56 | 6.88E−03 |
| miR-126* | −1.91 | 0.46 | −1.55 | 0.41 | −0.36 | 7.08E−03 |
| miR-199a* | 0.56 | 1.04 | −0.10 | 0.41 | 0.66 | 1.00E−02 |
| miR-224 | 5.02 | 1.19 | 6.03 | 1.35 | −1.01 | 1.03E−02 |
| miR-25 | −0.99 | 1.06 | −0.31 | 0.67 | −0.68 | 1.34E−02 |
| miR-331 | 3.34 | 0.62 | 4.22 | 1.64 | −0.88 | 1.55E−02 |
| let-7b | −2.11 | 0.87 | −1.57 | 0.51 | −0.54 | 1.58E−02 |
| miR-140 | 0.69 | 0.75 | 1.17 | 0.50 | −0.48 | 1.61E−02 |
| miR-142-5p | 2.06 | 0.70 | 2.56 | 0.68 | −0.50 | 1.68E−02 |
| miR-296 | 4.39 | 1.06 | 5.20 | 1.25 | −0.80 | 2.15E−02 |
| miR-382 | 5.43 | 1.64 | 4.33 | 1.39 | 1.09 | 2.29E−02 |
| miR-210 | 3.00 | 0.86 | 2.46 | 0.74 | 0.55 | 2.35E−02 |
| miR-146b | 0.47 | 0.74 | 0.04 | 0.47 | 0.43 | 2.54E−02 |
| miR-130a | −0.18 | 0.85 | 0.67 | 1.71 | −0.85 | 2.78E−02 |
| miR-30b | −0.24 | 0.47 | −0.70 | 0.98 | 0.46 | 3.31E−02 |
| miR-423 | −3.16 | 11.84 | 2.09 | 1.32 | −5.25 | 5.50E−02 |
| miR-345 | 1.63 | 0.76 | 2.04 | 0.69 | −0.41 | 5.59E−02 |
| miR-638 | 2.79 | 1.53 | 3.57 | 1.16 | −0.78 | 6.91E−02 |
| miR-422a | 4.35 | 0.81 | 4.86 | 1.14 | −0.51 | 7.14E−02 |
| miR-99a | 5.42 | 1.38 | 4.71 | 1.33 | 0.72 | 7.36E−02 |
| miR-335 | 2.72 | 0.87 | 2.26 | 0.84 | 0.45 | 7.49E−02 |
| miR-425 | 3.69 | 0.69 | 3.38 | 0.40 | 0.31 | 7.61E−02 |
| miR-326 | 7.62 | 0.83 | 7.15 | 0.99 | 0.46 | 9.43E−02 |
| miR-16 | −7.89 | 1.09 | −7.39 | 0.98 | −0.50 | 1.03E−01 |
| miR-93 | −2.67 | 0.84 | −3.06 | 0.76 | 0.38 | 1.09E−01 |
| miR-7 | 3.86 | 1.34 | 3.29 | 1.00 | 0.57 | 1.17E−01 |
| miR-29c | 1.63 | 0.80 | 2.01 | 0.58 | −0.39 | 1.24E−01 |
| miR-197 | 1.46 | 1.02 | 0.97 | 1.03 | 0.49 | 1.30E−01 |
| miR-196a | 6.93 | 1.59 | 6.32 | 0.77 | 0.61 | 1.34E−01 |
| miR-99b | 5.22 | 1.04 | 4.76 | 1.07 | 0.46 | 1.43E−01 |
| miR-100 | 5.71 | 1.29 | 5.12 | 1.46 | 0.59 | 1.53E−01 |
| miR-376a | 6.17 | 1.40 | 5.55 | 1.41 | 0.62 | 1.55E−01 |
| miR-375 | 5.57 | 1.53 | 6.23 | 1.12 | −0.66 | 1.58E−01 |
| let-7c | 2.30 | 0.82 | 2.64 | 0.94 | −0.34 | 1.84E−01 |
| miR-24 | −1.88 | 0.57 | −2.05 | 0.26 | 0.17 | 2.27E−01 |
| miR-132 | 3.11 | 0.70 | 2.82 | 1.01 | 0.29 | 2.48E−01 |
| miR-660 | 0.78 | 0.80 | 1.05 | 0.75 | −0.27 | 2.71E−01 |
| miR-127 | 5.26 | 1.68 | 4.75 | 1.41 | 0.51 | 2.75E−01 |
| miR-10b | 4.88 | 1.23 | 4.54 | 0.85 | 0.34 | 2.89E−01 |
| miR-139 | 4.84 | 1.06 | 5.14 | 1.01 | −0.31 | 3.32E−01 |
| miR-18d | 2.43 | 0.69 | 2.66 | 1.18 | −0.23 | 3.97E−01 |
| miR-497 | 4.88 | 1.15 | 5.19 | 1.21 | −0.31 | 4.00E−01 |
| miR-361 | 3.25 | 0.74 | 3.10 | 0.47 | 0.15 | 4.52E−01 |
| miR-1 | 5.58 | 1.86 | 5.15 | 1.83 | 0.43 | 4.54E−01 |
| miR-10a | 4.86 | 1.31 | 4.58 | 1.33 | 0.28 | 4.96E−01 |
| miR-584 | 4.39 | 1.15 | 4.16 | 1.36 | 0.23 | 5.51E−01 |
| miR-324-3p | 3.34 | 1.02 | 3.54 | 1.55 | −0.20 | 6.11E−01 |
| miR-151 | 1.86 | 0.75 | 1.96 | 0.67 | −0.10 | 6.44E−01 |
| miR-30a-3p | 5.24 | 1.02 | 5.09 | 1.29 | 0.15 | 6.56E−01 |
| miR-202 | 4.66 | 1.69 | 4.45 | 1.36 | 0.21 | 6.58E−01 |
| miR-194 | 1.98 | 8.64 | 2.79 | 0.90 | −0.81 | 6.85E−01 |
| miR-501 | 5.23 | 1.58 | 5.40 | 1.09 | −0.17 | 6.94E−01 |

TABLE 35-continued

Expression of miRNAs in serum from patients having lung cancer and from normal subjects.

| miRNA ID | Cancer mean dCt | Cancer SD | Normal mean dCt | Normal SD | Cancer − Normal ddCt | ttest p-value |
|---|---|---|---|---|---|---|
| miR-23b | 4.90 | 0.94 | 5.00 | 1.59 | −0.10 | 7.88E−01 |
| miR-125a | 2.86 | 0.92 | 2.76 | 1.73 | 0.10 | 7.93E−01 |
| miR-20a | −3.56 | 0.99 | −3.50 | 0.79 | −0.06 | 8.34E−01 |
| miR-92 | −5.77 | 0.94 | −5.74 | 0.74 | −0.02 | 9.22E−01 |

Based on analysis of differentially expressed miRNA pairs, 27 miRNAs were selected for further validation in serum samples from an additional 55 lung cancer patients and from 75 cancer-free, presumed normal individuals (Table 36).

TABLE 36

Lung cancer patient, tumor pathology, and normal subject information.

| Specimen ID | Age | Sex | Cell Type | TNM Stage | AJCC Stage | Smoking History |
|---|---|---|---|---|---|---|
| 1 | 80 | M | Normal | NA | NA | Yes |
| 2 | 66 | M | Normal | NA | NA | Yes |
| 3 | 78 | M | Normal | NA | NA | No |
| 4 | 70 | M | Normal | NA | NA | Yes |
| 5 | 38 | M | Normal | NA | NA | No |
| 6 | 66 | M | Normal | NA | NA | Yes |
| 7 | 67 | F | Normal | NA | NA | No |
| 8 | 62 | M | Normal | NA | NA | Yes |
| 9 | 63 | F | Normal | NA | NA | Yes |
| 10 | 69 | M | Normal | NA | NA | Yes |
| 11 | 82 | M | Normal | NA | NA | Yes |
| 12 | 55 | F | Normal | NA | NA | No |
| 13 | 55 | M | Normal | NA | NA | Yes |
| 14 | 79 | M | Normal | NA | NA | Yes |
| 15 | 71 | F | Normal | NA | NA | No |
| 16 | 62 | F | Normal | NA | NA | No |
| 17 | 79 | M | Normal | NA | NA | Yes |
| 18 | 77 | M | Normal | NA | NA | Yes |
| 19 | 78 | M | Normal | NA | NA | Yes |
| 20 | 69 | M | Normal | NA | NA | Yes |
| 21 | 62 | M | Normal | NA | NA | Yes |
| 22 | 55 | F | Normal | NA | NA | Yes |
| 23 | 56 | M | Normal | NA | NA | Yes |
| 24 | 55 | F | Normal | NA | NA | Yes |
| 25 | 79 | M | Normal | NA | NA | Yes |
| 26 | 77 | M | Normal | NA | NA | Yes |
| 27 | 79 | M | Normal | NA | NA | Yes |
| 28 | 55 | F | Normal | NA | NA | Yes |
| 29 | 51 | M | Normal | NA | NA | Yes |
| 30 | 56 | M | Normal | NA | NA | Yes |
| 31 | 78 | F | Normal | NA | NA | No |
| 32 | 52 | M | Normal | NA | NA | Yes |
| 33 | 75 | M | Normal | NA | NA | Yes |
| 34 | 68 | F | Normal | NA | NA | Yes |
| 35 | 57 | M | Normal | NA | NA | No |
| 36 | 67 | M | Normal | NA | NA | Yes |
| 37 | 85 | M | Normal | NA | NA | Yes |
| 38 | 76 | M | Normal | NA | NA | Yes |
| 39 | 53 | M | Normal | NA | NA | Yes |
| 40 | 51 | M | Normal | NA | NA | Yes |
| 41 | 65 | M | Normal | NA | NA | Yes |
| 42 | 78 | F | Normal | NA | NA | Yes |
| 43 | 83 | M | Normal | NA | NA | Yes |
| 44 | 72 | M | Normal | NA | NA | Yes |
| 45 | 61 | F | Normal | NA | NA | Yes |
| 46 | 69 | M | Normal | NA | NA | No |
| 47 | 55 | F | Normal | NA | NA | Yes |
| 48 | 51 | M | Normal | NA | NA | Yes |
| 49 | 56 | F | Normal | NA | NA | Yes |
| 50 | 70 | M | Normal | NA | NA | Yes |
| 51 | 57 | M | Normal | NA | NA | Yes |
| 52 | 63 | M | Normal | NA | NA | Yes |
| 53 | 73 | M | Normal | NA | NA | Yes |
| 54 | 70 | M | Normal | NA | NA | Yes |
| 55 | 75 | F | Normal | NA | NA | Yes |
| 56 | 73 | F | Normal | NA | NA | Yes |
| 57 | 57 | F | Normal | NA | NA | Yes |
| 58 | 78 | M | Normal | NA | NA | Yes |
| 59 | 63 | M | Normal | NA | NA | Yes |
| 60 | 74 | M | Normal | NA | NA | Yes |
| 61 | 79 | M | Normal | NA | NA | Yes |
| 62 | 55 | M | Normal | NA | NA | Yes |
| 63 | 84 | F | Normal | NA | NA | Yes |
| 64 | 54 | F | Normal | NA | NA | Yes |
| 65 | 56 | F | Normal | NA | NA | Yes |
| 66 | 82 | M | Normal | NA | NA | Yes |
| 67 | 64 | F | Normal | NA | NA | Yes |
| 68 | 77 | M | Normal | NA | NA | Yes |
| 69 | 51 | F | Normal | NA | NA | Yes |
| 70 | 37 | M | Normal | NA | NA | Yes |
| 71 | 54 | M | Normal | NA | NA | Yes |
| 72 | 68 | F | Normal | NA | NA | Yes |
| 73 | 54 | M | Normal | NA | NA | Yes |
| 74 | 62 | F | Normal | NA | NA | Yes |
| 75 | 54 | F | Normal | NA | NA | No |
| 76 | 77 | M | ADCA | T1N1 | IIA | Yes |
| 77 | 77 | M | SCCA | T2N0 | IB | Yes |
| 78 | 84 | M | SCCA | T2N0 | IB | Yes |
| 79 | 52 | M | SCCA | TN2 | IIIA | Yes |
| 80 | 49 | F | ADCA | T1N1 | IIA | Yes |
| 81 | 60 | M | ADCA | T2N0M0 | IB | Yes |
| 82 | 66 | F | ADCA/BA | T1N0 | IA | Yes |
| 83 | 69 | M | SCCA | T2N1M0 | IIB | Yes |
| 84 | 68 | M | ADCA | N2 | IIIA | Yes |
| 85 | 56 | M | SCCA | T2N1M0 | IIB | Yes |
| 86 | 85 | M | ADCA | T2N0 | IB | Yes |
| 87 | 68 | F | SCCA | T2N1M0 | IIB | Yes |
| 88 | 66 | M | SCCA | T2N0M0 | IB | Yes |
| 89 | 61 | M | SCCA | T2N1 | IIB | Yes |
| 90 | 58 | M | ADCA | M1 | IV | Yes |
| 91 | 64 | F | ADCA | T1N0M0 | IA | Yes |
| 92 | 72 | F | SCCA | T2N0 | IB | Yes |
| 93 | 67 | M | ADCA | T1Nx | IA | Yes |
| 94 | 63 | F | ADCA | T1N0 | IA | Yes |
| 95 | 80 | M | ADCA | T2N0 | IB | Yes |
| 96 | 63 | F | ADCA | T1N0M0 | IA | Yes |
| 97 | 48 | F | ADCA/BA | T1N0M0 | IA | Yes |
| 98 | 70 | F | SCCA | T1N0M0 | IA | Yes |
| 99 | 71 | M | SCCA | T3N0 | IIB | Yes |
| 100 | 73 | F | SCCA | T3N0M0 | IIB | Yes |
| 101 | 72 | M | ADCA/BA | T2N0 | IB | Yes |
| 102 | 74 | M | SCCA | T2N0 | IB | Yes |
| 103 | 51 | F | ADCA | T1N0 | IA | Yes |
| 104 | 83 | M | SCCA | T1N0 | IA | Yes |
| 105 | 66 | M | ADCA | T2N1M0 | IIB | Yes |
| 106 | 65 | F | SCCA | T2N0 | IB | Yes |
| 107 | 74 | F | ADCA | T1N0M0 | IA | Yes |
| 108 | 77 | M | SCCA | T2N1M0 | IIB | Yes |
| 109 | 82 | F | SCCA | T2N0 | IB | Yes |
| 110 | 67 | M | ADCA | T1N0 | IA | Yes |
| 111 | 61 | M | ADCA | TN2 | IIIA | Yes |
| 112 | 82 | F | SCCA | T2N1M0 | IIB | Yes |
| 113 | 58 | M | SCCA | T1N0M1 | IV | Yes |
| 114 | 78 | M | ADCA | T1N0M0 | IA | Yes |
| 115 | 77 | M | ADCA | T1N2 | IIIA | Yes |
| 116 | 72 | M | ADCA | T2N0 | IB | Yes |
| 117 | 59 | F | ADCA | T2N0 | IB | Yes |
| 118 | 72 | M | SCCA | T1N0M0 | IA | Yes |
| 119 | 71 | F | ADCA | T2N1 | IIB | Yes |
| 120 | 72 | F | SCCA | T2N0 | IB | Yes |
| 121 | 73 | F | ADCA | T2N2M0 | IIIA | Yes |
| 122 | 69 | M | SCCA | T2N0 | IB | Yes |
| 123 | 66 | F | SCCA | T2N1M0 | IIB | Yes |
| 124 | 55 | M | ADCA | T4 | IIIB | Yes |
| 125 | 68 | F | ADCA/BA | T1N0M0 | IA | Yes |
| 126 | 64 | F | ADCA | T2N0M0 | IB | Yes |
| 127 | 77 | M | SCCA | T1N0 | IA | Yes |
| 128 | 76 | F | ADCA | N2 | IIIA | Yes |

TABLE 36-continued

Lung cancer patient, tumor pathology, and normal subject information.

| Specimen ID | Age | Sex | Cell Type | TNM Stage | AJCC Stage | Smoking History |
|---|---|---|---|---|---|---|
| 129 | 60 | F | ADCA | T1N0 | IA | Yes |
| 130 | 66 | M | SCCA | T2N0M0 | IB | Yes |

TNM Stage (Sobin and Wittekind, 2002);
AJCC Stage (Greene, 2002);
ADCA, adenocarcinoma;
ADCA/BA, adenocarcinoma of the bronchoalveolar;
SCCA, squamous cell carcinoma;
NA, not applicable.

The 27 miRNAs were evaluated for their ability to distinguish lung cancer patient samples from normal subject samples shown in Table 36. Table 37 shows the mean Ct values and standard deviation for each miRNA for the cancer and the normal group. The dCt values represent the difference of the Cts between the cancer and the normal group. The miRNAs are arranged in increasing t-test p-value. Twenty-four of the 27 miRNAs were differentially expressed at a high statistical significance level, having t-test p-values of less than 0.001. These twenty-four miRNAs can be used for diagnosing lung cancer.

TABLE 37

Expression of miRNAs in serum from patients having lung cancer or from normal subjects.

| miRNA ID | Normal mean Ct | Normal SD | Cancer mean Ct | Cancer SD | Cancer – Normal dCt | ttest p-value |
|---|---|---|---|---|---|---|
| miR-15b | 27.90 | 1.52 | 30.80 | 1.41 | 2.91 | 1.78E−20 |
| miR-182 | 32.99 | 1.72 | 35.75 | 1.26 | 2.76 | 4.19E−17 |
| miR-15a | 31.21 | 1.68 | 33.90 | 1.52 | 2.68 | 5.00E−16 |
| miR-30b | 27.20 | 1.27 | 29.07 | 1.23 | 1.87 | 7.33E−14 |
| let-7i | 27.32 | 1.56 | 29.38 | 1.13 | 2.06 | 1.01E−13 |
| miR-26b | 26.12 | 1.51 | 28.10 | 1.10 | 1.98 | 1.38E−13 |
| miR-106b | 27.63 | 1.70 | 29.84 | 1.30 | 2.21 | 3.94E−13 |
| let-7g | 26.69 | 1.54 | 28.61 | 1.02 | 1.92 | 6.04E−13 |
| miR-106a | 25.45 | 1.59 | 27.51 | 1.48 | 2.05 | 9.07E−12 |
| miR-142-3p | 25.50 | 1.64 | 27.41 | 1.25 | 1.90 | 4.43E−11 |
| miR-301 | 31.56 | 1.36 | 33.29 | 1.46 | 1.73 | 1.98E−10 |
| miR-150 | 27.65 | 0.97 | 28.92 | 1.18 | 1.28 | 4.28E−10 |
| miR-181c | 34.36 | 1.41 | 36.01 | 1.41 | 1.65 | 1.52E−09 |
| miR-25 | 27.31 | 1.98 | 29.23 | 1.62 | 1.92 | 3.44E−08 |
| miR-324-3p | 31.65 | 2.19 | 33.48 | 1.69 | 1.83 | 8.72E−07 |
| miR-126 | 26.29 | 1.41 | 27.45 | 1.37 | 1.16 | 6.02E−06 |
| miR-27a | 28.64 | 1.64 | 29.97 | 1.59 | 1.33 | 8.30E−06 |
| miR-126* | 26.46 | 1.25 | 27.37 | 1.14 | 0.92 | 3.56E−05 |
| miR-660 | 25.55 | 3.36 | 27.78 | 3.26 | 2.23 | 2.43E−04 |
| miR-346 | 35.86 | 1.61 | 36.94 | 1.59 | 1.08 | 3.60E−04 |
| miR-422a | 32.34 | 1.71 | 33.48 | 1.57 | 1.13 | 3.81E−04 |
| miR-30d | 27.92 | 1.72 | 29.02 | 1.66 | 1.10 | 3.83E−04 |
| miR-30a-5p | 27.06 | 1.75 | 28.12 | 1.64 | 1.06 | 6.27E−04 |
| miR-422b | 32.47 | 2.02 | 33.57 | 1.45 | 1.10 | 8.28E−04 |
| miR-30e-5p | 28.41 | 2.61 | 29.70 | 1.70 | 1.30 | 1.65E−03 |
| miR-27b | 31.89 | 1.48 | 32.59 | 1.33 | 0.70 | 6.25E−03 |
| miR-92 | 25.84 | 3.71 | 25.47 | 3.05 | −0.37 | 5.46E−01 |

Receiver Operator Characteristic (ROC) analysis was used to identify the miRNA pairs having the capacity to distinguish serum samples of lung cancer patients from those of normal patients. Select differentially-expressed pairs that distinguished normal patients from cancer patients are shown in Table 38 and are arranged in decreasing AUC ranging from 0.99 to 0.74.

TABLE 38 miRNA biomarker pairs that can be used to identify serum from lung cancer patients.

| miRNA Biomarker Pair | Cancer mean – Normal mean | Cancer mean | Cancer SD | Normal mean | Normal SD | AUC ROC | ttest p-value |
|---|---|---|---|---|---|---|---|
| miR-126*,miR-15b | −1.99 | −3.43 | 0.89 | −1.44 | 0.67 | 0.99 | 6.21E−25 |
| miR-15b,miR-27b | 2.21 | −1.78 | 0.86 | −3.99 | 0.95 | 0.98 | 7.97E−27 |
| miR-126,miR-15b | −1.74 | −3.35 | 1.12 | −1.61 | 0.76 | 0.97 | 3.30E−16 |
| miR-126*,miR-15a | −1.80 | −6.55 | 0.81 | −4.76 | 0.87 | 0.94 | 1.49E−22 |
| miR-15b,miR-27a | 1.57 | 0.83 | 0.93 | −0.74 | 0.74 | 0.94 | 1.47E−17 |
| miR-106b,miR-30a-5p | 1.15 | 1.72 | 0.56 | 0.57 | 0.55 | 0.93 | 2.58E−21 |
| miR-15b,miR-30a-5p | 1.84 | 2.68 | 1.10 | 0.84 | 0.68 | 0.93 | 6.13E−18 |
| miR-15b,miR-30d | 1.81 | 1.79 | 1.08 | −0.02 | 0.69 | 0.93 | 6.96E−18 |
| miR-15a,3 miR-30a-5p | 1.64 | 5.79 | 0.84 | 4.15 | 0.83 | 0.92 | 8.12E−20 |
| miR-15a,miR-27b | 2.00 | 1.33 | 0.90 | −0.68 | 1.13 | 0.92 | 8.07E−21 |
| miR-15b,miR-30b | 1.03 | 1.73 | 0.76 | 0.70 | 0.71 | 0.92 | 2.58E−12 |
| miR-126*,miR-26b | −1.07 | −0.73 | 0.52 | 0.34 | 0.64 | 0.92 | 7.36E−19 |
| miR-126,miR-15a | −1.56 | −6.48 | 1.10 | −4.93 | 0.92 | 0.92 | 1.32E−13 |
| miR-15a,miR-30d | 1.62 | 4.91 | 0.87 | 3.29 | 0.85 | 0.91 | 1.04E−18 |
| miR-15b,miR-26b | 0.92 | 2.71 | 0.79 | 1.78 | 0.41 | 0.91 | 1.33E−11 |
| miR-106b,miR-30d | 1.12 | 0.83 | 0.61 | −0.29 | 0.60 | 0.91 | 2.69E−18 |
| miR-106b,miR-126* | 1.30 | 2.47 | 0.63 | 1.18 | 0.72 | 0.91 | 8.20E−20 |
| miR-15a,miR-422a | 1.56 | 0.46 | 0.99 | −1.10 | 0.80 | 0.91 | 4.86E−16 |
| miR-106a,miR-30a-5p | 0.99 | −0.62 | 0.58 | −1.60 | 0.44 | 0.91 | 8.79E−18 |
| miR-106a,miR-30d | 0.96 | −1.51 | 0.57 | −2.47 | 0.45 | 0.91 | 2.49E−17 |
| miR-15b,miR-301 | 1.18 | −2.48 | 0.85 | −3.66 | 0.54 | 0.91 | 3.59E−14 |
| miR-26b,miR-27b | 1.28 | −4.49 | 0.56 | −5.77 | 0.87 | 0.90 | 4.08E−18 |

TABLE 38-continued miRNA biomarker pairs that can be used to identify serum from lung cancer patients.

| miRNA Biomarker Pair | Cancer mean − Normal mean | Cancer mean | Cancer SD | Normal mean | Normal SD | AUC ROC | ttest p-value |
|---|---|---|---|---|---|---|---|
| miR-182,miR-27b | 2.14 | 3.19 | 1.07 | 1.05 | 1.35 | 0.90 | 6.45E−18 |
| miR-106b,miR-27b | 1.51 | −2.74 | 0.72 | −4.25 | 1.03 | 0.90 | 2.49E−17 |
| miR-142-3p,miR-27b | 1.20 | −5.18 | 0.58 | −6.38 | 0.94 | 0.89 | 3.90E−15 |
| miR-106a,miR-126* | 1.14 | 0.13 | 0.62 | −1.00 | 0.66 | 0.89 | 1.28E−17 |
| let-7i,miR-126* | 1.14 | 2.01 | 0.63 | 0.87 | 0.79 | 0.89 | 8.05E−16 |
| miR-27b,miR-30b | −1.17 | 3.51 | 0.58 | 4.69 | 1.02 | 0.89 | 1.67E−13 |
| miR-126*,miR-182 | −1.85 | −8.32 | 1.02 | −6.47 | 1.15 | 0.88 | 7.45E−17 |
| miR-15a,miR-27a | 1.40 | 3.97 | 0.84 | 2.57 | 0.87 | 0.88 | 1.13E−15 |
| miR-106b,miR-126 | 1.05 | 2.39 | 0.89 | 1.35 | 0.79 | 0.88 | 2.41E−10 |
| miR-142-3p,miR-15b | −1.00 | −3.40 | 0.81 | −2.39 | 0.70 | 0.88 | 3.57E−11 |
| let-7i,miR-27b | 1.36 | −3.21 | 0.70 | −4.57 | 0.99 | 0.88 | 1.07E−15 |
| miR-126*,miR-30b | −0.96 | −1.70 | 0.62 | −0.75 | 0.71 | 0.88 | 3.01E−13 |
| miR-150,miR-15b | −1.63 | −1.88 | 1.18 | −0.25 | 0.94 | 0.87 | 2.68E−13 |
| miR-15b,miR-422a | 1.68 | −2.71 | 1.40 | −4.40 | 0.73 | 0.87 | 5.28E−12 |
| miR-182,miR-422a | 1.67 | 2.31 | 1.22 | 0.64 | 1.04 | 0.86 | 6.23E−13 |
| miR-182,miR-30a-5p | 1.71 | 7.63 | 1.20 | 5.92 | 1.10 | 0.86 | 2.75E−13 |
| miR-15b,miR-422b | 1.79 | −2.77 | 1.52 | −4.55 | 0.96 | 0.86 | 2.69E−11 |
| miR-182,miR-30d | 1.70 | 6.72 | 1.20 | 5.02 | 1.05 | 0.86 | 1.78E−13 |
| miR-126,miR-26b | −0.82 | −0.65 | 0.84 | 0.17 | 0.76 | 0.86 | 9.36E−08 |
| miR-126,miR-182 | −1.62 | −8.29 | 1.21 | −6.67 | 1.27 | 0.85 | 2.19E−11 |
| let-7g,miR-126* | 1.00 | 1.23 | 0.65 | 0.24 | 0.86 | 0.85 | 8.28E−12 |
| miR-15a,miR-422b | 1.59 | 0.35 | 1.33 | −1.24 | 1.02 | 0.85 | 4.27E−11 |
| miR-27b,miR-301 | −1.03 | −0.70 | 0.66 | 0.33 | 0.88 | 0.85 | 6.93E−12 |
| miR-126,miR-30b | −0.71 | −1.62 | 0.80 | −0.92 | 0.82 | 0.85 | 3.08E−06 |
| miR-Let-7g,miR-15b | −0.99 | −2.20 | 0.91 | −1.21 | 0.68 | 0.85 | 7.70E−10 |
| miR-126*,miR-142-3p | −0.98 | −0.03 | 0.73 | 0.95 | 0.85 | 0.84 | 7.76E−11 |
| miR-106a,miR-27b | 1.35 | −5.08 | 0.79 | −6.43 | 1.15 | 0.84 | 8.96E−13 |
| miR-25,miR-30a-5p | 0.85 | 1.10 | 0.71 | 0.25 | 0.63 | 0.84 | 1.37E−10 |
| miR-15a,miR-30e-5p | 1.42 | 4.23 | 1.01 | 2.81 | 1.97 | 0.83 | 4.57E−07 |
| miR-106b,miR-422a | 1.02 | −3.63 | 0.93 | −4.65 | 0.65 | 0.83 | 3.79E−10 |
| miR-182,miR-422b | 1.71 | 2.18 | 1.37 | 0.47 | 1.30 | 0.83 | 8.37E−11 |
| miR-106b,miR-27a | 0.88 | −0.13 | 0.66 | −1.01 | 0.72 | 0.83 | 4.90E−11 |
| let-7i,miR-15b | −0.84 | −1.42 | 0.80 | −0.58 | 0.55 | 0.83 | 1.23E−09 |
| miR-126,miR-142-3p | −0.74 | 0.05 | 0.96 | 0.78 | 0.85 | 0.83 | 1.50E−05 |
| miR-Let-7g,miR-27b | 1.21 | −3.98 | 0.82 | −5.20 | 1.08 | 0.82 | 2.59E−11 |
| miR-30a-5p,miR-324-3p | −0.77 | −5.36 | 0.55 | −4.59 | 0.75 | 0.82 | 5.20E−10 |
| miR-150,miR-182 | −1.50 | −6.84 | 1.22 | −5.34 | 1.09 | 0.82 | 7.73E−11 |
| miR-182,miR-27a | 1.51 | 5.82 | 1.14 | 4.31 | 1.26 | 0.82 | 8.04E−11 |
| miR-150,miR-15a | −1.45 | −5.01 | 1.20 | −3.56 | 1.14 | 0.81 | 2.31E−10 |
| miR-15b,miR-30e-5p | 1.61 | 1.10 | 1.25 | −0.51 | 1.89 | 0.81 | 4.18E−08 |
| miR-15b,miR-181c | 1.18 | −5.28 | 1.11 | −6.46 | 0.88 | 0.81 | 2.59E−09 |
| miR-106b,miR-422b | 1.09 | −3.73 | 1.05 | −4.82 | 0.89 | 0.81 | 1.03E−08 |
| miR-25,miR-30d | 0.82 | 0.21 | 0.76 | −0.61 | 0.63 | 0.80 | 2.41E−09 |
| miR-15b,miR-92 | 3.30 | 5.34 | 2.87 | 2.04 | 3.38 | 0.80 | 1.98E−08 |
| miR-126*,miR-301 | −0.81 | −5.91 | 0.80 | −5.10 | 0.57 | 0.80 | 6.31E−09 |
| miR-106a,miR-126 | 0.89 | 0.06 | 0.90 | −0.83 | 0.89 | 0.80 | 1.44E−07 |
| miR-15a,miR-301 | 0.99 | 0.64 | 0.98 | −0.35 | 0.77 | 0.79 | 1.09E−08 |
| miR-106a,miR-15b | −0.85 | −3.30 | 0.99 | −2.44 | 0.59 | 0.79 | 1.75E−07 |
| miR-106b,miR-30e-5p | 0.92 | 0.14 | 0.70 | −0.77 | 1.82 | 0.79 | 1.34E−04 |
| miR-30d,miR-324-3p | −0.74 | −4.46 | 0.67 | −3.73 | 0.81 | 0.79 | 1.00E−07 |
| miR-15a,miR-92 | 3.03 | 8.43 | 2.93 | 5.41 | 3.39 | 0.79 | 2.74E−07 |
| let-7i,miR-126 | 0.90 | 1.93 | 1.00 | 1.04 | 0.97 | 0.79 | 1.30E−06 |
| miR-142-3p,miR-15a | −0.82 | −6.53 | 0.84 | −5.71 | 0.70 | 0.79 | 4.66E−08 |
| miR-181c,miR-27b | 1.00 | 3.47 | 0.89 | 2.48 | 0.88 | 0.79 | 5.18E−09 |
| miR-106a,miR-422a | 0.90 | −5.94 | 1.00 | −6.83 | 0.69 | 0.78 | 1.35E−07 |
| miR-106b,miR-92 | 2.60 | 4.38 | 2.93 | 1.78 | 3.40 | 0.78 | 7.78E−06 |
| let-7i,miR-30d | 0.97 | 0.37 | 1.03 | −0.60 | 0.82 | 0.78 | 9.84E−08 |
| miR-26b,miR-30d | 0.89 | −0.92 | 0.94 | −1.80 | 0.77 | 0.78 | 1.06E−07 |
| miR-182,miR-30e-5p | 1.55 | 6.08 | 1.22 | 4.53 | 2.07 | 0.78 | 4.58E−07 |
| miR-26b,miR-30a-5p | 0.92 | −0.02 | 0.95 | −0.94 | 0.75 | 0.78 | 4.19E−08 |
| miR-182,miR-92 | 3.07 | 10.21 | 3.02 | 7.15 | 3.41 | 0.78 | 3.08E−07 |
| let-7i,miR-30a-5p | 1.00 | 1.26 | 1.06 | 0.26 | 0.82 | 0.77 | 7.13E−08 |
| miR-182,miR-301 | 1.12 | 2.51 | 1.20 | 1.39 | 1.01 | 0.77 | 1.69E−07 |
| miR-15b,3 miR-46 | 1.79 | −6.11 | 2.03 | −7.89 | 1.58 | 0.77 | 4.01E−07 |
| miR-106a,miR-92 | 2.41 | 2.04 | 2.87 | −0.37 | 3.43 | 0.77 | 2.71E−05 |
| miR-27a,miR-27b | 0.63 | −2.62 | 0.52 | −3.25 | 0.71 | 0.77 | 3.97E−08 |
| miR-15a,miR-346 | 1.69 | −3.02 | 1.97 | −4.71 | 1.47 | 0.77 | 5.42E−07 |
| miR-15a,miR-324-3p | 0.90 | 0.47 | 0.85 | −0.44 | 1.00 | 0.77 | 1.49E−07 |
| miR-106b,miR-15b | −0.69 | −0.96 | 0.87 | −0.27 | 0.44 | 0.77 | 6.62E−07 |

TABLE 38-continued miRNA biomarker pairs that can be used to identify serum from lung cancer patients.

| miRNA Biomarker Pair | Cancer mean − Normal mean | Cancer mean | Cancer SD | Normal mean | Normal SD | AUC ROC | ttest p-value |
|---|---|---|---|---|---|---|---|
| miR-15b,miR-324-3p | 1.07 | −2.68 | 1.11 | −3.75 | 0.96 | 0.76 | 7.93E−08 |
| miR-126*,miR-181c | −0.75 | −8.65 | 0.87 | −7.91 | 0.71 | 0.76 | 1.01E−06 |
| let-7g,miR-126 | 0.75 | 1.16 | 0.92 | 0.41 | 1.01 | 0.76 | 2.14E−05 |
| miR-15a,miR-181c | 1.00 | −2.15 | 0.97 | −3.15 | 1.02 | 0.76 | 9.88E−08 |
| miR-142-3p,miR-27a | 0.57 | −2.57 | 0.68 | −3.14 | 0.68 | 0.75 | 5.81E−06 |
| miR-106b,miR-150 | 0.94 | 0.92 | 0.82 | −0.02 | 1.11 | 0.75 | 1.68E−07 |
| miR-182,miR-346 | 1.67 | −1.27 | 1.82 | −2.94 | 1.66 | 0.75 | 4.51E−07 |
| miR-126*,miR-25 | −1.00 | −1.85 | 1.03 | −0.85 | 1.07 | 0.75 | 4.15E−07 |
| miR-26b,miR-27a | 0.65 | −1.87 | 0.75 | −2.52 | 0.78 | 0.75 | 4.13E−06 |
| miR-25,miR-92 | 2.29 | 3.76 | 2.85 | 1.47 | 3.48 | 0.75 | 6.64E−05 |
| miR-15a,miR-26b | 0.72 | 5.82 | 0.84 | 5.10 | 0.67 | 0.74 | 7.99E−07 |
| let-7g,miR-182 | −0.88 | −7.11 | 1.06 | −6.23 | 0.99 | 0.74 | 4.23E−06 |
| miR-15a,miR-30b | 0.84 | 4.85 | 0.87 | 4.01 | 0.95 | 0.74 | 8.58E−07 |
| let-7i,miR-92 | 2.44 | 3.92 | 2.98 | 1.47 | 3.30 | 0.74 | 2.17E−05 |
| miR-106a,miR-27a | 0.72 | −2.47 | 0.73 | −3.19 | 0.91 | 0.74 | 1.75E−06 |
| miR-142-3p,miR-182 | −0.92 | −8.40 | 0.97 | −7.48 | 1.11 | 0.74 | 1.67E−06 |
| miR-182,miR-30b | 0.89 | 6.69 | 0.98 | 5.80 | 0.98 | 0.74 | 1.27E−06 |
| miR-324-3p,miR-422a | 0.68 | −0.02 | 0.94 | −0.70 | 0.87 | 0.74 | 5.00E−05 |
| let-7i,miR-182 | −0.80 | −6.40 | 1.03 | −5.59 | 0.90 | 0.74 | 1.03E−05 |
| miR-182,miR-26b | 0.79 | 7.63 | 0.91 | 6.84 | 0.94 | 0.74 | 4.74E−06 |
| let-7g,miR-30a-5p | 0.85 | 0.49 | 1.07 | −0.37 | 0.98 | 0.74 | 8.75E−06 |

In addition to the differential paired analysis of miRNA (Table 38), several miRNA biomarker based classifier models that discriminated lung-cancer from normal (cancer free) subjects were evaluated. Classifier models were designed with data obtained from the samples described in Table 34. When applied to the unrelated samples shown in Table 36, the models demonstrated good performance in discriminating lung cancer patients from normal subjects.

Specifically, the simple Welch's t-test and Relief (Kira and Rendel, Proc 10$^{th}$ Natl Conf on Artificial Intelligence, MIT Press, pp. 129-134 (1992)) methods were used to select features (i.e., miRNAs) as inputs, and the Linear Discriminant Analysis (LDA) and Linear Support vector machines (LSVM) were used as the classifiers during training (Burges, *Data Mining and Drug Discovery* 2:121-167 (1998)). Table 39 shows representative examples of classifier models that distinguished lung cancer from cancer free subjects in both training and test sets.

TABLE 39

Performance of classification models and feature selection in training set and test set of normal subjects and lung cancer patients.

| Name | Classifier | Feature Selection Method | Number of Features (miRNAs) | Training Set AUC | Test Set AUC |
|---|---|---|---|---|---|
| LSVM Train r + TTest + 4 | LSVM Train | TTest | 4 | 1.000 | 0.919 |
| LSVM Train + TTest + 5 | LSVM Train | TTest | 5 | 1.000 | 0.890 |
| LSVM Train + TTest + 6 | LSVM Train | TTest | 6 | 1.000 | 0.879 |
| LSVM Train + TTest + 7 | LSVM Train | TTest | 7 | 1.000 | 0.831 |
| LSVM Train + Relief + 4 | LSVM Train | Relief | 4 | 0.996 | 0.958 |
| LSVM Train + Relief + 5 | LSVM Train | Relief | 5 | 0.997 | 0.958 |
| LSVM Train + Relief + 6 | LSVM Train | Relief | 6 | 0.997 | 0.933 |
| LSVM Train + Relief + 7 | LSVM Train | Relief | 7 | 0.997 | 0.931 |
| LDA Train + TTest + 4 | LDA Train | TTest | 4 | 1.000 | 0.886 |
| LDA Train + TTest + 5 | LDA Train | TTest | 5 | 1.000 | 0.875 |
| LDA Train + TTest + 6 | LDA Train | TTest | 6 | 0.998 | 0.816 |
| LDA Train + TTest + 7 | LDA Train | TTest | 7 | 0.998 | 0.785 |
| LDA Train + Relief + 4 | LDA Train | Relief | 4 | 0.996 | 0.939 |
| LDA Train + Relief + 5 | LDA Train | Relief | 5 | 0.997 | 0.908 |
| LDA Train + Relief + 6 | LDA Train | Relief | 6 | 0.996 | 0.908 |
| LDA Train + Relief + 7 | LDA Train | Relief | 7 | 0.996 | 0.917 |

The model's performance was estimated on training data by performing 25 repetitions of 5-fold cross validation on the training samples and measuring the ROC AUC values as previously described in Example 5. The frequency of appearance of miRNA pairs in each of the classification models is shown in Table 40.

TABLE 40

Prevalence of paired biomarkers in classifier generation. The classification models are as indicated.

| LSVM Train + TTest + 7 | | LSVM Train + Relief + 7 | | LDA Train + TTest + 7 | | LDA Train + Relief + 7 | |
|---|---|---|---|---|---|---|---|
| miRNA Pair | Pair Frequency | miRNA Pair | Pair Frequency | miRNA Pair | Pair Frequency | miRNA Pair | Pair Frequency |
| 106a,15b | 125 | 106a,26b | 125 | 106a,15b | 125 | 106a,26b | 125 |
| 106a,422b | 125 | 126*,26b | 125 | 106a,422b | 125 | 126*,26b | 125 |
| 15b,30a-5p | 125 | let-7i,26b | 115 | 15b,30a-5p | 125 | let-7i,26b | 115 |
| 126*,15b | 101 | 126*,15b | 104 | 126*,15b | 101 | 126*,15b | 104 |
| 106a,26b | 95 | 106a,15b | 101 | 106a,26b | 95 | 106a,15b | 101 |
| let-7g,106a | 79 | 126*,30b | 50 | let-7g,106a | 79 | 126*,30b | 50 |
| 106a,106b | 55 | 26b,30a-5p | 49 | 106a,106b | 55 | 26b,30a-5p | 49 |
| 181c,30e-5p | 45 | 106a,422b | 38 | 181c,30e-5p | 45 | 106a,422b | 38 |
| 106a,142-3p | 40 | 30d,30e-5p | 27 | 106a,142-3p | 40 | 30d,30e-5p | 27 |
| 106a,182 | 20 | 26b,30e-5p | 25 | 106a,182 | 20 | 26b,30e-5p | 25 |
| 182,30a-5p | 9 | 422a,422b | 16 | 182,30a-5p | 9 | 422a,422b | 16 |
| 106a,15a | 8 | 126,15b | 14 | 106a,15a | 8 | 126,15b | 14 |
| 142-3p,30a-5p | 6 | 15b,30a-5p | 12 | 142-3p,30a-5p | 6 | 15b,30a-5p | 12 |
| 126*,26b | 5 | 106a,30b | 10 | 126*,26b | 5 | 106a,30b | 10 |
| 15b,30e-5p | 5 | 26b,27b | 10 | 15b,30e-5p | 5 | 26b,27b | 10 |
| 182,30e-5p | 5 | 106a,15a | 9 | 182,30e-5p | 5 | 106a,15a | 9 |
| 15b,25 | 4 | let-7i,15b | 9 | 15b,25 | 4 | let-7l,15b | 9 |
| 126,30e-5p | 3 | 26b,27a | 6 | 126,30e-5p | 3 | 26b,27a | 6 |
| 126*,422b | 3 | 30e-5p,422b | 6 | 126*,422b | 3 | 30e-5p,422b | 6 |
| 142-3p,27b | 3 | 106a,106b | 4 | 142-3p,27b | 3 | 106a,106b | 4 |
| 181c,27b | 3 | 15b,25 | 4 | 181c,27b | 3 | 15b,25 | 4 |
| 26b,27a | 3 | 15b,30e-5p | 3 | 26b,27a | 3 | 15b,30e-5p | 3 |
| 422a,422b | 3 | 106a,324-3p | 2 | 422a,422b | 3 | 106a,324-3p | 2 |
| 30a-5p,422b | 2 | 181c,30e-5p | 2 | 30a-5p,422b | 2 | 181c,30e-5p | 2 |
| 106a,126 | 1 | let-7i,422b | 2 | 106a,126 | 1 | let-7i,422b | 2 |
| 106a,181c | 1 | 106a,182 | 1 | 106a,181c | 1 | 106a,182 | 1 |
| 106a,324-3p | 1 | 126*,422b | 1 | 106a,324-3p | 1 | 126*,422b | 1 |
| | | 15b,27b | 1 | | | 15b,27b | 1 |
| | | 25,26b | 1 | | | 25,26b | 1 |
| | | 30b,30e-5p | 1 | | | 30b,30e-5p | 1 |
| | | let-7i,15a | 1 | | | let-7i,15a | 1 |
| | | let-7i,30b | 1 | | | let-7i,30b | 1 |

The unique miRNAs that were most frequently associated with the classifier models from Table 40 and that distinguished lung cancer from cancer free subjects are shown in Table 41. These miRNAs can be used to distinguish patients with lung cancer from cancer free subjects, and therefore can be used in the characterization or diagnosis of lung cancer.

TABLE 41 miRNAs that can be used to distinguish patients with lung cancer from cancer free subjects

| LSVM Train + TTest + 7 | LSVM Train + Relief + 7 | LDA Train + TTest + 7 | LDA Train + Relief + 7 |
|---|---|---|---|
| 106a | 106a | 106a | 106a |
| 106b | | 106b | |
| 126* | 126* | 126* | 126* |
| 142-3p | | 142-3p | |
| 15b | 15b | 15b | 15b |
| 181c | | 181c | |
| 182 | | 182 | |
| 26b | 26b | 26b | 26b |
| 30a-5p | 30a-5p | 30a-5p | 30a-5p |
| | 30b | | 30b |
| | 30d | | 30d |
| 30e-5p | 30e-5p | 30e-5p | 30e-5p |

TABLE 41-continued miRNAs that can be used to distinguish patients with lung cancer from cancer free subjects

| LSVM Train + TTest + 7 | LSVM Train + Relief + 7 | LDA Train + TTest + 7 | LDA Train + Relief + 7 |
|---|---|---|---|
| 422b | 422b | 422b | 422b |
| | let-7i | | let-7i |
| let-7g | | let-7g | |

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All references cited herein are incorporated herein by reference in their entirety. To the extent publications and patents or patent applications incorporated by reference contradict the invention contained in the specification, the specification will supersede any contradictory material.

What is claimed is:

1. A method for characterizing a lung disease in a patient with a lung tumor or lesion as cancerous or benign, comprising the steps of:
   a. reverse transcribing a miRNA in a serum sample;
   b. amplifying the miRNA;
   c. measuring the level of the miRNA, wherein the miRNA is miR-142-3p; and
   d. detecting whether the level of miR-142-3p is reduced, as compared to a level of miR-142-3p in serum from a cohort or cohorts that do not have the lung disease, thereby characterizing the lung disease in the patient as cancerous if miR-142-3p is reduced.

2. The method of claim 1, wherein the lung cancer is small cell or non-small cell lung cancer.

3. The method of claim 1, wherein the patient has previously been screened for lung disease.

4. The method of claim 3, wherein the screening was by CT scan or chest x-ray.

5. The method of claim 1, wherein the patient is suspected of having lung cancer or is at risk of developing lung cancer.

6. The method of claim 1, wherein the amplification is by quantitative reverse transcriptase polymerase chain reaction.

7. The method of claim 1, further comprising reverse transcribing, amplifying, measuring, and detecting a reduced or elevated level of a second miRNA in the serum sample, as compared to a level of the second miRNA in serum from a cohort or cohorts that do not have the lung disease, whereby the lung disease is characterized as cancerous if miR-142-3p is reduced and the second miRNA is reduced or elevated.

8. The method of claim 1, wherein the reverse transcription comprises a reverse transcription primer that includes a portion complementary to the miRNA and a 5' non-complementary portion.

9. The method of claim 1, wherein the amplification comprises a first primer that includes a portion complementary to the miRNA and a 5' non-complementary portion.

10. The method of claim 9, wherein the amplification comprises a second primer complementary to the 5' non-complementary portion of the first primer.

11. The method of claim 1, wherein the amplification comprises a first primer that includes a portion complementary to a cDNA copy of the miRNA and a 5' non-complementary portion.

12. The method of claim 11, wherein the amplification comprises a second primer complementary to the 5' non-complementary portion of the first primer.

13. A method for characterizing a lung disease in a patient comprising the steps of:
 a. reverse transcribing a first miRNA and a second miRNA in a serum sample;
 b. amplifying the first miRNA and the second miRNA;
 c. measuring the level of the first miRNA and the second miRNA, wherein the first miRNA is miR-142-3p; and
 d. detecting whether the level of the first miRNA is reduced and detecting whether the level of the second miRNA is reduced or elevated, as compared to miRNA levels in serum from a cohort or cohorts that do not have the lung disease,
 thereby characterizing the lung disease in the patient.

14. The method of claim 13, wherein the second miRNA is chosen from miR-22, miR-23a, miR-24, miR-27b, miR-30a-5p, miR-92, miR-99b, miR-125a, miR-130b, miR-132, miR-145, miR-146a, miR-150, miR-151, miR-181a, miR-181b, miR-181d, miR-186, miR-191, miR-202, miR-210, miR 320, miR-328, miR-342, miR-345, miR-378, miR-422a, miR-425, miR-486, and miR-518b.

15. The method of claim 13, wherein the lung disease is cancer.

16. The method of claim 15, wherein the cancer is small cell or non-small cell lung cancer.

17. The method of claim 13, wherein the patient has a lung tumor or lesion.

18. The method of claim 13, wherein the patient has previously been screened for lung disease.

19. The method of claim 13, wherein the amplification is by quantitative reverse transcriptase polymerase chain reaction.

20. The method of claim 13, wherein the patient is male.

21. The method of claim 13, wherein the patient is female.

22. The method of claim 13, wherein the reverse transcription comprises a reverse transcription primer that includes a portion complementary to the first or second miRNA and a 5' non-complementary portion.

23. The method of claim 13, wherein the amplification comprises a first primer that includes a portion complementary to the first or second miRNA and a 5' non-complementary portion.

24. The method of claim 23, wherein the amplification comprises a second primer complementary to the 5' non-complementary portion of the first primer.

25. The method of claim 13, wherein the amplification comprises a first primer that includes a portion complementary to a cDNA copy of the first or second miRNA and a 5' non-complementary portion.

26. The method of claim 25, wherein the amplification comprises a second primer complementary to the 5' non-complementary portion of the first primer.

27. The method of claim 13, wherein the patient has a lung tumor or lesion, and the method comprises characterizing the lung tumor or lesion as cancerous if miR-142-3p is reduced and the second miRNA is reduced or elevated.

28. The method of claim 27, wherein the cancer is small cell or non-small cell lung cancer.

29. The method of claim 27, wherein miR-142-3p and the second miRNA are expressed at reduced levels in serum from a patient with lung cancer.

30. The method of claim 27, wherein miR-142-3p is expressed at a reduced level and the second miRNA is expressed at an elevated level in serum from a patient with lung cancer.

31. The method of claim 13, wherein a progression of the lung disease is characterized based on the level of miR-142-3p and the second miRNA.

32. The method of claim 13, wherein a prognosis or aggressiveness of the lung disease is characterized based on the level of miR-142-3p and the second miRNA.

33. The method of claim 13, wherein the second miRNA is miR-27b.

34. The method of claim 13, wherein the second miRNA is miR-15b.

35. The method of claim 13, wherein the second miRNA is miR-21.

36. The method of claim 13, wherein the second miRNA is miR-205.

37. The method of claim 13, wherein the second miRNA is miR-126*.

* * * * *